US010247672B2

(12) United States Patent
Betzig et al.

(10) Patent No.: US 10,247,672 B2
(45) Date of Patent: Apr. 2, 2019

(54) NON-LINEAR STRUCTURED ILLUMINATION MICROSCOPY

(71) Applicant: Howard Hughes Medical Institute, Ashburn, VA (US)

(72) Inventors: Robert E. Betzig, Ashburn, VA (US); Dong Li, Ashburn, VA (US)

(73) Assignee: Howard Hughes Medical Institute, Ashburn, VA (US)

( * ) Notice: Subject to any disclaimer, the term of this patent is extended or adjusted under 35 U.S.C. 154(b) by 0 days.

(21) Appl. No.: 14/869,968

(22) Filed: Sep. 29, 2015

(65) Prior Publication Data

US 2016/0305883 A1 Oct. 20, 2016

Related U.S. Application Data

(60) Provisional application No. 62/210,871, filed on Aug. 27, 2015, provisional application No. 62/057,220, filed on Sep. 29, 2014.

(51) Int. Cl.
*G01N 21/64* (2006.01)
*G02B 21/16* (2006.01)
(Continued)

(52) U.S. Cl.
CPC ..... *G01N 21/6458* (2013.01); *G01N 21/6428* (2013.01); *G02B 21/06* (2013.01);
(Continued)

(58) Field of Classification Search
CPC ........... G01N 21/6428; G01N 21/6458; G01N 2021/6439
See application file for complete search history.

(56) References Cited

U.S. PATENT DOCUMENTS 5,245,619 A 9/1993 Kronberg et al.
5,856,049 A 1/1999 Lee et al.
(Continued)

FOREIGN PATENT DOCUMENTS

WO 2016054118 A1 4/2016

OTHER PUBLICATIONS

Hoffman et al., "Breaking the diffraction barrier in fluorescence microscopy at low light intensities by using reversibly photoswitchabe proteins," PNAS, vol. 102, No. 49, pp. 17565-17569, Dec. 6, 2005; Retrieved from the internet [Apr. 29, 2017]; Retrieved from url <www.pnas.org/cgi/doi/10.1073/pnas.0506010102>.*

(Continued)

*Primary Examiner* — Yara B Green
(74) *Attorney, Agent, or Firm* — Brake Hughes Bellermann LLP

(57) ABSTRACT

A method includes: (a) providing spatially-patterned activation radiation to a sample that includes phototransformable labels, where an optical parameter of the spatially-patterned activation radiation varies periodically in space; (b) providing spatially-patterned excitation radiation to the sample, where an optical parameter of the spatially-patterned excitation radiation varies periodically in space, where (a) and (b) create a non-linear fluorescence emission pattern within the sample, the pattern including H modulation harmonics, with H>1. The method includes (c) detecting radiation emitted from the activated and excited labels, (d) storing detected radiation data, and (e) spatially shifting one or both of the spatially-patterned excitation radiation and the spatially-patterned activation radiation with respect to the sample to spatially shift the non-linear fluorescence emission pattern within the sample, and (f) repeating (a)-(e) at least N times, with N>2. Then, a sub-diffraction-limited final image of the sample is generated based on the stored data for the N positions of the non-linear fluorescence emission pattern within the sample.

95 Claims, 63 Drawing Sheets

(51) Int. Cl.
*G02B 21/06* (2006.01)
*G02B 21/36* (2006.01)

(52) U.S. Cl.
CPC .......... *G02B 21/16* (2013.01); *G02B 21/367* (2013.01); *G01N 2021/6439* (2013.01)

(56) References Cited

U.S. PATENT DOCUMENTS

| | | | |
|---|---|---|---|
| 6,480,524 | B1 | 11/2002 | Smith et al. |
| 7,626,695 | B2 | 12/2009 | Betzig et al. |
| 7,626,703 | B2 | 12/2009 | Betzig et al. |
| 7,710,563 | B2 | 5/2010 | Betzig et al. |
| 7,782,457 | B2 | 8/2010 | Betzig et al. |
| 8,599,376 | B2 | 12/2013 | Betzig et al. |
| 2004/0027889 | A1 | 2/2004 | Occhipinti et al. |
| 2005/0036136 | A1 | 2/2005 | Opsal et al. |
| 2006/0257089 | A1 | 11/2006 | Mueth et al. |
| 2008/0068588 | A1* | 3/2008 | Hess ............ G01N 21/6458 356/36 |
| 2008/0111086 | A1* | 5/2008 | Betzig ............ G01N 21/6458 250/459.1 |
| 2008/0123713 | A1 | 5/2008 | Kamiyama et al. |
| 2008/0158551 | A1* | 7/2008 | Hess ............ G01B 9/04 356/73 |
| 2009/0250632 | A1* | 10/2009 | Kempe ............ G01N 21/6458 250/459.1 |
| 2010/0193673 | A1* | 8/2010 | Power ............ G02B 21/32 250/251 |
| 2010/0265575 | A1 | 10/2010 | Lippert et al. |
| 2011/0036996 | A1* | 2/2011 | Wolleschensky .. G01N 21/6458 250/459.1 |
| 2011/0205339 | A1 | 8/2011 | Pavani et al. |
| 2011/0205352 | A1 | 8/2011 | Pavani et al. |
| 2013/0088776 | A1 | 4/2013 | Nakayama et al. |
| 2013/0126759 | A1 | 5/2013 | Betzig et al. |
| 2013/0286181 | A1 | 10/2013 | Betzig et al. |
| 2013/0314717 | A1* | 11/2013 | Yi ............ G02B 21/0032 356/479 |
| 2014/0042340 | A1* | 2/2014 | Hell ............ G01N 21/645 250/459.1 |
| 2014/0049817 | A1 | 2/2014 | Yang |
| 2015/0037812 | A1* | 2/2015 | Schreiter ............ G01N 33/84 435/7.1 |
| 2016/0054553 | A1* | 2/2016 | Pantazis ............ G02B 21/0032 250/459.1 |
| 2016/0124208 | A1* | 5/2016 | Best ............ G02B 21/0076 359/363 |

OTHER PUBLICATIONS

Rego et al., "Nonlinear structured-illumination microscopy with a photoswitchable protein reveals cellular structures at 50-nm resolution," PNAS, vol. 109, No. 3, p. E135-E143, Jan. 17, 2012; Retrieved from the internet [Apr. 25, 2017]; Retrieved from url <www.pnas.org/cgi/doi/10.1073/pnas.1107547108>.*
International Search Report and Written Opinion received for PCT Patent Application No. PCT/US2015/053050, mailed on Jan. 14, 2016, 10 pages.
Botcherby, et al., "Scanning Two Photon Fluorescence Microscopy with Extended Depth of Field", ScienceDirect, Accepted Jul. 14, 2006, Jun. 28, 2006, pp. 253-260.
Huisken, et al., "Selective Plane Illumination Microscopy Techniques in Developmental Biology", Development 136, 2009, pp. 1963-1975.
So, "Two-Photon Fluorescence Light Microscopy", Encyclopedia of Life Sciences, 2002, pp. 1-5.
Berning, et al., "Nanoscopy in a living mouse brain", Science, vol. 335, Feb. 3, 2012, p. 551.
Chen, et al., "Lattice light sheet microscopy: imaging molecules to embryos at high spatiotemporal resolution", sciencemag.org, vol. 346, Issue 6208, Oct. 24, 2014, 13 pages.
Chmyrov, et al., "Nanoscopy with more than 100,000 'doughnuts'", Nature Methods, vol. 10, Issue 8, 2013, pp. 737-740.
Fiolka, et al., "Time-lapse two-color 3D imaging of live cells with doubled resolution using structured illumination", PNAS, vol. 109, No. 14, Apr. 3, 2012, pp. 5311-5315.
Grotjohann, et al., "rsGFP2 enables fast RESOLFT nanoscopy of living cells", eLife 1, e00248, 2012, 14 pages.
Gustafsson, "Nonlinear structured-illumination microscopy: widefield fluorescence imaging with theoretically unlimited resolution", PNAS, vol. 102, No. 37, Sep. 13, 2005, pp. 13081-13806.
Gustafsson, "Surpassing the lateral resolution limit by a factor of two using structured illumination microscopy", Journal of Microscopy, vol. 198, Pt 2, May 2000, pp. 82-87.
Hein, et al. "Stimulated emission depletion (STED) nanoscopy of a fluorescent protein-labeled organelle inside a living cell", PNAS, vol. 105, No. 38, Sep. 23, 2008, pp. 14271-14276.
Ji, et al. "Advances in the Speed and Resolution of Light Microscopy", Current Opinion in Neurobiology 18, 2008, pp. 605-616.
Jones, et al., "Fast, three-dimensional super-resolution imaging of live cells", Nature Methods, vol. 8, 2011, pp. 499-505.
Kner, et al., "Super-resolution video microscopy of live cells by structured illumination", Nature Methods, vol. 6, 2009, pp. 339-342.
Lavoie-Cardinal, et al., "Two-color RESOLFT nanoscopy with green and red fluorescent photochromic proteins", ChemPhysChem 15, 2014, pp. 655-663.
Parton, et al., "The multiple faces of caveolae", Nat. Rev. Mol. Cell Biol, vol. 8, 2007, pp. 185-194.
Rego, et al., "Nonlinear structured illumination microscopy with a photoswitchable protein reveals cellular structures at 50-nm resolution", PNAS, vol. 109, No. 3, Jan. 17, 2012, pp. E135-E143.
Schermelleh, et al., "A guide to super-resolution fluorescence microscopy", J. Cell Biol., vol. 190, No. 2, 2010, pp. 165-175.
Schnell, et al., "Immunolabeling artifacts and the need for live-cell imaging", Nat. Methods, vol. 9, No. 2, Feb. 2012, pp. 152-158.
Shao, et al., "Super-resolution 3D microscopy of live whole cells using structured illumination", Nature Methods, vol. 3, No. 12, Dec. 2011, pp. 1044-1046.
Shim, et al., "Super-resolution fluorescence imaging of organelles in live cells with photoswitchable membrane probes", PNAS, vol. 109, No. 35, Aug. 28, 2012, pp. 13978-13983.
Shroff, et al., "Live-cell photoactivated localization microscopy of nanoscale adhesion dynamics", Nature Methods, vol. 5, 2008, pp. 417-423.
Testa, et al., "Nanoscopy of living brain slices with low light levels", Neuron 75, Sep. 20, 2012, pp. 992-1000.
Westphal, et al., "Video-rate far-field optical nanoscopy dissects synaptic vesicle movement", Science, vol. 320, Apr. 11, 2008, pp. 246-249.
Xu, et al., "Dual-objective Storm reveals three-dimensional filament organization in the actin cytoskeleton", Nat. Methods, vol. 9, 2012, 9 pages.

* cited by examiner

Incoherent vs. Coherent Structured and Swept Light Sheets single Bessel-like beam

| sweep incoherent swept light sheet incoherent structured
sheet from stepped beam

| sweep incoherent swept light sheet coherent structured sheet
from first side-lobes
overlapping

| sweep coherent swept light sheet

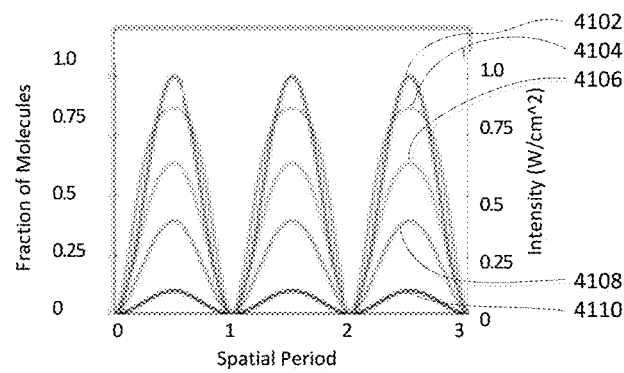
FIG. 41
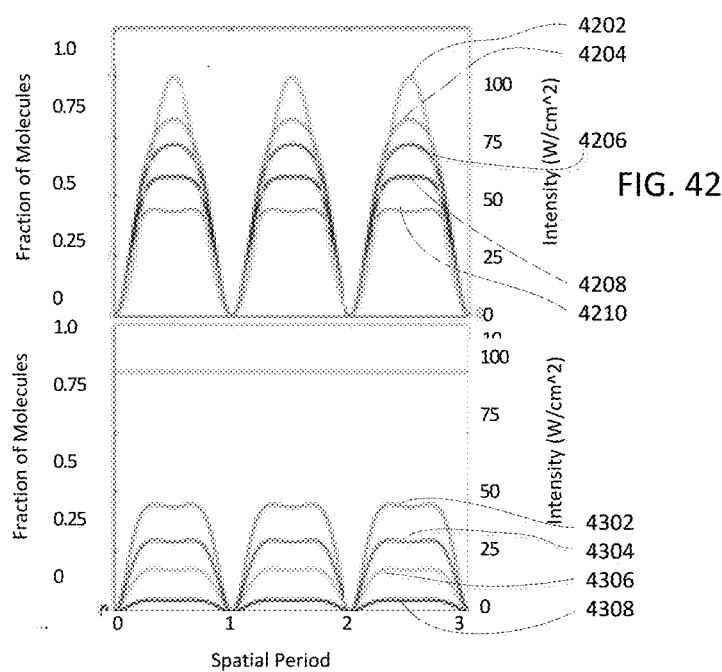
FIG. 42
FIG. 43
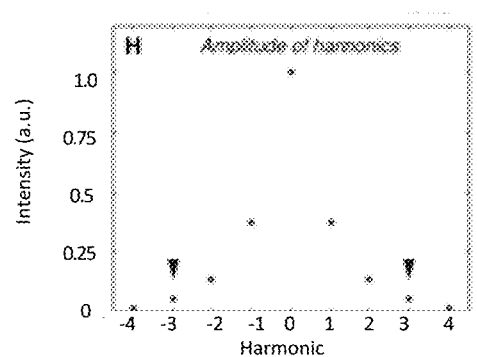
FIG. 44

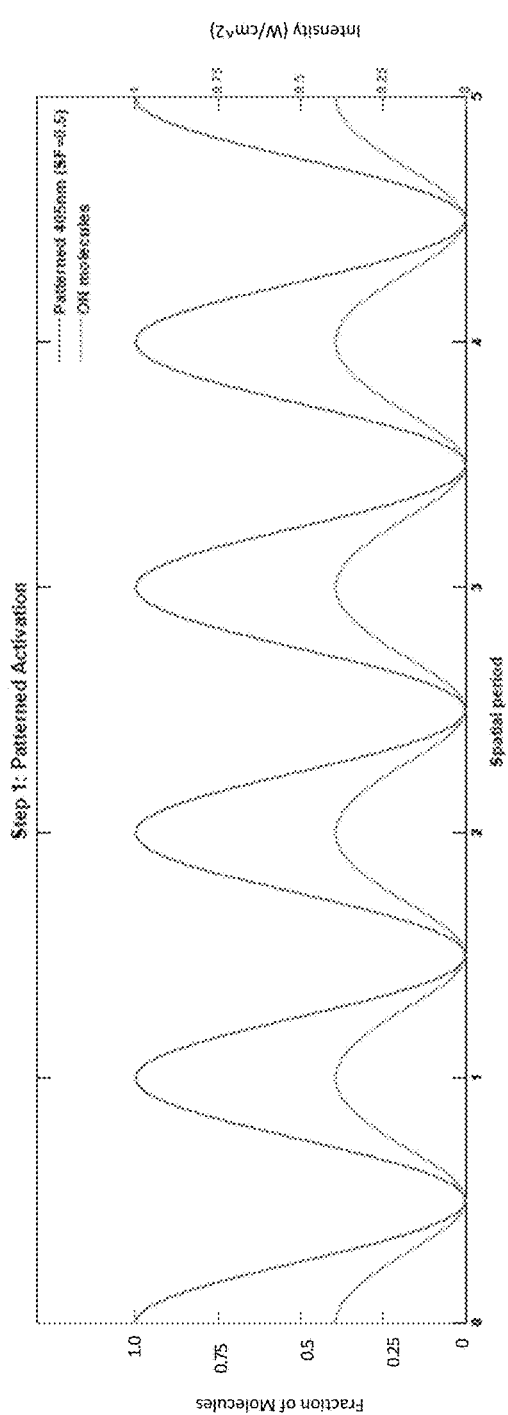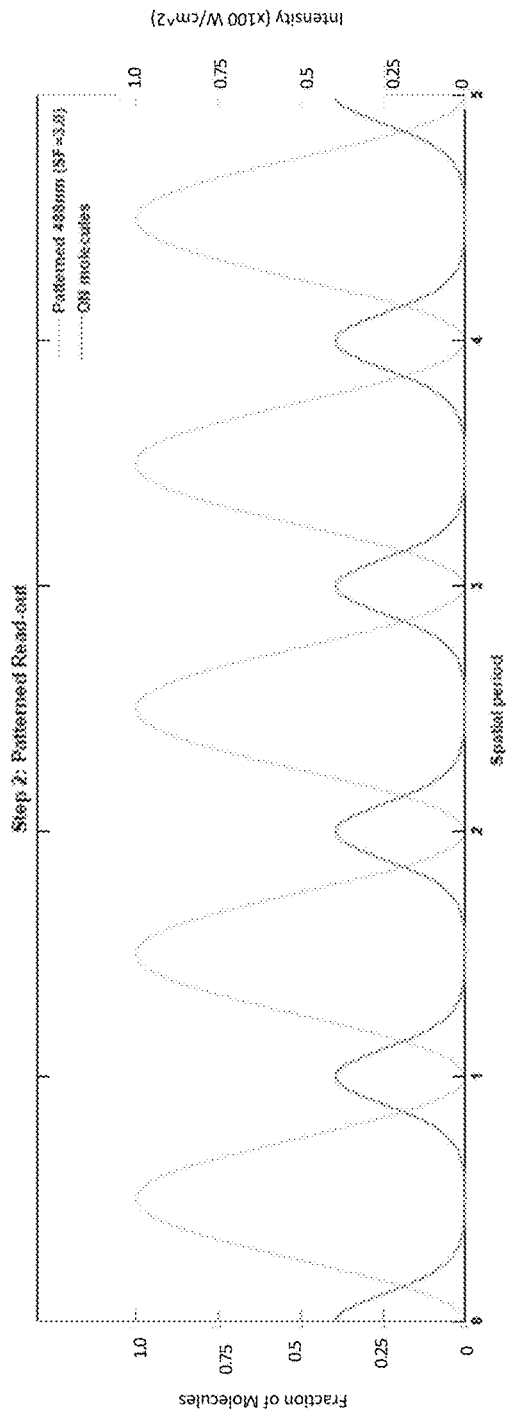

NON-LINEAR STRUCTURED ILLUMINATION MICROSCOPY

CROSS-REFERENCE TO RELATED APPLICATIONS

This application claims priority to U.S. Provisional Patent Application No. 62/057,220, entitled "NON-LINEAR LATTICE LIGHT SHEET MICROSCOPY," filed Sep. 29, 2014, and to U.S. Provisional Patent Application No. 62/210,871, entitled "NON-LINEAR STRUCTURED ILLUMINATION MICROSCOPY," filed Aug. 27, 2015. The subject matter of each of these earlier filed applications is hereby incorporated by reference.

TECHNICAL FIELD

This disclosure relates to microscopy and, in particular, to structured plane illumination microscopy.

BACKGROUND

Several imaging technologies are commonly used to interrogate biological systems. Widefield imaging floods the specimen with light, and collects light from the entire specimen simultaneously, although high resolution information is only obtained from that portion of the sample close to the focal plane of the imaging objective lens. Confocal microscopy uses the objective lens to focus light within the specimen, and a pinhole in a corresponding image plane to pass to the detector only that light collected in the vicinity of the focus. The resulting images exhibit less out-of-focus background information on thick samples than is the case in widefield microscopy, but at the cost of slower speed, due to the requirement to scan the focus across the entire plane of interest.

For biological imaging, a powerful imaging modality is fluorescence, since specific sub-cellular features of interest can be singled out for study by attaching fluorescent labels to one or more of their constituent proteins. Both widefield and confocal microscopy can take advantage of fluorescence contrast. One limitation of fluorescence imaging, however, is that fluorescent molecules can be optically excited for only a limited period of time before they are permanently extinguished (i.e., "photobleach"). Not only does such bleaching limit the amount of information that can be extracted from the specimen, it can also contribute to photo-induced changes in specimen behavior, phototoxicity, or even cell death.

Unfortunately, both widefield and confocal microscopy excite fluorescence in every plane of the specimen, whereas the information rich, high resolution content comes only from the vicinity of the focal plane. Thus, both widefield and confocal microscopy are very wasteful of the overall fluorescence budget and potentially quite damaging to live specimens. A third approach, two photon fluorescence excitation (TPFE) microscopy, uses a nonlinear excitation process, proportional to the square of the incident light intensity, to restrict excitation to regions near the focus of the imaging objective. However, like confocal microscopy, TPFE requires scanning this focus to generate a complete image. Furthermore, the high intensities required for TPFE can give rise to other, nonlinear mechanisms of photodamage in addition to those present in the linear methods of widefield and confocal microscopy.

Thus, there is a need for the ability to: reduce photodamage and photobleaching, as well as to reduce out-of-focus background and use widefield detection, to obtain images rapidly.

SUMMARY

In one general aspect, a method includes: (a) providing spatially-patterned activation radiation to a sample that includes phototransformable optical labels ("PTOLs"), where an optical parameter of the spatially-patterned activation radiation varies periodically in space within the sample and (b) providing spatially-patterned excitation radiation to the sample, where an optical parameter of the spatially-patterned excitation radiation varies periodically in space within the sample, where (a) and (b) create a non-linear fluorescence emission pattern within the sample, the pattern including H modulation harmonics, with H>1. The method further includes (c) detecting radiation emitted from the activated and excited PTOLs within the sample, (d) storing detected radiation data for generating an image of the sample based on the detected radiation, and (e) spatially shifting one or both of the spatially-patterned excitation radiation and the spatially-patterned activation radiation with respect to the sample to spatially shift the non-linear fluorescence emission pattern within the sample, and (f) repeating (a)-(e) at least N times, with N>2. Then, a sub-diffraction-limited final image of the sample is generated based on the stored data for the N positions of the non-linear fluorescence emission pattern within the sample.

Implementations can include one or more of the following features, which can be included individually, or in combination with one or more other features.

A spatial period, $\Lambda$, of the periodic variation of the optical parameters of the activation and excitation radiation can be the same. The periodic variation of both the activation radiation and the excitation radiation can be a sinusoidal variation. The patterns of the activation and excitation radiation can be in-phase, and the patterns of the activation and excitation radiation can be out of phase (e.g., 180 degrees out of phase). When the the patterns of the activation and excitation radiation are out of phase, providing the spatially-patterned excitation radiation to the sample, can include: providing first spatially-patterned excitation radiation to the sample, where the first spatially-patterned excitation radiation has a first phase, $\varphi_1$, relative to the pattern of the activation radiation and providing second spatially-patterned excitation radiation to the sample, where the second spatially-patterned excitation radiation has a second phase, $\varphi_2$, relative to the pattern of the activation radiation, where in $\varphi_1 \neq \varphi_2$. The phase difference $\varphi_1 - \varphi_2$ can be 180 degrees.

Providing the spatially-patterned excitation radiation to the sample, can include: providing first spatially-patterned excitation radiation to the sample, where the first spatially-patterned excitation radiation has a phase of 180 degrees relative to the pattern of the activation radiation and providing second spatially-patterned excitation radiation to the sample, where the second spatially-patterned excitation radiation is in phase with the pattern of the activation radiation.

In some implementations, $H \geq 2$, and the detected signal can include spatial frequency components at $-2\Lambda$, $-\Lambda$, $0$, $\Lambda$, and $2\Lambda$. In some implementations, where $H \geq 3$, and the detected signal includes spatial frequency components at $-3\Lambda$, $-2\Lambda$, $-\Lambda$, $0$, $\Lambda$, $2\Lambda$, and $3\Lambda$.

The periodically varied optical parameter of the excitation and activation radiation can be the intensity of the radiations and the intensities of both the activated and excited radiation can be below the saturation limit. The periodically varied optical parameter of the excitation and activation radiation can be the intensity of the radiations and the intensity of the activated radiation can be above the saturation limit. The periodically varied optical parameter of the excitation and activation radiation can be the intensity of the radiations and the intensity of the excitation radiation can be above the saturation limit. The periodically varied optical parameter of the excitation and activation radiation can be the intensity of the radiations and the intensities of both the activated and excited radiation can be above the saturation limit.

The excitation radiation can have a wavelength, $\lambda$, and the detected radiation can have a wavelength $\lambda/2$. The activation radiation can have a wavelength, $\lambda'$, and the PTOLs can be activated through a two-photon activation process.

In some implementations, $N \geq 7$.

Providing the spatially-patterned activation radiation can include modulating a beam of activation radiation with a wavefront modulating element (WME) to provide a desired pattern of activation radiation in the sample, where the WME can include a spatial light modulator (SLM) or a digitial micromirror.

Providing the spatially-patterned excitation radiation can include modulating a beam of excitation radiation with a WME to provide a desired pattern of excitation radiation in the sample. The beams of activating and excitation radiation can be modulated by the same WME. The activating and excitation radiation can have different wavelengths, and a pattern on the WME used to modulate the excitation radiation can have a different period than a pattern on the WME used to modulate the activation radiation. The different patterns for the different wavelengths on the WME can be chosen to provide patterns of excitation and activation radiation at the sample that have the same period.

Providing the spatially-patterned activation radiation can include providing the activation radiation via TIRF illumination of the sample. Providing the spatially-patterned excitation radiation can include providing the excitation radiation via TIRF illumination of the sample. Providing the spatially-patterned activation radiation can icludes providing a beam of activation radiation, sweeping the beam of activation radiation in the direction parallel to the plane of a first sheet, and varying the optical parameter of the activation radiation while sweeping the beam Providing the spatially-patterned excitation radiation in which an optical parameter of a second sheet varies periodically can include providing a beam of excitation radiation, sweeping the beam of excitation radiation in the direction parallel to the plane of the first sheet, and varying the optical parameter of the excitation radiation while sweeping the beam of excitation radiation. The beam of excitation radiation can include a Bessel-like beam. The Bessel-like beam can have a ratio of a Rayleigh length, $z_R$ to a minimum beam waist, $w_o$, of more than $2\pi w_o/\lambda$ and less than $100\pi w_o/\lambda$, where $\lambda$ represents the wavelength of the excitation radiation. the Bessel-like beam has a non-zero ratio of a minimum numerical aperture to a maximum numerical aperture of less than 0.95 or of less than 0.90. The Bessel-like beam can have a minimum numerical aperture greater than zero and a ratio of energy in a first side lobe of the beam to energy in the central lobe of the beam of less than 0.5. Providing the spatially-patterned excitation radiation in which an optical parameter of the second sheet varies periodically can include providing the beam of excitation radiation in the form of a light sheet. The light sheet can include a lattice light sheet.

In some implementations, (a)-(f) can be repeated at a plurality of sequential times, and a plurality of sub-diffraction-limited final images of the sample can be generated for each of the sequential times based on the stored data for each of the sequential times and for the N positions of the non-linear fluorescence emission pattern within the sample. The activation and excitation radiation can be provided to substantially the same plane in the sample at each of the sequential times. The activation and excitation radiation can be provided to different planes in the sample at each of the sequential times, while the activation and excitation radiation are provided to the same plane in the sample at each of the sequential times, each of the different planes being substantially parallel to each other.

An intensity of the excitation radiation can be less than about 125 W/cm$^2$ or less than about 500 W/cm$^2$. In some implementations, (f) can be performed in less than 0.5 seconds.

Deactivating radiation can be provided each time that (a)-(e) are repeated. The deactivating radiation can be provided to the activated PTOLs to deactivate a portion of the activated PTOLs, such that the non-linear fluorescence emission pattern within the sample includes H>2 modulation harmonics. The deactivating radiation can have a wavelength that is different from the activating wavelength. The deactivation radiation can include the spatially-patterned excitation radiation that is provided to the sample.

Spatially shifting one or both of the spatially-patterned excitation radiation and the spatially-patterned activation radiation can include spatially shifting one or both of the spatially-patterned excitation radiation and the spatially-patterned activation in a linear direction with respect to the sample to spatially shift the non-linear fluorescence emission pattern within the sample in the linear direction, and the method can further include shifting a rotational orientation of the non-linear fluorescence emission pattern within the sample a number, M, of times; repeating (a)-(e) at least N times, with N>2 for each rotational orientation of the pattern. In some implementations, $M \geq 2H+1$.

In another general aspect, an apparatus includes a stage configured for supporting a sample, a first light source and beam-forming optics configured for providing spatially-patterned activation radiation to a sample that includes phototransformable optical labels ("PTOLs"), where an optical parameter of the spatially-patterned activation radiation varies periodically in space within the sample, and a second light source and beam-forming optics configured for providing spatially-patterned excitation radiation to the sample, where an optical parameter of the spatially-patterned excitation radiation varies periodically in space within the sample. The first and second light sources and beam-forming optics are configured for providing the spatially-patterned activation and excitation radiation to create a non-linear fluorescence emission pattern within the sample, where the pattern includes H modulation harmonics, with H>1. The stage and/or the first and second beam forming optics are configured for spatially shifting one or both of the spatially-patterned excitation radiation and the spatially-patterned activation radiation with respect to the sample to spatially shift the non-linear fluorescence emission pattern within the sample to at least N different positions, with N>2. The apparatus includes a detector configured for detecting radiation emitted from the non-linear fluorescence emission, memory for storing detected radiation data for generating an image of the sample based on the detected radiation, and one or more processors configured for generating a sub-diffraction-limited final image of the sample based on the stored data for the N positions of the non-linear fluorescence emission pattern within the sample.

Implementations can include one or more of the following features, which can be included individually, or in combination with one or more other features.

A spatial period, $\Lambda$, of the periodic variation of the optical parameters of the activation and excitation radiation can be the same. The periodic variation of both the activation radiation and the excitation radiation can be a sinusoidal variation. The patterns of the activation and excitation radiation can be in-phase, and the patterns of the activation and excitation radiation can be out of phase (e.g., 180 degrees out of phase). When the the patterns of the activation and excitation radiation are out of phase, providing the spatially-patterned excitation radiation to the sample, can include: providing first spatially-patterned excitation radiation to the sample, where the first spatially-patterned excitation radiation has a first phase, $\varphi_1$, relative to the pattern of the activation radiation and providing second spatially-patterned excitation radiation to the sample, where the second spatially-patterned excitation radiation has a second phase, $\varphi_2$, relative to the pattern of the activation radiation, where in $\varphi_1 \neq \varphi_2$. The phase difference $\varphi_1 - \varphi_2$ can be 180 degrees.

Providing the spatially-patterned excitation radiation to the sample, can include: providing first spatially-patterned excitation radiation to the sample, where the first spatially-patterned excitation radiation has a phase of 180 degrees relative to the pattern of the activation radiation and providing second spatially-patterned excitation radiation to the sample, where the second spatially-patterned excitation radiation is in phase with the pattern of the activation radiation.

In some implementations, H≥2, and the detected signal can include spatial frequency components at $-2\Lambda$, $-\Lambda$, $0$, $\Lambda$, and $2\Lambda$. In some implementations, where H≥3, and the detected signal includes spatial frequency components at $-3\Lambda$, $-2\Lambda$, $-\Lambda$, $0$, $\Lambda$, $2\Lambda$, and $3\Lambda$.

The periodically varied optical parameter of the excitation and activation radiation can be the intensity of the radiations and the intensities of both the activated and excited radiation can be below the saturation limit. The periodically varied optical parameter of the excitation and activation radiation can be the intensity of the radiations and the intensity of the activated radiation can be above the saturation limit. The periodically varied optical parameter of the excitation and activation radiation can be the intensity of the radiations and the intensity of the excitation radiation can be above the saturation limit.

The excitation radiation can have a wavelength, $\lambda$, and the detected radiation can have a wavelength $\lambda/2$. The activation radiation can have a wavelength, $\lambda'$, and the PTOLs can be activated through a two-photon activation process.

In some implementations, N≥7.

The apparatus can include a wavefront modulating element (WME) configured for modulating a beam of activation radiation to provide a desired pattern of activation radiation in the sample. The beams of activating and excitation radiation can be modulated by the same WME. The activating and excitation radiation can have different wavelengths, and a pattern on the WME used to modulate the excitation radiation can have a different period than a pattern on the WME used to modulate the activation radiation. The different patterns for the different wavelengths on the WME can be chosen to provide patterns of excitation and activation radiation at the sample that have the same period.

Providing the spatially-patterned activation radiation can include providing the activation radiation via TIRF illumination of the sample. Providing the spatially-patterned excitation radiation can include providing the excitation radiation via TIRF illumination of the sample. Providing the spatially-patterned activation radiation can includes providing a beam of activation radiation, sweeping the beam of activation radiation in the direction parallel to the plane of a first sheet, and varying the optical parameter of the activation radiation while sweeping the beam.

Providing the spatially-patterned excitation radiation in which an optical parameter of a second sheet varies periodically can include providing a beam of excitation radiation, sweeping the beam of excitation radiation in the direction parallel to the plane of the first sheet, and varying the optical parameter of the excitation radiation while sweeping the beam of excitation radiation. The beam of excitation radiation can include a Bessel-like beam. The Bessel-like beam can have a ratio of a Rayleigh length, $z_R$ to a minimum beam waist, $w_o$, of more than $2\pi w_o/\lambda$ and less than $100\pi w_o/\lambda$, where $\lambda$ represents the wavelength of the excitation radiation. the Bessel-like beam has a non-zero ratio of a minimum numerical aperture to a maximum numerical aperture of less than 0.95 or of less than 0.90. The Bessel-like beam can have a minimum numerical aperture greater than zero and a ratio of energy in a first side lobe of the beam to energy in the central lobe of the beam of less than 0.5. Providing the spatially-patterned excitation radiation in which an optical parameter of the second sheet varies periodically can include providing the beam of excitation radiation in the form of a light sheet. The light sheet can include a lattice light sheet.

The processor can be further configured to generate a plurality of sub-diffraction-limited final images of the sample for each of a plurality of sequential times based on the stored data for each of the sequential times and for the N positions of the non-linear fluorescence emission pattern within the sample. The activation and excitation radiation can be provided to substantially the same plane in the sample at each of the sequential times. The activation and excitation radiation can be provided to different planes in the sample at each of the sequential times, where the activation and excitation radiation are provided to the same plane in the sample at each of the sequential times, each of the different planes being substantially parallel to each other.

An intensity of the excitation radiation can be less than about 125 W/cm² or less than about 500 W/cm².

The apparatus can include a third light source for providing deactivating radiation. The deactivating radiation can be provided to the activated PTOLs to deactivate a portion of the activated PTOLs, such that the non-linear fluorescence emission pattern within the sample includes H>2 modulation harmonics. The deactivating radiation can have a wavelength that is different from the activating wavelength. The apparatus can provide deactivation radiation in the form of the spatially-patterned excitation radiation that is provided to the sample.

Spatially shifting one or both of the spatially-patterned excitation radiation and the spatially-patterned activation radiation can include spatially shifting one or both of the spatially-patterned excitation radiation and the spatially-patterned activation in a linear direction with respect to the sample to spatially shift the non-linear fluorescence emission pattern within the sample in the linear direction, and the method can further include shifting a rotational orientation of the non-linear fluorescence emission pattern within the sample a number, M, of times; repeating (a)-(e) at least N times, with N>2 for each rotational orientation of the pattern. In some implementations, M≥2H+1.

The details of one or more implementations are set forth in the accompanying drawings and the description below. Other features will be apparent from the description and drawings, and from the claims.

BRIEF DESCRIPTION OF THE DRAWINGS

FIG. 21A illustrates a cross-sectional profile in the X-Z plane of a Bessel like beam propagating in the Y direction. FIG. 21B illustrates the electric field, in the X-Z plane, of a structured light sheet formed by coherent sum of a linear, periodic array of Bessel-like beams that propagate in the Y direction. FIG. 21C illustrates the electric field, in the XZ plane, of the structured light sheet of FIG. 21B after a Gaussian envelope function has been applied to the field of the light sheet to bound the light sheet in the Z direction. FIG. 21D illustrates the pattern of phase shifts applied to individual pixels of a binary spatial light modulator to generate the field shown in FIG. 21C. FIG. 21E illustrates the cross-sectional point spread function, in the X-Z plane, of the structured plane of excitation radiation that is produced in the sample by the coherent array of Bessel-like beams, which are generated by the pattern on the spatial light modulator shown in FIG. 21D. FIG. 21F illustrates the excitation beam intensity that is produced in the sample when the array of Bessel-like beams is swept or dithered in the X direction.

FIG. 22A illustrates a cross-sectional profile in the X-Z plane of a Bessel like beam propagating in the Y direction. FIG. 22B illustrates the electric field, in the X-Z plane, of a structured light sheet formed by a coherent sum of a linear, periodic array of Bessel-like beams that propagate in the Y direction. FIG. 22C illustrates the electric field, in the XZ plane, of the structured light sheet of FIG. 22B after a Gaussian envelope function has been applied to the field of the light sheet to bound the light sheet in the Z direction. FIG. 22D illustrates the pattern of phase shifts applied to individual pixels of a binary spatial light modulator to generate the field shown in FIG. 22C. FIG. 22E illustrates the cross-sectional point spread function, in the X-Z plane, of the structured plane of excitation radiation that is produced in the sample by the coherent array of Bessel-like beams, which are generated by the pattern on the spatial light modulator shown in FIG. 22D. FIG. 22F illustrates the modulation transfer function, which corresponds to the point spread functions shown in FIG. 22E.

FIG. 23A is a cross-sectional in the X-Z plane of a Bessel-like beam propagating in the Y direction. FIG. 23B is a schematic diagram of the time-averaged intensities in the X-Z plane that results from sweeping the Bessel-like beam of FIG. 23A in the X direction. FIG. 23C is a cross-sectional in the X-Z plane of a superposition of incoherent Bessel-like beams propagating in the Y direction, such as would occur if the single Bessel-like beam in FIG. 23A were moved in discrete steps. FIG. 23D is a schematic diagram in the X-Z plane of the time-averaged intensity that results from moving multiple instances of the array of Bessel-like beams of FIG. 23C in small increments in the X direction and integrating the resulting signal on a camera. FIG. 23E is a cross-section in the X-Z plane of a superposition of coherent Bessel-like beams propagating in the Y direction. FIG. 23F is a schematic diagram of the time-averaged intensity in the X-Z plane that results from sweeping or dithering the array of Bessel-like beams of FIG. 23E.

FIG. 25A illustrates a cross-sectional profile in the X-Z plane of an ideal two-dimensional fundamental hexagonal lattice that is oriented in the Z direction. FIG. 25B illustrates the electric field, in the XZ plane, of the optical lattice of FIG. 25A after a Gaussian envelope function has been applied to the optical lattice to bound the lattice in the Z direction. FIG. 25C illustrates the pattern of phase shifts applied to individual pixels of a binary spatial light modulator to generate the field shown in FIG. 25B. FIG. 25D illustrates the cross-sectional point spread function, in the X-Z plane, of the structured plane of excitation radiation that is produced in the sample by the optical lattice, which is generated by the pattern on the spatial light modulator shown in FIG. 25C, and then filtered by an annular apodization mask that limits the maximum NA of the excitation to 0.55 and the minimum NA of the excitation to 0.44. FIG. 25E illustrates the excitation beam intensity that is produced in the sample when the bound optical lattice pattern in FIG. 25D is swept or dithered in the X direction. Higher intensities are shown by whiter regions.

FIG. 26A a schematic diagram of the pattern of phase shifts applied to individual pixels of a binary spatial light modulator to generate the field shown in FIG. 25B. FIG. 26B a schematic diagram of the intensity of light that impinges on an apodization mask downstream from a SLM. FIG. 26C a schematic diagram of the transmission function of an apodization mask. FIG. 26D a schematic diagram of the intensity of light immediately after the apodization mask. FIG. 26E is a schematic diagram of an optical lattice that results at the sample when then the pattern of the light that exists just after the apodization mask is focused by an excitation objective to the focal plane within the sample. FIG. 26F is a schematic diagram of the intensity patter that results when the optical lattice of FIG. 26E is swept or dithered in the X direction.

FIG. 27A is a schematic diagram of a cross-sectional profile in the X-Z plane of a two-dimensional fundamental hexagonal lattice that is oriented in the Z direction. FIG. 27B is a schematic diagram of the electric field, in the XZ plane, of the optical lattice of FIG. 27A after a Gaussian envelope function has been applied to the optical lattice to bound the lattice in the Z direction. FIG. 27C is a schematic diagram of the pattern of phase shifts applied to individual pixels of a binary spatial light modulator to generate the field shown in FIG. 27B. FIG. 27D is a schematic diagram of the cross-sectional point spread function, in the X-Z plane, of the structured plane of excitation radiation that is produced in the sample by the optical lattice, which is generated by the pattern on the spatial light modulator shown in FIG. 27C, and then filtered by an annular apodization mask that limits the maximum NA of the excitation to 0.60 and the minimum NA of the excitation to 0.54. FIG. 27E is a schematic diagram of the modulation transfer function, in reciprocal space, which corresponds to the intensity pattern shown FIG. 27D.

FIG. 28A is a schematic diagram of the pattern of phase shifts applied to individual pixels of a binary spatial light modulator to generate the field shown in FIG. 27B. FIG. 28B is a schematic diagram of the intensity of light that impinges on the apodization mask downstream from the SLM when the SLM includes the pattern of FIG. 28A. FIG. 28C is a schematic diagram of the transmission function of the apodization mask. FIG. 28D is a schematic diagram of the intensity of light immediately after the apodization mask. FIG. 28E is a schematic diagram of an optical lattice that results from the pattern of the light shown in FIG. 28D being focused by an excitation objective to the focal plane within a sample. FIG. 28F is a schematic diagram of the modulation transfer function for this lattice shown in FIG. 28E.

FIG. 29A is a schematic diagram of the intensity of the optical lattice to which a wide, or weak, envelope function is applied. FIG. 29B is a schematic diagram of the intensity profiles of a light sheet created by sweeping or dithering the lattice of FIG. 29A. FIG. 29C is a schematic diagram of the intensity of the optical lattice to which a medium-wide envelope function is applied. FIG. 29D is a schematic diagram of the intensity profiles of a light sheet created by sweeping or dithering the lattice of FIG. 29C. FIG. 29E is a schematic diagram of the intensity of the optical lattice to which a medium-narrow envelope function is applied to the ideal optical lattice pattern. FIG. 29F is a schematic diagram of the intensity profiles of a light sheet created by sweeping or dithering the lattice of FIG. 29E. FIG. 29G is a schematic diagram of the intensity of the optical lattice to which a narrow, or strong, envelope function is applied to the ideal optical lattice pattern. FIG. 29H is a schematic diagram of the intensity profiles of a light sheet created by sweeping or dithering the lattice of FIG. 29G.

FIGS. 41, 42, 43, and 44 illustrate a process of saturated PA NL-SIM, in accordance with the techniques describe herein

FIGS. 52A, 52B, and FIG. 52C are schematic diagrams, showing an example of spatially-structured excitation pattern being provided out of phase with a spatially-structured activation pattern, and the resulting fraction of molecules in the activated state.

DETAILED DESCRIPTION

Figure 2:
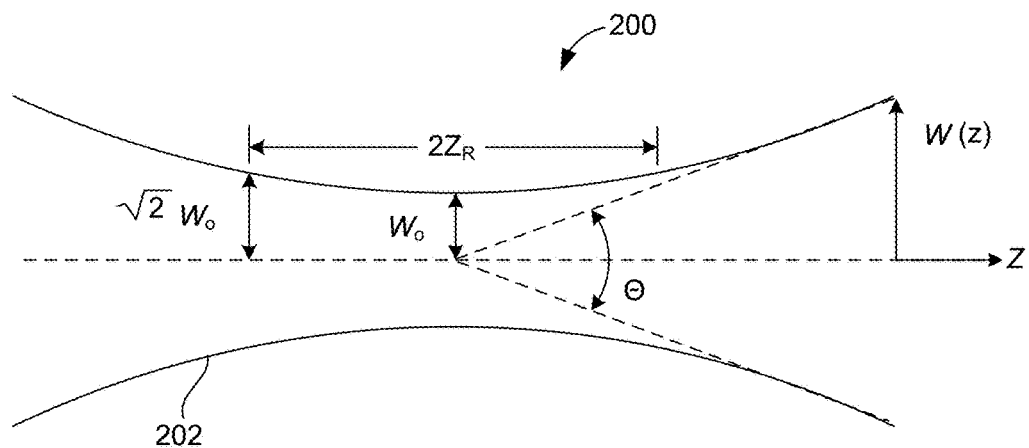
FIG. 2 is a schematic diagram of a profile of a focused beam of light.

This description discloses microscopy and imaging apparatus, systems, methods and techniques, which enable a light sheet or pencil beam to have a length that can be decoupled from its thickness, thus allowing the illumination of large fields of view (e.g., tens or even hundreds of microns) across a plane having a thickness on the order of, or smaller than, the depth of focus of the imaging objective by using illumination beams having a cross-sectional field distribution that is similar to a Bessel function. Such illumination beams can be known as Bessel beams. Such beams are created by focusing light, not in a continuum of azimuthal directions across a cone, as is customary, but rather at a single azimuthal angle or range of azimuthal angles with respect to the axis of the focusing element. Bessel beams can overcome the limitations of the diffraction relationship shown in FIG. 2, because the relationship shown in FIG. 2 is only valid for lenses (cylindrical or objectives) that are uniformly illuminated.

Figure 1:
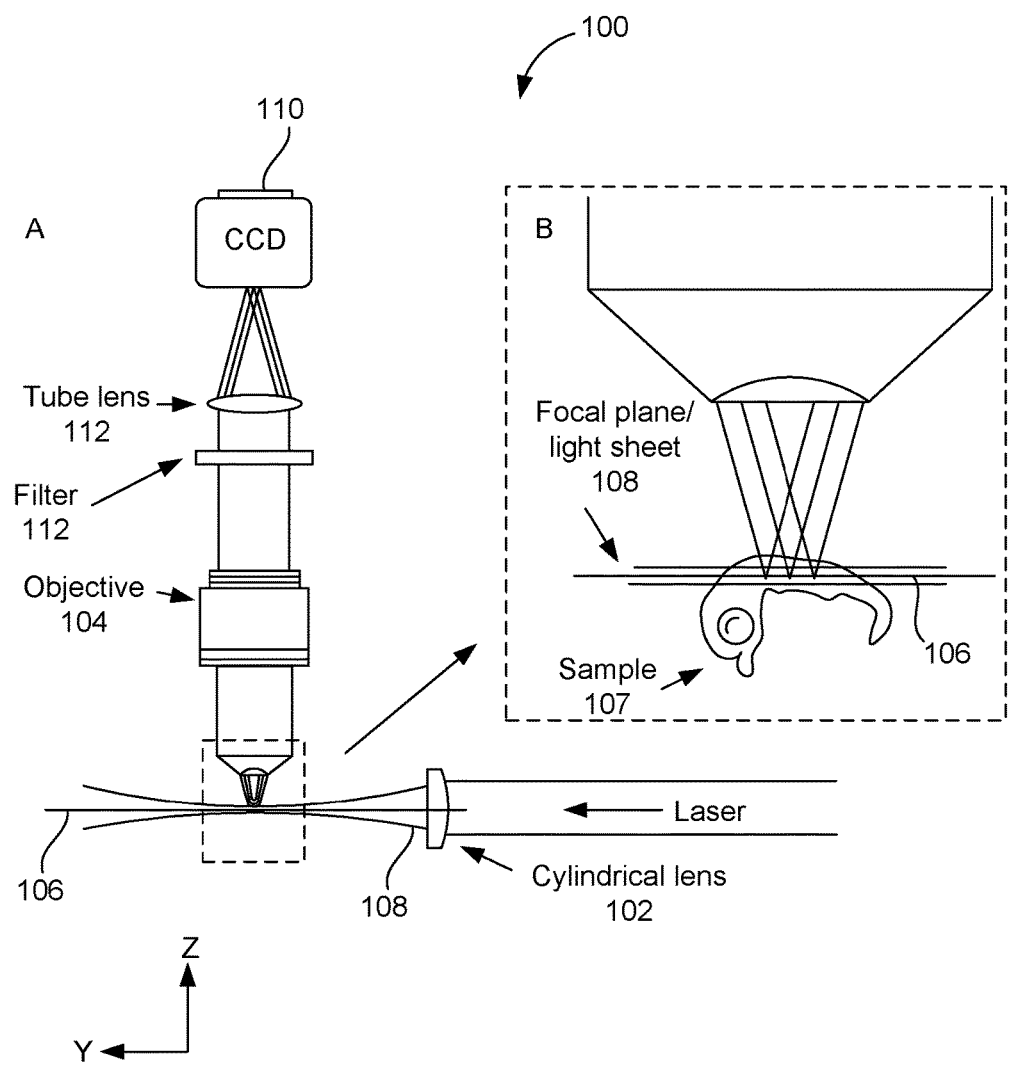
FIG. 1 is a schematic diagram of a light sheet microscopy (LSM) system.

This description also discloses microscopy and imaging apparatus, systems, methods and techniques, which can create a non-linear relationship between a parameter (e.g., intensity) of light used to excite fluorescence emission in a sample and the amount of fluorescence emission from the sample. This can be exploited to extended the resolution of images of the sample created based on the detected fluorescence emission beyond the diffraction limit of the optics used to image the fluorescence emission FIG. 1 is a schematic diagram of a light sheet microscopy (LSM) system 100. As shown in FIG. 1, LSM uses a beam-forming lens 102, external to imaging optics, which includes an objective 104, to illuminate the portion of a specimen 107 in the vicinity of the focal plane 106 of the objective. In one implementation, the lens 102 that provides illumination or excitation light to the sample 107 is a cylindrical lens that focuses light in only one direction, thereby providing a beam of light 108 that creates a sheet of light coincident with the objective focal plane 106. A detector 110 then records the signal generated across the entire illuminated plane of the specimen 107. Because the entire plane is illuminated at once, images can be obtained very rapidly.

In another implementation, termed Digital Laser Scanned Light Sheet Microscopy (DSLM), the lens 102 can be a circularly symmetric multi-element excitation lens (e.g., having a low numerical aperture (NA) objective) that corrects for optical aberrations (e.g., chromatic and spherical aberrations) that are prevalent in cylindrical lenses. The illumination beam 108 of light then is focused in two directions to form a pencil beam of light coincident with the focal plane 106 of the imaging objective 104. The width of the pencil beam is proportional to the 1/NA, whereas its length is proportional to $1/(NA)^2$. Thus, by using the illumination lens 102 at sufficiently low NA (i.e., NA<<1), the pencil beam 108 of the excitation light can be made sufficiently long to encompass the entire length of the desired field of view (FOV). To cover the other direction defining the lateral width of the FOV, the pencil beam can be scanned across the focal plane (e.g., with a galvanometer, as in confocal microscopy) while the imaging detector 110 integrates the signal that is collected by the detection optics 112 as the beam sweeps out the entire FOV.

A principal limitation of these implementations is that, due to the diffraction of light, there is a tradeoff between the XY extent of the illumination across the focal plane of the imaging objective, and the thickness of the illumination in the Z direction perpendicular to this plane. In the coordinate system used in FIG. 1, the X direction is into the page, the Y direction is in the direction of the illumination beam, and the Z direction is in the direction in which imaged light is received from the specimen.

FIG. 2 is a schematic diagram of a profile 200 of a focused beam of light. As shown in FIG. 2, illumination light 202 of wavelength, $\lambda$, that is focused to a minimum beam waist, $2w_o$, within the specimen will diverge on either side of the focus, increasing in width by a factor of $\sqrt{2}$ in a distance of $z_R = \pi w_o^2/\lambda$, the so-called Rayleigh range. Table 1 shows specific values of the relationship between the usable FOV, as defined by $2z_R$, and the minimum thickness $2w_o$ of the illumination sheet, whether created by a cylindrical lens, or by scanning a pencil beam created by a low NA objective.

TABLE 1

| $2w_o$ (μm, for $\lambda$ = 500 nm) | $2z_R$ (μm, for $\lambda$ = 500 nm) |
|---|---|
| 0.2 | 0.06 |
| 0.4 | 0.25 |
| 0.6 | 0.57 |
| 0.8 | 1.00 |
| 1.0 | 1.57 |
| 2.0 | 6.28 |
| 5.0 | 39.3 |
| 10.0 | 157 |
| 20.0 | 628 |

From Table 1 it can be seen that, to cover FOVs larger than a few microns (as would be required image even small single cells in their entirety) the sheet thickness must be greater than the depth of focus of the imaging objective (typically, <1 micron). As a result, out-of-plane photobleaching and photodamage still remain (although less than in widefield or confocal microscopy, provided that the sheet thickness is less than the specimen thickness). Furthermore, the background from illumination outside the focal plane reduces contrast and introduces noise which can hinder the detection of small, weakly emitting objects. Finally, with only a single image, the Z positions of objects within the image cannot be determined to an accuracy better than the sheet thickness.

Figure 3:
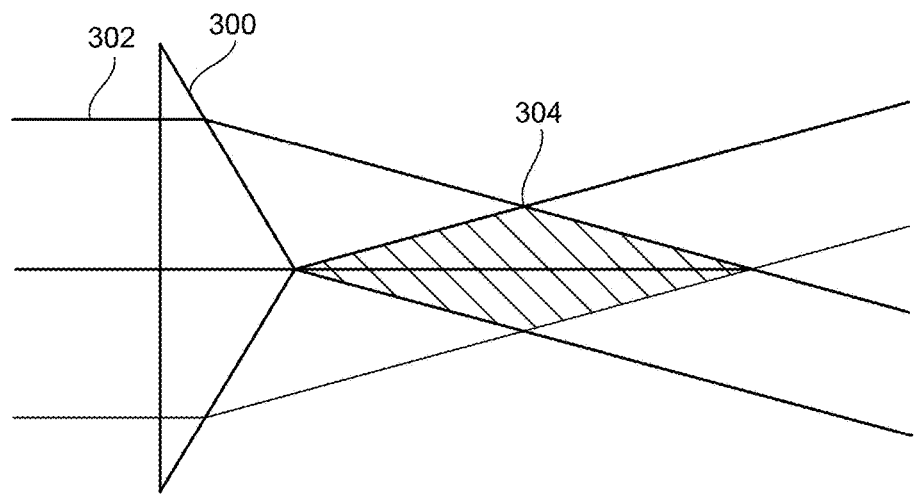
FIG. 3 is a schematic diagram of a Bessel beam formed by an axicon.

FIG. 3 is a schematic diagram of a Bessel beam formed by an axicon 300. The axicon 300 is a conical optical element, which, when illuminated by an incoming plane wave 302 having an approximately-Gaussian intensity distribution in directions transverse to the beam axis, can form a Bessel beam 304 in a beam that exits the axicon.

Figure 4:
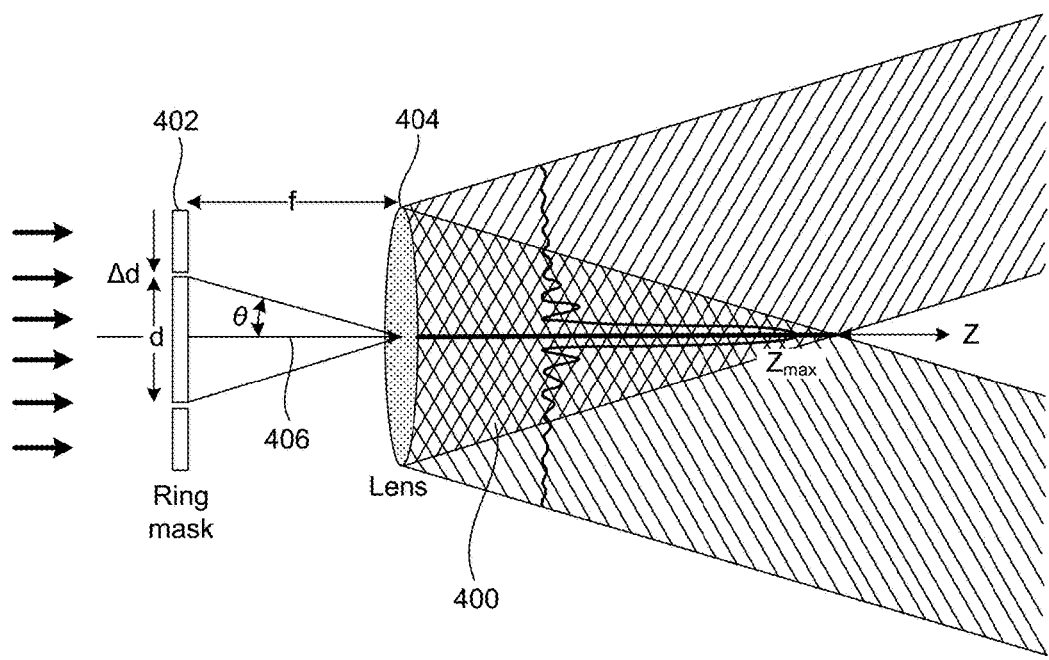
FIG. 4 is a schematic diagram of a Bessel beam formed by an annular apodization mask.

FIG. 4 is a schematic diagram of a Bessel beam 400 formed by an annular apodization mask 402, where the annular mask 402 is illuminated to create a thin annulus of light at the back focal plane of a conventional lens 404. The mask 402 is separated from the lens 404 by the focal length, f. An angle, θ, can be defined as the inverse tangent of half the distance, d, from the center of the annular ring to a point within the ring divided by the focal length, where $d_o$ can be used to denote the minimum diameter of the annular ring. Ideally, in either case shown by FIG. 3 or by FIG. 4, the axial wavevectors $k_z$ of all rays converging to the focus are the same, and hence there is no variation of the beam along this direction. In practice, the finite diameter of the axicon 300, or the finite width, Δd, of the annular ring in the apodization mask 402 restricts the Bessel beam to a finite length. The optical system of the annular apodization mask 402 and the lens 404 can be characterized by a minimum and maximum numerical aperture, where the maximum numerical aperture is proportional to $d_o + \Delta d$, and the minimum numerical aperture is proportional to $d_o$. In other implementations, different optical elements, other than an axicon or an apodization mask, can be used to create an annulus of light. For example, a binary phase mask or a programmable spatial light modulator can be used to create the annulus of light.

Figure 5:
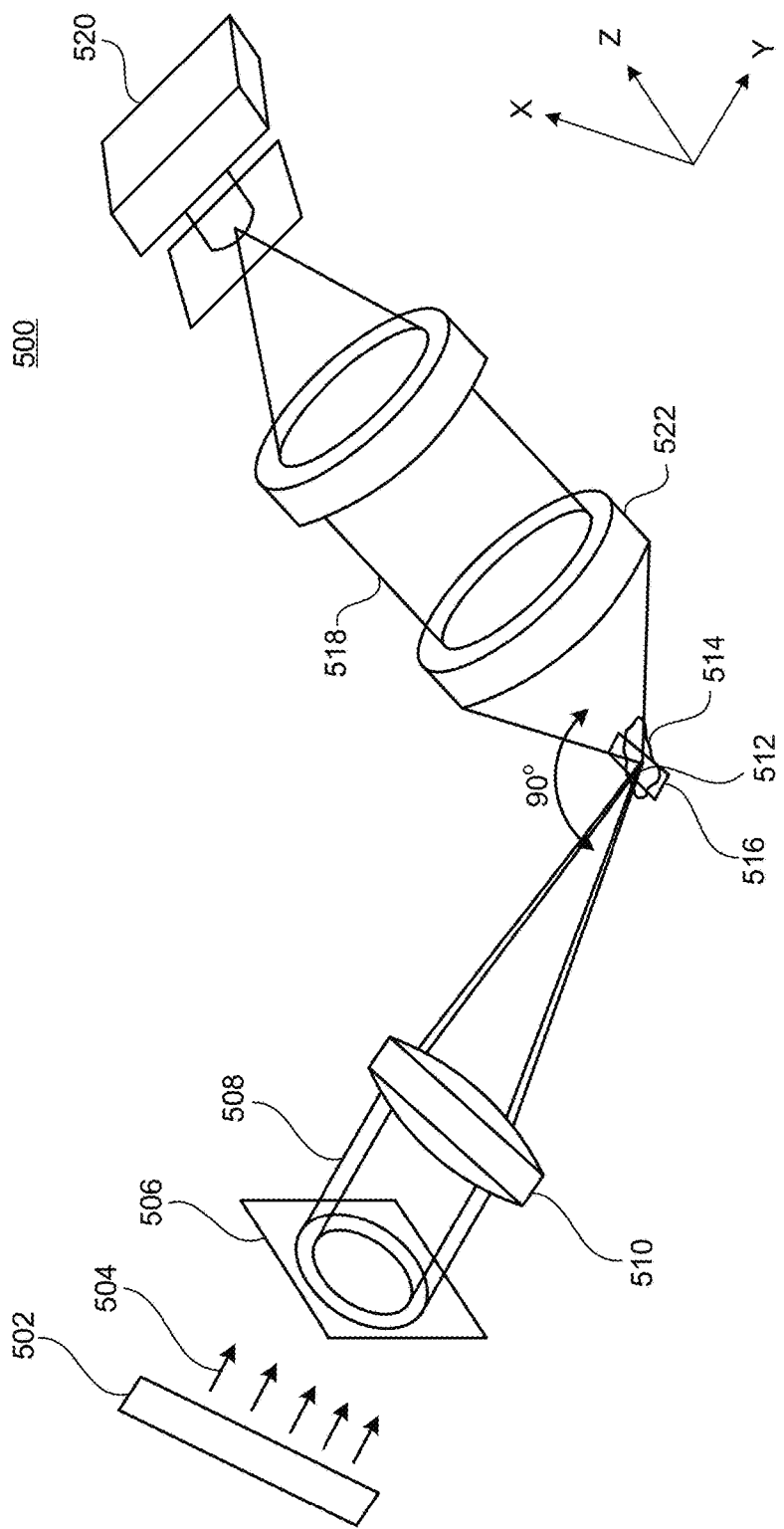
FIG. 5 is a schematic diagram of a system for Bessel beam light sheet microscopy.

FIG. 5 is a schematic diagram of a system 500 for Bessel beam light sheet microscopy. A light source 502 emits a light beam 504 that strikes an annular apodization mask 506. An annulus of excitation light 508 illuminates the back focal plane of microscope objective 510 to create an elongated Bessel beam 512 of light in a sample 514. By scanning this beam in a plane 516 transverse to the axis of the Bessel beam 512 and coincident with the focal plane of a detection objective 504 while simultaneously integrating the collected signal 518 with a camera 520 located at a corresponding image plane of imaging optics 522, an image is obtained from a much thinner slice within the sample than is the case when either conventional light sheet microscopy or DSLM is used.

Figure 6A:
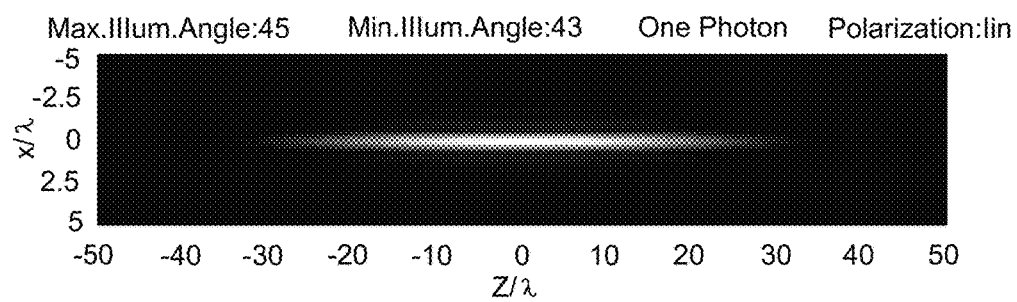
FIG. 6A is a plot of the intensity profile of a Bessel beam.
Figure 6B:
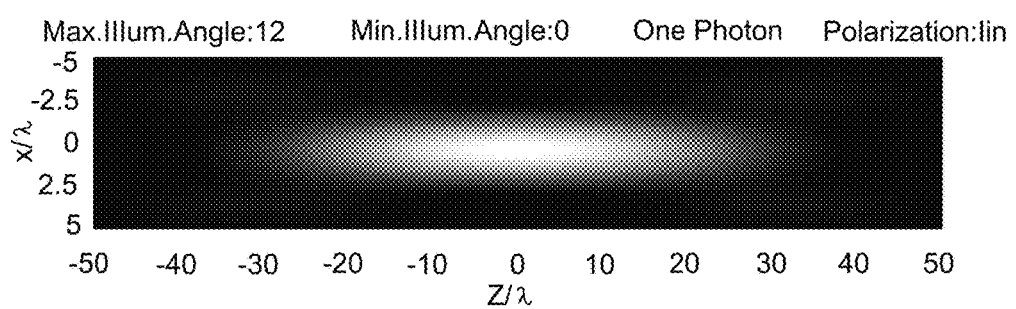
FIG. 6B shows a plot of the intensity profile of a conventional beam.
Figure 7A:
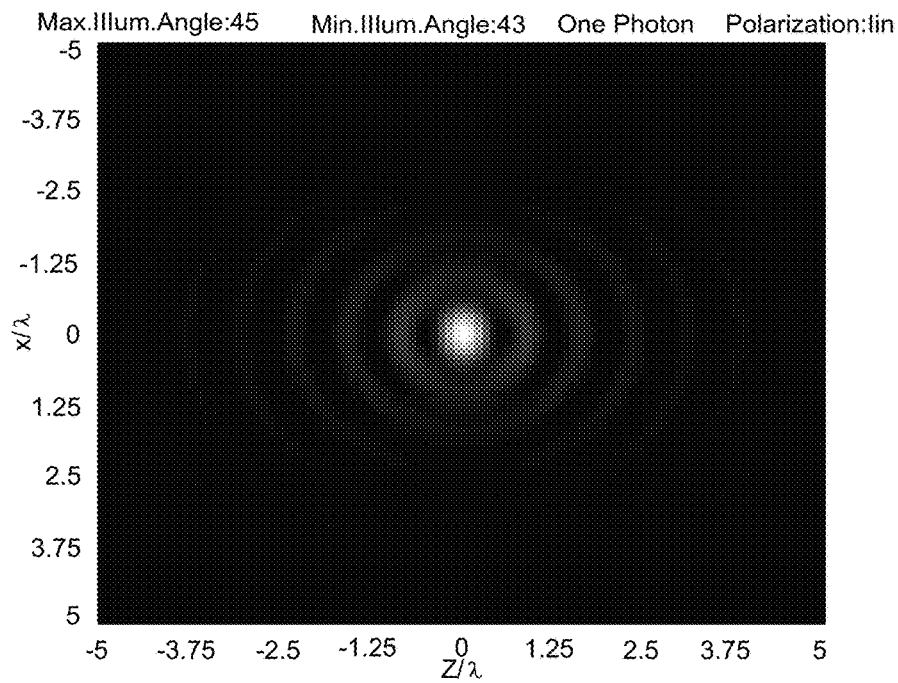
FIG. 7A is a plot of the intensity profile of a Bessel beam of FIG. 6A in the directions transverse to the propagation direction of the beam.
Figure 7B:
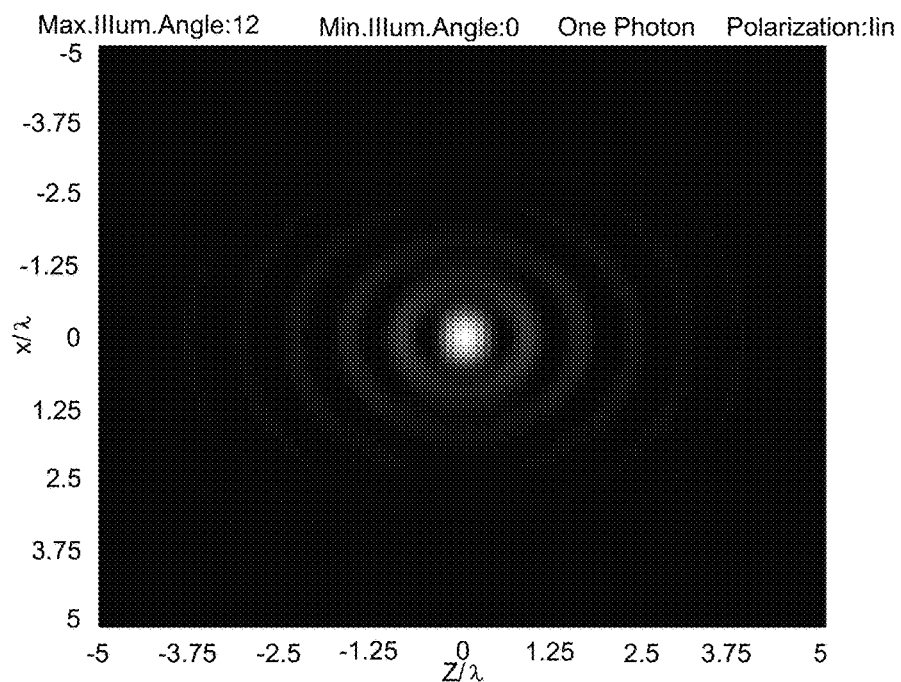
FIG. 7B is a plot of the intensity profile of the conventional beam of FIG. 6B in the directions transverse to the propagation direction of the beam.

How much thinner the sheet of excitation light can be with Bessel beam illumination than with conventional light sheet microscopy or DSLM can be seen from a comparison of FIG. 6A, which shows a plot of the intensity profile of a Bessel beam, and FIG. 6B, which shows a plot of the intensity profile of a conventional beam. In the plots of FIGS. 5 and 6, Y is along the axis of the propagation direction of the beam, X is the direction of the excitation polarization (when linearly polarized light is used), and Z is along the axis of detection optics objective 522 and is orthogonal to X and Y. FIG. 7A is a plot of the intensity profile of a Bessel beam of FIG. 6A in the directions transverse to the propagation direction of the beam, and FIG. 7B is a plot of the Gaussian intensity profile of the conventional beam of FIG. 7A in the directions transverse to the propagation direction of the beam.

As seen in FIG. 6A, annular illumination across a small range of angles (θ=43 to 45 degrees) results in a Bessel-like beam approximately 50 wavelengths $\lambda$ long in the Y direction, or roughly the same length obtained by conventional illumination using a plane wave having a Gaussian transverse intensity profile that is focused by a lens into an illumination beam having a cone half-angle of 12 degrees, as seen in FIG. 6b. However, the thickness of the Bessel beam is much narrower than the thickness of the conventional beam, yielding a much thinner sheet of excitation when scanned across a plane.

Figure 8A:
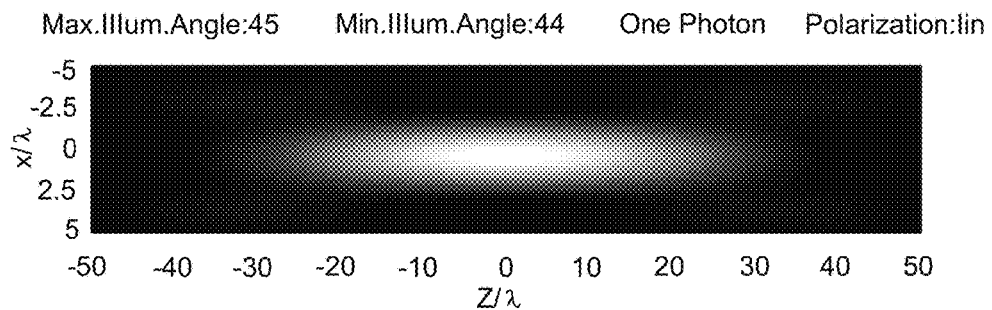
FIG. 8A is a plot of the intensity profile in the YZ plane of a Bessel beam generated from an annular mask having a thinner annulus in the annulus used to generate the intensity profile of the Bessel beam of FIG. 6A.
Figure 8B:
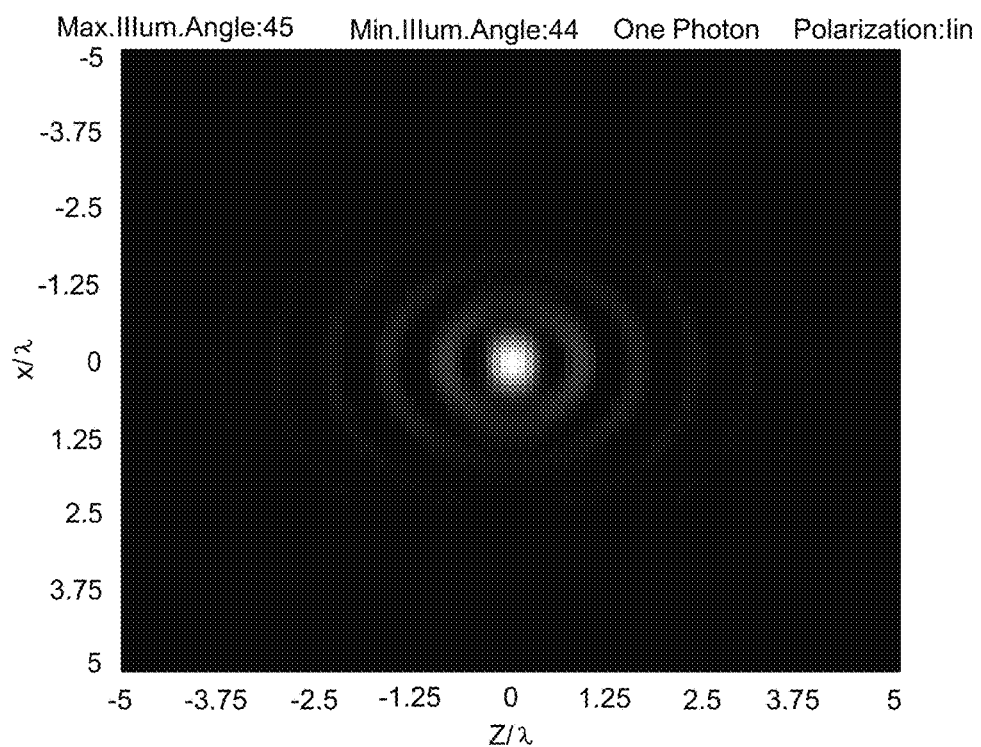
FIG. 8B is a plot of the transverse intensity profile in the XZ directions for the beam of FIG. 8A.

Furthermore, even longer Bessel-like beams can be made without compromising their cross-sectional width simply by restricting the annular illumination over an even smaller range of angles. FIG. 8A is a plot of intensity profile in the YZ directions of a Bessel beam generated from an annular mask having a thinner annulus than is used to generate the intensity profile of the Bessel-like beam of FIG. 6A, and FIG. 8B is a plot of the transverse intensity profile for the beam in the XZ directions. As shown in FIG. 8A, annular illumination across a small range of angles (θ=44 to 45 degrees) results in in the YZ intensity profile of the Bessel-like beam shown in FIG. 8A, where the Bessel-like beam has a length of approximately 100 wavelengths in the Y direction. However, the transverse intensity profile of the longer Bessel beam is relatively unchanged compared with shorter Bessel beam, as can be seen from a comparison of FIG. 7A and FIG. 8B, and the thickness of the beam is not significantly greater than the thickness of the beam whose intensity profile is shown in FIG. 6A. In contrast, with conventional illumination the usual approach of lengthening the beam by reducing the NA results in an unavoidably larger diffraction limited cross-section, roughly in accordance with Table 1.

Figure 9A:
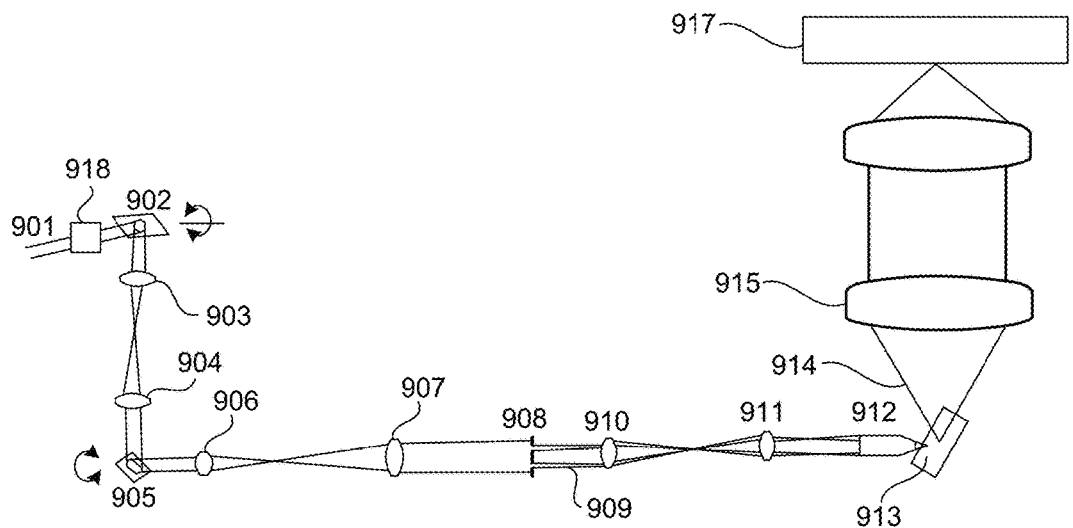
FIG. 9A is a schematic diagram of another system for implementing Bessel beam light sheet microscopy.

FIG. 9A is a schematic diagram of another system 900 for implementing Bessel beam light sheet microscopy. Collimated light 901, such as a laser beam having a Gaussian intensity profile, is reflected from first galvanometer-type mirror 902 and then imaged by relay lens pair 903 and 904 onto a second galvanometer-type mirror 905 positioned at a point optically conjugate to the first galvanometer-type mirror 902. A second lens pair 906 and 907 then relays the light to annular apodization mask 908 conjugate with the second galvanometer-type mirror 905. The annular light beam transmitted through this mask 908 is then relayed by a third lens pair 910 and 911 onto a conjugate plane coincident with the back focal plane of excitation objective 912. Finally, the annular light is focused by objective 912 to form a Bessel-like beam 913 that is used to provide excitation light to a specimen.

The rotational axis of galvanometer mirror 902 is positioned such that tilting this galvanometer-type mirror 902 causes the Bessel-like beam 913 to sweep across the focal plane of detection objective 915 (i.e., in the X direction), whose axis is orthogonal to (or whose axis has an orthogonal component to) the axis of the excitation objective 912. The signal light 914 can be directed by detection optics, including the detection objective 915, to a detection camera 917. The galvanometers-type mirrors 902, 905 can provide sweep rates of up to about 2 kHz, and with resonant galvanometer-type mirrors (e.g., Electro-Optical Products Corp, model SC-30) sweep rates can exceed 30 kHz. Extremely high frame rate imaging is then possible when the system is used in conjunction with a high frame rate detection camera (e.g., 500 frames/sec with an Andor iXon+DU-860 EMCCD, or >20,000 frames/sec with a Photron Fastcam SA-1 CMOS camera coupled to a Hamamatsu C10880-03 image intensifier/image booster).

The rotational axis of the galvanometer mirror 905 is positioned such that tilting of this mirror causes Bessel-like beam 913 to translate along the axis of detection objective 915. By doing so, different planes within a specimen can be accessed by the Bessel beam, and a three dimensional (3D) image of the specimen can be constructed, with much higher axial resolution than in conventional light sheet microscopy, due to the much narrower sheet of excitation afforded by Bessel-like excitation. In order to image each plane in focus, either detection objective 915 must be moved synchronously with the motion of the Bessel beam 913 imparted by the tilt of galvanometer-type mirror 905 (such as with a piezoelectric transducer (e.g., Physik Instrumente P-726)), or else the effective plane of focus of the detection objective 915 must be altered, such as by using a second objective to create a perfect image of the sample. Of course, if 3D image stacks are not desired, the second galvanometer 905 and relay lenses 906 and 907 can be removed from the system shown in FIG. 9A, and the first galvanometer 902 and relay lenses 903 and 904 can be repositioned so that the apodization mask 908 is at a conjugate plane relative to galvanometer-type mirror 902. An acousto-optical tunable filter (AOTF) 918 can be used to block all excitation light from reaching the specimen when desired.

The system in FIG. 9A is typically quite wasteful of the energy in light beam 901, because most of this light is blocked by apodization mask 908. If greater efficiency is desired, a diffractive optical element such as a binary phase mask or spatial light modulator and a collimating lens can be used to create an approximately annular light beam prior to more exact definition of this beam and removal of higher diffractive orders by the apodization mask 908.

Figure 9B:
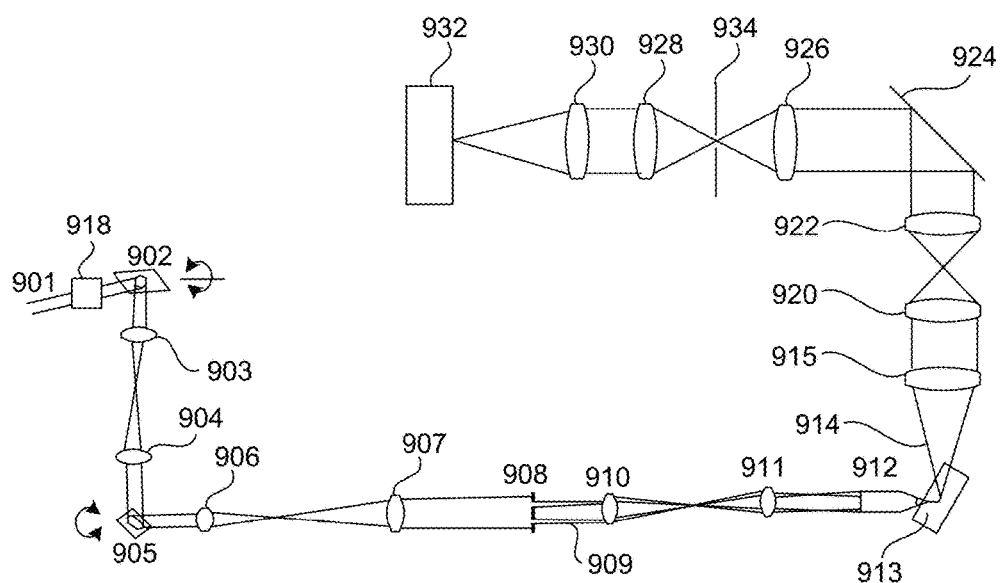
FIG. 9B is a schematic diagram of another system for implementing Bessel beam light sheet microscopy.

In another implementation, shown in FIG. 9B, signal light 914 received by detection objective 915 can be transmitted through relay lenses 920, 922 and reflected off a galvanometer-type mirror 924 and then transmitted through relay lenses 926 and 928 and focused by a tube lens 930 onto a detector 932. An aperture mask (e.g., an adjustable slit) 934 can be placed at a focal plane of lens 926, and the when the mask defines a slit the width of the slit 934 can be selected to block signal light from positions in the sample corresponding to side lobes of the Bessel-like beam illumination light, while passing signal light from positions in the sample corresponding to the central peak of the Bessel-like beam illumination light. The galvanometer-type mirror 924 can be rotated in conjunction with galvanometer-type mirror 902, so that when the Bessel-like beam is scanned in the X direction within the sample signal light from different positions within the sample passes through the slit 934.

Figure 10:
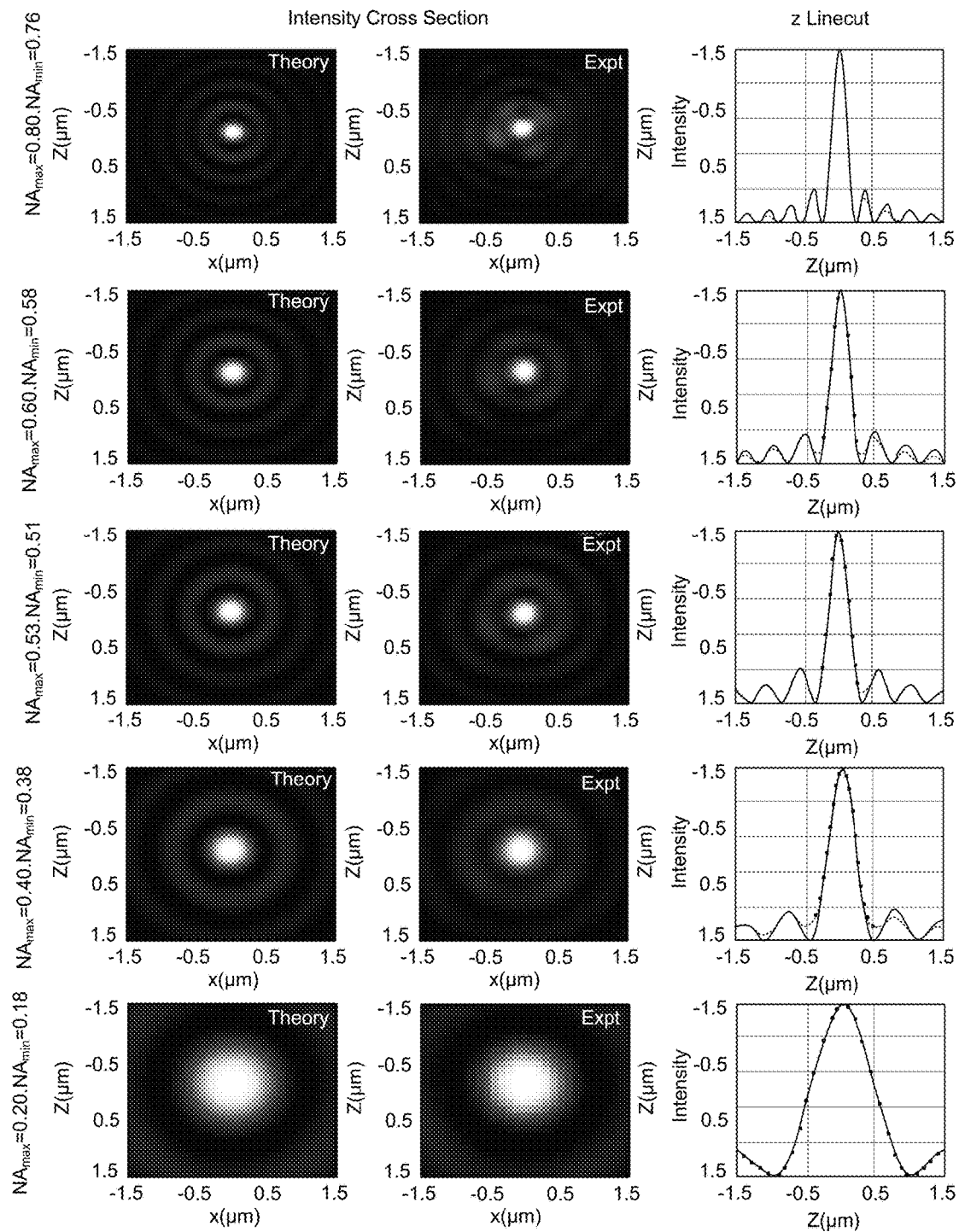
FIG. 10 shows a number of transverse intensity profiles for different Bessel-like beams.

Bessel-like beams include excitation intensity in rings other than the central excitation maximum, which are evident in FIGS. 7A and 8B, and substantial energy resides in the side lobes of a Bessel-like beam. Indeed, for an ideal Bessel beam of infinite extent, each side lobe contains energy equal to that in the central peak. Also, for an ideal Bessel beam, the ratio of the Rayleigh length of the beam to the minimum waist size of the beam is infinite. FIG. 10 shows a number of transverse intensity profiles for different Bessel-like beams. In FIG. 10, the first column shows theoretical two-dimensional intensity plots in the XZ plane, the second column shows experimental intensity plots in the third column shows a one-dimensional intensity profile at the X=0 plane. Different rows in FIG. 10 correspond to Bessel-like beams that are created using different annular apodization masks. Each row indicates the maximum and minimum numerical aperture of the annular ring of the mask. In the first row, the maximum numerical aperture is 0.80, and the minimum numerical aperture is 0.76. In the second row, the maximum numerical aperture is 0.60, and the minimum numerical aperture is 0.58. In a third row, the maximum numerical aperture is 0.53 and the minimum numerical aperture is 0.51. In the fourth row the maximum numerical aperture is 0.40, and the minimum numerical aperture is 0.38. In the fifth row, the maximum numerical aperture is 0.20, and the minimum numerical aperture is 0.18.

Figure 11A:
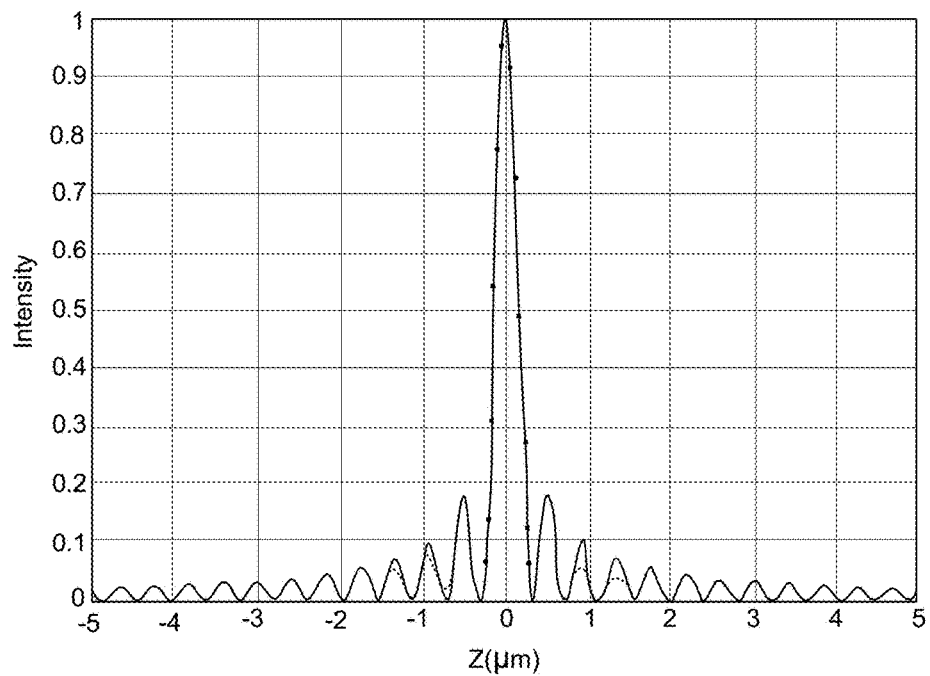
FIG. 11A shows the theoretical and experimental one-dimensional intensity profile of a Bessel-like beam at the X=0 plane.
Figure 11B:
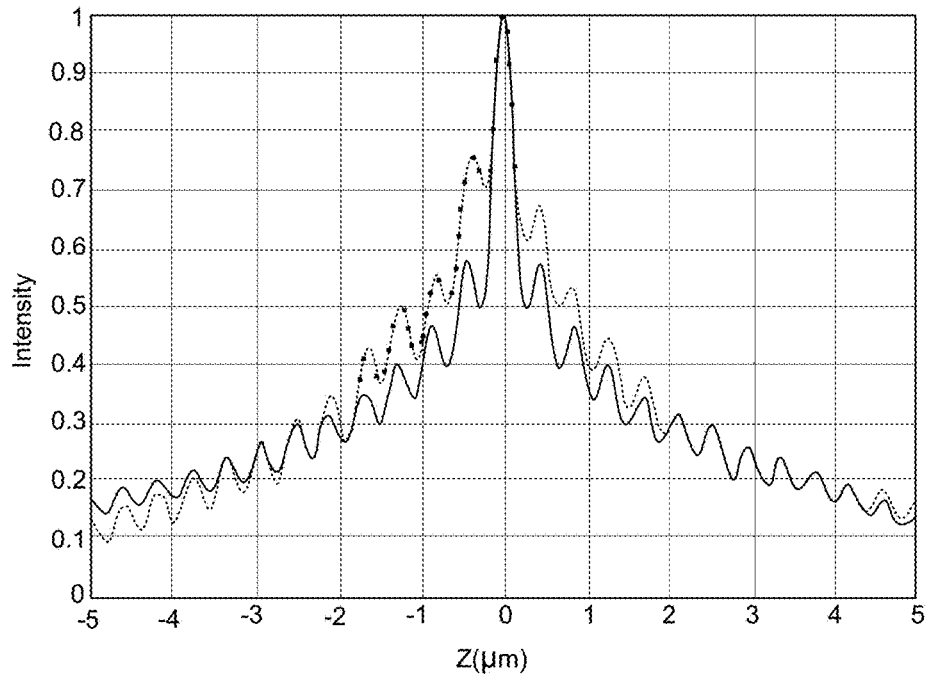
FIG. 11B shows an integrated intensity profile when the Bessel beam of FIG. 11 A is swept in the X direction.

Because of the intensity in the side lobes, the integrated fluorescence excitation profile after the beam is swept in the X direction exhibits broad tails, as shown in FIG. 11. FIG. 11A shows the theoretical and experimental intensity profile in the Z direction of a Bessel-like beam, when the center of the beam is fixed at the X=0 and Z=0 plane, where experimental values are shown by dots and theoretical values are shown by solid lines. The intensity profile shown in FIG.

11A is representative of a Bessel-like beam formed from an annular apodization mask that generates an annulus of 488 nm light at a rear pupil of an excitation objective, where the annulus has a maximum numerical aperture of 0.60 and a minimum numerical aperture of 0.58. When this Bessel-like beam is swept in the X direction to create a sheet of excitation light centered on the Z=0 plane, integrated fluorescence excitation profile shown in FIG. 11B results because of the side lobes in the beam. Thus, the side lobes of the Bessel beam can contribute out-of-focus background fluorescence and premature photobleaching of the sample. A number of techniques can be used to mitigate the effect of these lobes.

Figure 12A:
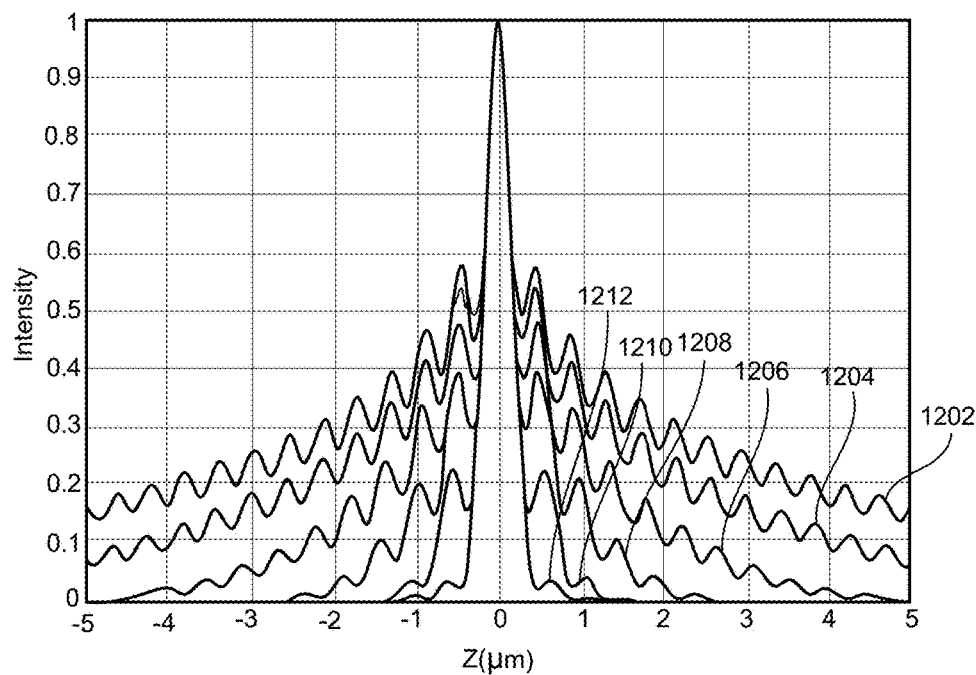
FIG. 12A shows plots of the width of fluorescence excitation profiles of a swept beam, where the beam that is swept is created from annuli that have different thicknesses.
Figure 12B:
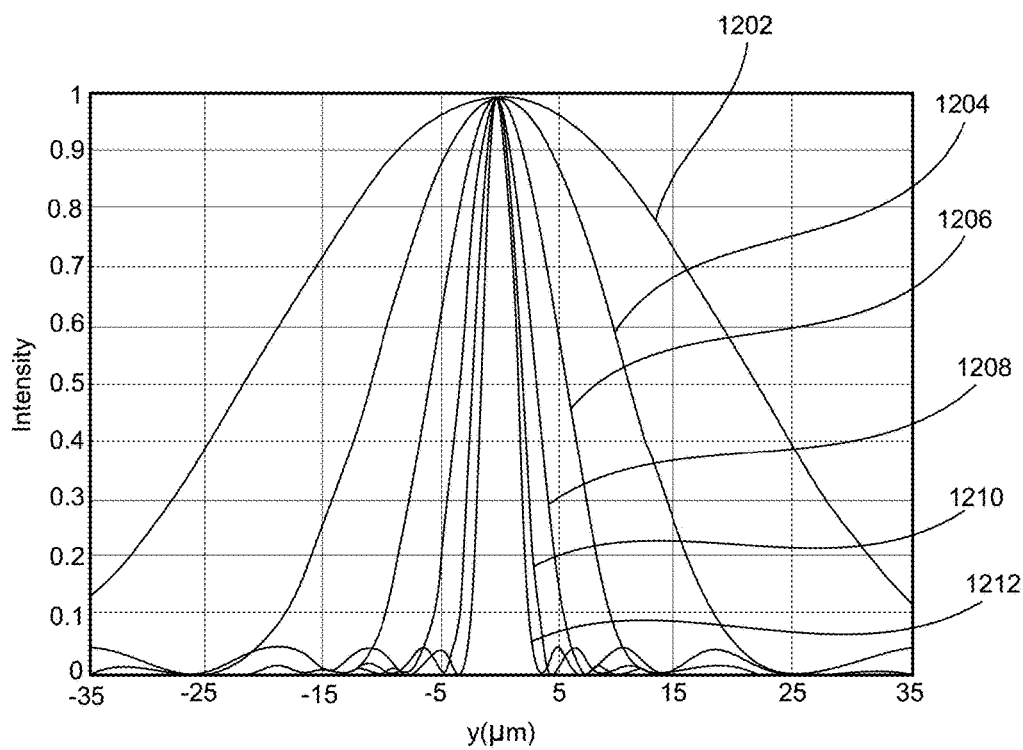
FIG. 12B shows plots of the axial intensity profile of the beam that is swept in the Z direction.

Choosing a thicker annulus in the annular mask 506 suppresses these tails, but it does so at the expense of the length of the beam, as the beam becomes more Gaussian and less Bessel-like in character. This effect can be seen in FIG. 12A and FIG. 12B. FIG. 12A shows plots of the width of fluorescence excitation profiles of beams swept in the X direction in the Z=0 plane, where the beams that are swept are created from annuli that have different thicknesses. FIG. 12B shows plots of the axial intensity profiles (i.e., in the Y direction) of the beams that are swept. For each of the beams whose intensity profiles are plotted in FIG. 12A and FIG. 12B, the maximum numerical aperture is 0.60. A beam with an intensity profile 1202 has a minimum numerical aperture equal to 0.58. A beam with an intensity profile 1204 has a minimum numerical aperture equal to 0.56. A beam with an intensity profile 1206 has a minimum numerical aperture people equal to 0.52. The beam with an intensity profile 1208 has a minimum numerical aperture equal to 0.45. A beam with an intensity profile 1210 has a minimum numerical aperture equal to 0.30. A beam with an intensity profile 1212 as a minimum numerical aperture equal to 0.00, i.e., it is equivalent to the Gaussian beam that fully illuminates a circular aperture.

Thus, as can be seen from a comparison of the plot FIG. 12A and FIG. 12B, a trade-off exists between minimizing the deleterious effects of the side lobes of the beam and maximizing the axial length of the field of view of the beam. Therefore, by selecting an annulus having a thickness that achieves a length of the field of view that is just sufficient to cover a region of interest in a specimen, but that is not substantially longer than the region of interest, the deleterious effects of the side lobes can be minimized. Therefore, the system 500 shown in FIG. 5, can include a plurality of different apodization masks 506 in which the thickness of the open annular region varies, and a particular one of the apodization masks 506 can be selected to image a region of the specimen 514, where the selected mask is chosen such that the length of the field of view of beam just covers the region of interest. When referring to FIG. 4, the different apodization masks can have open regions with different widths, Δd.

Thus, a comparison of the plots in FIG. 12A and FIG. 12B shows the profiles of the beam changing from a profile that best approximates that of a lowest order ($J_0$) Bessel function (plot 1202) to a Gaussian profile (1212). This comparison indicates that the deleterious effect of the side lobes can be reduced by using a beam having a profile that is not substantially similar to that of a Bessel function, at the expense of having a beam with a shorter axial length. This means that it can be advantageous to select a beam profile having a minimum length necessary to create the desired image, so that the effect of the side lobes of the beam, which create background haze and photobleaching, can be minimized. Thus, the beam that may be selected may not have a profile that approximates that of a Bessel function, but the beam also may not have a profile of a Gaussian beam, because the annular mask 506 blocks the portion of the incoming light 504 on the axis of the excitation objective 510 such that the $k_z=0$ of the beam 516 are removed. In particular, in one implementation, the selected beam can have a ratio of a Rayleigh length, $z_R$ to a minimum beam waist, $w_o$, of more than $2\pi w_o/\lambda$ and less than $100\pi w_o/\lambda$. In another implementation, the selected beam can have a non-zero ratio of a minimum numerical aperture to a maximum numerical aperture of less than 0.95. In another implementation, the selected beam can have a non-zero ratio of a minimum numerical aperture to a maximum numerical aperture of less than 0.9. In another implementation, the selected beam can have a ratio of a minimum numerical aperture to a maximum numerical aperture of less than 0.95 and greater than 0.80. In another implementation, the selected beam can have a non-zero ratio of a minimum numerical aperture to a maximum numerical aperture of less than 0.9. In another implementation, the selected beam can have a ratio of a minimum numerical aperture to a maximum numerical aperture of less than 0.95 and greater than 0.80. In another implementation, the selected beam can have a ratio of energy in a first side lobe of the beam to energy in the central lobe of the beam of less than 0.5.

The length of the beam 516 that is necessary to image a specimen can be reduced by tilting a cover slip that supports the specimen with respect to the direction of the incoming beam 516. For example, if a specimen that resides on a cover slip is 5 µm thick in the direction normal to the cover slip and has lateral dimensions of 50 µm×50 µm then, if the cover slip lies in the Z=0 plane, the beam 516 would have to be 50 µm long to span the specimen. However, by tilting the plane of the cover slip at a 45° angle to the direction of the incoming beam 516, then the beam would only need to be 5 µm×√2 long to span the sample. Thus, by placing a thin specimen on a cover slip and tilting the cover slip with respect to the direction of the incoming beam, a shorter length beam can be used, which has the advantage of reducing the effect of background haze and photobleaching due to side lobes of the beam. To image the specimen on a tilted cover slip, the beam 516 can be scanned in the X direction by tilting the galvanometer-type mirror 902, and can be scanned in the Z direction either by introducing a third galvanometer (not shown) and a third pair of relay lenses (not shown) into the system 900 shown in FIG. 9A to scan the beam 516 in the Z direction or by translating the Z position of the specimen, e.g., via a piezoelectric transducer (not shown and FIG. 9A) coupled to the cover slide that supports the specimen. This mode of operation in which a specimen on a cover slip is imaged when the cover slip is tilted (e.g., at an angle between 10 and 80 degrees) with respect to the direction of the incoming illumination beam can be used to image thin (e.g., less than 10 µm thick) specimens, such as individual cells that are mounted or cultured on to the cover slip.

Another approach to isolate the central peak fluorescence from that generated in the side lobes is to exclude the latter via confocal filtering with a virtual slit. When the detector includes a plurality of individual detector elements, only those elements of the detector which an image the portion of the sample that is illuminated by the central lobe of the illumination beam can be activated to record information that is used to generate an image, while the individual detector elements upon which an image of the portion of the sample that is illuminated by side lobes of the illumination beam are not activated, such that they do not record information that is used to generate an image.

Figure 13A:
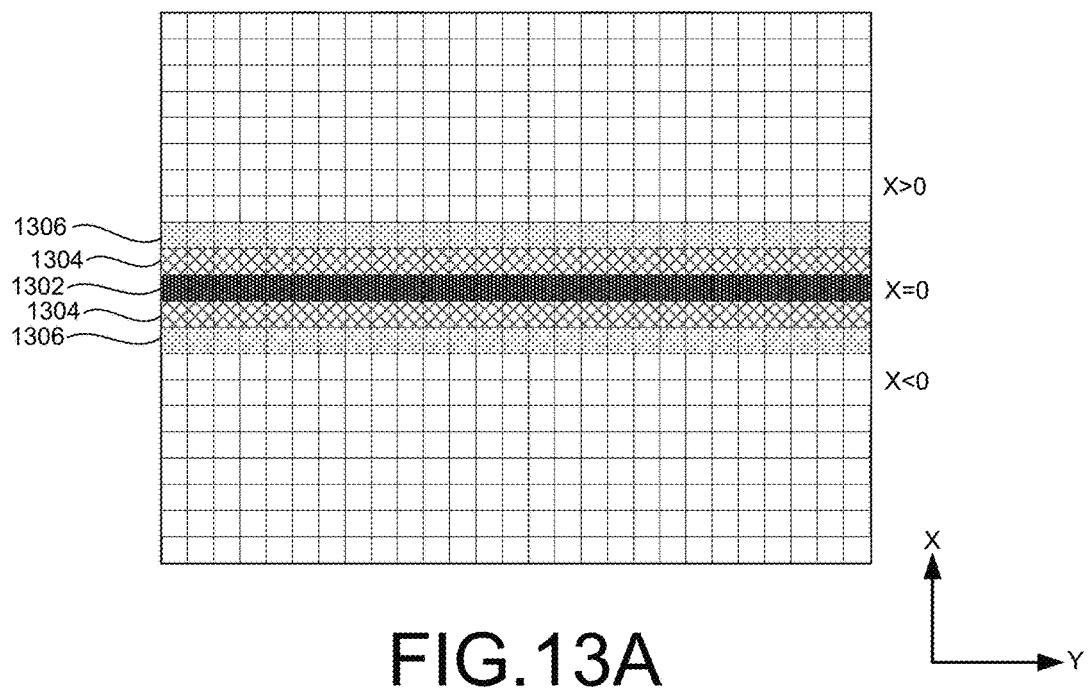
FIG. 13A is a schematic diagram of a surface of a detector having a two-dimensional array of individual detector elements in the X-Y plane.

For example, FIG. 13A is a schematic diagram of a surface of a detector having a two-dimensional array of individual detector elements in the XY plane. When the center of the central lobe of the excitation beam is located at X=0 and side lobes are located at X>0 and X<0, then the detector elements 1302 onto which fluorescence or detection light is focused from the X=0 position within the specimen at the focal plane of the detection objective 915 (or detector elements corresponding to the smallest absolute value of X for a particular Y position) can be activated to record information, while neighboring detector elements corresponding to higher absolute values of X for the particular Y position can be un-activated such that they do not record information that is used to generate an image. As shown in FIG. 13A, detector elements 1302 located on the detector surface at positions that correspond most closely with fluorescence light from X=0 positions within the specimen can be activated to record information, while neighboring detector elements 1304, 1306 are unactivated, so they do not record fluorescence light from positions within the sample that are not illuminated by the central portion of the excitation beam.

Figure 13B:
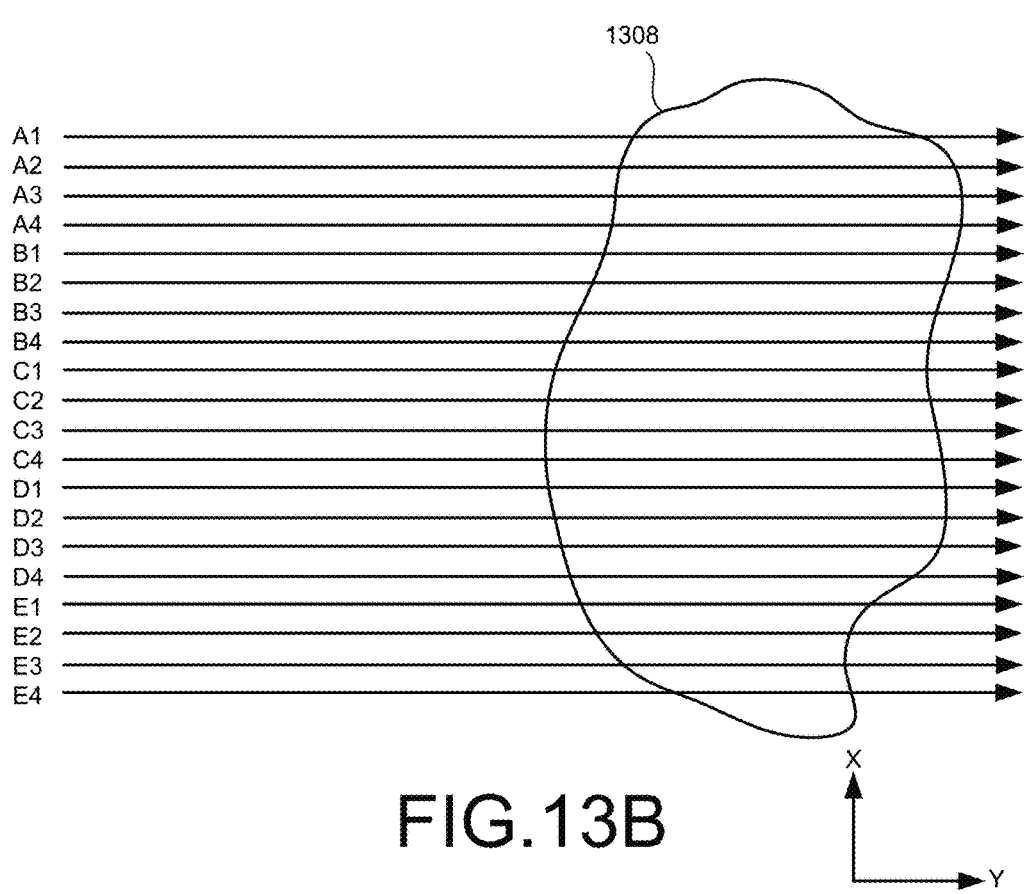
FIG. 13B is a schematic diagram of "combs" of multiple Bessel-like excitation beams that can be created in a given Z plane, where the spacing in the X direction between different beams is greater than the width of the fluorescence band generated by the side lobes of the excitation beams.

FIG. 13B is a schematic diagram of "combs" of multiple Bessel-like excitation beams that can be created in a given Z plane. A comb of beams can be created by inserting a diffractive optical element (DOE, not shown) in the beam path between the light source and the galvanometer-type mirrors 902, 905, where the DOE diffracts a plurality of beams at different angles from the DOE, which end up being parallel to and spatially shifted from each other within the specimen. In the specimen at the focal plane of the detection objective, the spacing in the X direction between different beams of the comb is greater than the width of the fluorescence band generated by the side lobes of the beams. This allows information to be recorded simultaneously from rows of individual detector elements corresponding to the centers of the different beams of the comb, without the side lobes of neighboring beams interfering with the recorded signal for a particular beam.

For example, as shown in FIG. 13B, a comb of beams that illuminate a plane of a specimen 1308 can include the beams A1, B1, C1, D1, and E1, where the beams are separated by distances great enough so that side lobes of one beam in the comb do not overlap with a central portion of a neighboring beam. In this manner, multiple "stripes" of an image can be simultaneously recorded. This process is then repeated, with additional images collected as the comb of Bessel-like illumination beams is translated in discrete steps having a width that corresponds to the spacing in the X direction between individual detector elements until all "stripes" of the final image have been recorded. For example, the beams can be moved to new positions of A2, B2, C2, D2, and E2, where the spacing between the positions A1 and A2, the spacing between positions B1 and B2, etc. corresponds to the spacing between neighboring individual detector elements in the detector. Thus, fluorescence light from the beam position C1 could be detected at a detector element 1302, while fluorescence light from the beam position C2 can be detected at individual detector elements 1304. The image is then digitally constructed from the information in all of the different stripes of the image. An acousto-optical tunable filter (AOTF) 918 can be used to block all excitation light from reaching the specimen between steps.

Another technique to reduce the influence of the side lobes and to reduce the Z-axis size of the field of view from which detection light is received is to employ structured illumination (SI) based optical sectioning. In a widefield microscopy implementation of SI, a periodic excitation pattern can be projected through an epi-illumination objective to the focal plane of the objective, and three images of a sample, $I_n$ (n=1, 2, 3), are acquired as the pattern is translated in steps of ⅓ of the period of the pattern. Since the observable amplitude of the pattern decreases as it becomes increasingly out of focus (i.e., in a direction perpendicular to the focal plane), combining the images according to:

$$I_{final} = \left| \sum_{n=1}^{N} I_n \exp(2\pi i n/N) \right| \quad (1)$$

with N=3 removes the weakly modulated out-of-focus component and retains the strongly modulated information near the focal plane. In equation (1), I is an intensity at a point in the image, and n is an index value indicating an image from which $I_n$ is taken. Equation (1) is but one example of a linear combination of the individual images that will remove the weakly modulated out-of-focus component and retain the strongly modulated information near the focal plane.

To use SI using a Bessel-like beam with a wavelength, λ, that illuminates a thin plane of a specimen and where light is emitted in a direction perpendicular to (or in a direction with a component perpendicular to) the illumination plane, the beam may not be swept continuously, but rather can be moved in discrete steps to create a pattern of illumination light from which an image $I_n$ can be generated. When the stepping period is larger than or approximately equal to the minimum period of $\lambda/2NA_{Bessel}^{max}$ required to produce a resolvable grating, but smaller than or approximately equal to $\lambda/NA_{Bessel}^{max}$, the imposed pattern of illumination light contains a single harmonic, as required for the three-image, three-phase SI algorithm.

Thus, referring to FIG. 9A, the Bessel-like beam 913 can be moved across the X direction in discrete steps having a period greater than or approximately equal to $\lambda/2NA_{Bessel}^{max}$ and less than or approximately equal to $\lambda/NA_{Bessel}^{max}$ by controlling the position of the galvanometer-type mirror 902, and detection light can be received and signals corresponding to the detected light can be recorded by the detector 917 when the beam 913 is in each of the positions. While the galvanometer-type mirror is being moved from one position to the next position, the illumination light can be blocked from reaching the sample by the AOTF. In this manner, an image $I_1$ can be generated from the detected light that is received when the illumination beam 913 is at each of its different positions. Then, additional images, $I_2 \ldots I_N$, can be created by again stepping the beam 913 across the specimen in the X direction to create a pattern of illumination light, but with the patterns spatially shifted from the position of the first pattern by (i−1)/N of the period of the pattern, for i=2 to N. A final image of the specimen then can be constructed from the recorded signals through the use of equation (1).

Figure 14A:
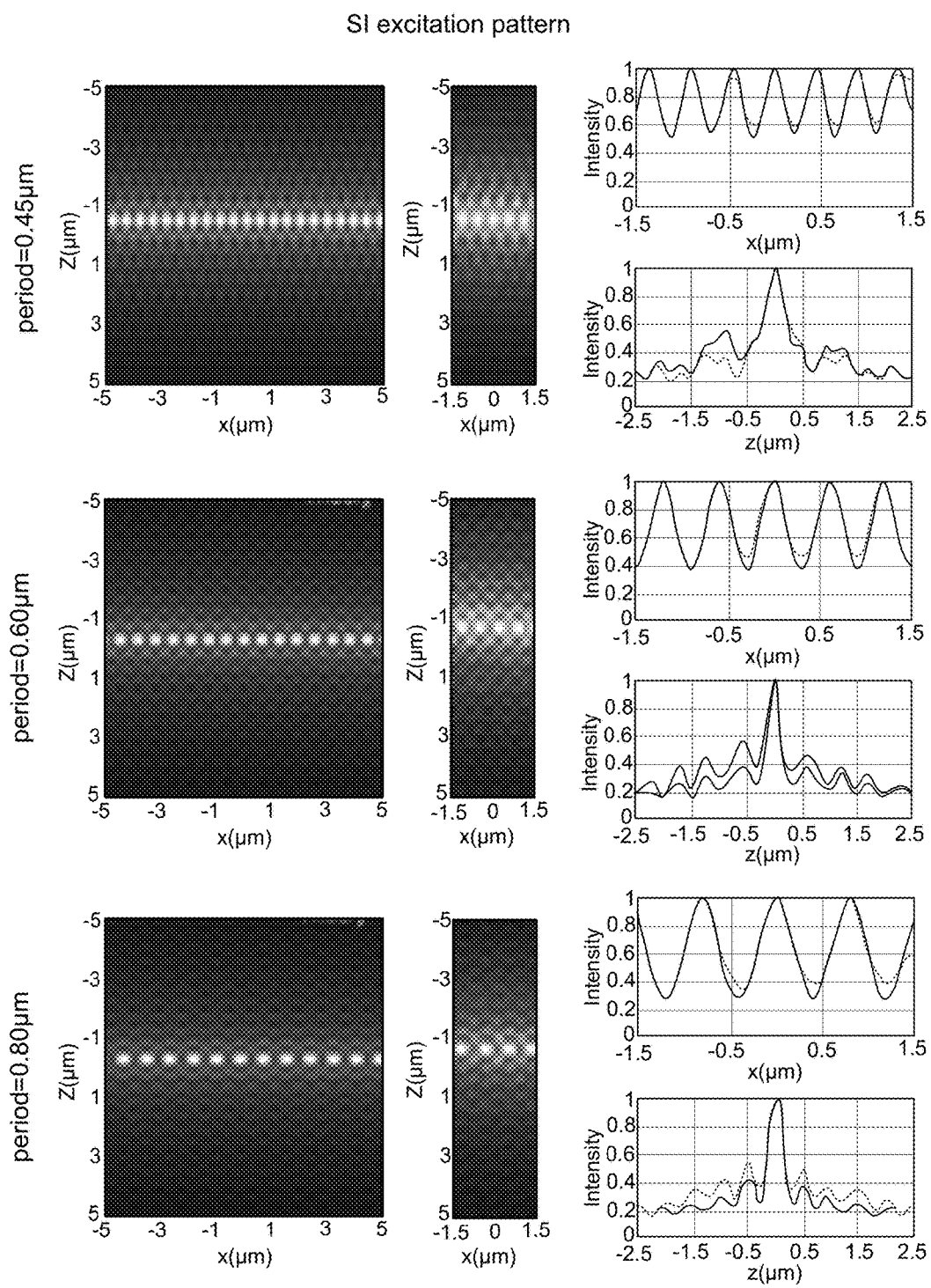
FIG. 14A shows theoretical and experimental single-harmonic structured illumination patterns that can be created with Bessel-like beams having a maximum numerical aperture of 0.60 and the minimum vertical aperture of 0.58, which are created with 488 nm light.
Figure 14B:
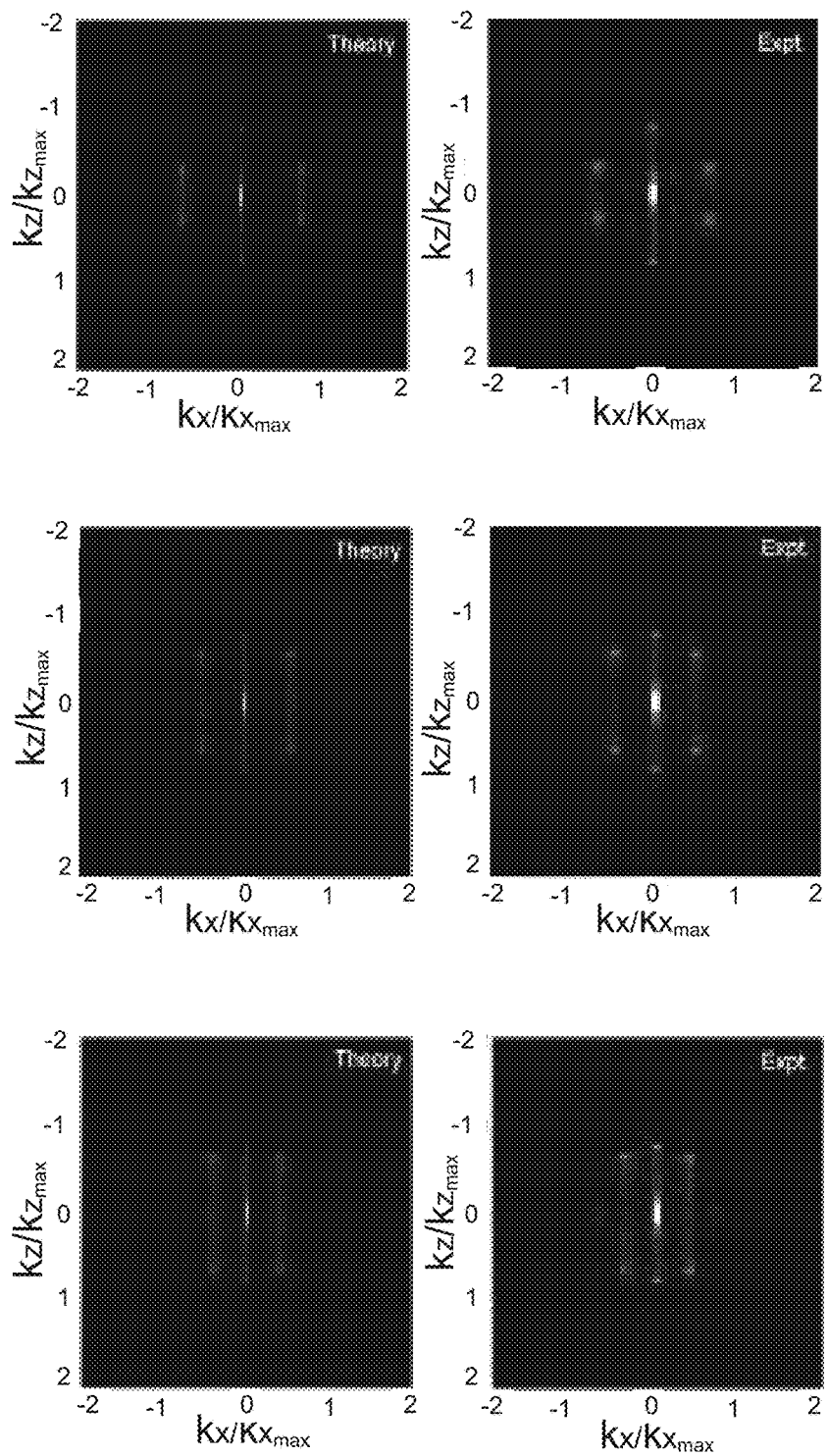
FIG. 14B shows theoretical and experimental modulation transfer functions in reciprocal space, which correspond to the point spread functions shown in the two left-most columns of FIG. 14A.

FIG. 14A shows theoretical and experimental structured illumination patterns that can be created with a 488 nm light Bessel-like beam having a maximum numerical aperture of 0.60 and the minimum numerical aperture of 0.58, that is moved across the X direction in discrete steps. The leftmost column of figures shows theoretical patterns of the point spread functions of the excitation light produced by stepping the beam across the X direction in discrete steps. The middle column shows experimentally-measured patterns, and the third column shows one-dimensional intensity patterns for the Z=0 plane (top figure) and the X=0 (bottom figure) plane, respectively, in each of the three rows of FIG. 14A. In the first row of FIG. 14A, the period the pattern (i.e., the spacing between successive positions of the center of the Bessel-like being as the beam is stepped in the X direction) is 0.45 µm. In the second row, the period of the pattern is 0.60 µm. In the third row the period of the pattern is 0.80 µm. FIG. 14B shows theoretical and experimental modulation transfer functions (MTFs) in reciprocal space, which correspond to the point spread functions shown in the two left-most columns of FIG. 14A. All of the MTFs are normalized to the maximum frequency, $k_{max}=2NA_{exc}^{max}/\lambda$ set by Abbe's Law, with $NA_{exc}^{max}=0.8$ for the excitation objective.

As described above, rather than stepping a single beam across the X direction, a comb of multiple Bessel-like beams, which are spaced by more than the width of the fringes of the beams in the comb, can be used to illuminate the specimen simultaneously, and then the comb of beams can be stepped in the X direction using the step size described above, so that different stripes of the specimen can be imaged in parallel and then an image of the specimen can be constructed from the multiple stripes.

The excellent optical sectioning of the single harmonic SI mode results from the removal of the $k_x=0$ band in the excitation modulation transfer function (MTF) under application of Eq. (1). However, due to the energy in the Bessel side lobes, considerably more spectral energy exists in this band than in the two side bands, so that its removal proves wasteful of the photon budget and reduces the SNR of the final images substantially. Somewhat more energy can be transferred to the side bands using single harmonic excitation having a period far beyond the $\lambda/2NA_{detect}^{max}$ Abbe limit, but at the expense of proportionally poorer optical sectioning capability.

Figure 15A:
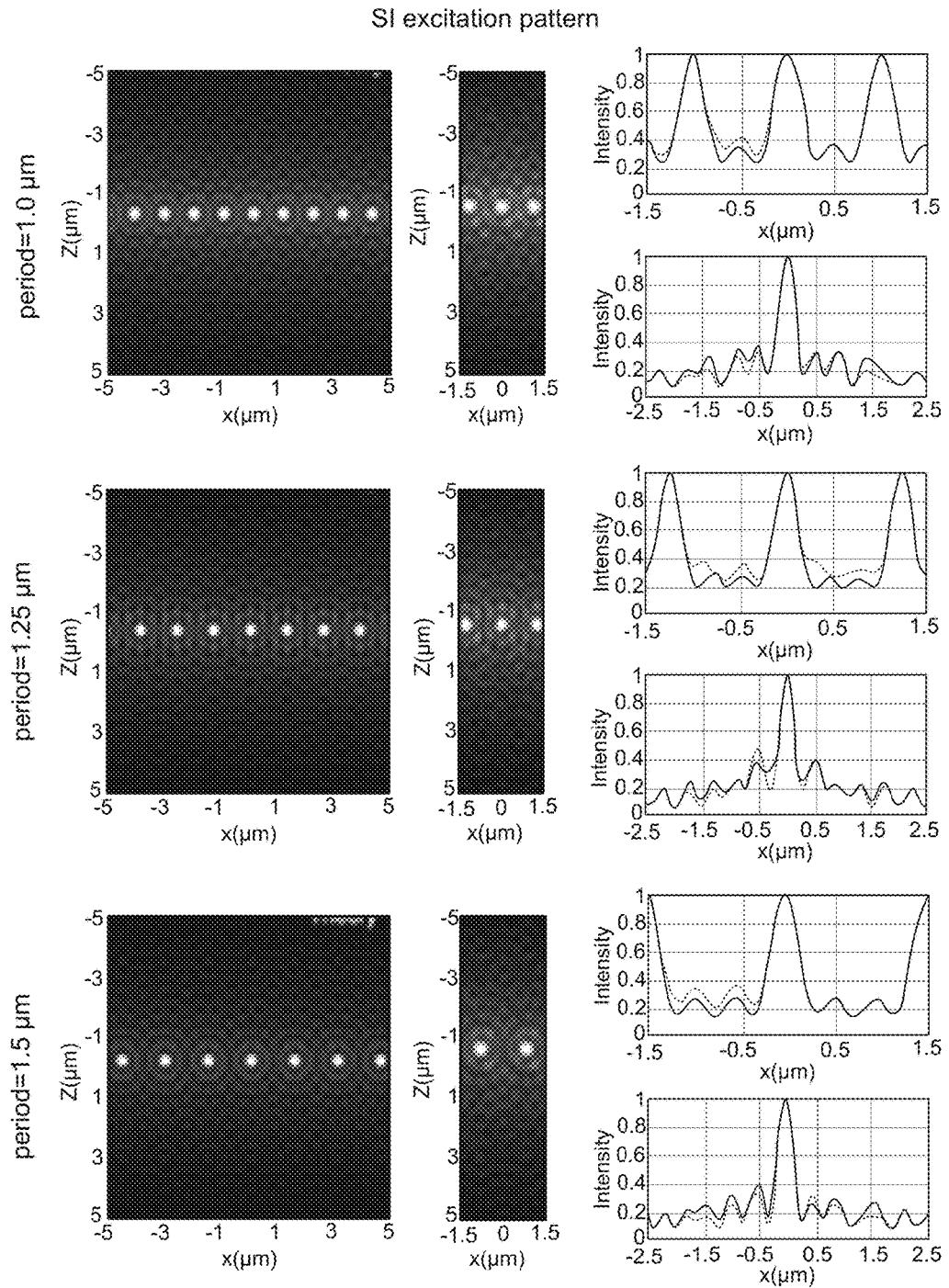
FIG. 15A shows theoretical and experimental higher-order harmonic structured illumination patterns that can be created with Bessel-like beams having a maximum numerical aperture of 0.60 and the minimum vertical aperture of 0.58, which are created with 488 nm light.

An alternative that can better retain both signal and axial resolution is to create a multi-harmonic excitation pattern by stepping the beam at a fundamental period larger than $\lambda/NA_{Bessel}^{max}$, as seen in FIG. 15A, which shows theoretical and experimental higher-order harmonic structured illumination patterns that can be created with Bessel-like beams having a maximum numerical aperture of 0.60 and the minimum vertical aperture of 0.58, which are created with 488 nm light. To create a single SI image with a pattern having H harmonics, Eq. (1) is again used, except with N≥H+2 images, each with the pattern phase shifted by $2\pi/N$ relative to its neighbors.

Figure 15B:
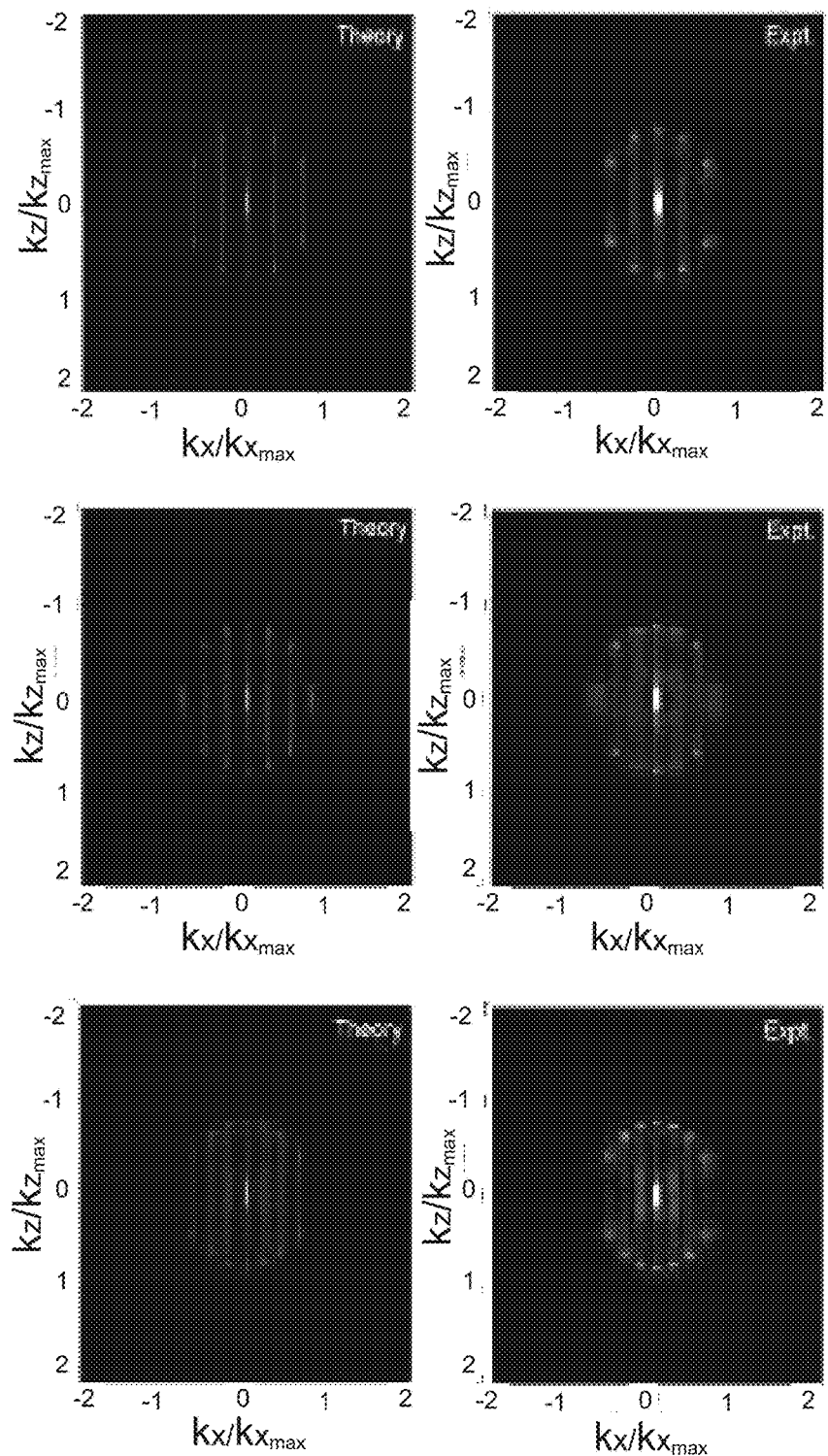
FIG. 15B shows theoretical and experimental modulation transfer functions (MTFs) in reciprocal space, which correspond to the point spread functions shown in the two left-most columns of FIG. 15A.

FIG. 15B shows theoretical and experimental modulation transfer functions (MTFs) in reciprocal space, which correspond to the point spread functions shown in the two left-most columns of FIG. 15A. As shown in FIG. 15B, with increasing H, more side bands are generated in the MTF that contain a greater combined fraction of the total spectral energy relative to the $k_x=0$ band, thus yielding higher signal-to-noise (SNR) images. Due to the greater weighting of these sidebands to lower $k_z$, axial resolution (i.e., along the axis of the detection objective 915) of this multi-harmonic SI mode is slightly less (0.29 µm FWHM for N=9 phases) than in the single harmonic case, yet images of fixed and living cells still exhibit isotropic 3D resolution, albeit at the cost of more data frames required per image plane, and thus lower speed.

In addition to this speed penalty, both single-harmonic and multi-harmonic SI modes still generate some excitation beyond the focal plane, and are thus not optimally efficient in their use of the photon budget. Both these issues can be addressed using two-photon excitation (TPE), which suppresses the Bessel side lobes sufficiently such that a thin light sheet can be obtained even with a continuously swept beam. As a result, high axial resolution and minimal out-of-focus excitation is achieved in fixed and living cells with only a single image per plane. Some additional improvement is also possible with TPE-SI, but the faster TPE sheet mode can be preferred for live cell imaging. The benefits of TPE are not limited to structured illumination excitation of the specimen, but are beneficial during other modes of Bessel-like beam plane illumination of the specimen to reduce out of focus excitation and photo damage by the illumination beam. Other forms of non-linear excitation with a Bessel like beam, such as coherent anti-Stokes Raman scattering (CARS), can also reap similar benefits.

Thus, the improved confinement of the excitation light to the vicinity of the focal plane of the detection objective made possible by Bessel beam plane illumination leads to improved resolution in the axial direction (i.e., in the direction along the axis of the detection objective) and reduced photobleaching and phototoxicity, thereby enabling extended observations of living cells with isotropic resolution at high volumetric frame rates. For example, extended imaging of the endoplasmic reticulum in a live human osteosarcoma cell (U2OS cell line) in the linear multi-harmonic SI mode was performed. Despite the fact that over three-hundred image slices were required to construct each 3D image stack, the dynamics of the ER could be followed over 45 minutes at a rate of 1 stack/min with axial resolution of ~0.3 µm.

Even longer duration observations were found to be possible in the TPE sheet mode. For example, portions of three consecutive image stacks from a series of one hundred such stacks showed the evolution of numerous filopodia on the apical surface of a HeLa cell transfected with mEmerald/Lifeact. Significantly, the imaging speeds achievable in this mode (51.4 image planes/sec, 6 sec stack interval) enable even complex, rapid 3D cellular processes to be visualized with sufficient time resolution. This is further underscored by consecutive images of the retrograde flow of membrane ruffles formed at the leading edge of a transformed African green monkey kidney cell (COS-7 cell line, transfected with mEmerald/c-src). Such ruffles can surround and engulf extracellular fluid to create large intracellular vacuoles, a process known as macropinocytosis, which was directly demonstrated using the techniques described herein. The visualization of these processes in four dimensional spatiotemporal detail (0.12×0.12×0.15 µm×12.3 sec stack interval) across 15 minutes cannot currently be achieved with other fluorescence microscopy techniques.

For sufficiently bright samples, the pixel rate of EMCCD cameras becomes a limiting factor. To achieve even higher imaging speeds in such cases, a scientific CMOS camera (125 MHz, Hamamatsu Orca Flash 2.8) can be used. To exploit the full speed of the camera, a third galvanometer-type mirror that can be tilted can be placed at a plane conjugate to the rear pupil of the detection objective and used to tile several image planes across the width of the detector, which were then are read out in parallel.

Figure 16:
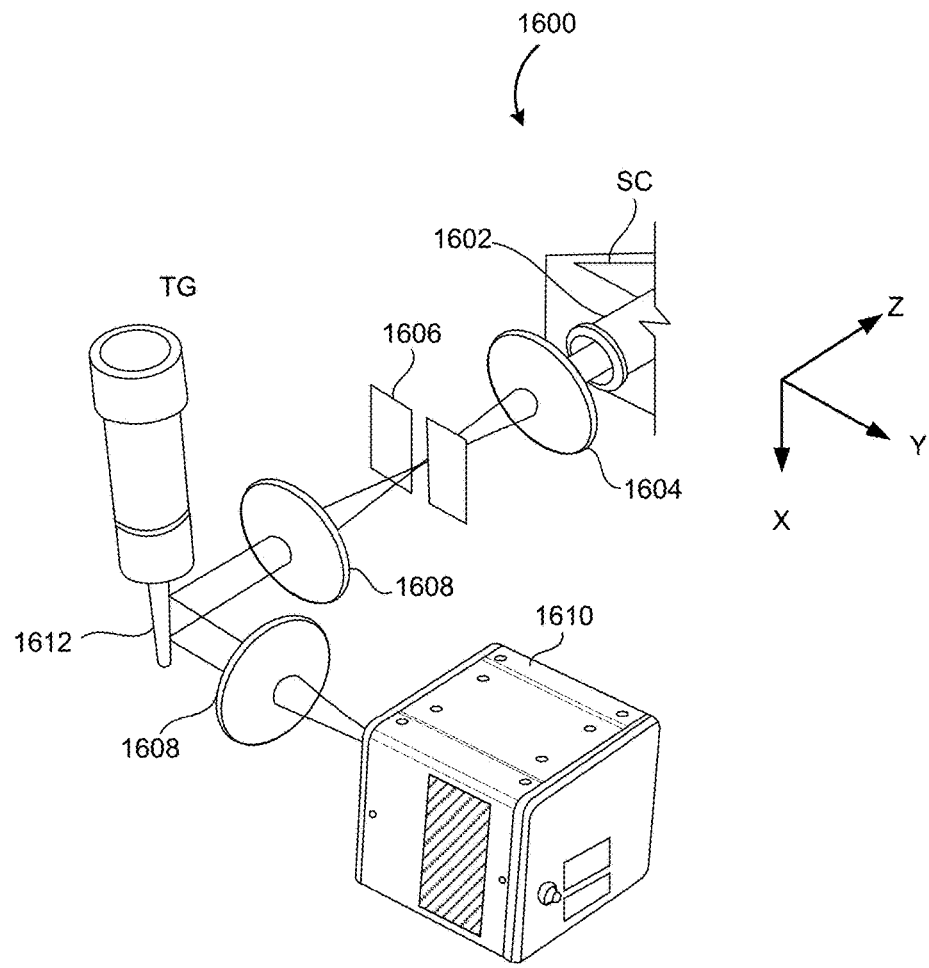
FIG. 16 shows a system with a galvanometer-type mirror placed at a plane that is conjugate to the detection objective between the detection objective and the detector.

FIG. 16 shows a system 1600 with a mirror placed at a plane that is conjugate to the detection objective between the detection objective and the detector. In the system 1600, detection light collected by detection objective 1602 can be focused by a tube lens 1604 to form an image at the plane of an adjustable slit 1606. The image cropped by the adjustable slit 1606 is reimaged by relay lenses 1608 onto a high-speed detection camera 1610. A galvanometer-type mirror 1612 is placed the plane between the relay lenses

1608 that is conjugate to the back focal plane of the detection objective 1612. By changing the angle of galvanometer-type mirror, multiple images can be exposed across the surface of the detection camera 1610 and then read out in parallel to exploit the full speed of the detection camera 1610.

With this configuration, the 3D dynamics of chromatid separation in early anaphase could be studied in the TPE sheet mode at rates of 1 volume/sec. Significantly, even at these imaging rates, the excitation did not arrest mitosis. Moreover, the intracellular trafficking of vesicles in a COS-7 cell could be observed over the course of 7000 frames acquired in a single plane at 191 frames/sec.

Three-dimensional live cell imaging can be performed with Bessel-like beams with the use of fluorescent proteins to highlight selected portions of a specimen. A key aspect of fluorescent proteins (FPs) is that their spectral diversity permits investigation of the dynamic interactions between multiple proteins in the same living cell. For example, after transfection with mEmerald/MAP4 and tdTomato/H2B, microtubules in a pair of U2OS cells surrounding their respective nuclei, were imaged in the linear, nine-phase multi-harmonic SI mode. Nevertheless, although many vectors are available for linear imaging, the need for N frames of different phase per image plane can limits the use of SI with Bessel-like beams to processes which evolve on a scale that matches the time required to collect frames at the desired spatial resolution. Of course, this limitation does not apply for fixed cells, where the linear SI mode is preferred, due to its superior axial resolution and the availability of a wider array of fluorescent dyes as well as FPs for protein specific labeling. For example, three-color isotropic 3D imaging of the actin cytoskeleton of an LLC-PK1 cell stained with Alexa Fluor 568 phalloidin, the nuclear envelope tagged with mEmerald/lamin B1, and nuclear histones tagged with mNeptune/H2B was performed.

For imaging multiple proteins exhibiting faster dynamics, the TPE sheet mode can be used. However, this presents its own challenges: orange/red FPs such as tdTomato and mCherry do not have the same TPE brightness and photostability of green FPs such as EGFP or mEmerald and require a second expensive ultrafast light source, since the time required to retune and realign a single source is prohibitive for live cell imaging. Fortunately, the 3D isotropic resolution of the Bessel TPE sheet mode permits multiple proteins tagged with the same FP to be imaged simultaneously, as long as they are known a priori to be spatially segregated. For example, the fragmentation of the Golgi apparatus between metaphase (t=0 min) and anaphase (t=10 min) was observed, as identified by chromosome morphology (green), and the re-constitution of the Golgi (t=20 min) around the daughter nuclei in telophase (t=40 min).

As described herein, Bessel beam plane illumination microscopy techniques offer 3D isotropic resolution down to ~0.3 µm, imaging speeds of nearly 200 planes/sec, and the ability, in TPE mode, to acquire hundreds of 3D data volumes from single living cells encompassing tens of thousands of image frames. Nevertheless, additional improvements are possible. First, substantially greater light collection making still better use of the photon budget is obtained by using a detection objective with a numerical aperture of 1.0 or greater. Although mechanical constraints would thereby force the use of an excitation objective with a numerical aperture of less than 0.8 thus lead to a somewhat anisotropic point spread function (PSF), the volumetric resolution would remain similar, since the slight loss of axial resolution would be offset by the corresponding transverse gain.

As noted above, SI using the algorithm in Eq. (1) is also photon inefficient, as it achieves high axial resolution by removing substantial spectral energy that resides in the $k_x=0$ band of the MTF. An alternative would be to use the algorithms of 3D superresolution SI, which assign the sample spatial frequencies down-modulated by all bands of the excitation to their appropriate positions in an expanded frequency space. By doing so, shorter exposure times and fewer phases are needed to record images of acceptable SNR, making linear Bessel SI a more viable option for high speed multicolor imaging. In addition, resolution can be extended to the sum of the excitation and detection MTF supports in each direction—an argument in favor of using three mutually orthogonal objectives. Indeed, the marriage of Bessel beam plane illumination and 3D superresolution SI permits the latter to be applied to thicker, more densely fluorescent specimens than the conventional widefield approach, while more efficiently using the photon budget.

Superresolution SI can be performed by extending the structured illumination techniques described above with respect to FIG. 14 and FIG. 15. By illuminating the sample with a structured illumination pattern, normally inaccessible high-resolution information in an image of a sample can be made accessible in the form of Moiré fringes. A series of such images can be processed to extract this high-frequency information and to generate reconstruction of the image with improved resolution compared to the diffraction limited resolution.

Figures 17A, 17B, 17C, 17D, 17E:
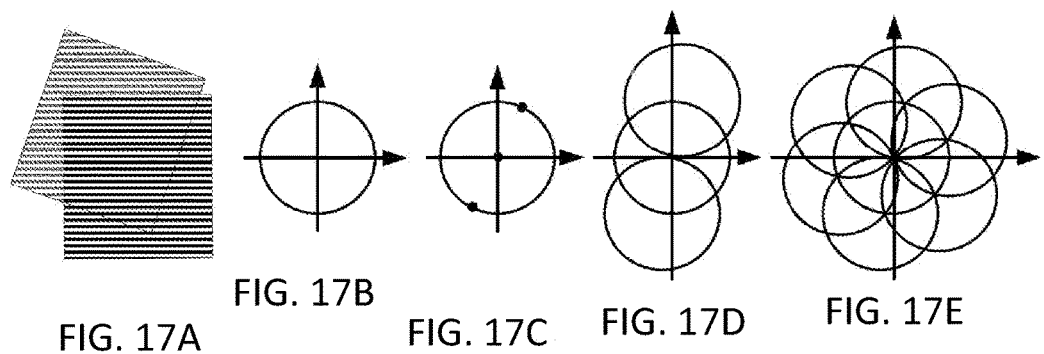
FIG. 17A shows two overlapping structured patterns.
FIG. 17B shows a reciprocal space representation of one of the patterns of FIG. 17A.
FIG. 17C shows shows a reciprocal space representation of the other pattern of FIG. 17A.
FIG. 17D shows an observable region of a reciprocal space representation of specimen structure shifted from the reciprocal space origin.
FIG. 17E shows observable regions of reciprocal space representations of specimen structure shifted from the reciprocal space origin, where the different representations correspond to different orientations and/or phases of a structured pattern overlayed with the specimen structure.

The concept of super resolution SI exploits the fact that when two patterns are superimposed multiplicatively a beat pattern will appear in the product of the two images, as seen in FIG. 17A. In the case of Bessel-like beam plane illumination microscopy, one of the patterns can be the unknown sample structure, for example, the unknown spatial distribution of regions of the sample that receive illumination light and that emit signal light—and the other pattern can be the purposely structured pattern of excitation light that is written in the form of parallel Bessel-like beams. Because the amount of signal light emitted from a point in the sample is proportional to the product of the local excitation light intensity and the relevant structure of the sample, the observed signal light image that is detected by the detector will show the beat pattern of the overlap of the two underlying patterns. Because the beat pattern can be coarser than those of the underlying patterns, and because the illumination pattern of the Bessel-like beams is known, the information in the beat pattern can be used to determine the normally unresolvable high-resolution information about the sample.

The patterns shown in FIG. 17A can be Fourier transformed into reciprocal space. For example, the Fourier transform of the structure of a sample that is imaged by an a convention widefield optical system is constrained by the Abbe resolution limit would be represented by a circle having a radius of $2NA/\lambda$, as shown in FIG. 17B, where the low resolution components of the sample are close to the origin, and the high-resolution components are close to the edge of the circle. The Fourier transform of a 2D illumination pattern that consists of a sinusoidal variation in the illumination light in one dimension and having a period equal to the diffraction limit of the optical system has three non-zero points that lie on the circle shown in FIG. 17C. One point resides at the origin and the other two points are offset from the origin in a direction defined by the orientation of the illumination pattern by distances proportional to the inverse of the spatial period of the pattern. When the specimen is illuminated by structured illumination, the resulting beat pattern between the specimen structure and the illumination structure represents information that has changed position in reciprocal space, such that the observable region of the sample in physical space then contains new high-frequency information represented by the two regions and FIG. 17D that are offset from the origin. For example, the regions of the offset circles in FIG. 17D that fall outside the central circle represent new information that is not accessible with a conventional widefield technique. When a sequence of such images is obtained using structured excitation radiation that is oriented in different directions multiple circles that lie outside the central circle are produced, as shown in FIG. 17E. From this plurality of images, information can be recovered from an area that can be twice the size of the normally observable region, to increase the lateral resolution by up to a factor of two is compared with widefield techniques.

In an implementation using a structured illumination pattern of Bessel-like beams, as explained above with respect to FIG. 14 and FIG. 15, N images can be recorded with the spatial phase of the illumination pattern between each image shifted by Λ/N in the X direction, where Λ is the spatial period of the pattern and N is the number of harmonics in reciprocal space. Then, a Fourier transform can be performed on each of the N images, and the reciprocal space images can moved to their true positions in reciprocal space, combined through a weighted-average in reciprocal space, and then the weight-averaged reciprocal space image can be re-transformed to real space to provide an image of the sample. In this manner, a superresolution image of the sample can be obtained, where the resolution of the image in both the X and Z directions can be enhanced over the Abbe diffraction limited resolution. The resolution enhancement in the X direction can be up to a factor of two when the NA of the structured excitation and the NA of the detection are the same. However, the excitation lens NA is usually lower than that of the detection lens, so the extension beyond the Abbe limit is usually less than a factor of two but more than a factor of one. In the Z direction, the resolution improvement can be better than a factor of two, since the transverse Z resolution of the excitation can exceed the transverse Z resolution of the detection.

In another implementation, more than one excitation objective can be used to provide a structured illumination pattern to the sample, where the different excitation objectives can be oriented in different directions, so that super resolution of the sample can be obtained in the directions transverse to the Bessel-like beams of each of the orientation patterns. For example, a first excitation objective can be oriented with its axis along the Y direction (as described above) and can illuminate the sample with an illumination pattern of Bessel-like beams that provides a superresolution image of the sample in the X and Z directions, and a second excitation objective can be oriented with its axis along the X direction and can illuminate the sample with an illumination pattern of Bessel-like beams that provides a superresolution image of the sample in the Y and Z directions. The super-resolution information that can be derived from illumination patterns from the different excitation objectives can be combined to yield extended resolution in all three directions.

In another implementation, highly inclined, objective-coupled sheet illumination has been used to image single molecules in thicker regions of the cell where autofluorescence and out-of-focus excitation would be otherwise prohibitive under widefield illumination. With the thinner light sheets possible with Bessel beam plane illumination, only in-focus molecules would be excited, while out-of-focus ones would not be prematurely bleached. As such, it would be well suited to live cell 3D particle tracking and fixed cell photoactivated localization microscopy.

At the other extreme, the TPE sheet mode may be equally well suited to the imaging of large, multicellular specimens, since it combines the self-reconstructing property of Bessel beams with the improved depth penetration in scattering media characteristic of TPE. In addition to large scale 3D anatomical mapping with isotropic resolution, at high frame rates it might be fruitfully applied to the in vivo imaging of activity in populations of neurons. When the sample is excited with two-photon excitation radiation, additional spatial frequencies are introduced to images generated from detected light that is emitted from the sample, and the additional spatial frequencies can provide additional information that may be exploited to enhance the resolution of a final image of the sample generated through the super resolution structured illumination techniques described herein. The infrared excitation light used in TPE can penetrate tissue with reduced scattering and aberration, and the out-of-focus emission from the side lobes of the excitation beam can be suppressed. Similarly, the suppression of the side lobes confines the TPE excitation radiation more closely to the Z=0 plane permitting substantial axial resolution improvement when applied to SR-SIM.

Figure 18A:
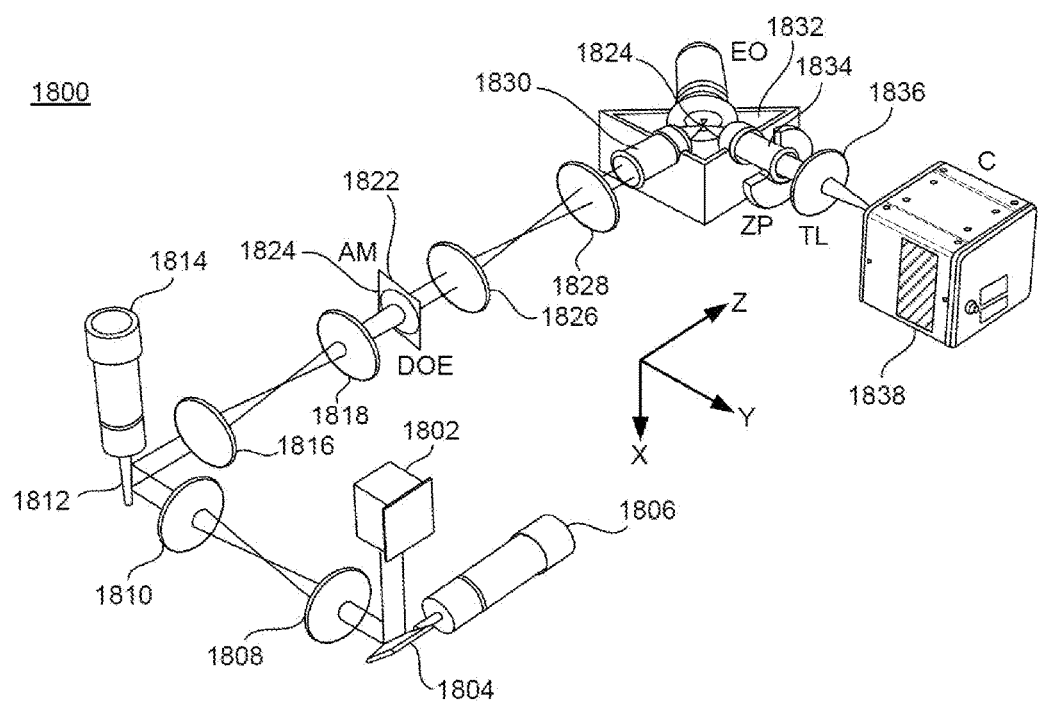
FIG. 18A is a schematic diagram of a system for producing an array of Bessel-like beams in a sample.

FIG. 18A is a schematic diagram of a system 1800 for generating and providing an array of Bessel-like excitation beams to a sample, similar to the comb of beams show in FIG. 13B, and for imaging the light emitted from the sample due to interaction between the Bessel-like beams and the sample.

As shown in FIG. 18A, a light source 1802 (e.g., a laser) can produce coherent, collimated light such as a beam having a Gaussian intensity profile, which can be reflected from first galvanometer-type mirror 1804. The mirror 1804 can be controlled by a fast motor 1806 that is used to rotate the mirror and steer the beam in the X direction. After the beam is reflected from the mirror 1804, it is imaged by relay lens pair 1808 and 1810 onto a second galvanometer-type mirror 1812 positioned at a point optically conjugate to the first galvanometer-type mirror 1804. The mirror 1812 can be controlled by a fast motor 1814 that is used to rotate the mirror and steer the beam in the Z direction.

A second lens pair 1816 and 1818 then can relay the light to a diffractive optical element (DOE) 1824 located just in front of an annular apodization mask (AM) 1822 that is conjugate with the second galvanometer-type mirror 1812. The DOE 1820 can be, for example, a holographic diffractive optical element, that creates, in the far field from the DOE, a fan of Gaussian beams. In some implementations, the DOE can create a fan of seven beams. The apodization mask 1822, located just after the DOE 1820, can be used in combination with the DOE to generate an array of Bessel-like beams in the sample 1840.

The annular light beams transmitted through the AM 1822 are relayed by a third lens pair 1826 and 1828 onto a conjugate plane coincident with the back focal plane of excitation objective 1830. Finally, the annular light beams are focused by the objective 1830 to form a fan of Bessel-like beam s that are used to provide excitation light to the sample 1840. The sample 1840 can be placed in an enclosed sample chamber 1832 that can be filled with aqueous media and that can be temperature controlled. Signal light emitted from the sample can be collimated by a detection objective

1834 and focused by a tube lens 1836 onto a position sensitive detector 1838. The signal light emitted from the sample can be generated through a non-linear signal generation process. For example, in one implementation, the signal light may be generated through a two-photon process, such that the signal light has a wavelength that is one half the wavelength of the excitation light of the Bessel-like beams.

Figure 18B:
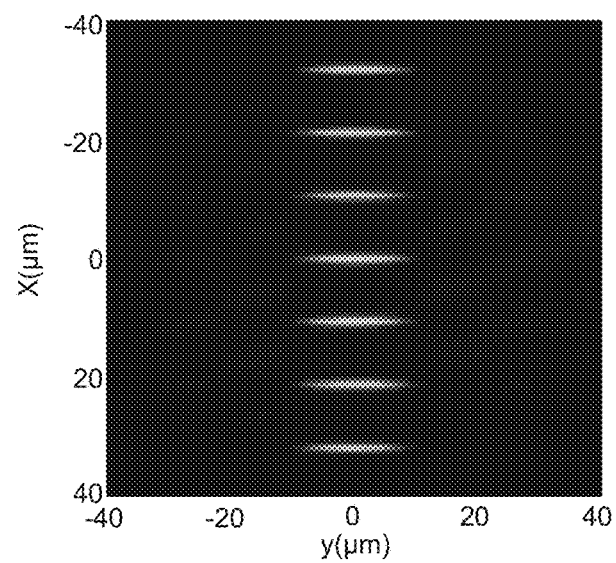
FIG. 18B is a view of an array of Bessel-like beams.
Figure 18C:
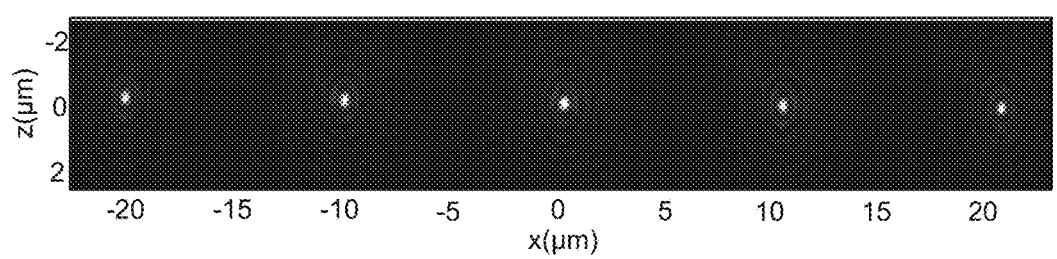
FIG. 18C is another view of the array of Bessel-like beams shown in FIG. 18B.
Figure 18D:
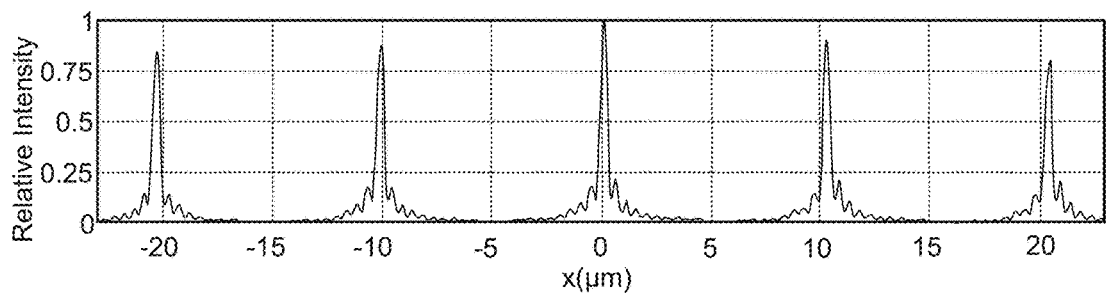
FIG. 18 D is a plot of the relative intensity of light produced by the array of Bessel-like beams shown in FIG. 18B and FIG. 18C along a line in which the beams lie.

FIGS. 18B and 18C, are example diagrams showing an array of substantially parallel Bessel-like beams produced by the system 1800. FIG. 18B shows the array of beams in the X-Y plane, and FIG. 18C shows the array of beams in the X-Z plane, although FIG. 18C shows only five of the seven Bessel-like beams. In one implementation, a diffractive optical element that produces seven beams in combination with the other beam-forming optics of system 1800, including the apodization mask 1822 and the excitation objective 1830, can create the array of seven Bessel-like beams shown in FIGS. 18B and 18C. As shown in FIGS. 18B and 18C, the beams, for particular parameters and configurations of the beam-forming optics of system 1800, including the dimensions of the apodization mask, the numerical aperture of the excitation objective 1830, etc. the Bessel-like beams that are produced in the sample can extend over a length of approximately 10 μm, and can have central lobes with diameters on the order of 1 μm. FIG. 18D is a schematic figure showing a relative intensity plots of five of the seven Bessel-like beams along the X-axis at the Y=0, Z=0 plane. As shown in FIG. 18D, in this implementation, the intensity profiles of neighboring Bessel-like beams do not substantially overlap. Nevertheless, use of the array of N non-overlapping beams spreads the excitation energy over N beams instead of concentrating the energy in just one beam, and, therefore, the sample is subject to less damage. In addition an array having a plurality of beams can be stepped across the sample to create an incoherent structured illumination pattern over a given field of view faster than one beam can be stepped.

The rotational axis of galvanometer mirror 1804 can be positioned such that tilting this galvanometer-type mirror 1804 causes the array of Bessel-like beams to sweep across the focal plane of detection objective 1834 (i.e., in the X direction), whose axis is orthogonal to (or whose axis has an orthogonal component to) the axis of the excitation objective 1830. Thus, through control of the galvanometer-type mirror 1804, the array of Bessel-like beams can be swept in the X direction to produce a thin sheet of light in a plane.

The signal light emitted from the sample 1840 can be directed by detection optics, including the detection objective 1834, to a detector 1838. The galvanometers-type mirrors 1804, 1812 can provide sweep rates of up to about 2 kHz, and with resonant galvanometer-type mirrors (e.g., Electro-Optical Products Corp, model SC-30) sweep rates can exceed 30 kHz. Extremely high frame rate imaging is then possible when the system is used in conjunction with a high frame rate detection camera.

The rotational axis of the galvanometer mirror 1812 can be positioned such that tilting of this mirror causes the array of Bessel-like beams to translate along the Z axis of detection objective 1834. By doing so, different planes within a specimen can be accessed by the Bessel beam, and a three dimensional (3D) image of the specimen can be constructed, with much higher axial resolution than in conventional light sheet microscopy, due to the much narrower sheet of excitation afforded by array of Bessel-like excitation. In order to image each plane in focus, either detection objective 1834 must be moved synchronously with the motion of the array of Bessel-like beams imparted by the tilt of galvanometer-type mirror 1812 (such as with a piezoelectric transducer), or else the effective plane of focus of the detection objective 1834 must be altered, such as by using a second objective to create a perfect image of the sample. In another implementation, the excitation plane and the detection plane can remain fixed and the sample can be moved through the planes, for example, by using a piezoelectric transducer to move the sample through the beam to cover different z planes. For relatively flat samples, this allows the use of a shorter Bessel-like beams in the Y-direction with less energy in the side-lobes.

The plurality of Bessel-like beams can lie in a plane within the sample and can be equally spaced from neighboring beams, such that the plurality of beams form a pattern in the plane having a spatial period, Λ. The array of beams can be scanned in a direction perpendicular to their propagation direction (e.g., in the X direction). In some implementations, the array of beams can be scanned in a series of discrete steps. For example, the array of beams can be scanned from its original position in N−1 discrete steps, where N is an integer, and the steps can have a length of (N−1)·Λ/N. Images of the sample can be recorded based on light emitted from the sample when the array of Bessel-like beams is in each of the N different positions within the sample (i.e., in the original position and in the N−1 scanned positions). Then, a final image of the sample can be generated through a linear combination of the N individual images of the sample. For example, the linear combination of the different images can be created according to $$I_{final} = \left| \sum_{n=1}^{N} I_n \exp(2\pi i n/N) \right|.$$

where $I_{final}$ is an intensity of the final image at a particular position within the sample, n is an index variable corresponding to the different individual images that are generated, and In is an intensity of the particular position within the sample in the nth individual image.

In some implementations, the array of the Bessel-like beams can be spatially dithered (i.e., rapidly changed in a periodic manner) at a dither frequency back and forth in the plane of the array of beams. For example, the galvanometer-type mirror 1804 can be tilted back and forth to dither the spatial position of the array of Bessel-like beams. The array of Bessel-like beams can be spatially dithered over a distance greater than or approximately equal to the spatial period, Λ, of the pattern of the array of Bessel-like beams. While dithering the array, the Bessel-like beams can be moved in the plane at the array (e.g., along the X axis) at a substantially constant rate, so that the time-averaged intensity of light in the plane of the array is substantially constant. When the inverse of the dither frequency is greater than the integration time of the detector 1838, the excitation light provided by the array of Bessel-like beams in the sample can appear to the detector as a uniform sheet of excitation light.

The system in FIG. 18A is typically quite wasteful of the energy in light beam 1801, because most of this light is blocked by apodization mask 1808. If greater efficiency is desired, a diffractive optical element such as a binary phase mask or spatial light modulator and a collimating lens can be used to create an approximately annular light beam prior to more exact definition of this beam and removal of higher diffractive orders by the apodization mask 1808.

The different, substantially parallel Bessel-like beams that are produced from the light of the light source and the beam-forming optics shown in FIG. 18A, can be created from a single source of coherent light, and the beam-forming optics can be held in stable positions, such that fixed phase relationships exist between the different substantially parallel Bessel-like beams in the sample. In some implementations, for example, in the implementation shown in FIGS. 18B, 18C, and 18D, the different Bessel-like beams can be spaced apart from the other with the spacing that is great enough so that the light from neighboring Bessel beams does not interact substantially.

Structured Illumination Microscopy with an Array of Bessel-Like Beams

Another technique to reduce the influence of the side lobes and to improve the Z-axis resolution of images obtained of a sample is to employ structured illumination using a coherent array of Bessel-like beams that are provided simultaneously to the sample, such that interference between the beams of the coherent array improves the Z-axis confinement of the plane of structured illumination that is used to provide excitation radiation to the sample. One way to imagine the creation of such a structured illumination plane is to think of the plane being created by different beams that are spaced apart from their neighboring beams by distances small enough for neighboring beams to overlap and interfere with each other. For example, in some implementations neighboring Bessel-like beams can be spaced by distances that are less than or comparable to a diameter of a first side lobe of the Bessel-like beams. Interference between the beams then creates a structured light sheet of high modulation depth within the desired Z=0 plane, improving the performance in optically sectioned or superresolution structured plane illumination. In addition, destructive interference between the side lobes outside the Z=0 plane reduces the out-of focus excitation from the side lobes, reducing phototoxicity and decreasing the thickness of the light sheet created by sweeping or dithering the structured light sheet.

Figure 19:
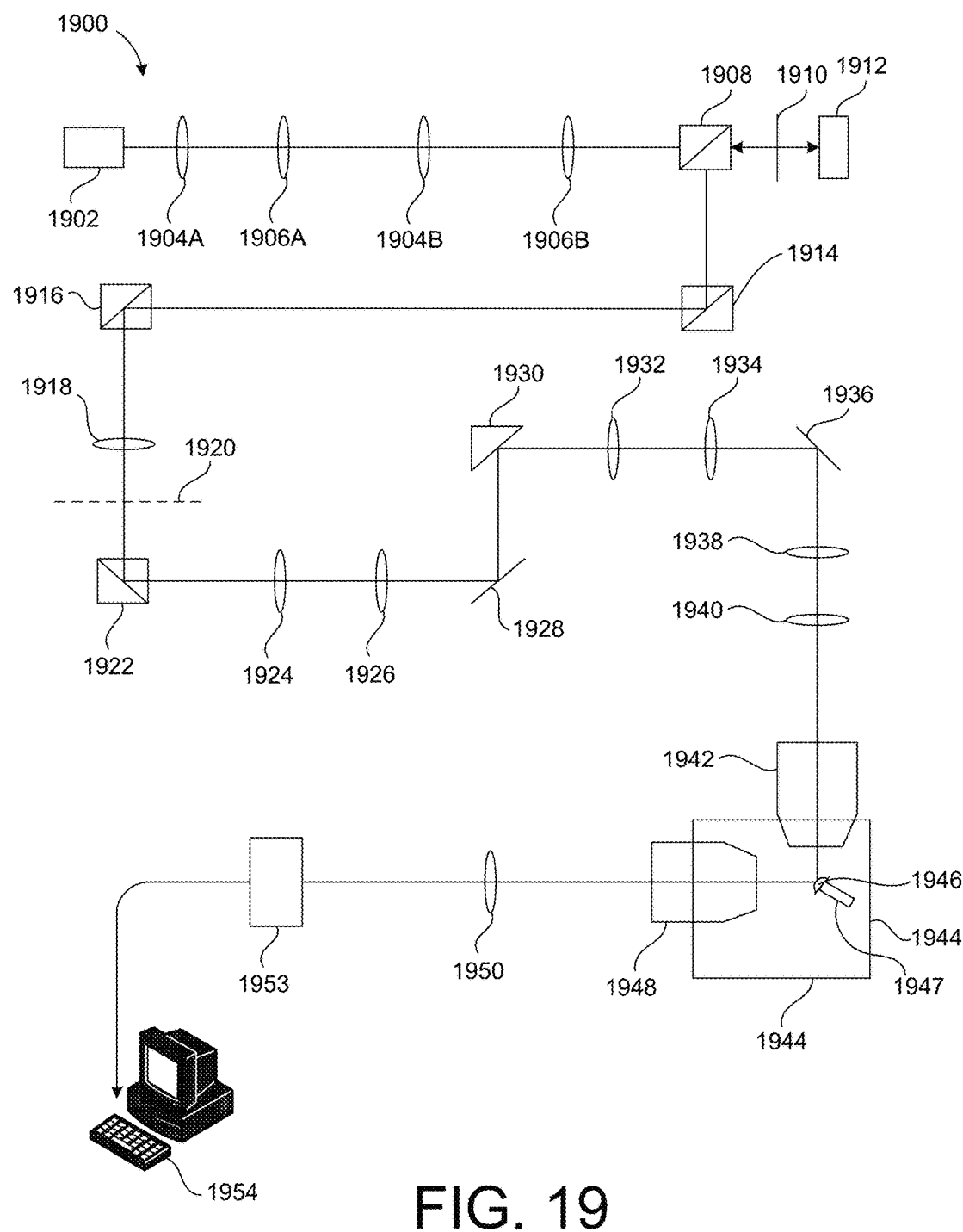
FIG. 19 is a schematic diagram of another system for producing an array of Bessel-like beams in a sample.

FIG. 19 is a schematic diagram of another system 1900 for producing an array of Bessel-like beams in a sample. As shown in FIG. 19, the light beam from the light source 1902 can be spatially expanded in the X direction by a pair of cylindrical lenses 1904A, 1904B and can be spatially reduced in the Z direction by a pair of cylindrical lenses 1906A, 1906B to produce a beam having an intensity profile that is wide in the X direction and narrow in the Z direction.

The beam can pass through a beam splitter 1908 half-wave plate 1910 and then impinge on a wavefront modulating element (WME) 1912 that independently modulates individual portions of the entire wavefront. The insertion of the half-wave plate 1910 in the beam path can make the WME 1912 operate as a phase modulator of portions of the beam that strike the WME. In some implementations, the WME can include a liquid-crystal phase-only spatial light modulator. In another implementation, the WME can include a ferroelectric binary spatial light modulator. In other implementations, the WME 1912 can include a deformable mirror (e.g., a piston-tip-tilt mirror) or an array of micromirrors. By controlling the WME 1912 (e.g., by control of the individual pixels of a spatial light modulator or individual mirrors within an array of micrometers or control of individual elements of a piston-tip-tilt mirror), the wavefront of the light reflected from the WME 1912, and consequently the wavefront(s) of downstream beam(s) (e.g., beams in the sample 1946), can be controlled. For example, the WME 1912 can be programmed to modulate the wavefront of the incoming light beam such that the outgoing light beam from the WME subsequently defines an array of coherent Bessel-like beams that overlap and interfere with each other to create a plane of structured illumination in the sample 1946. The WME 1912 can be optically conjugated to the sample 1946, so that modulations introduced by the WME can be propagated to the sample.

The WME 192 can be used to control the relative phases of individual beamlets (or portions of the incoming wavefront) that are reflected from the WME. For example, the WME 1912 can be used to control the relative phases of individual portions of the wavefront that strike the WME 1912 and that then propagate into the sample 1946. In some implementations, this relative phase control of individual portions of the reflected wave front can result in control of relative phases of individual Bessel-like beams in array of beams in the sample 1946.

In some implementations, the WME 1912 can include a spatial light modulator, and in some implementations the spatial light modulator can be a binary spatial light modulator, in which each pixel of the spatial light modulator can have one of two different states that affect the light modulated by the pixel. In some implementations, the WME 1912 can be used to scan the array of Bessel-like beams within the sample—either within the plane of the array or perpendicular to the plane (e.g. in the Z axis direction).

An advantage of using a reflective spatial light modulator (SLM) as the WME is that, with a high number of pixels (e.g., 1024×1280 pixels), it can be readily divided into many subregions, and in part because the subregions are truly independent, and not mechanically coupled, as in a deformable mirror.

After modulation by the WME 1912, the light reflected from the WME can be reflected by the beam splitter 1908 and reflected by mirrors 1914, 1916. Then, the light can be imaged by a lens 1918 onto an apodization mask 1920 that is conjugate to the rear pupil of the excitation objective 1942. After the apodization mask 1920, the light can be reflected off of a mirror 1922, transmitted through relay lenses 1924, 1926, reflected off galvanometer mirror 1928, mirror 1930, transmitted through relay lenses 1932, 1934, reflected off galvanometer mirror 1936, and transmitted through relay lenses 1938, 1940 to the rear pupil plane of excitation objective 1942. Then, the light can be focused by excitation objective 1942 onto the sample 1946 that is housed in chamber 1944.

Mirror 1928 can operate as a galvanometer-type mirror to translate the structured plane illumination in the X direction within the sample, and the mirror 1928 can be conjugated to the apodization mask 1920 by relay lenses 1924, 1926. Mirror 1936 can operate as a galvanometer-type mirror to translate the structured plane illumination in the Z direction within the sample, and the mirror 1936 can be conjugated to mirror 1928 by relay lenses 1932, 1934. The rear pupil plane of excitation objective 1942 can be conjugated to mirror 1936 by relay lenses 1938 and 1940. The combination of lenses 1918, 1924, 1926, 1932, 1934, 1938, and 1940 as well as excitation objective 1942 then serve to conjugate WME 1912 to an excitation plane within the sample 1946. The sample 1946 can be supported on a translation stage 1947 that can be used to translate the sample in space. In some implementations, the translation stage 1947 can translate the sample 1946 with respect to a beam of radiation that is provided to the sample, while the position of the beam remains fixed.

Light emitted from the sample 1946 due to the interaction of the excitation light with the sample can be collected by the detection objective 1948 and then focused by lens 1950 onto a detector 1952. Information collected by the detector 1952 can be sent to a computing device 1954, which may include one or more processors and one or more memories. The computing device may process the information from the detector 1952 to create images of the sample 1946 based on the information provided by the detector 1952.

The WME 1912 can control the wavefront of the light leaving the WME, such that the plurality of Bessel-like beams is created in the sample 1946. Furthermore, the WME 1912 can control the relative phases of the individual Bessel-like beams in the sample. The relative phases of the individual Bessel-like beams can be controlled such that neighboring Bessel-like beams interfere destructively with each other at positions that are out of the plane of the array of Bessel-like beams. For example, the destructive interference can occur within the Z≠0 plane when the array of Bessel-like beams is in the Z=0 plane. For example, the first side lobes of neighboring Bessel-like beams can destructively interfere where they intersect with each other at locations that are not in the plane of the array. For example, the intersection point can occur at a position that is closer to the plane of the array than a diameter of the first side lobe of the Bessel-like beams. Techniques for using a spatial light modulator WME to create structured light sheets within the sample are described in more detail below.

Figure 20:
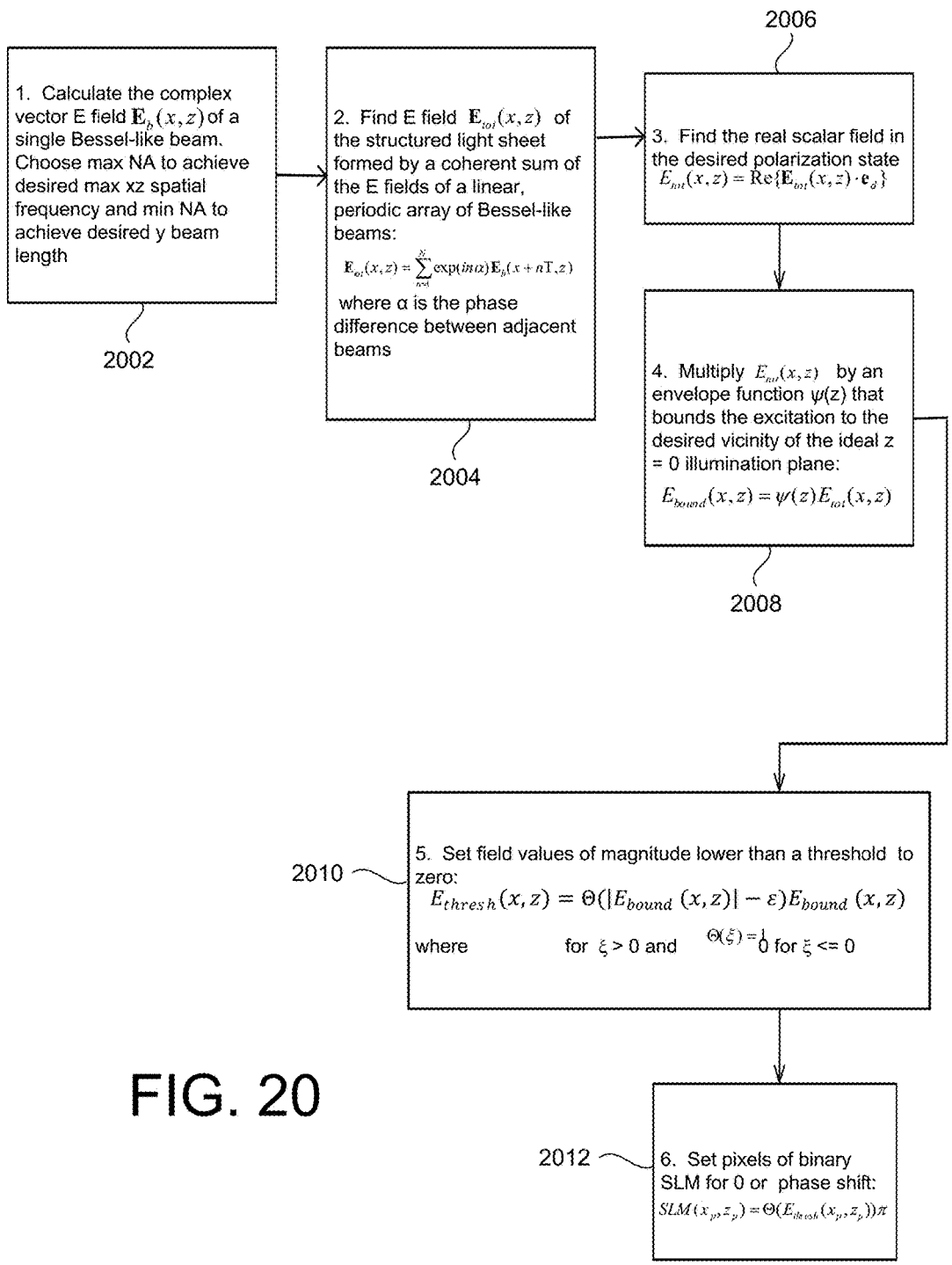
FIG. 20 is a flowchart of a process of determining a pattern to apply to a binary spatial light modulator, which will produce a coherent structured light sheet having a low height in the Z direction over a sufficient length in the Y direction to image samples of interest.

FIG. 20 is a flowchart of a process 2000 of determining a pattern to apply to a binary spatial light modulator, which will produce a coherent structured light sheet having a relatively low thickness in the Z direction over a sufficient length in the Y direction to image samples of interest. In the process 2000, the complex electric field $$E_b(x,z)$$

of a single Bessel-like beam propagating in the Y direction into the sample is calculated (step 2002). The complex electric field is chosen based on a maximum NA to achieve a desired maximum X-Z spatial frequency and based on a minimum NA to achieve a desired beam length in the Y direction. Then, the complex electric field $$E_{tot}(x,z)$$

of the structured light sheet that is formed by a coherent sum of a plurality of Bessel-like beams in a linear periodic array of Bessel-like beams can be calculated (step 2004). The total complex electric field of the array of beams can be expressed as:

$$E_{tot}(x,z) = \sum_{n=1}^{N} \exp(in\alpha) E_b(x+nT, z)$$

where $\alpha$ is the phase difference between adjacent beams in the array, and for T is the spatial period of the array of beams. In some implementations, $\alpha$ can be set equal to 0 or $\pi$ (i.e., all beams can have the same phase, or beams can have alternating opposite phases). Then, the real scalar field in the desired polarization state can be determined (step 2006), where the real scalar field is given by:

$$E_{tot}(x,z) = Re\{E_{tot}(x,z) \cdot e_d\}.$$

Next, the real scalar field can be multiplied by an envelope function $\psi(z)$ that bounds the excitation light to the desired vicinity of the ideal Z=0 illumination plane (step 2008). The product of the real scalar field and the envelope function gives the function for the bound field:

$$E_{bound}(x,z) = \psi(z) E_{tot}(x,z).$$

In some implementations, the envelope function can be a Gaussian function:

$$\psi(z) = \exp(-z^2/a^2)$$

Then, the field values having a magnitude lower than a threshold value, $\epsilon$, can be set to zero (step 2010). The thresholding step can be expressed mathematically as:

$$E_{thresh}(x,z) = \Theta(|E_{bound}(x,z)| - \epsilon) E_{bound}(x,z)$$

where $\Theta(\xi)=1$, for $\xi>0$ and 0 for $\xi<0$. Then, individual pixels values of a binary SLM that is used as the WME 1912 can be set to impose a 0 or $\pi$ phase shift on light that interacts with the SLM (step 2012), according to:

$$SLM(x_p, z_p) = \Theta(E_{thresh}(x_p, z_p))\pi,$$

where the "p" subscript references an individual pixel of the SLM.

Figure 21A:
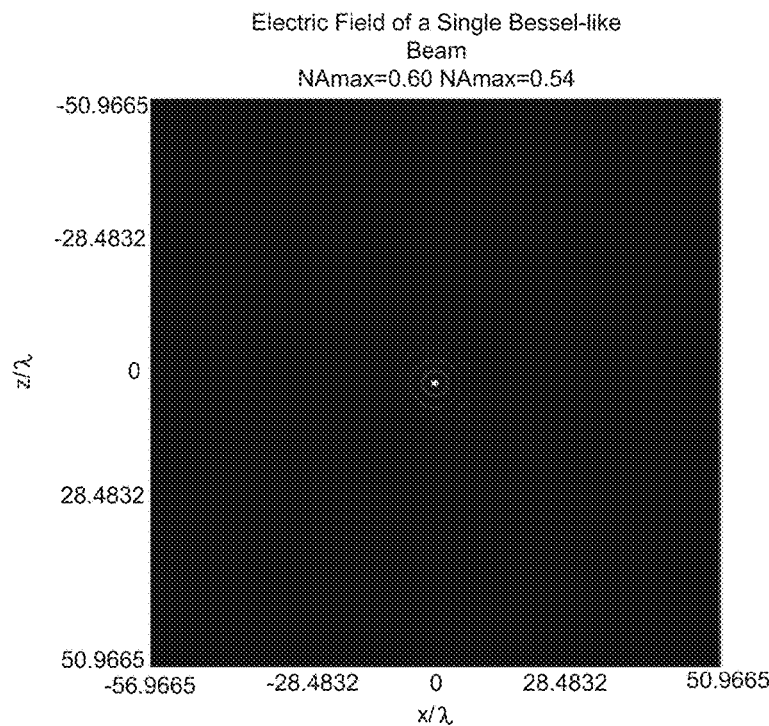
FIGS. 21A-21F show a series of graphical illustrations of the process of FIG. 20.

FIGS. 21A-21F shows a series of graphical illustrations of the process 2000, when the processes used to generate a thin array of structured excitation radiation is swept in the X direction to generate a plane of excitation illumination. FIG. 21A illustrates a cross-sectional profile in the X-Z plane of a Bessel like beam propagating in the Y direction. The particular cross section shown in FIG. 21A is for a Bessel-like beam having a maximum numerical aperture of 0.60 and a minimum numerical aperture of 0.54. Higher electric field strengths are shown by whiter regions in FIG. 21A.

Figure 21B:
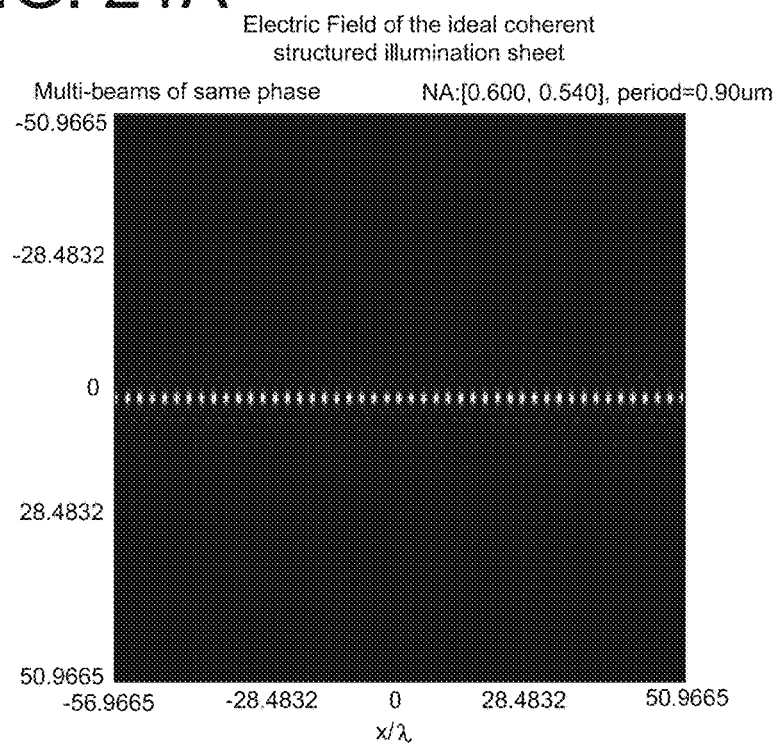

FIG. 21B illustrates the electric field, in the X-Z plane, of a structured light sheet formed by coherent sum of a linear, periodic array of Bessel-like beams that propagate in the Y direction. The individual Bessel-like beams have a maximum numerical aperture of 0.60 and a minimum numerical aperture is 0.54. The wavelength of the light is 488 nm, and the period of the array of beams is 0.90 µm, and the individual beams of the array all have the same phase. Higher electric field strengths are shown by whiter regions in FIG. 21B. The lengths shown on the axes of all of the panels of FIGS. 21A-21F are normalized the wavelength of light in the medium within the sample chamber 1944.

Figure 21C:
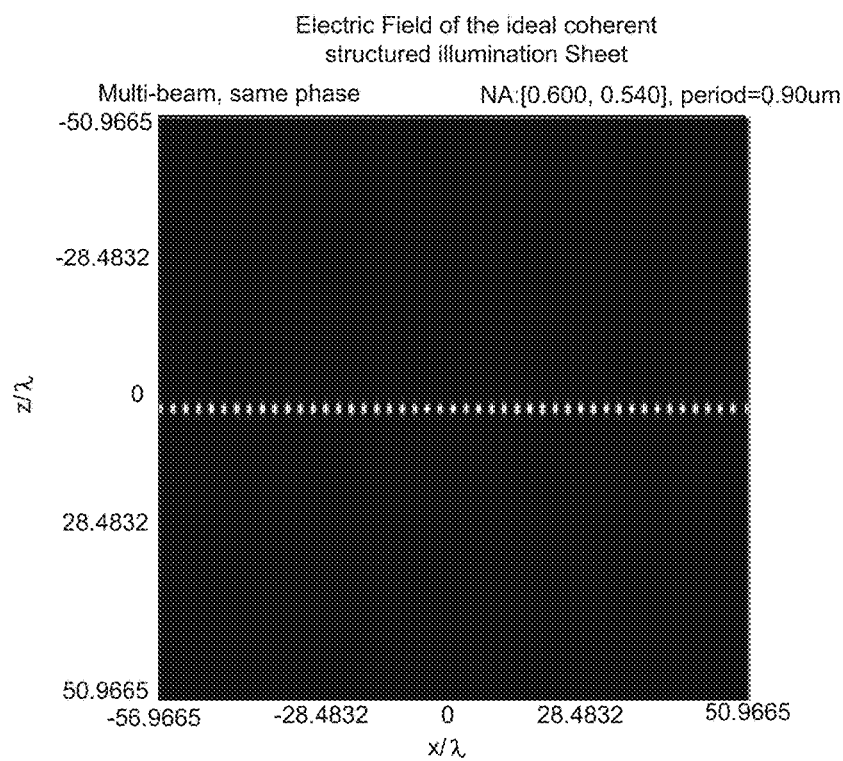
Figure 21D:
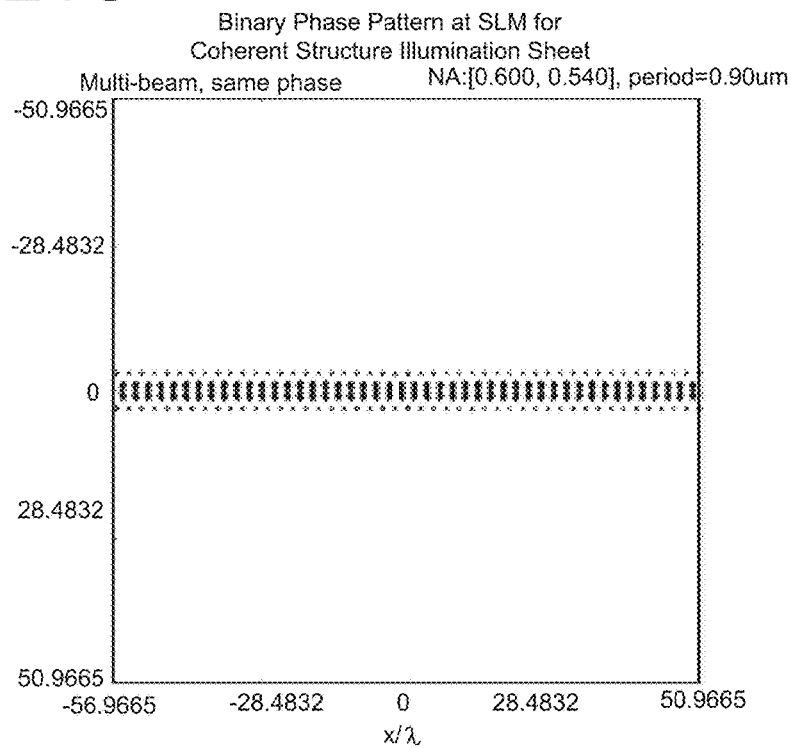
Figure 21E:
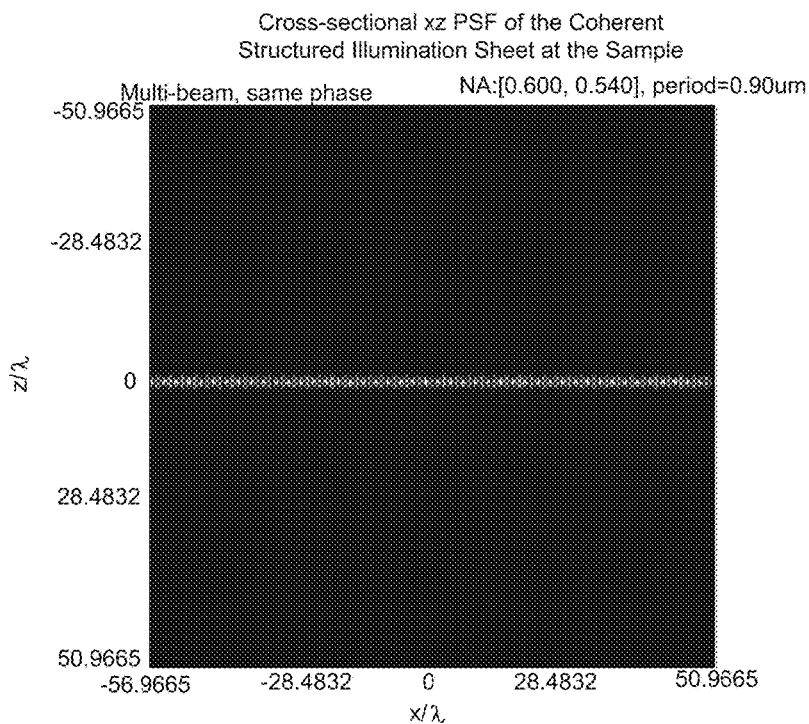
Figure 21F:
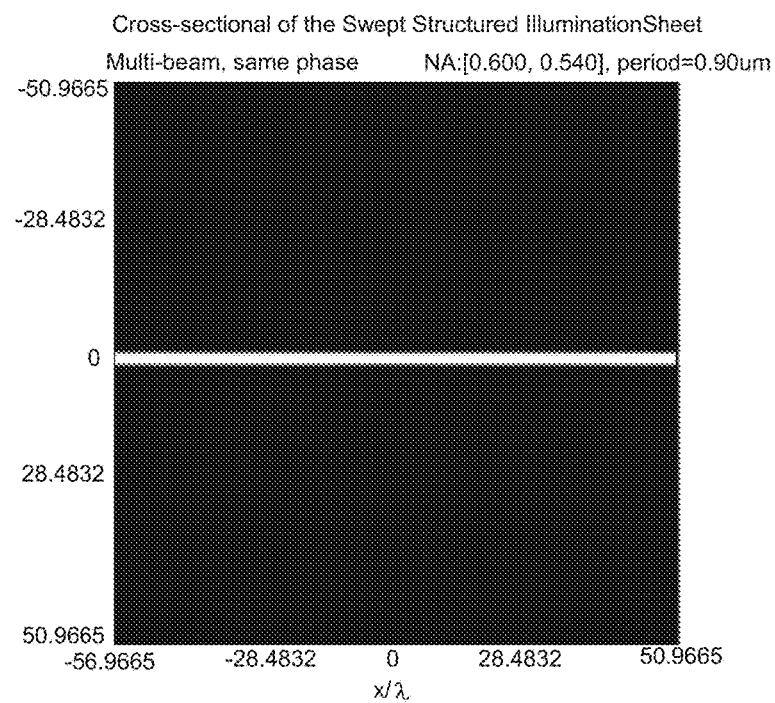

FIG. 21C illustrates the electric field, in the XZ plane, of the structured light sheet of FIG. 21B after a Gaussian envelope function has been applied to the field of the light sheet to bound the light sheet in the Z direction. Higher electric field strengths are shown by whiter regions. FIG. 21D illustrates the pattern of phase shifts applied to individual pixels of a binary spatial light modulator to generate the field shown in FIG. 21C. Pixels generating a phase shift of $\pi$ are shown in black, and pixels generating a phase shift of zero are shown in white. FIG. 21E illustrates the cross-sectional point spread function, in the X-Z plane, of the structured plane of excitation radiation that is produced in the sample by the coherent array of Bessel-like beams, which are generated by the pattern on the spatial light modulator shown in FIG. 21D. Higher light intensities are shown by whiter regions. FIG. 21F illustrates the excitation beam intensity that is produced in the sample when the array of Bessel-like beams is swept or dithered in the X direction. Higher intensities are shown by whiter regions.

Changing the period of the array of the coherent Bessel-like beams can affect the overall electric field pattern resulting from the interference of the plurality of beams. In particular, for different periods of the array, the resulting electric field interference pattern can extend relatively more or less in the Z direction. This effect can be exploited to determine parameters of the coherent array that can be useful for generating images of the sample using super resolution structured illumination techniques as well as using a thin sheet of structured illumination that is swept in the X direction.

Figure 22A:
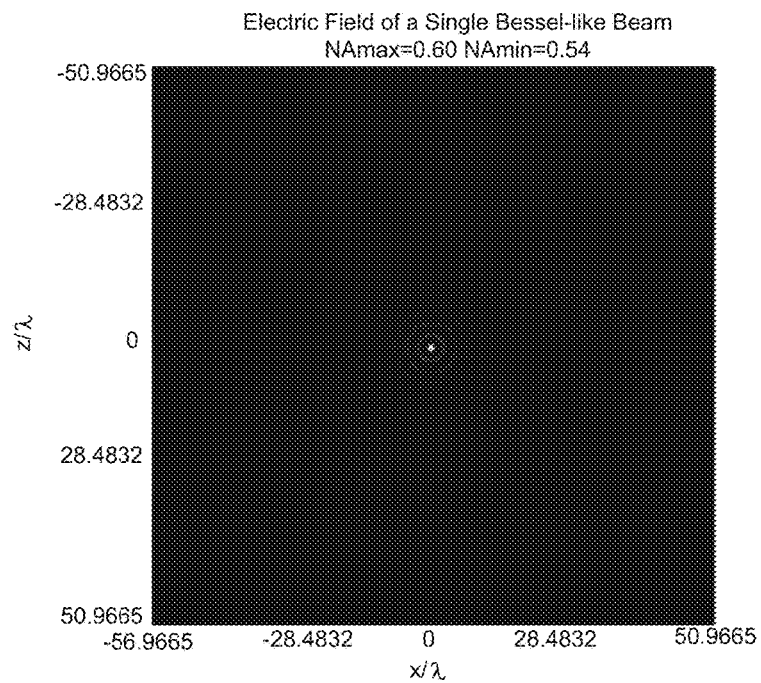
FIGS. 22A-22F show a series of graphical illustrations of the process shown in FIG. 20.

FIGS. 22A-22F shows a series graphical illustrations of the process 2000, when the plane is used to generate an array of structured excitation radiation that is used to generate images of the sample using super resolution structured illumination techniques. Like FIG. 21A, FIG. 22A illustrates a cross-sectional profile in the X-Z plane of a Bessel like beam propagating in the Y direction. The particular cross section shown in FIG. 22A is identical to that of FIG. 21A and is for a Bessel-like beam having a maximum numerical aperture of 0.60 and a minimum numerical aperture of 0.54. The lengths shown on the axes of all of the panels of FIGS. 22A-22F are normalized the wavelength of light in the medium within the sample chamber 1944.

Figure 22B:
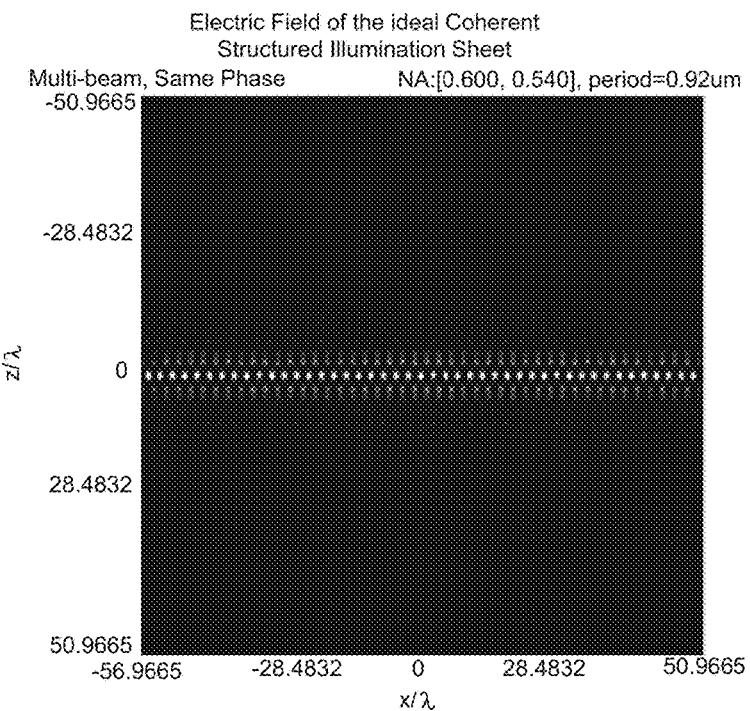

FIG. 22B illustrates the electric field, in the X-Z plane, of a structured light sheet formed by a coherent sum of a linear, periodic array of Bessel-like beams that propagate in the Y direction. The individual Bessel-like beams have a maximum numerical aperture of 0.60 and a minimum numerical aperture is 0.54. The wavelength of the light is 488 nm, and the period of the array of beams is 0.92 μm and the individual beams of the array all have the same phase. Thus, the period of the array illustrated in FIG. 22B is 0.02 μm longer than the period of the array illustrated in FIG. 21B.

Figure 22C:
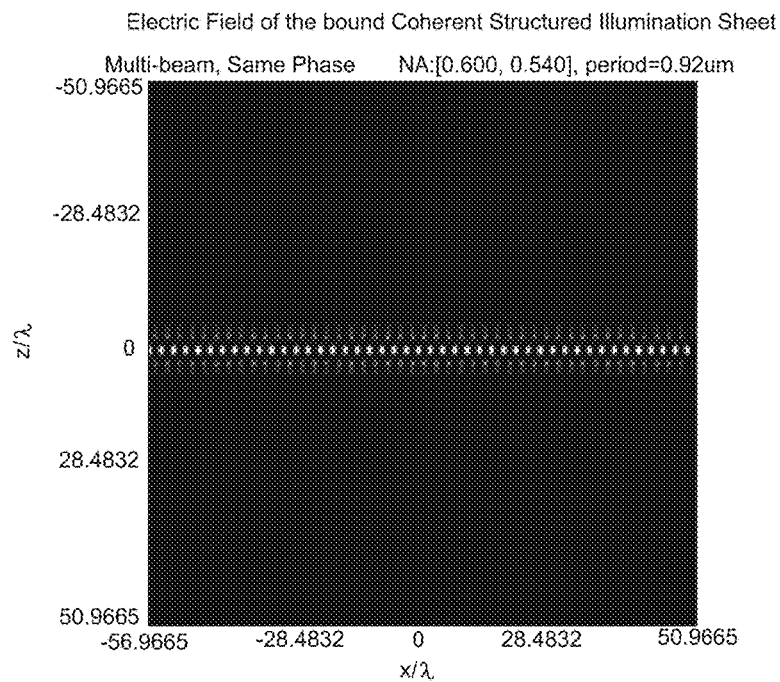

FIG. 22C illustrates the electric field, in the XZ plane, of the structured light sheet of FIG. 22B after a Gaussian envelope function has been applied to the field of the light sheet to bound the light sheet in the Z direction. Because the structured light sheets shown in FIGS. 22A-22F are to be used for super resolution structured illumination microscopy, in which it may be desirable to have the electric field extend further in the Z direction then when using the light sheet in a swept sheet mode, and therefore the envelope (or "bounding") function used in FIG. 22C may be relatively more relaxed than the bounding function used in FIG. 21C.

Figure 22D:
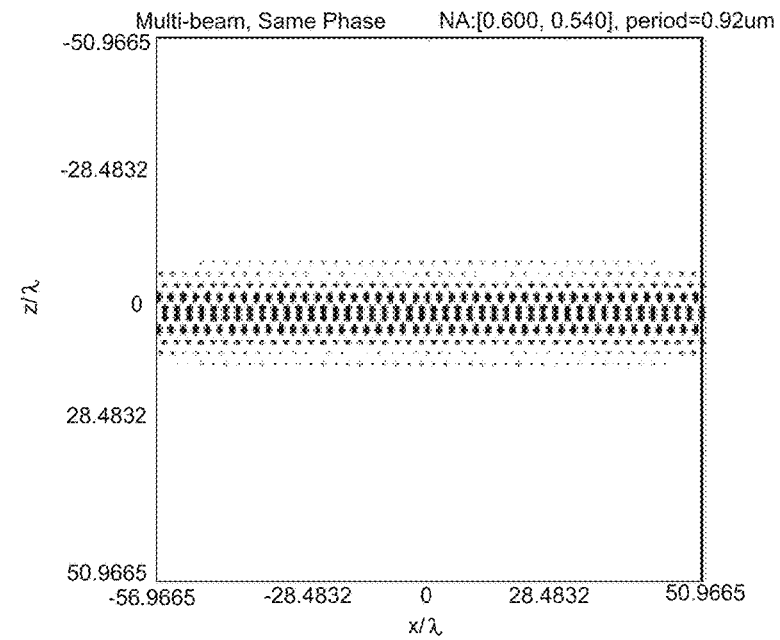
Figure 22E:
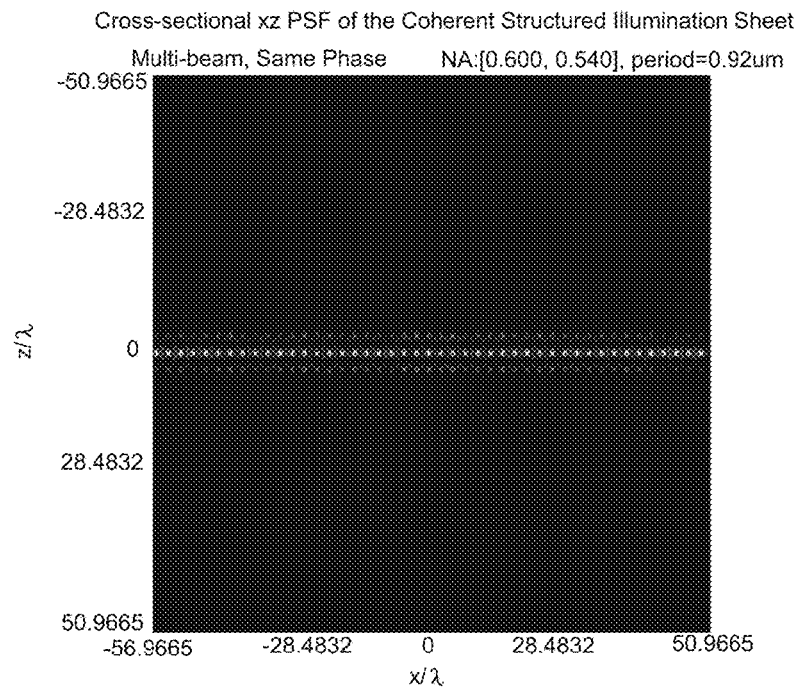
Figure 22F:
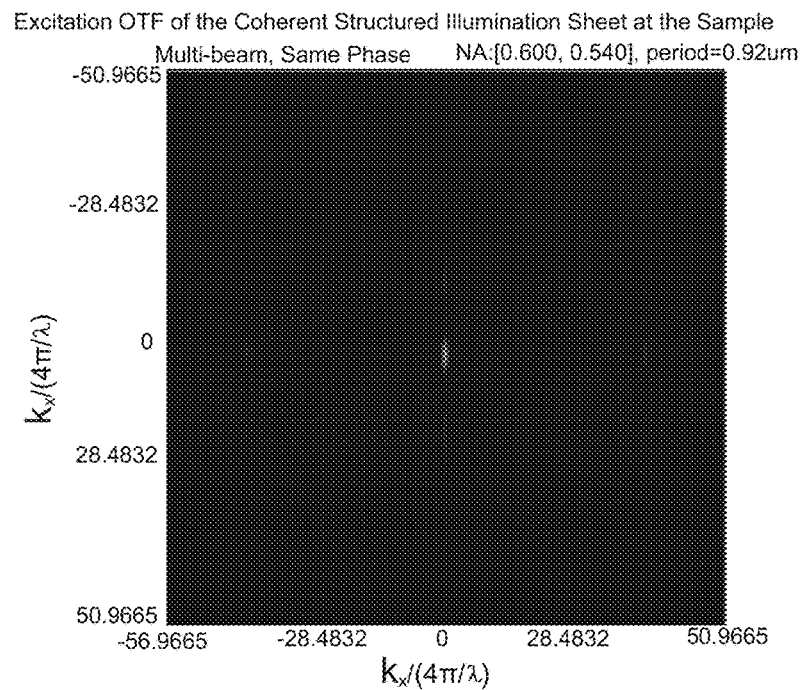

FIG. 22D illustrates the pattern of phase shifts applied to individual pixels of a binary spatial light modulator to generate the field shown in FIG. 22C. Pixels generating a phase shift of $\pi$ are shown in black, and pixels generating a phase shift of zero are shown in white. FIG. 22E illustrates the cross-sectional point spread function, in the X-Z plane, of the structured plane of excitation radiation that is produced in the sample by the coherent array of Bessel-like beams, which are generated by the pattern on the spatial light modulator shown in FIG. 22D. FIG. 22F illustrates the modulation transfer function, which corresponds to the point spread functions shown in FIG. 22E. All of the MTFs are normalized to $4\pi/\lambda$, where $\lambda$ is the wavelength of light in the medium within the sample chamber 1944.

As can be seen from the electric field patterns and point spread function patterns in FIGS. 21 and 22, the coherent superposition of a plurality of Bessel-like beams bears little resemblance to the electric field patterns and point spread function patterns of individual Bessel-like beams. As is evident from a comparison of FIGS. 21A-21F and FIG. 22, changing the period of the array of beams causes large changes in optical properties of the optical lattices (e.g., the period, symmetry, and degree of bounding in the Z direction of the lattices) that result from interference between the beams of the array. Instead, the coherent superposition of an array of Bessel-like beams, in general, forms a spatially-structured plane of excitation radiation that can be used to excite optical labels within a sample, which then emit light that is detected and used to generate an image of the sample. In some implementations, the spatially-structured plane of excitation radiation can be swept in a direction parallel to the plane to generate a thin sheet of excitation radiation. In some implementations, the spatially-structured plane of excitation radiation can be translated in discrete steps in a direction parallel to the plane and emitted light can be detected when the plane is in each of the different positions. Then, the light detected from the sample when the plane is in each of the different positions can be algorithmically combined to generate a super resolution image of the sample.

Figure 23A:
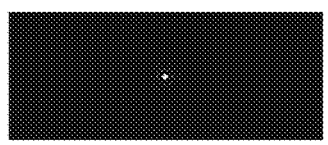
FIGS. 23A-23F are schematic diagrams of the intensities of different modes of excitation radiation that is provided to the sample.
Figure 23B:
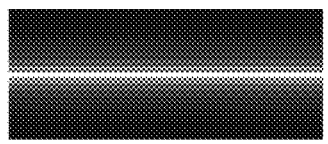
Figure 23C:
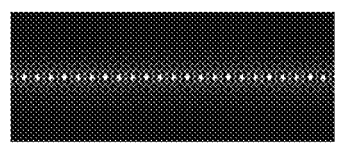
Figure 23D:
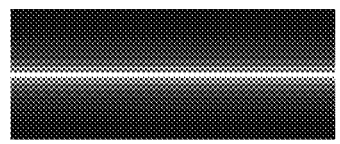
Figure 23E:
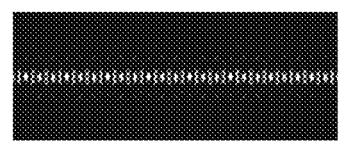
Figure 23F:
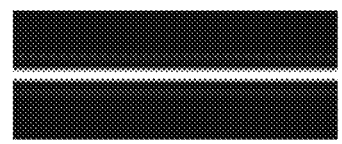

FIGS. 23A-23F are schematic diagrams of the intensities of different modes of excitation radiation that is provided to the sample. FIG. 23A is a cross-sectional in the X-Z plane of a Bessel-like beam propagating in the Y direction. The particular cross section shown in FIG. 23A is for a Bessel-like beam having a wavelength of 488 nm and having a maximum numerical aperture of 0.60 and a minimum numerical aperture of 0.54. Higher intensities are shown by whiter regions. When the Bessel-like beam of FIG. 23A is swept in the X direction, then the time-averaged intensities in the X-Z plane shown in FIG. 23B results. FIG. 23C is a cross-sectional in the X-Z plane of a superposition of incoherent Bessel-like beams propagating in the Y direction, such as would occur if the single Bessel-like beam in FIG. 23A were moved in discrete steps. The pattern shown in FIG. 23C is for a 488 nm Bessel-like beam having a maximum numerical aperture of 0.60 and a minimum numerical aperture of 0.54, stepped in units of 0.90 μm. When multiple instances of the array of Bessel-like beams of FIG. 23C are moved in small increments in the X direction and the resulting signal integrate don a camera, then the time-averaged intensity in the X-Z plane shown in FIG. 23D results. FIG. 23E is a cross-section in the X-Z plane of a superposition of coherent Bessel-like beams propagating in the Y direction. The pattern shown in FIG. 23E is for an array of 488 nm Bessel-like beams having a maximum numerical aperture of 0.60 and a minimum numerical aperture of 0.54, with individual beams of the array being spaced 0.90 μm from each other. When the array of Bessel-like beams of FIG. 23E is swept or dithered in the X direction, then the time-averaged intensity in the X-Z plane shown in FIG. 23F results. As can be seen by a comparison of FIG. 23B, FIG. 23D, and FIG. 23F, the coherent array of Bessel-like beams can result in a light sheet that is more tightly confined in the Z direction that a light sheet that is produced by sweeping a single Bessel-like beams (FIG. 23B) or a light sheet that is produced by sweeping an incoherent array of Bessel-like beams (FIG. 23D).

Referring again to the electric field patterns in FIGS. 21B and 22B, and point spread function intensity patterns in FIGS. 21E and 22E, it can be seen that the coherent superposition of a plurality of Bessel-like beams forms a spatially-structured plane of excitation radiation. These patterns can be viewed as optical lattices that are created by interference within the sample between different beamlets of the beam that is modulated by the spatial light modulator 1912 shown in FIG. 19 and then enter the sample 1946 through the excitation objective 1942. Therefore, in some implementations, a pattern can be applied to the WME 1912 that creates an optical lattice within the sample, which can be used to generate a spatially-structured plane of excitation radiation that can be used to generate images of the sample 1946.

Figure 24:
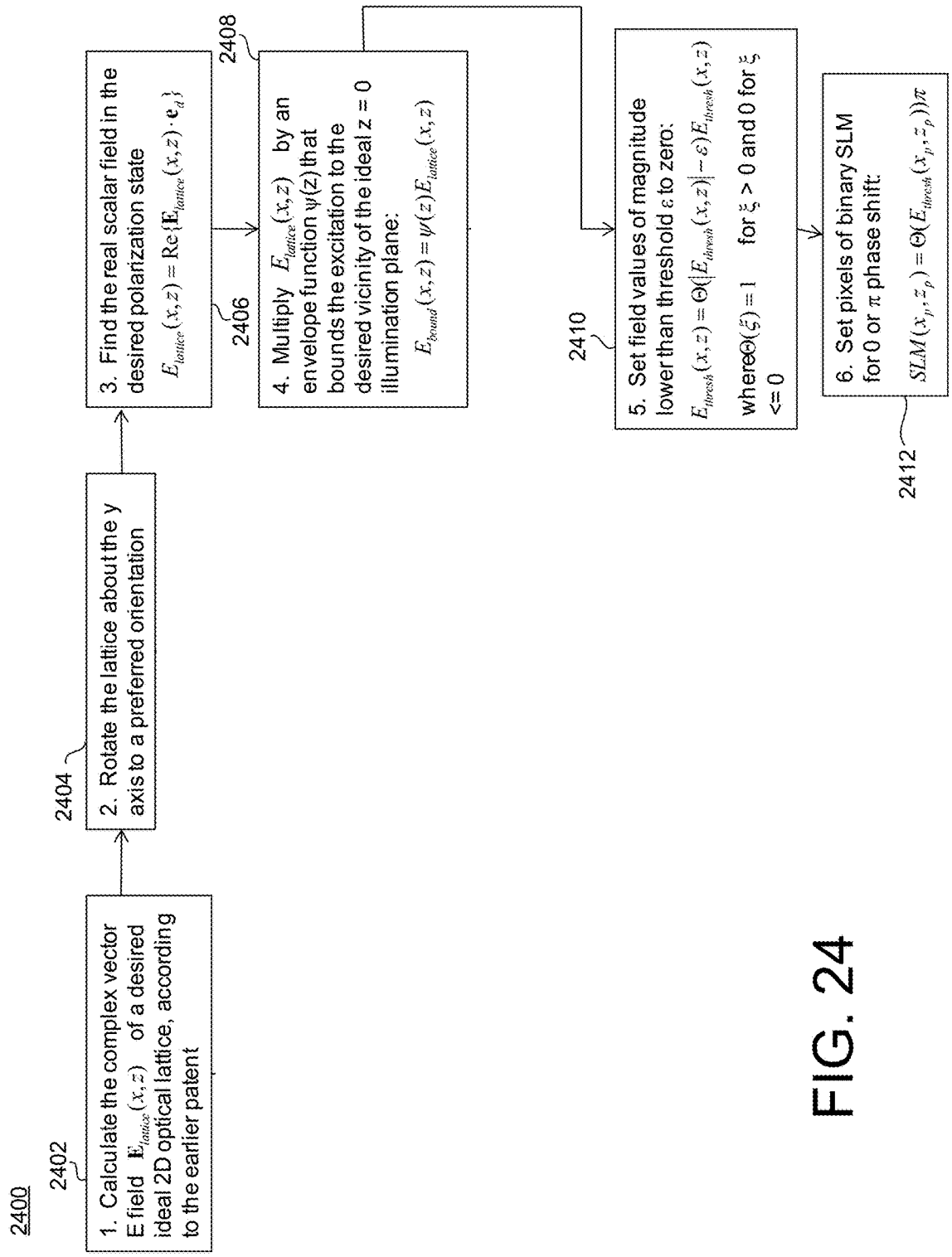
FIG. 24 is a flowchart of a process of determining a pattern to apply to a binary spatial light modulator, which will produce an optical lattice within the sample, where the optical lattice can be used as a coherent structured light sheet having a relatively low thickness extent in the Z direction over a sufficient length in the Y direction to image samples of interest.

FIG. 24 is a flowchart of a process 2400 of determining a pattern to apply to a binary spatial light modulator, which will produce an optical lattice within the sample, where the optical lattice can be used as a coherent structured light sheet having a relatively low thickness extent in the Z direction over a sufficient length in the Y direction to image samples of interest. In the process 2400, the complex electric field $E_{lattice}(x,z)$ of a selected two-dimensional 2D optical lattice can be calculated (step 2402). The selected optical lattice can be, for example, a fundamental lattice, a sparse lattice, a composite lattice, or a maximally symmetric composite lattice, as described in U.S. Pat. No. 7,609,391, entitled "Optical Lattice Microscopy," issued on Oct. 27, 2009, which is incorporated herein by reference. In some implementations, a maximally symmetric composite lattice can be selected to provide tight confinement of the excitation radiation in the Z direction when generating images of the sample using the swept sheet mode and to provide high spatial frequency components in the XZ plane when generating images of the sample using the super resolution, structured illumination mode. In some implementations, maximally symmetric composite hexagonal and square lattices can be used, because they can provide more wavevectors than lattices with other symmetry.

Then, the lattice can be rotated about the Y axis to a desired orientation (step 2404). For example, an orientation of the lattice in which lattice wavevectors lie along the X axis facilitates the construction of structured light sheets that are tightly confined in the Z direction. In another example, an orientation of the optical lattice in which a line of lattice intensity maxima lies along the x-axis can be desirable. In another example, an optical lattice having a periodicity and orientation such that adjacent lines of the lattice maximum along the X direction are separated by more than the desired light sheet thickness in the Z direction can be useful when using the lattice to generate images of the sample with the swept sheet mode. However, the lines of lattice maximum along the X direction should be separated by less than the desired light sheet thickness when using the super resolution, structured illumination mode to generate images of the sample.

After the orientation of the lattice is determined, the real scalar field of the optical lattice can be determined (step 2406), where the real scalar field is given by:

$$E_{lattice}(x,z) = Re\{E_{lattice}(x,z) \cdot e_d\},$$

Where $e_d$ is a vector in the direction of the desired polarization of the electric field. Next, the real scalar field of the optical lattice can be multiplied by an envelope function $\psi(z)$ that bounds the excitation light to the desired vicinity of the ideal Z=0 illumination plane (step 2408). The product of the real scalar field and the envelope function gives the function for the bound field:

$$E_{bound}(x,z) = \psi(z) E_{lattice}(x,z).$$

In some implementations, the envelope function can be a Gaussian function:

$$\psi(z) = \exp(-z^2/a^2)$$

Then, the field values having a magnitude lower than a threshold value, $\epsilon$, can be set to zero (step 2410). The thresholding step can be expressed mathematically as:

$$E_{thresh}(x,z) = \Theta(|E_{bound}(x,z)| - \epsilon) E_{bound}(x,z)$$

where $\Theta(\xi)=1$, for $\xi>0$ and 0 for $\xi<0$. Then, individual pixels values of a binary SLM that is used as the WME 1912 can be set to impose a 0 or $\pi$ phase shift on light that interacts with the SLM (step 2412), according to:

$$SLM(x_p, z_p) = \Theta(E_{thresh}(x_p, z_p))\pi,$$

where the "p" subscript references an individual pixel of the SLM. This pattern imposed on the SLM, which is conjugate to the sample 1946, will create an optical lattice within the sample.

Figure 25A:
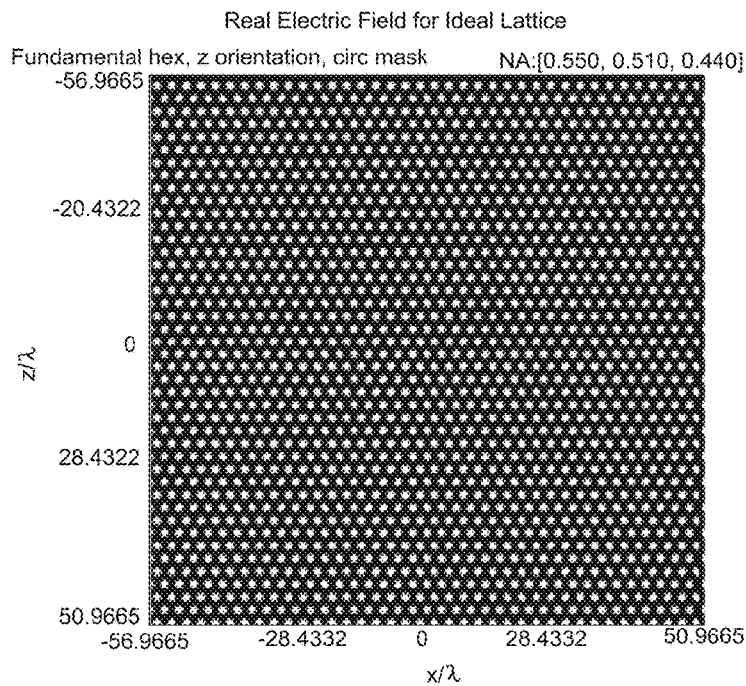
FIGS. 25A-25E show a series of graphical illustrations of the process shown in FIG. 24, when the process is used to generate an optical lattice of structured excitation radiation that is swept in the X direction to generate a plane of excitation illumination.

FIGS. 25A-25E show a series of graphical illustrations of the process 2400, when the process is used to generate an optical lattice of structured excitation radiation that is swept in the X direction to generate a plane of excitation illumination. FIG. 25A illustrates a cross-sectional profile in the X-Z plane of an ideal two-dimensional fundamental hexagonal lattice that is oriented in the Z direction. The optical lattice is formed by the coherent superposition of a plurality of beams that all converge on a cone corresponding to a numerical aperture of 0.51. The profile shows the real electric field strengths in the optical lattice, with higher electric field strengths being shown by whiter regions. The lengths shown on the axes of all of the panels of FIGS. 25A-25E are normalized the wavelength of light in the medium within the sample chamber 1944.

Figure 25B:
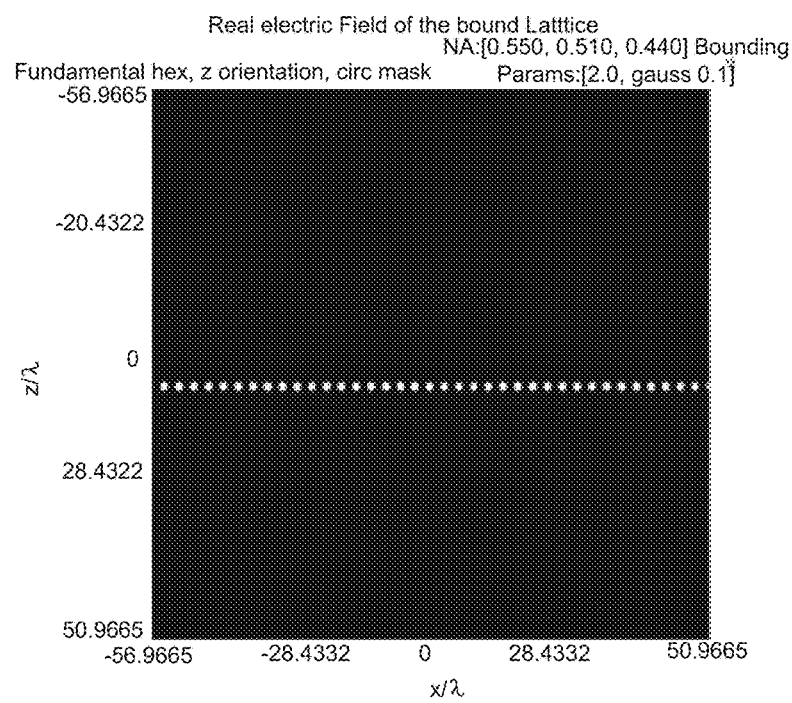
Figure 25C:
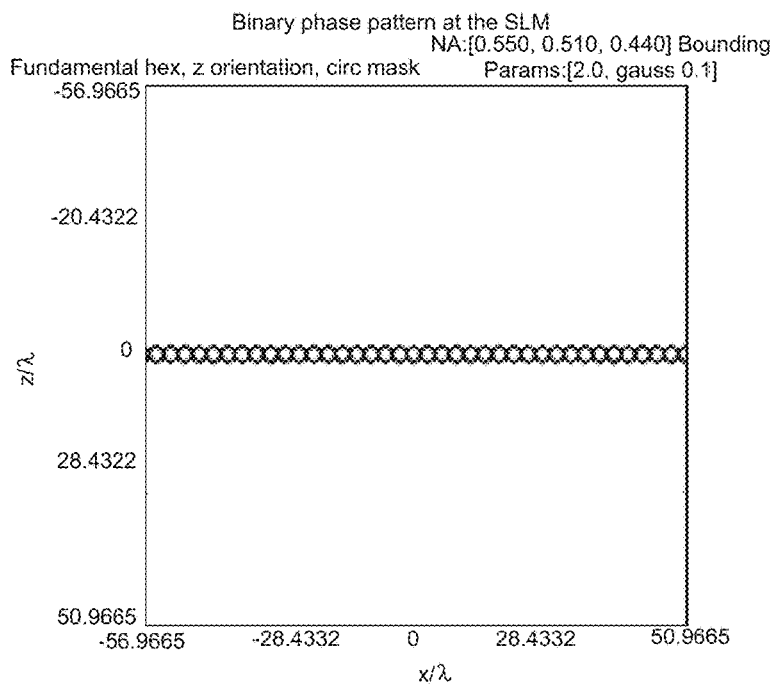
Figure 25D:
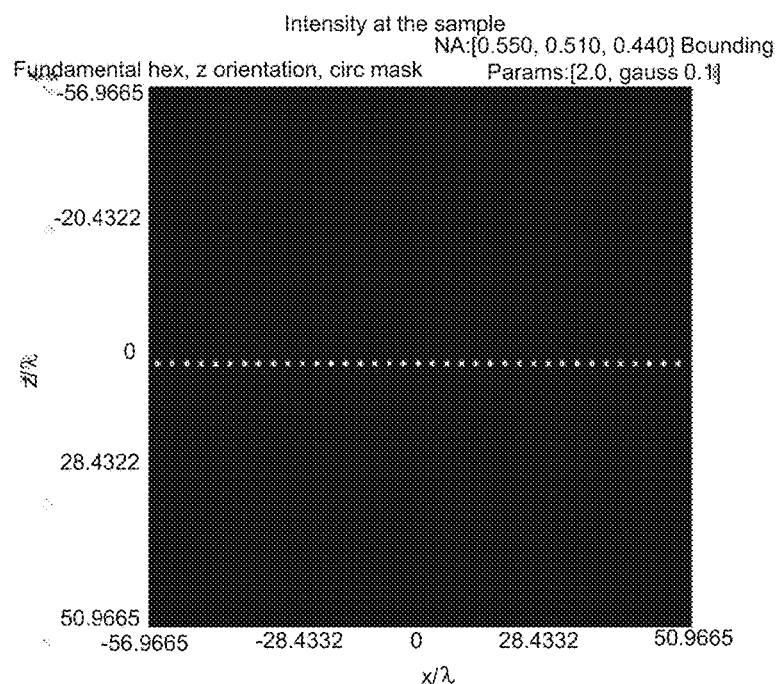
Figure 25E:
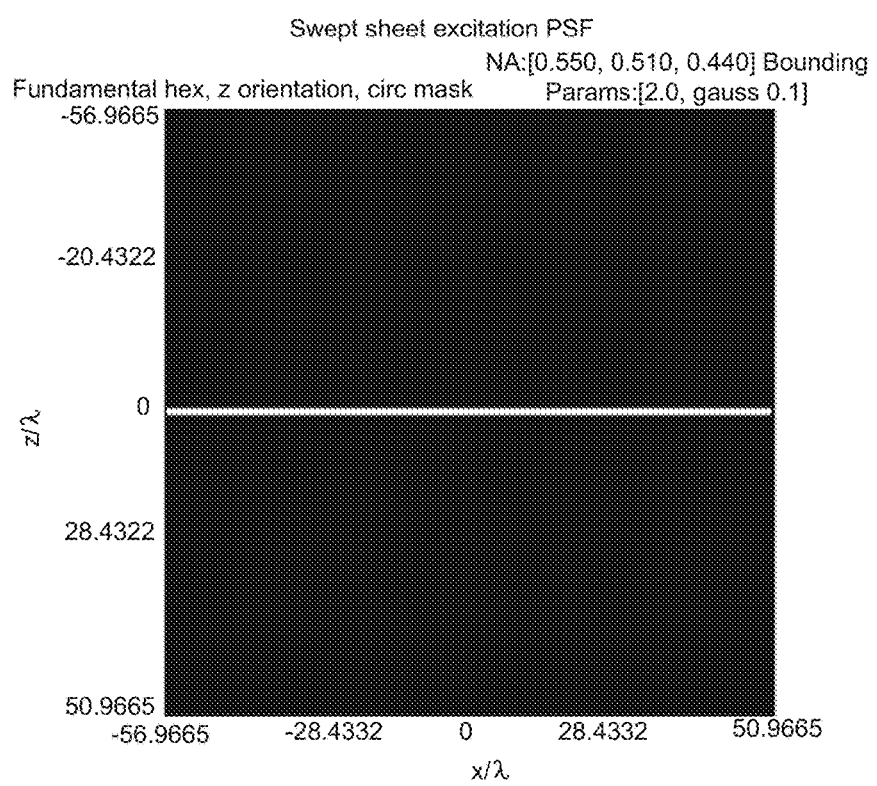

FIG. 25B illustrates the electric field, in the XZ plane, of the optical lattice of FIG. 25A after a Gaussian envelope function has been applied to the optical lattice to bound the lattice in the Z direction. Higher electric field strengths are shown by whiter regions. FIG. 25C illustrates the pattern of phase shifts applied to individual pixels of a binary spatial light modulator to generate the field shown in FIG. 25B. Pixels generating a phase shift of $\pi$ are shown in black, and pixels generating a phase shift of zero are shown in white. FIG. 25D illustrates the cross-sectional point spread function, in the X-Z plane, of the structured plane of excitation radiation that is produced in the sample by the optical lattice, which is generated by the pattern on the spatial light modulator shown in FIG. 25C, and then filtered by an annular apodization mask that limits the maximum NA of the excitation to 0.55 and the minimum NA of the excitation to 0.44. Higher intensities are shown by whiter regions. FIG. 25E illustrates the excitation beam intensity that is produced in the sample when the bound optical lattice pattern in FIG. 25D is swept or dithered in the X direction. Higher intensities are shown by whiter regions.

Figure 26A:
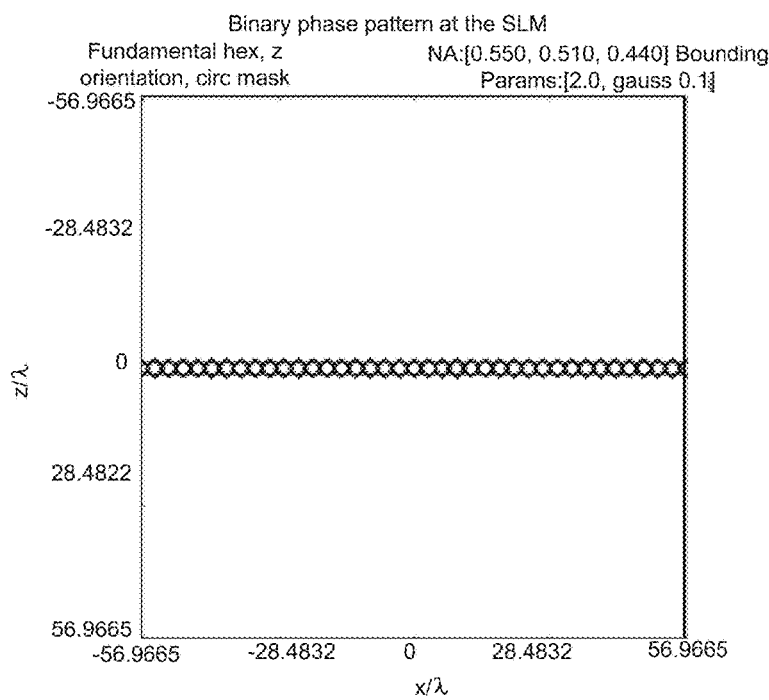
FIGS. 26A-26F illustrates the light patterns of at a plurality of locations along the beam path shown in FIG. 19 when the pattern shown in FIG. 25C is used on the SLM of FIG. 19.
Figure 26B:
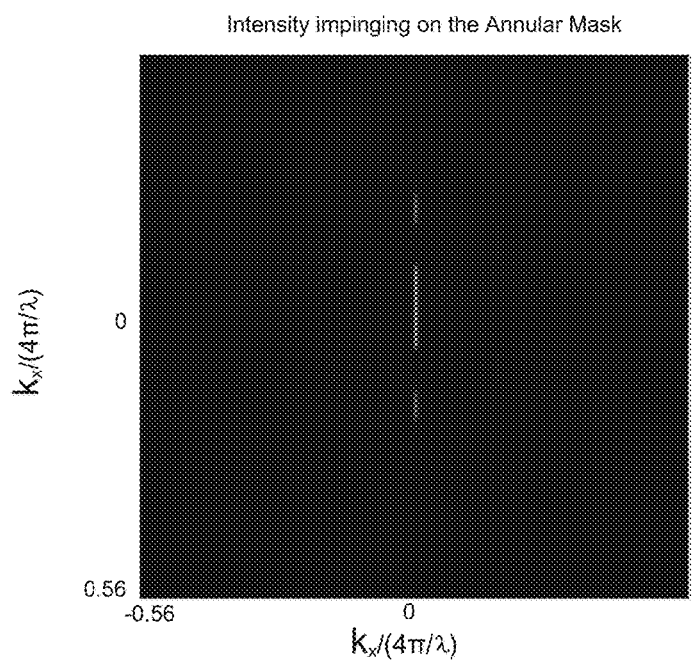
Figure 26C:
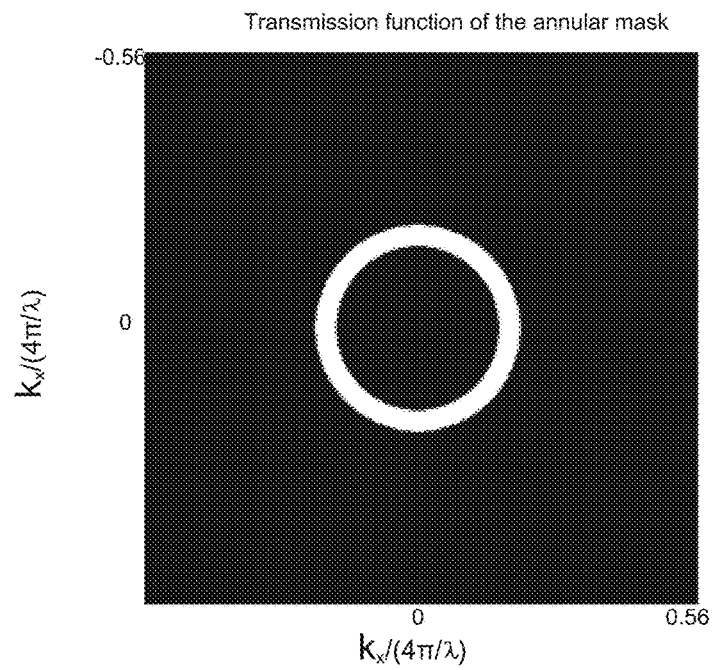
Figure 26D:
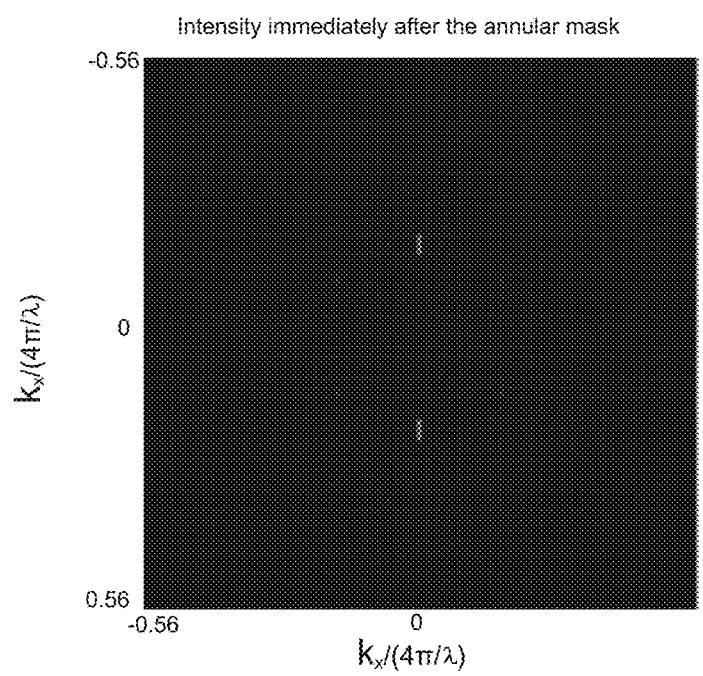
Figure 26E:
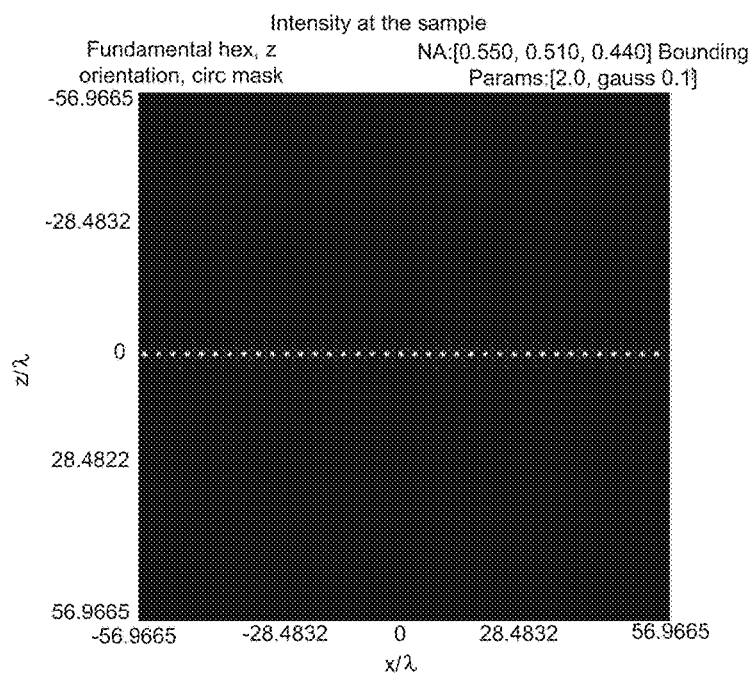
Figure 26F:
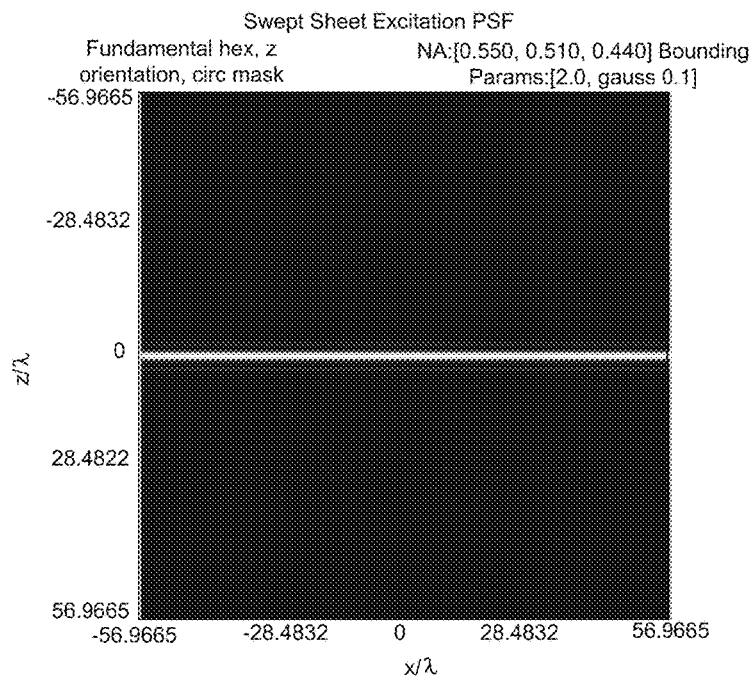

FIGS. 26A-26F illustrates the light patterns at a plurality of locations along the beam path shown in FIG. 19 when the pattern shown in FIG. 25C is used on the SLM 1912. For example, FIG. 26A is identical to FIG. 25C and illustrates the pattern of phase shifts applied to individual pixels of a binary spatial light modulator 1912 to generate the field shown in FIG. 25B. FIG. 26B illustrates the intensity of light that impinges on the apodization mask 1920 downstream from the SLM 1912. FIG. 26C illustrates the transmission function of the apodization mask 1920, and FIG. 26D illustrates the intensity of light immediately after the apodization mask 1920. As shown in FIG. 26D, the pattern of the light that exists just after the apodization mask 1920, which is conjugate to the rear pupil of the excitation objective, is a plurality of six vertical slits located on a surface of a cone, and when this pattern is focused by the excitation objective 1942 to the focal plane within the sample, the optical lattice shown in FIG. 26E (which is identical to the pattern shown in FIG. 25D) results. When this optical lattice is swept or dithered in the X direction, the sheet of excitation radiation shown in FIG. 26F results. The lengths shown on the axes of all of the panels of FIGS. 26A-26F are normalized the wavelength of light in the medium within the sample chamber 1944.

Figure 27A:
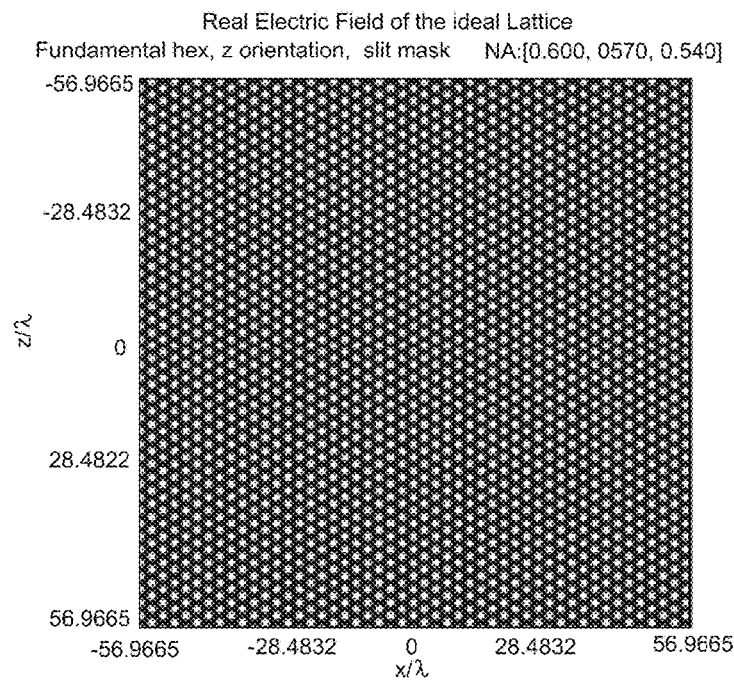
FIGS. 27A-27E show a series of graphical illustrations of the process, when the processes used to generate an optical lattice of structured excitation radiation that is translated in the X direction in discrete steps to generate images of the sample using superresolution, structured illumination techniques.

FIGS. 27A-27E show a series of graphical illustrations of the process 2400, when the processes used to generate an optical lattice of structured excitation radiation that is translated in the X direction in discrete steps to generate images of the sample using superresolution, structured illumination techniques. FIG. 27A illustrates a cross-sectional profile in the X-Z plane of a two-dimensional fundamental hexagonal lattice that is oriented in the Z direction. The optical lattice is formed by the coherent superposition of a plurality of beams that all converge on a cone corresponding to a numerical aperture of 0.57. The lengths shown on the axes of all of the panels of FIGS. 27A-27E are normalized to the wavelength of light in the medium within the sample chamber 1944.

Figure 27B:
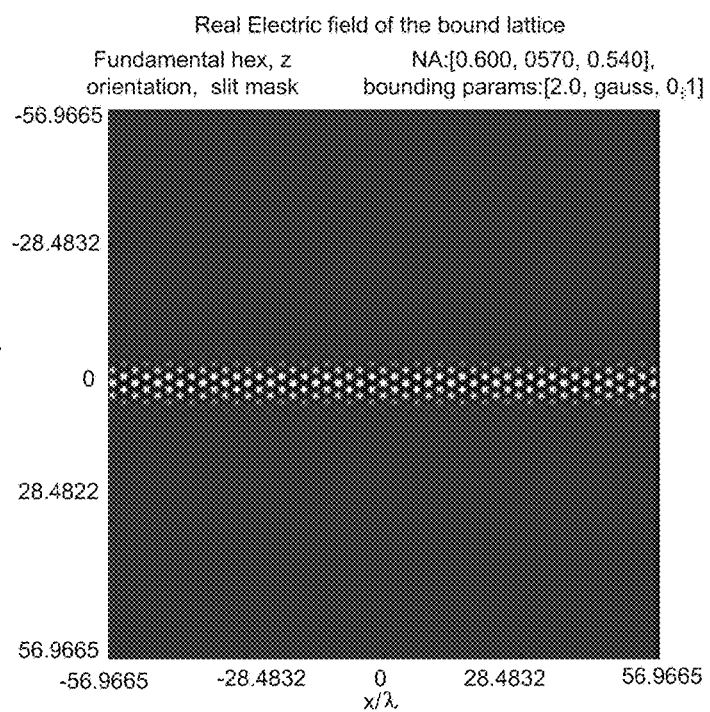
Figure 27C:
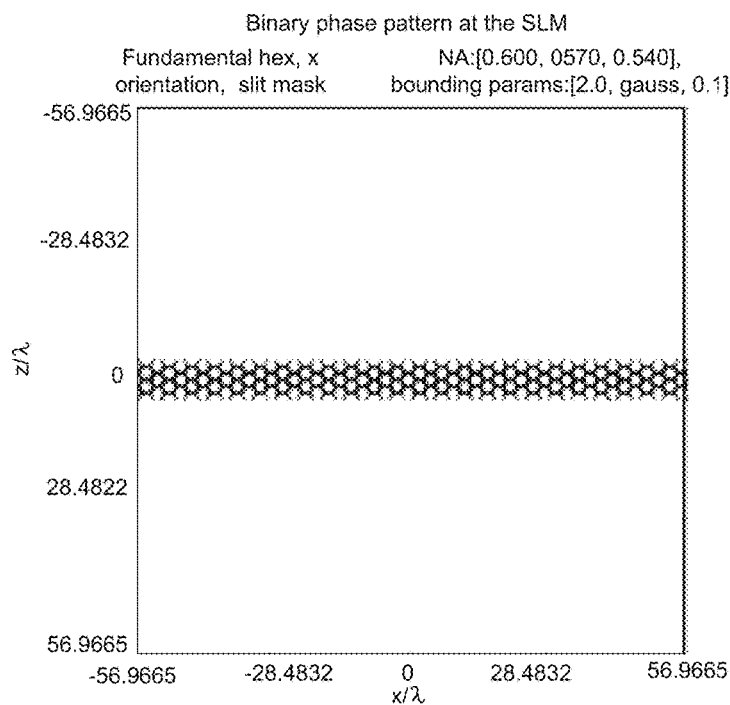
Figure 27D:
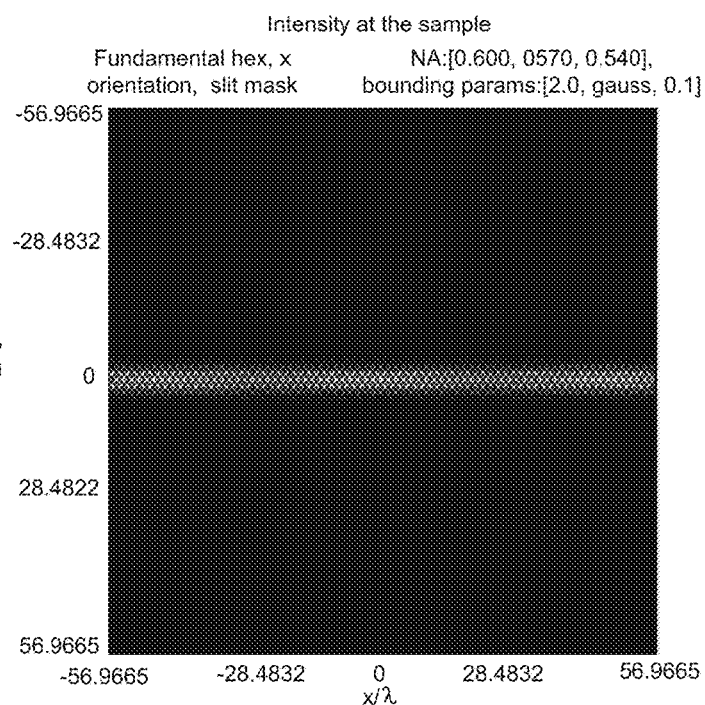
Figure 27E:
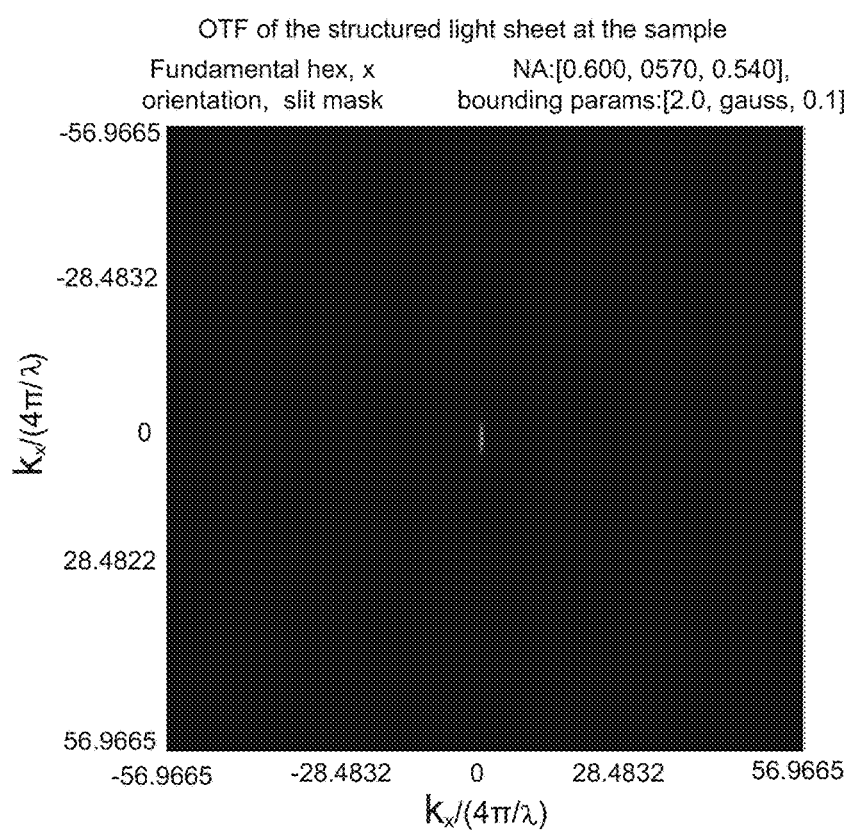

FIG. 27B illustrates the electric field, in the XZ plane, of the optical lattice of FIG. 27A after a Gaussian envelope function has been applied to the optical lattice to bound the lattice in the Z direction. Higher electric field strengths are shown by whiter regions. The envelope function used for FIG. 27B confines the lattice less tightly in the Z direction that the envelope function used for FIG. 25B. FIG. 27C illustrates the pattern of phase shifts applied to individual pixels of a binary spatial light modulator to generate the field shown in FIG. 27B. Pixels generating a phase shift of π are shown in black, and pixels generating a phase shift of zero are shown in white. FIG. 27D illustrates the cross-sectional point spread function, in the X-Z plane, of the structured plane of excitation radiation that is produced in the sample by the optical lattice, which is generated by the pattern on the spatial light modulator shown in FIG. 27C, and then filtered by an annular apodization mask that limits the maximum NA of the excitation to 0.60 and the minimum NA of the excitation to 0.54. Higher intensities are shown by whiter regions. FIG. 27E illustrates the modulation transfer function, in reciprocal space, which corresponds to the intensity pattern shown FIG. 27D. The MTF is normalized to $4\pi/\lambda$, where $\lambda$ is the wavelength of the excitation radiation. Higher spectral powers are shown by whiter regions.

Figure 28A:
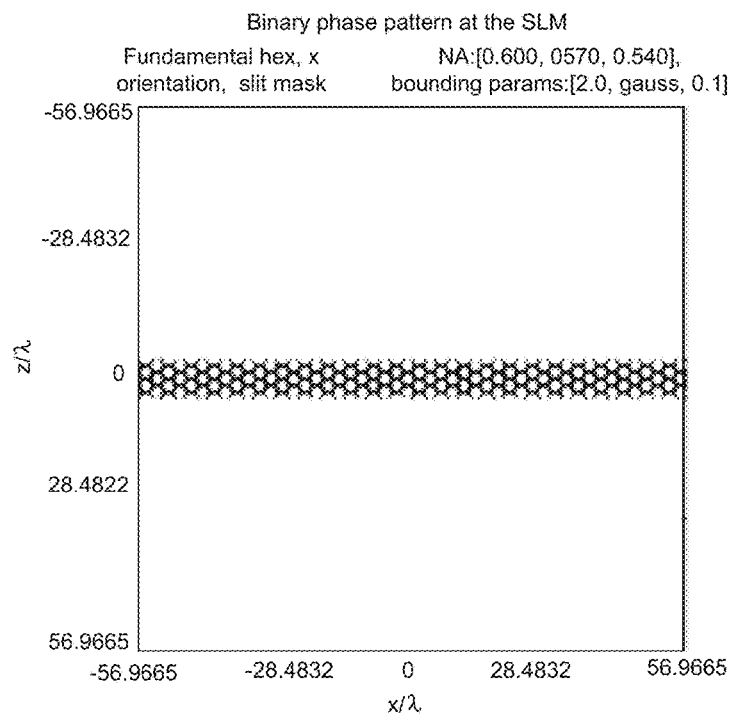
FIGS. 28A-28F illustrates the light patterns at a plurality of locations along the beam path shown in FIG. 19 when the pattern shown in FIG. 27C is used on the SLM of FIG. 19.
Figure 28B:
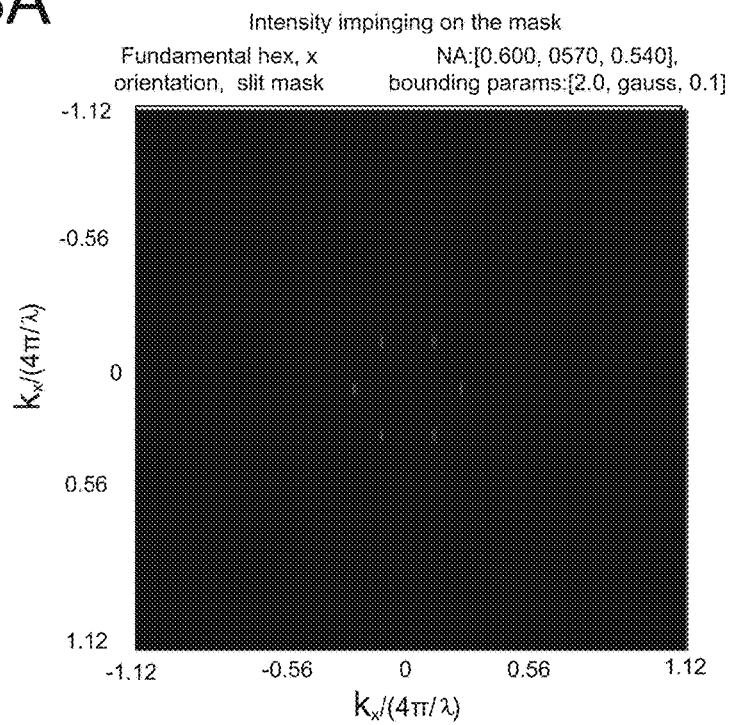
Figure 28C:
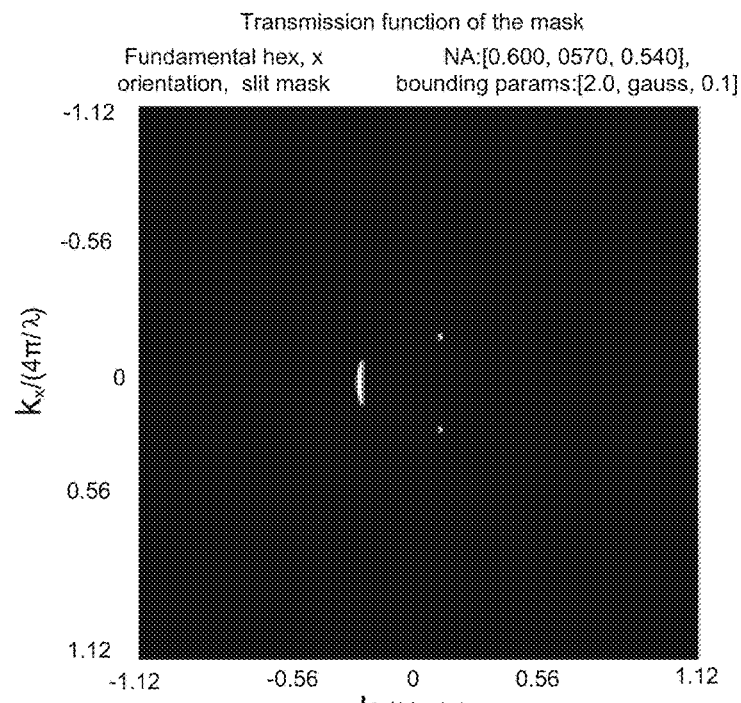
Figure 28D:
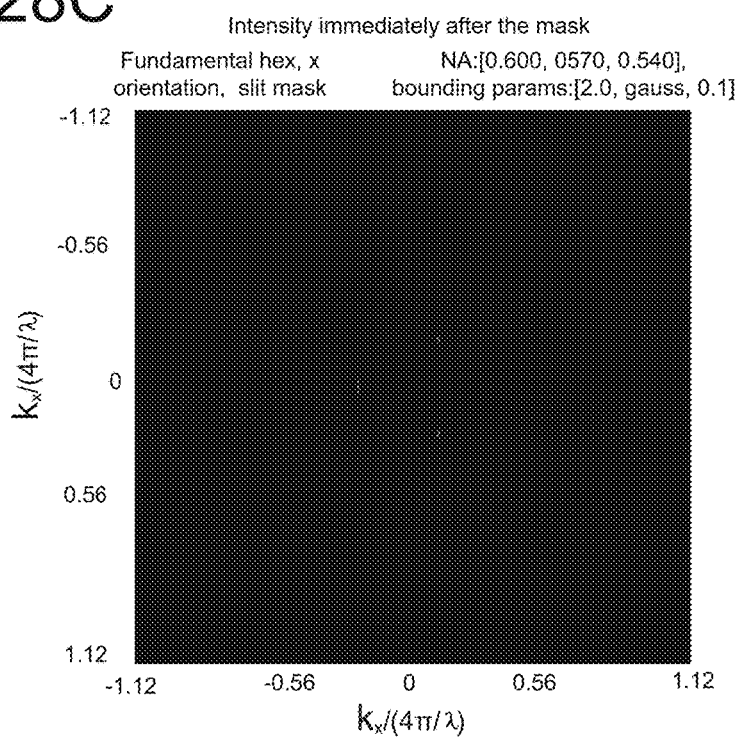
Figure 28E:
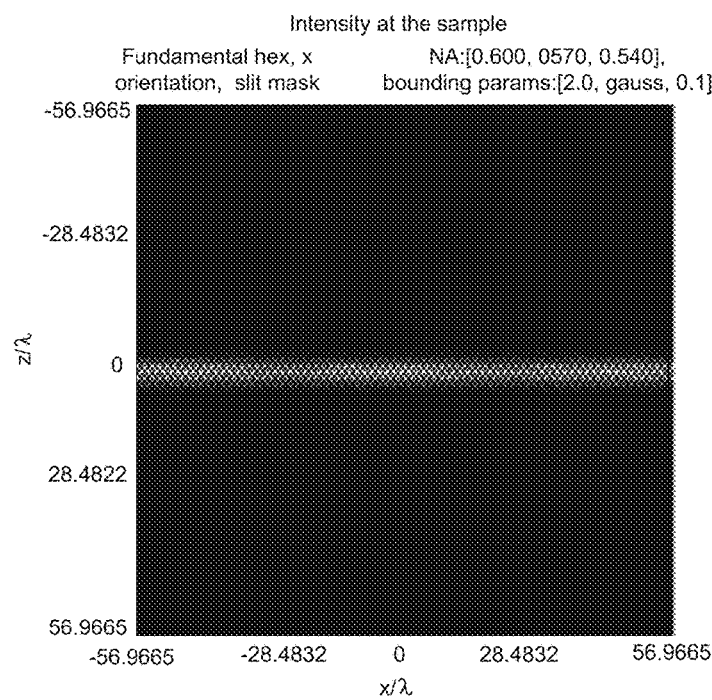
Figure 28F:
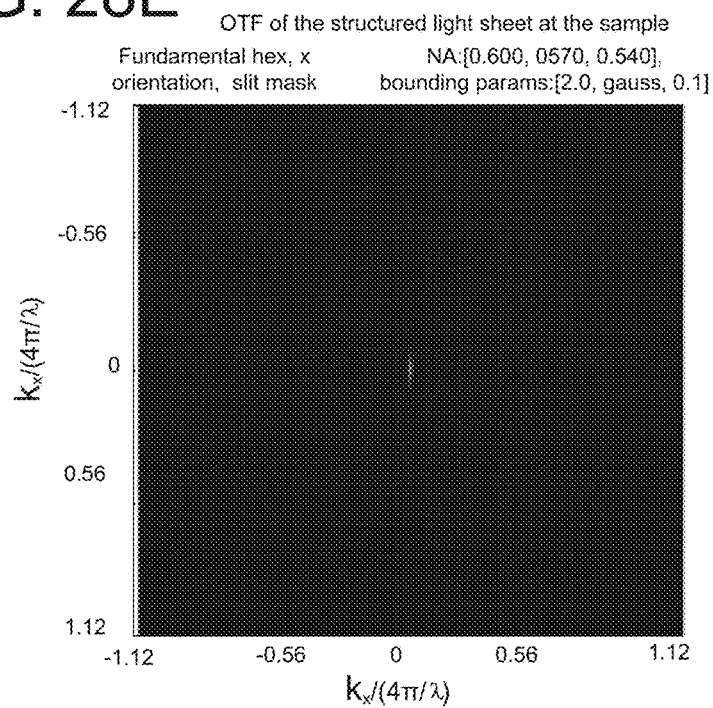

FIGS. 28A-28F illustrates the light patterns at a plurality of locations along the beam path shown in FIG. 19 when the pattern shown in FIG. 27C is used on the SLM 1912. For example, FIG. 28A is identical to FIG. 27C and illustrates the pattern of phase shifts applied to individual pixels of a binary spatial light modulator 1912 to generate the field shown in FIG. 27B. FIG. 28B illustrates the intensity of light that impinges on the apodization mask 1920 downstream from the SLM 1912 when the SLM includes the pattern of FIG. 28A. FIG. 28C illustrates the transmission function of the apodization mask 1920, and FIG. 28D illustrates the intensity of light immediately after the apodization mask 1920. The mask used to produce the transmission function shown in FIG. 28C includes the product of an annular mask and a mask having two slits, which transmits only three of the six beams shown in FIG. 28B. As shown in FIG. 28D, the pattern of the light that exists just after the apodization mask 1920, which is conjugate to the rear pupil of the excitation objective, is a plurality of three vertical slits located on a surface of a cone, and when this pattern is focused by the excitation objective 1942 to the focal plane within the sample, the optical lattice shown in FIG. 28E (which is identical to the pattern shown in FIG. 27D) results. The modulation transfer function for this lattice is shown in FIG. 28F. The lengths shown on the axes of all of the panels of FIGS. 28A-28F are normalized to the wavelength of light in the medium within the sample chamber 1944.

Referring again to FIG. 25, and, in particular, to FIG. 25B, the envelope function that are selected to bound the optical lattice to the vicinity of the Z=0 plane of the sample can have an effect on the intensity pattern of the swept light sheet shown in FIG. 25E. For example, when a strong envelope function is selected that tightly binds the optical lattice to the vicinity of the Z=0 plane, then the intensity of the optical lattice may be strongly confined to the line of intensity maxima along the Z=0 plane, but the extent of the individual maxima in the Z direction can be relatively large. On the other hand, when a weak envelope function is selected that only loosely binds the optical lattice to the vicinity of the Z=0 plane, then the optical lattice within the sample may include intensity maxima along the line of the Z=0 plane and also maxima along one or more lines that are displaced from the Z=0 plane. This phenomenon is shown in FIG. 29.

Figure 29A:
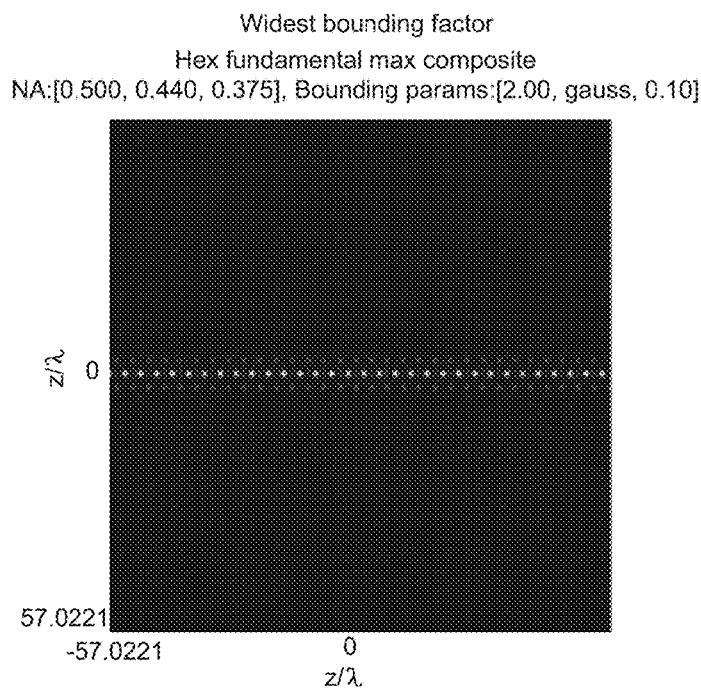
FIGS. 29A-29H are graphs illustrating the effect of the Z axis bounding of the optical lattice on the light sheets produced in the sample.
Figure 29B:
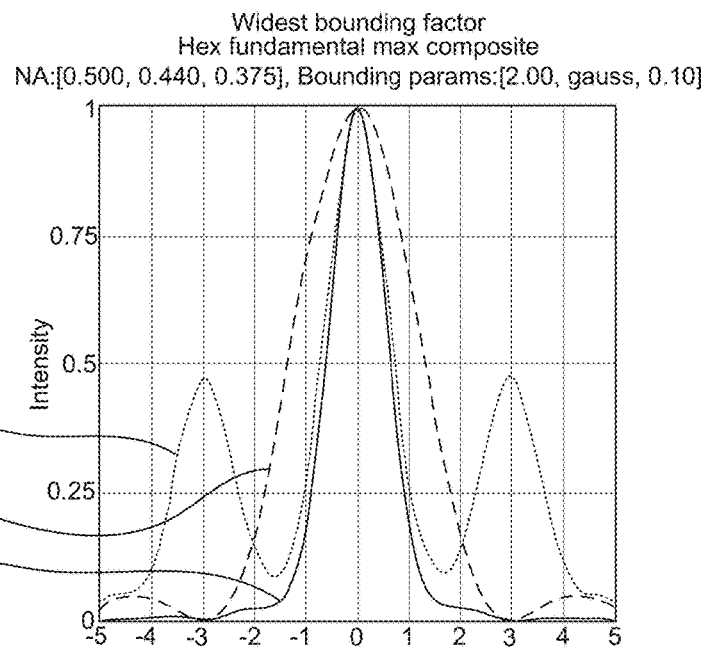

FIGS. 29A-29H are graphs illustrating the effect of the Z axis bounding of the optical lattice on the light sheets produced in the sample. FIG. 29A illustrates the intensity of the optical lattice to which a wide, or weak, envelope function is applied. As can be seen in FIG. 29A, intensity maxima exist along the Z=0 plane and also a positive and negative nonzero values of Z. Sweeping or dithering this pattern in the X direction creates a light sheet whose intensity profile along the Z direction is shown in the curve A of FIG. 29B. Curve A shows side lobes peaked at three wavelengths away from the Z=0 plane. Curve B shown in FIG. 29B shows the point spread function of the detection objective 1948, and the curve C in FIG. 29B shows the normalized product of curves A and B, which is the overall point spread function of the optical system in the Z direction. In some implementations, the numerical aperture of the excitation objective and the numerical aperture of the detection objective can be selected such that the maximum intensity of a side lobe of the sheet of excitation illumination occurs at a Z position that corresponds to a minimum in the point spread function of the detection objective. In this manner, the overall point spread function shown in curve C can minimize the effect of the excitation illumination side lobes on images generated from the sample. The lengths shown on the axes of all of the panels of FIGS. 29A-29H are normalized to the wavelength of light in the medium within the sample chamber 1944.

Figure 29C:
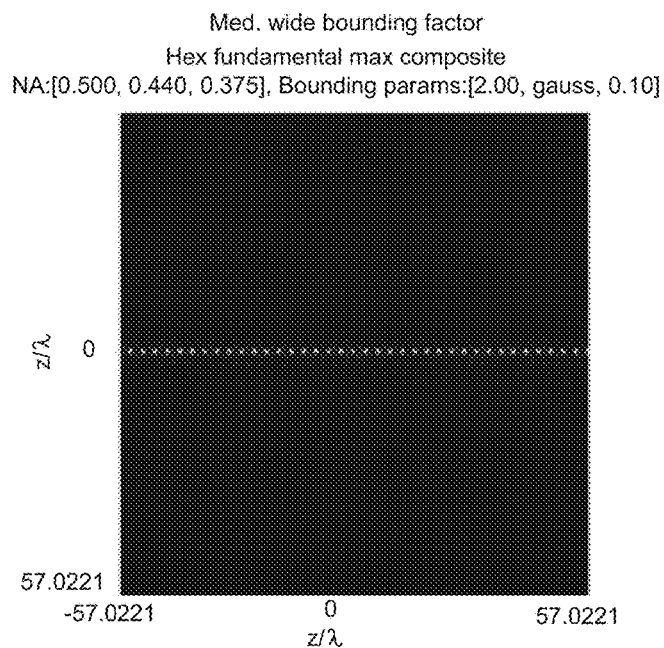
Figure 29D:
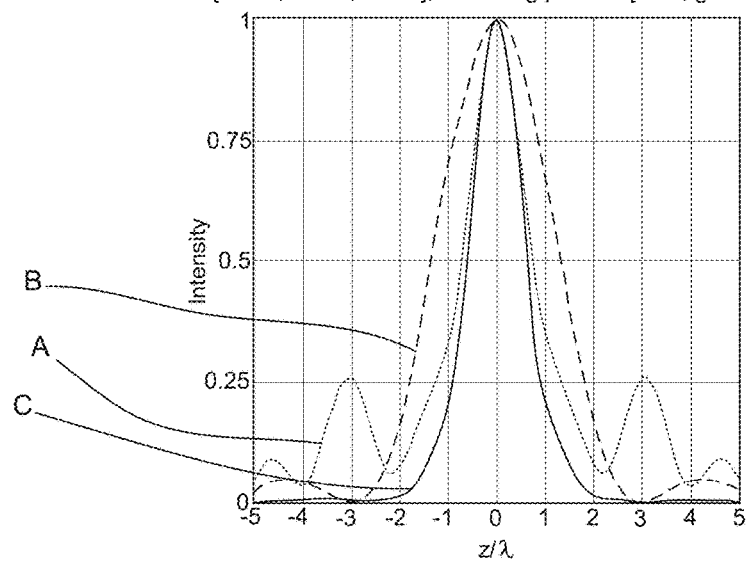
Figure 29E:
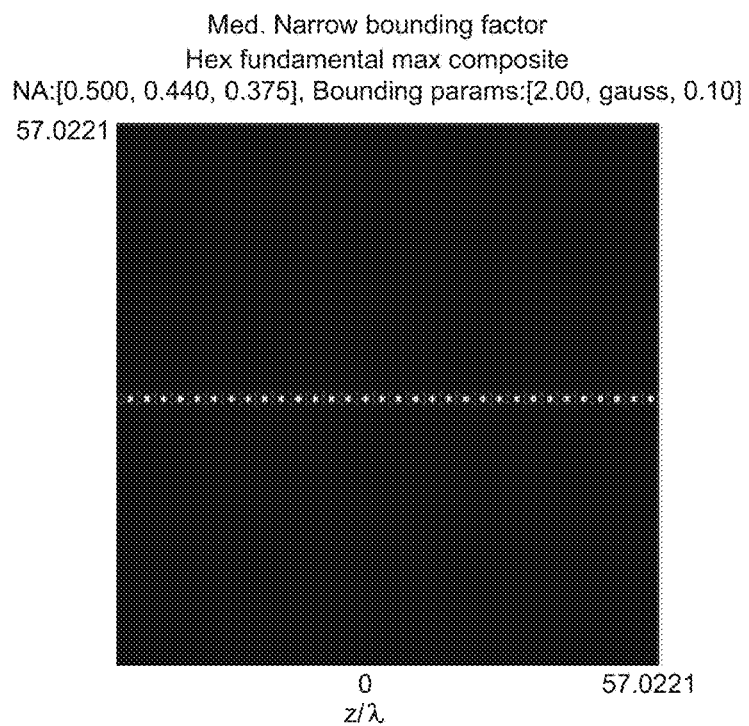
Figure 29F:
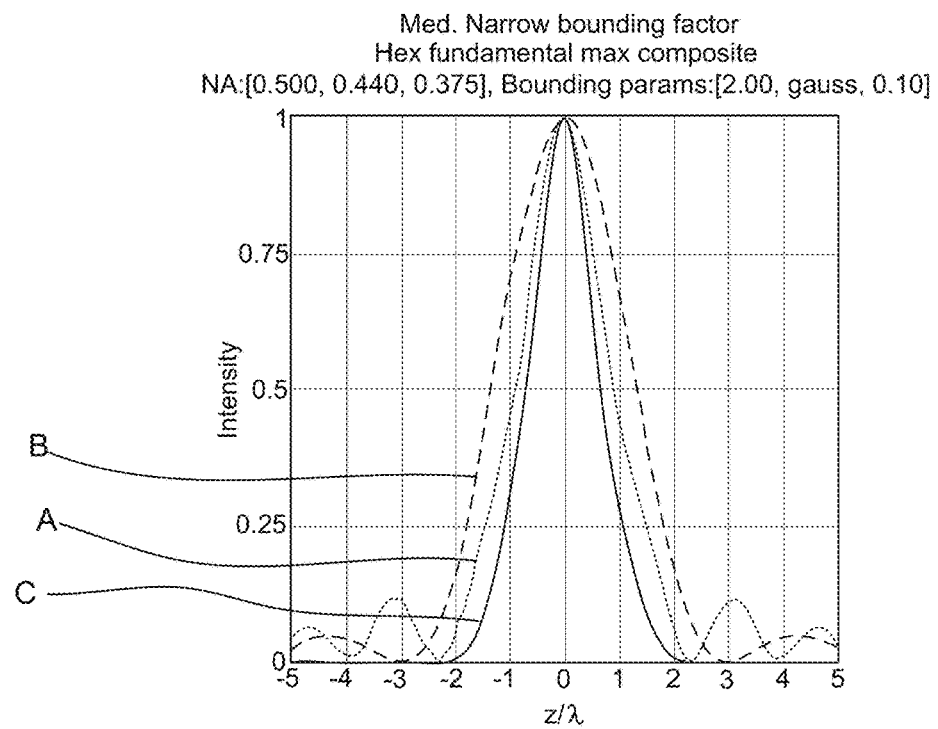
Figure 29G:
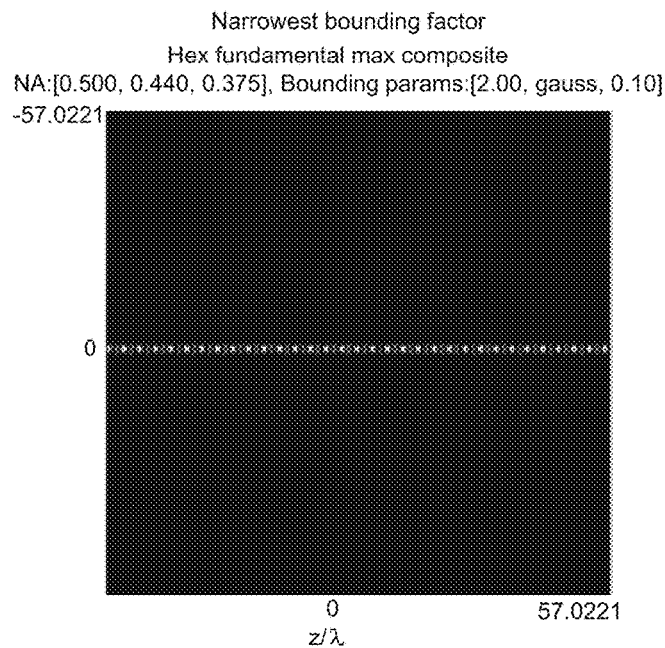
Figure 29H:
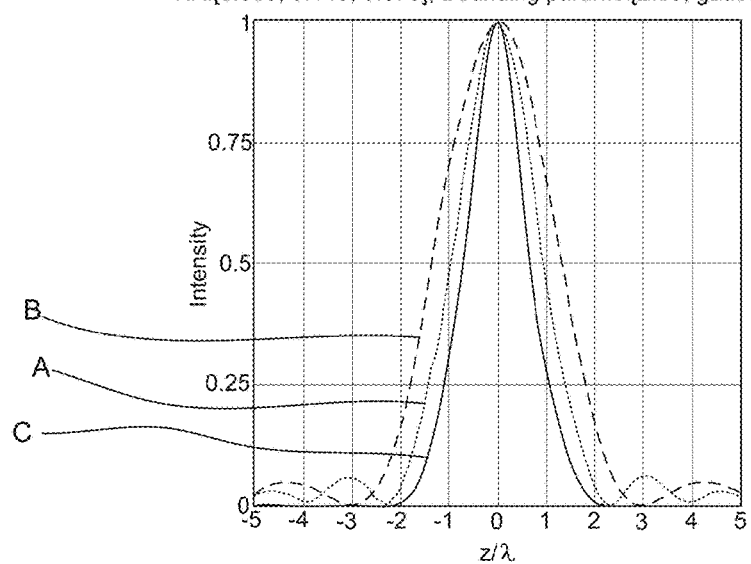

FIG. 29G illustrates the intensity of the optical lattice to which a narrow, or strong, envelope function is applied to the ideal optical lattice pattern. As can be seen in FIG. 29G, intensity maxima exist along the Z=0 plane, but there are no lines of intensity maxima along other planes. Sweeping or dithering this pattern in the X direction creates a light sheet whose intensity profile along the Z direction is shown in curve A of FIG. 29H. Curve A shows much smaller side lobes peaked at three wavelength away from the Z=0 plane than in FIG. 29B. Curve B shown in FIG. 29H shows the point spread function of the detection objective 1948, and curve C in FIG. 29H shows the normalized product of curves A and B, which is the overall point spread function of the optical system in the Z direction. As can be seen from a comparison of FIG. 29B and FIG. 29H, the central peak in curve A of FIG. 29B is narrower than the central peak in curve A of FIG. 29H, but the side lobes of FIG. 29B are larger than the side lobes and FIG. 29H. Thus, bound optical lattices having different parameters can be selected to image different samples using different techniques. FIG. 29C and FIG. 29D are similar to FIGS. 29A and 29B, respectively, and to FIGS. 29G and 29H, respectively, except that a medium-wide envelope function is used. FIG. 29E and FIG. 29F are similar to FIGS. 29A and 29B, respectively, and to FIGS. 29G and 29H, respectively, except that a medium-narrow envelope function is used.

Stochastic Excitation and Bessel-Like Beams

Another technique that can be used to create high-resolution images of a sample involves using stochastic activation and/or excitation of individual emitting labels within a sample (for example, such as described in U.S. Pat. No. 7,782,457, which is incorporated herein by reference) along with activation radiation and/or excitation radiation that is provided to the sample in the form of a thin sheet of radiation. In this manner, individual emitters within the sample can be individually resolved as their emission of signal light is turned on and off, and the thin sheet of activation and/or excitation radiation can limit the amount of signal light that is produced in portions of the sample that are not in the focal plane of the detection objective. During the stochastic activation of labels, as different emitting labels are turned on and off within a focal plane of the detection objective, an image of the sample at that plane can be built up over time. Also, the focal plane of the detection objective can be moved through the sample, and the thin sheet of activation and/or excitation radiation can be moved along with the focal plane, so that multiple planes of the sample can be imaged, which may allow generation of a three-dimensional image of the sample.

In some implementations, a sample can include a dense plurality of phototransformable or photoswitched optical labels ("PTOLs"), such as, for example, photoactivated or photoswitched fluorescent proteins ("FPs"), that are transformable from an inactive state (in which the labels do not produce significant detectable radiation when excited) to an activated state (in which the labels can emit radiation when excited) by virtue of the interaction of the transformable labels with their environment. With sufficient control over at least one activating environmental parameter, a controllable, sparse subset of the labels can be activated. These activated labels can then be excited into excited states, from which they can emit fluorescence radiation that can be imaged by an optical system. By controlling the activation environment and exciting radiation, the mean volume per activated and excited label that emits radiation can be greater than the diffraction-limited resolution volume ("DLRV") characteristic of the optical system. By detecting radiation from such a sparse subset of emitting labels, the location of the activated and excited PTOLs can be determined with super-resolution accuracy. Then, the activated labels can be deactivated, and another subset of transformable labels, statistically likely to be located at different positions within the sample, can be activated by controlling at least one activating environmental parameter, and fluorescence from the second subset of activated labels can be imaged, and their locations can be determined with superresolution accuracy. This process can be repeated to determine the location of more transformable labels within the sample with superresolution accuracy. The determined locations of all the transformable labels from the different images can be combined to build up a superresolution image of the sample.

Figure 30:
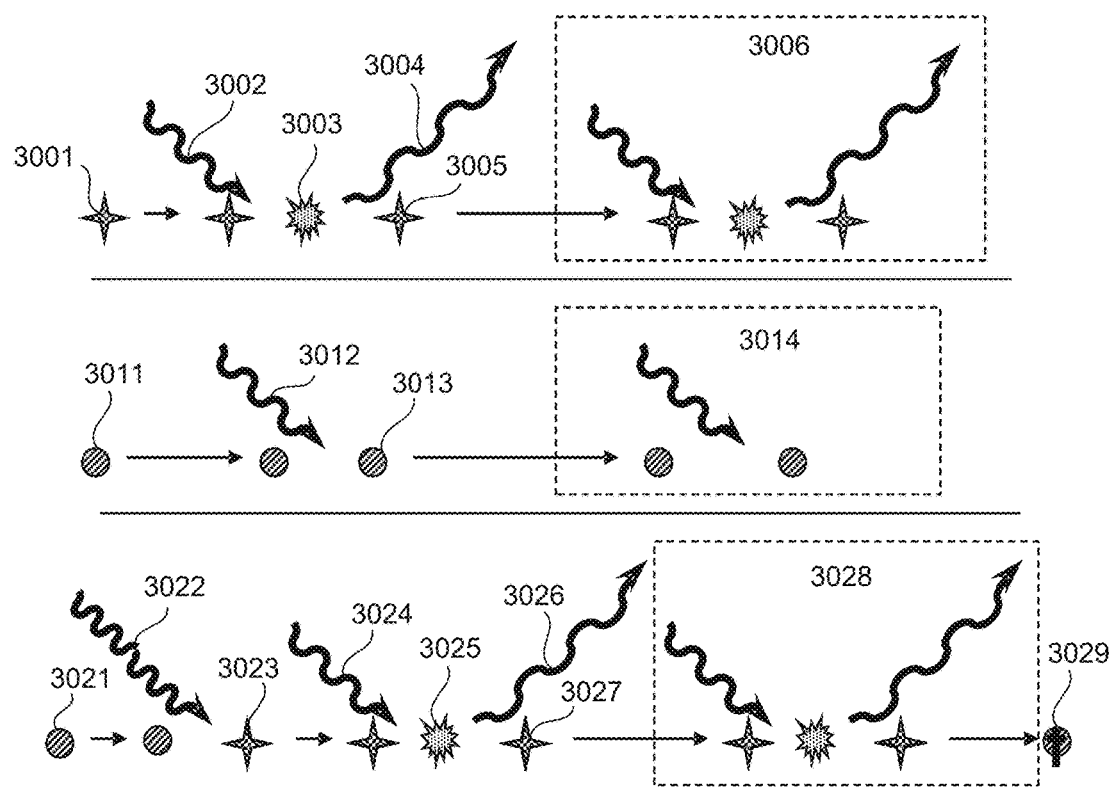
FIG. 30 is a schematic diagram illustrating a PTOLs (e.g., a fluorescent molecule) stimulated by excitation radiation from a ground state into an excited state that emits a portion of the energy of the excited state into a fluorescence radiation photon.

FIG. 30 is a schematic diagram illustrating a PTOLs (e.g., a fluorescent molecule) 3001 stimulated by excitation radiation 3002 from a ground state into an excited state 3003 that emits a portion of the energy of the excited state into a fluorescence radiation photon 3004. The molecule 3001 then reverts to the ground state 3005. This cycle of excitation of the molecule 3001 by radiation 3002 and emission of fluorescence radiation 3004 can be repeated many times 3006, and the fluorescence radiation can be accumulated by a microscope camera or detector. If there are many such fluorescent molecules 3001 within a diffraction limited resolution volume ("DLRV") of the imaging optics it might seem difficult to distinguish the fluorescence radiation of one molecule from another molecule.

However, in the case of a phototransformable optical label ("PTOL") molecule or emitter 3011, the ability of the PTOL to absorb excitation radiation and therefore to emit fluorescence radiation can be explicitly turned on by an activating signal, and in certain cases, can be turned off by a de-activating signal. In an inactivated state, a PTOL 3011 can be exposed to excitation radiation 3012 having a characteristic wavelength, but it will radiate little, if any, fluorescence radiation at a wavelength characteristic of an activated and excited PTOL. However, when the PTOL 3021 is irradiated with activation radiation 3022, the PTOL 3021 can be transformed into an excitable state 3023. The activation radiation 3022 often has a different wavelength than the wavelength of the excitation radiation, but for some PTOLs activation radiation and excitation radiation have the same wavelength and are distinguished by their intensities. After a PTOL is transformed into an excitable state 3023, subsequent illumination of the activated PTOL 3023 by excitation radiation 3024 generally results in detectable emission of fluorescence radiation 3026. This process of excitation and emission can be repeated numerous times 3028 for an activated PTOL 3027 until the PTOL eventually bleaches or deactivates, at which point the PTOL 3029 can no longer be excited and can no longer emit fluorescence radiation.

Thus, a PTOL 3021 can be illuminated with activation radiation 3022 to transform the PTOL into an activated state 3023. The activated PTOL 3023 can be illuminated with excitation radiation 3024 to excite the PTOL into an excited state 3025, from which the PTOL 3025 can emit radiation 3026. For some species of PTOL, the PTOL can be transformed from an activated state 3023 back to an unactivated state 3021, either through spontaneous decay to the unactivated state or through the application of de-activation radiation.

A fluorescent protein ("FP") is a particular kind of phototransformable optical label ("PTOL") whose optical properties can be altered by light and that can be used to label a portion of a sample to image optically the portion of the sample. As used herein "fluorescence" and "fluorescent" generally designate an optical response of the PTOL. In addition to the common understanding of fluorescence (e.g., emission of a photon from a substance in response to excitation by a more energetic photon) we include other properties that can characterize the PTOL. For example, we include emission of a photon in response to multi-photon excitation, or a large elastic optical cross section that can be activated or deactivated.

PTOLs useful for superresolution via localization of isolated PTOLs generally have one or more of the following distinguishing characteristics: a relatively high brightness (as defined by its excitation cross section and the quantum efficiency); a relatively high contrast ratio between luminescence generated in the activated state to that generated in the inactivated state (which might be improved through a judicious choice of the excitation wavelength and detection filter set); an excitation wavelength that reduces autofluorescence from other cellular material exposed to the excitation; an emission wavelength that is sufficiently different from the spectral range over which most autofluorescence occurs; and photostability that is large enough that a sufficient number of photons are collected from each PTOL to achieve the desired localization accuracy prior to irreversible bleaching, yet, for PTOLs other than the kindling proteins and Dronpa that can switch back to the deactivated state, is nevertheless still finite, so that a new population of individually resolvable activated PTOLs can be created after the current set is largely bleached. Indeed, to reduce possible phototoxicity related to irreversible photobleaching, an ideal PTOL would remain in the activated state until it is deactivated by choice using other means (e.g., illumination at a separate deactivation wavelength).

Photoactivatable fluorescent proteins useful for super-resolution microscopy include, for example, *Aequorea victoria* photoactivated green fluorescent protein ("PA-GFP"), Photoswitchable cyan fluorescent protein ("PS-CFP"), Kaede, Kindling fluorescent proteins ("KFP"), and Dronpa. Superresolution via localization has been demonstrated with the tetrameric PTOLs Kaede and Kikume, as well as the monomeric, dimeric, and tandem dimer forms of EosFP. These PTOLS have the common advantages of large wavelength spread between the inactivated and activated absorption and emission maxima, high brightness, and longer wavelength emission, where autofluorescence is typically lower. Monomeric EosFP has the added advantage of smaller physical size than tetrameric Kaede or Kikume, and may therefore be less perturbative of cellular structure and function. In practice, a particular FP could be selected from a number of different FPs based on a user's criteria for optimization for a given application. Given the diversity of PTOL species with different activation, excitation, and emission wavelengths and time constants, it is possible to construct separate images for each species of PTOLs. Thus, different components of a sample can be tagged with distinct labels, and each labeled object can then be independently identified in a super-resolution image that can be constructed as disclosed herein.

It is possible to label specific sample features of interest with PTOLs, such that the PTOLs, and therefore the specific sample features, can be imaged. For PTOLs that can be genetically expressed (e.g., the photoactivable fluorescent proteins), DNA plasmids can be created and inserted into the cell by transient transfection, so that fluorescent protein PTOLs are produced fused to specific proteins of interest. Likewise, stable transfections that permanently alter the genetic makeup of a cell line can be created, so that such cells produce fluorescent protein PTOLs. PTOLs also can be tagged to specific cellular features using immunolabeling techniques, or high-specificity small molecule receptor-ligand binding systems, such as biotin ligase.

Figure 31:
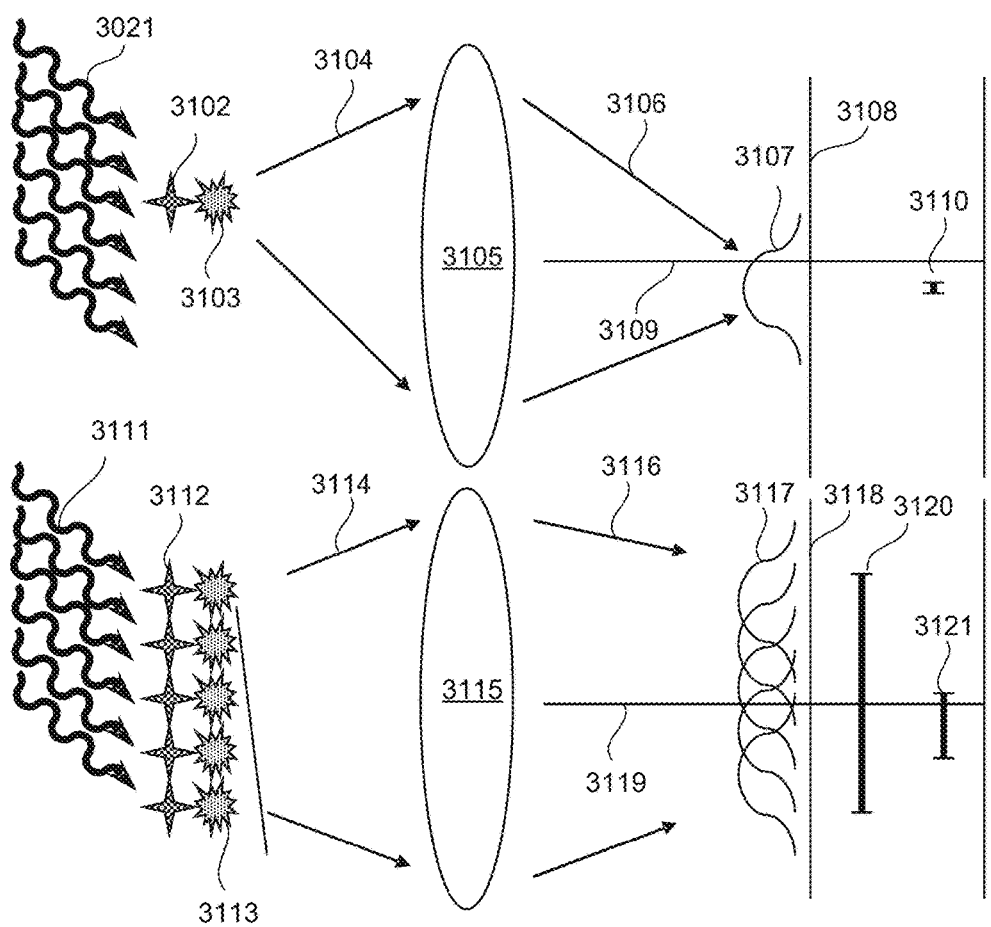
FIG. 31 is a schematic diagram illustration excitation radiation that can excite an isolated emitter into an excited state.

Radiation from molecules or emitters can be used for sub-diffractive localization of PTOLs when the radiating molecules or emitters are isolated and spaced further apart from each other than the diffraction limited length scale of the imaging optics. For example, as shown in FIG. 31, excitation radiation 3101 can excite an isolated emitter 3102 into an excited state 3103. Outgoing radiation 3104 emitted from the excited emitter 3103 can be collected by microscope optics including a detection objective 3105 and refocused 3106 onto a diffraction limited spot 3107. This spot profile is shown plotted on the axis of position 3108 versus emission intensity 3109 in the image plane 3108. The image and object plane are scaled by the magnification M. In the image plane 3108, the minimum spatial width of this spot is characterized by a fundamental limitation of resolution of microscopes and is given by the Abbe criteria $\Delta x \approx 0.5 * \lambda * M/NA$, where $\lambda$ is the wavelength of emission radiation 3104 and NA is the numerical aperture of the objective 3105. This magnified image of the isolated emitter can be used to localize the emitter to sub-diffractive precision by measuring the distribution of the emission at a detector such as a CCD camera. This data can then be fit or otherwise processed to find the center of the detected signal. For example, the emission intensity profile of light emitted from a PTOL and detected on a detector can be characterized by the discrete data set, $\{n_i\}$, where $n_i$ are the number of photons detected in the $i^{th}$ pixel of the detector located at position $x_i$. This data can be fit to a peaked function to determine a location of the PTOL. For example, a Gaussian function, $$n_i = \frac{N}{\sqrt{2\pi}\,\sigma} e^{-\frac{(x_i - x_c)^2}{2\sigma^2}},$$

can be used to perform the fit. A least squares fit of the data to the peaked function, for example, can find a value for the peak center location $x_c$. In addition other parameters, such as, for example, the total number of photons detected, N, and the peak width, $\sigma$, (which can be generally on the order of $\Delta x$) can also be deduced from the fit. Errors in $n_i$ can be expressed by a value, $\delta n_i$, and likewise the uncertainty in the center position, $x_c$, can be expressed as through a parameter, $\delta x$. In particular, when the system noise is limited by photon shot noise statistics (meaning $\delta n_i = \sqrt{n_i}$)) arising from the detected signal and N is the number of photons detected, then the accuracy to which this center can be localized is given by $\delta x = \Delta x/\sqrt{N}$. To the extent that N is much larger than unity, the localization accuracy 3110 can be significantly better than the diffraction limit 3121. The data also can be fit to other functions than the Gaussian function to determine a center location and width of the position of a PTOL.

However, it can be difficult to apply this technique to a set of continuously-emitting fluorescent molecules 3112 that are spaced so closely together that they are within $\Delta x$ of each other. In this case, the diffractive spots are highly overlapped, such that fitting of the image of a molecule to obtain a position of the molecule with superresolution accuracy is difficult. Thus, in this situation the resolution limit generally is given by standard Abbe criterion 3121, i.e. the width of the diffractive limited spot.

Figure 32:
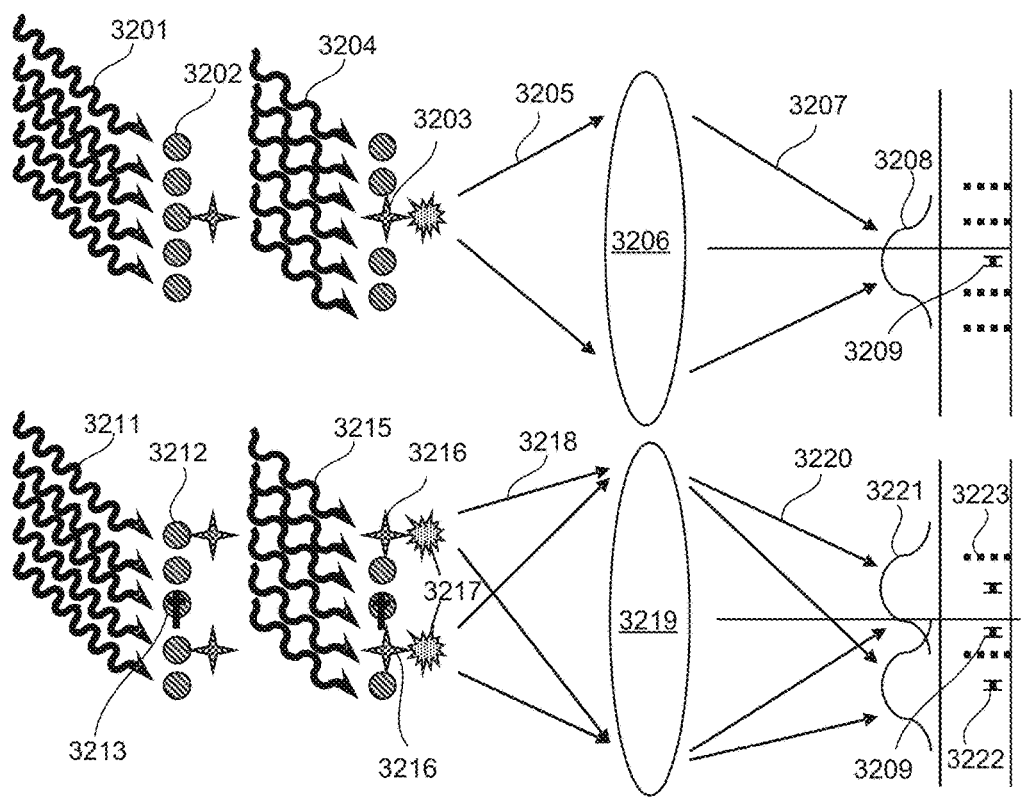
FIG. 32 is a schematic diagram illustrating how when weak intensity activation radiation bathes closely spaced PTOLs a small, statistically-sampled fraction of all the PTOLs that absorbs the activation radiation can be converted into a state that can be excited by excitation radiation.

However, by selectively activating and de-activating subsets of PTOLs within a dense set of PTOLs this localization concept can be used even when the optical labels are closely spaced. As shown in FIG. 32, when weak intensity activation radiation 3201 bathes closely spaced PTOLs 3202 a small, statistically-sampled fraction 3203 of all the PTOLs absorbs the activation radiation and is converted into a state 3203 that can be excited by the excitation radiation 3204. The emission radiation 3205, 3207 from this activated and excited subset is focused to a set of isolated, diffraction limited spots 3208 whose centers can be localized to sub-diffractive resolution 3209 as illustrated previously in FIG. 31. After enough photons are collected to generate sufficiently resolved images of the PTOLs that are members of the activated and excited subset, the activated PTOLs are either deactivated to return to an activatable state 3202 (as in the case of Dronpa or KFP) or are permanently photobleached to a dark form 3213, effectively removing them from the system. Another cycle of weak intensity activation radiation 3211 is then applied to activate a new subset 3216 of the remaining activatable PTOLs 3212. The PTOLs in this second subset in turn can be put into the excited state 3217 by excitation 3215. The radiated light 3218, 3220 is refocused by the microscope lens 3219 onto well-separated diffractive resolution limited spots 3221. Once again, fitting of each peak can define the sub-diffractive locations 3222 of the PTOLs in the second subset. Further cycles will extract sub-diffractive locations of other PTOLs, such as PTOL image locations 3223.

Figure 33:
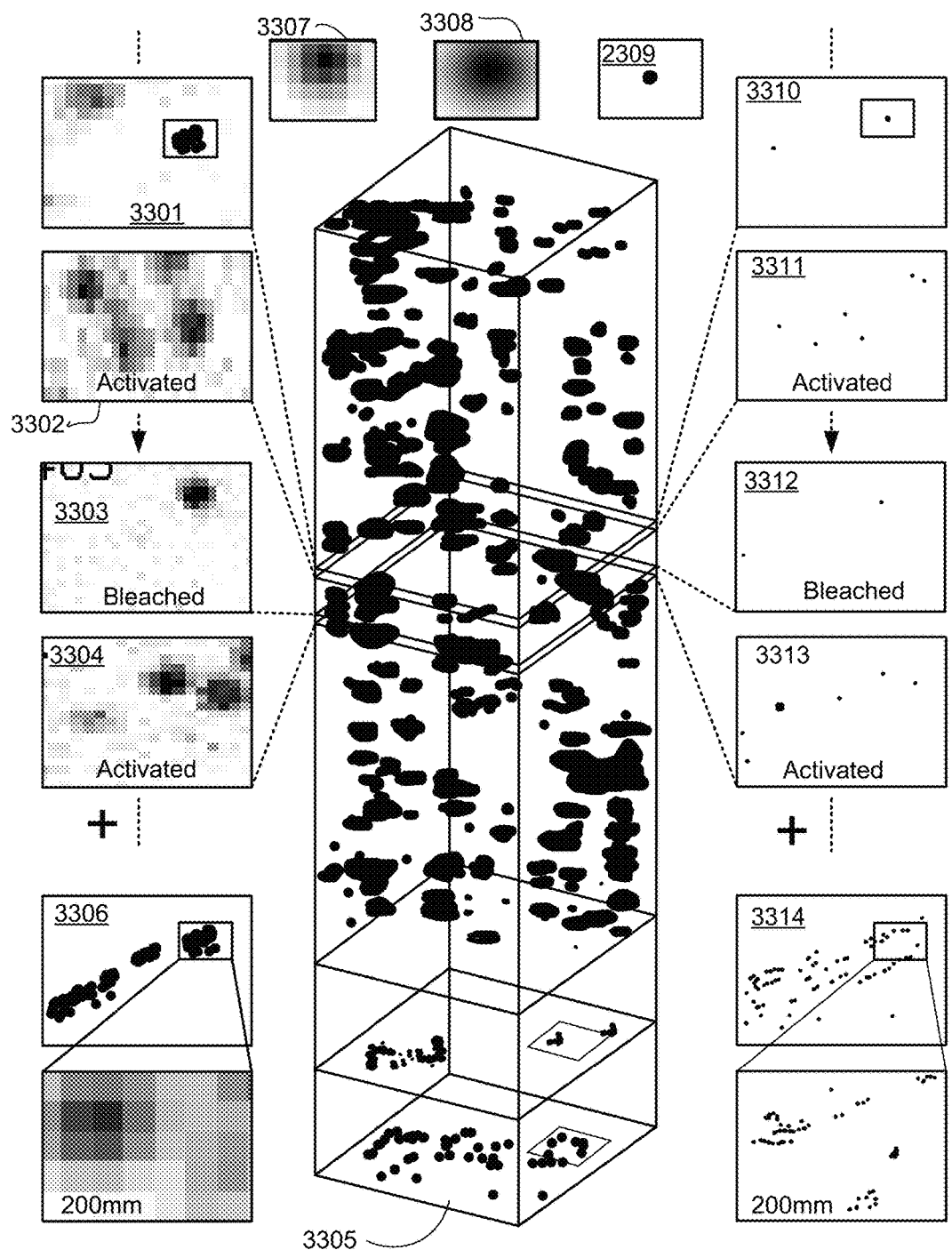
FIG. 33 is a schematic diagram illustrating how multiple sub-diffractive resolution images in two spatial dimensions, x and y, of individual PTOLs in a sample can be generated, and then the multiple images can be combined to generate a sub-diffraction limited resolution image of an x-y plane of the sample.

As shown in FIG. 33, multiple sub-diffractive resolution images in two spatial dimensions, x and y, of individual PTOLs in a sample can be generated, and then the multiple images can be combined to generate a sub-diffraction limited resolution image of an x-y plane of the sample. An initial image of a few discrete PTOLs emitting at a wavelength that is imaged by imaging optics is shown in frame 3301. After a subset of PTOLs is activated with an activation pulse of radiation having an activation wavelength different from the wavelength of radiation that is imaged, more PTOLs are detected, as shown in frame 3302. Several such frames are recorded until many of these initially-activated PTOLs bleach and can no longer emit, as shown in frame 3303. At this point, a new activation pulse can convert a new subset of PTOLs into an activated state, and this new subset of PTOLs can emit radiation at the imaging wavelength when the newly-activated PTOLs are excited, which results in the image of frame 3304. This cycle can be repeated to generate several hundred or thousands of such image frames, which can be considered to represent a 3D data stack 3305 of PTOL images, with the coordinates, x and y, on the horizontal plane and the time, t, on the vertical axis. Then all these individual image frames in the data stack can be summed to generate a total image that is equivalent to a long time exposure of a diffraction-limited image from a microscope, as shown in frame 3306.

When activated PTOLs are sufficiently sparse in the sample, the raw signal from each activated PTOL (e.g., the intensity of the signal on individual pixels of a CCD detector), as shown in frame 3307, can be fitted with an approximate point spread function (e.g., a Gaussian) to generate a smoothed, fitted signal, as shown in frame 3308, and the center x,y coordinates of each PTOL can be determined. The location of each PTOL can then be rendered in a new image as a Gaussian centered at the measured localization position, having a width defined by the uncertainty to which this location is known. This uncertainty can be significantly less than the original radius of the original, diffraction-limited PTOL image 3307 (typically by an approximate factor of sqrt(N), where N is the number of photons detected to generated the image of the PTOL). For example, if there were 3300 photons in the pixels of the image spot of a PTOL, the uncertainty of the fitted central location can be $\frac{1}{20}$ of the size of the original diffraction limited image of that PTOL.

Applying this process to images of all the activated PTOLs in frames 3301, 3302, 3303, and 3304 leads to the corresponding narrow rendered peaks in frames 3310, 3311, 3312, and 3313. The widths of these rendered peaks are given by their localization uncertainty. Applied to all activated PTOLs in all frames of the data stack 3305, this localization process results in a list of coordinates for many PTOLs within the sample. Alternatively, the rendered peaks can be accumulated (e.g., summed) to give a superresolution image 3314 of a dense set of PTOLs. The emission of any activated PTOL may persist over several frames until it is bleached or otherwise deactivated. For such a case, an implementation of this accumulation is to identify the coordinates across several frames of what is likely to be a common PTOL. This set of coordinates can be averaged or otherwise reduced to obtain a single, more accurately localized coordinate vector of that PTOL. A comparison of the diffraction limited image 3306 and the superresolution image 3314 illustrates the higher resolution achievable by this process.

This process of serial activation of different isolated PTOL subsets allows an effective way of localizing the positions of a dense set of PTOLs, such that superresolution images in 1, 2, or 3 spatial dimensions can be generated, as described in more detail herein. Furthermore, this process can also be independently repeated for different species of PTOLs within a sample, which have different activation, excitation, and/or emission wavelengths. Separate or combined superresolution images can then be extracted using each PTOL species. The extracted positional information of two or more different PTOLs that label two different binding proteins can describe co-localization and relative binding positions on a common or closely connected target. This can be useful for determining which proteins are related to each other.

Figure 34:
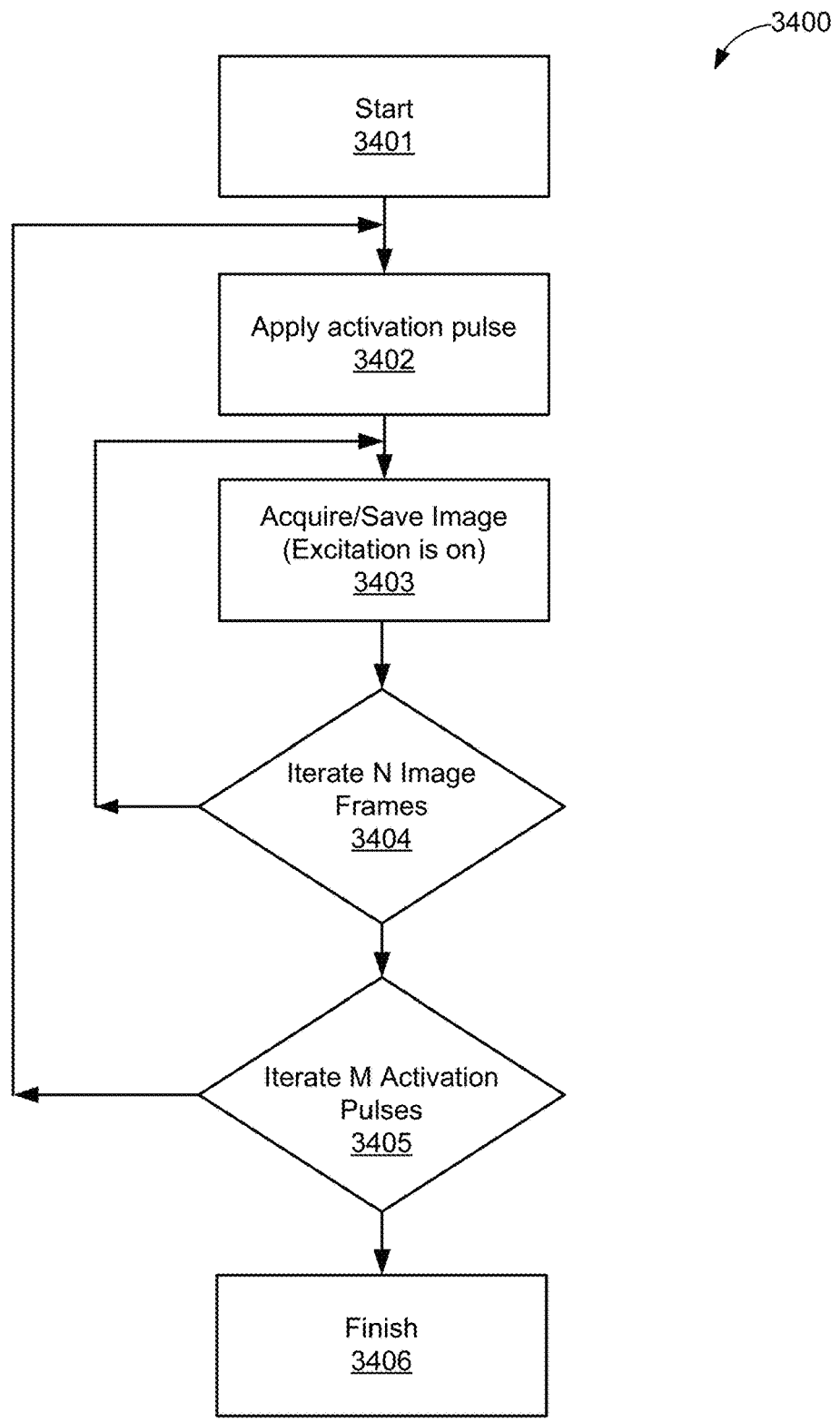
FIG. 34 is a flow chart of a process for creating an image of a sample containing multiple relatively densely-located PTOLs.

FIG. 34 is a flow chart of a process 3400 for creating an image of a sample containing multiple relatively densely-located PTOLs. Activation radiation having an activation wavelength can be directed onto a sample to transform a subset of PTOLs in the sample from an unactivated to an activated state (step 3402). Excitation radiation is applied to activated PTOLs in the sample at the excitation wavelength, and radiation that is emitted from activated and excited PTOLs and incident onto the imaging and detecting optics is acquired and saved (step 3403). Images of a set of activated PTOLs can be acquired and saved multiple times. For example, the controller can require that N images of a set of activated PTOLs are acquired, such that if N images have not yet been acquired (step 3404) image acquisition (step 3403) is repeated. The excitation radiation can be applied to the sample continuously or can be switched off between acquisitions of images.

After N images of the subset of activated PTOLs are acquired, and if more images are to be obtained from the sample (step 3405) another activation pulse can be applied to the sample to activate another set of PTOLs (step 3402). Excitation radiation can be applied to this other set of activated PTOLs, and radiation emitted from the activated and excited PTOLs can be acquired and saved (step 3403). Multiple sets of PTOLs can be activated. For example, the controller can require that M sets PTOLs be activated, such that if M sets have not yet been activated (step 3405) another activation pulse is applied (step 3403). Thus, the process of activating a set of PTOLs, exciting PTOLs within the activated set, and acquiring images from the activated and excited PTOLs can be repeated multiple times, for example, until the total pool of available PTOLs becomes exhausted or until a desired number of images of a desired number of different PTOLs within a spatial area or volume is achieved.

While applying the activation and excitation radiation, the number of iterations N between activation pulses, along with the intensity of the activation and excitation radiation can be controlled such that the mean volume per imaged PTOL in an individual image is generally more than the DLRV of the optical imaging system used to detect and localize the individual PTOLs. The density of activated PTOLs that are capable of emitting radiation is generally highest in images acquired immediately after the activation pulse and generally decreases as more PTOLs photobleach during the acquisition of the N image frames.

Furthermore, as the process 3400 progresses, and the number of activation pulses increases from 1 to M, PTOLs within the sample may photobleach, such that fewer and fewer PTOLs within the sample are available to be activated, excited, and imaged. Thus, in one implementation, the intensity and time length of individual activation pulses and the intensity and time length of excitation radiation can be controlled, to reduce the variation in density of activated PTOLs as the process progresses. For example, using less excitation radiation (possibly with fewer frames N between activation pulses) can reduce the decrease in imaged PTOLs from the first frame after an activation pulse to the Nth frame just preceding the next activation pulse. In another example, the intensity of individual activation pulses can increase as the process 3400 progresses from the first to the M$^{th}$ activation pulse. This would reduce the decrease in the number of imaged PTOLs in the first acquisition frame after the Mth activation pulse relative to the number of imaged PTOLs in the first acquisition frame after the first activation pulse, thereby compensating for the reduction in the number of activable PTOLs as the sequence of activation and image acquisition progresses. Thus, in the first example, the variation of activated and excitable PTOLs during an excitation sequence is reduced and in the second example the variation of activated and excitable PTOLs during the activation sequence is reduced. The reduced variation of activated and excitable PTOLs allows operation, where more PTOLs can be localized per unit time, while not exceeding the density criteria of more than one imaged PTOL per DLRV.

In one implementation, multiple species of PTOLs within the sample can be activated, excited, and imaged. For example, steps of applying the activation pulses (3402) and of exciting and imaging (3403) can include applying pulses of activation radiation and excitation radiation, respectively, having wavelengths corresponding to the different activation and excitation wavelengths of different PTOL species. A multiplicity of detectors and/or filters can also be used in the imaging step 3403 to image different wavelengths of radiation emitted from different PTOL species. In this manner, multiple independent data sets of images can be acquired. These independent data sets in turn can be reduced to corresponding super-resolution images of each PTOL species within a sample.

If the contrast ratio between activated and inactivated PTOLs is too low at a given initial density of target PTOLs to achieve the desired SNR and consequent localization accuracy, the contrast ratio can be improved by irreversibly bleaching a portion of the target PTOLs until the effective molecular density and resulting SNR is as desired. Other autofluorescent material in the sample can also be pre-bleached using the excitation light without affecting the bulk of the inactivated PTOLs. Further discrimination with respect to background might be obtained via appropriate spectral filtering, fluorescence lifetime measurements, or polarized excitation and/or polarization analyzed detection.

Figure 35:
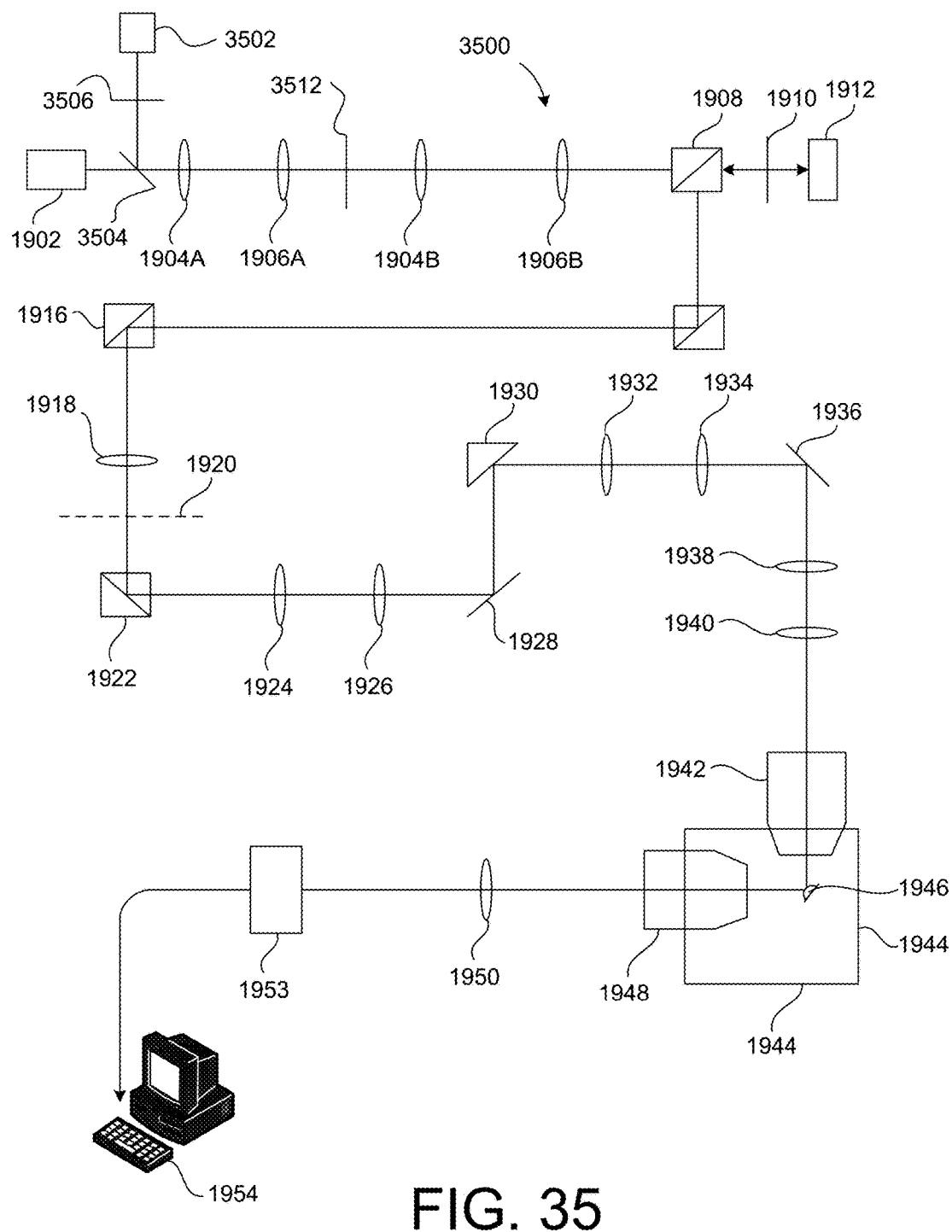
FIG. 35 is a schematic view of a system that can be used to implement the techniques described herein.

FIG. 35 is a schematic view of a system 3500 that can be used to implement the techniques described herein. The system 3500 is similar to the system 1900 also includes can include a source 3502 of the activation radiation in addition to the source 1902 of excitation radiation. The activation radiation can be coupled into the beam path of the excitation radiation the use of a beam splitter 3504 positioned between the source of excitation radiation 1902 and the lens 1904A. As shown in FIG. 35, in some implementations, the beam paths of the excitation radiation and the activation radiation can overlap and can be directed to the sample 1946 by at least some of the same beam-forming optics (e.g., galvanometer-mirrors 1928 and 1936, wavefront modulator 1912, etc.). In other implementations, the excitation radiation in the activation radiation may be provided to the sample 1946 from different directions. For example, the activation radiation may be provided to the sample 1946 through the detection objective 1948. In other implementations, the beam splitter 3504 that couples the activation radiation and the excitation radiation may be provided in a different position along the beam path shown in FIG. 35. For example, the beam splitter may be located between relay lens 1940 and excitation objective 1942, and the beam path for the activation radiation may include independent beam-forming optical elements to shape and direct the activation beam.

The light source 3502 can be directly modulated, or modulated via a shutter 3506 placed in the beam path of the activation radiation emitted by the light source 3502. The shutter can operate to admit or prevent activation radiation from passing from the light source 3502 to the sample 1946. In one implementation, the shutter can be a mechanical shutter that moves to selectively block the beam path. In another implementation, the shutter can be a material that can be modified electronically or acoustically to admit or prevent light from passing or to alter a beam path from the light source 3502. Similarly, excitation radiation that causes an activated PTOL to be transformed from a de-excited state to an excited state can also be passed from an excitation light source 1902 through a shutter 3512 to the sample 1946.

A controller (e.g., a general or special purpose computer or processor) can control one or more optical elements of the systems 1800, 1900, 3500. For example, a controller can be used to control parameters of the activation and excitation radiation (e.g., the wavelength, intensity, polarization, and duration of pulses of various radiation beams that reach the sample 1946 3501; and the timing of activation radiation pulses and excitation radiation pulses) during an image acquisition sequence. Of course, the optical elements can be arranged in other configurations. Data from images formed at the detector 1953 are communicated to a controller for storage and processing. For example, the controller can include a memory for recording or storing intensity data as a function of position on the detector for different image frames. The controller can also include a processor for processing the data (e.g., a general or special purpose computer or processor), for example, to fit the data recorded for an image of an individual PTOL to determine a location of the PTOL to sub-diffraction limited precision, or to combine the data about the locations of multiple PTOLs that are determined with superresolution accuracy to generate an image of the sample based on the locations of multiple PTOLs that have been located with superresolution accuracy.

Thus, in some implementations, the sample 1946 can include a dense plurality of photo transformable optical labels. The density of the optical labels in the sample can be greater than an inverse of the diffraction limited resolution volume of the detection optics of the system. Activation radiation can be provided to the sample to activate a statistically sampled subset of the labels in the sample. For example, the source 3502 can generate a beam of activation light having a first wavelength, and the activation light can be steered to the sample by optical elements shown in system 3500.

In some implementations, the activation radiation can be provided in the form of a Bessel-like beam that is swept in a direction having a component orthogonal to the propagation direction of the Bessel-like beam and having a component orthogonal to an optical axis of the detection objective 1948. In some implementations, the activation radiation can be provided in the form of an array of incoherent Bessel-like beams that are swept or dithered in a direction having components that are orthogonal both to the direction of propagation of the Bessel-like beams and orthogonal to an optical axis of detection objective 1948. In some implementations, the activation radiation can be provided in the form of an array of coherent Bessel-like beams that are swept or dithered in a direction having components that are orthogonal both to the direction of propagation of the Bessel-like beams and orthogonal to an optical axis of detection objective 1948. In some implementations, the Bessel-like beams of the array can be phase coherent with each other. In some implementations, the Bessel-like beams in an array of beams can partially overlap with neighboring beams in the array within the sample. In some implementations, the activation radiation can be provided in the form of a Gaussian-like beam that is swept in a direction having a component orthogonal to the propagation direction of the Bessel-like beam and having a component orthogonal to an optical axis of the detection objective 1948. The sweeping and/or dithering of the beam(s) of activation radiation can form a thin sheet of activation radiation near a focal plane of the detection objective 1948. In some implementations, the activation radiation can be provided in the form of a static thin sheet of activation radiation in a plane substantially perpendicular to the optical axis of the detection objective 1948. For example, the thin sheet of activation radiation can be formed through use of a cylindrical lens used to focus the activation radiation in one spatial direction. In some implementations, the activation radiation is not provided in the form of a thin light sheet, but rather provided through widefield techniques. The activation radiation can be controlled such that the density of activated labels in the subset is less than the inverse of the diffraction limited resolution volume of the detection optics. For example, the intensity of the activation radiation and/or the time for which the activation radiation is provided to the sample can be controlled such that the probability of the activation radiation activating a label convoluted with the density of the labels in the sample is such that the resulting density of activated labels is less than the inverse of the diffraction limited resolution volume of the detection optics.

Once the subset of activated labels is created, a thin sheet of excitation radiation can be provided to the at least some of the activated labels in the sample to excite at least some of the activated photo transformable optical labels. For example, the source 1902 can generate a beam of excitation light having a second wavelength, and the excitation light can be steered to the sample by optical elements shown in system 3500.

In some implementations, the excitation radiation can be provided in the form of a Bessel-like beam that is swept in a direction having a component orthogonal to the propagation direction of the Bessel-like beam and having a component orthogonal to an optical axis of the detection objective 1948. In some implementations, the excitation radiation can be provided in the form of an array of Bessel-like beams that are swept or dithered in a direction having components that are orthogonal both to the direction of propagation of the Bessel-like beams and orthogonal to an optical axis of detection objective 1948. In some implementations, the Bessel-like beams can be phase coherent with each other. In some implementations, Bessel-like beams in an array of beams can partially overlap with neighboring beams in the array within the sample.

In some implementations, the excitation radiation can be provided in the form of a Gaussian-like beam that is swept in a direction having a component orthogonal to the propagation direction of the Bessel-like beam and having a component orthogonal to an optical axis of the detection objective 1948. The sweeping and/or dithering of the beam(s) of excitation radiation can form a thin sheet of excitation radiation near a focal plane of the detection objective 1948. In some implementations, the excitation radiation can be provided in the form of a static thin sheet of excitation radiation in a plane substantially perpendicular to the optical axis of the detection objective 1948. For example, the thin sheet of excitation radiation can be formed through use of a cylindrical lens used to focus the excitation radiation in one spatial direction.

Radiation emitted from the activated and excited labels is imaged by imaging optics, including the detection objective 1948, onto a detector 1953. The detection objective has an axis along a direction that is substantially perpendicular to the sheet of excitation radiation. Locations of labels from which radiation is detected can be determined with super resolution accuracy by one or more processors or computing devices based on the detected radiation. The process of activating a statistical subset of transformable labels, exciting the activated labels, and detecting light from the activated and excited labels can be repeated, where different subsets of transformable labels are activated during different rounds of activation. Finally, a sub-diffraction-limited image of the sample can be generated by one or more processors of a computing system based on the determined locations of the labels.

Other planes of the sample 1946 can be imaged by moving the activation radiation and the excitation radiation and the focal plane of the detection objective 1948 to different positions within the sample. For example, in one implementation, the sample can be mounted on a movable stage 3506 that is configured to change the position of the sample with respect to the focal plane of the detection objective 1948. In another implementation, the activation radiation and the excitation radiation can be steered to different planes along the axial direction of the detection objective by the beam-forming optics of the system 3500 (e.g., by galvanometer-mirror 1928). When the activation and excitation radiation beams are steered to different positions within the sample, the focal plane of the detection objective can be changed correspondingly, such that committing optical labels from the newly positioned plane of excitation radiation can be imaged effectively by the detection objective 1948. When optical labels in different planes of the sample are activated, excited, and imaged, the locations of the optical labels in the different planes can be combined to generate a three-dimensional image of the sample.

Non-Linear Structured Illumination Microscopy

The structured illumination microscopy (SIM) techniques described above, in which spatially-structured excitation radiation is used to excite optical labels in the sample, can be extended to nonlinear SIM in which optically emitting labels are prepared using techniques in which spatially patterned light is used to create a nonlinear relationship between the intensity of the excitation light and the intensity of the fluorescence emission. With nonlinear SIM the resolution of images can be extended to the sub-100 nm regime, while retaining, to the greatest extent possible, the advantages which make it the preferred superresolution (SR) method for live cell imaging.

In describing the apparatuses, materials, and methods disclosed herein the following terms and abbreviations can be used for convenience:

PA NL-SIM: Patterned Activation Non-Linear Structured Illumination Microscopy.

High NA PA NL-SIM: High Numerical Aperture PA NL-SIM.

Saturated PA NL-SIM: Increases the dose of the patterned activation in PA NL-SIM until most, or a significant percentage, of the photoswitchable labels are activated at the maxima of the pattern. This can provide increase the resolution of the final image to 45 nm, but at the cost of high intensity, slower speed, and fewer image frames before photobleaching.

EM: Electron Microscopy.

TIRF: Total Internal Reflection Fluorescence. A method where the excitation light is confined to an evanescent field within about 200 nm of the substrate upon which the specimen rests. While this restricts the observable volume, it eliminates out-of-focus background, greatly reduces phototoxicitiy, and can be used to improve resolution, thanks to the high numerical aperture lenses required.

SIM: Structured Illumination Microscopy. A super-resolution method in which spatially patterned light is used to shift high resolution information about the sample encoded in spatial frequencies beyond the diffraction-limit to spatial frequencies which can be measured with conventional optics. A series of raw images at different orientations and phases of the patterned light are analyzed in Fourier space to reconstruct the final super-resolution image.

L-SIM: Linear SIM, which is a form of SIM, in which the intensity of the fluorescence emission from the specimen generally can be linearly proportional to the intensity of the spatially patterned excitation light. This approach can be faster and can use less intense light than other super-resolution methods, but its resolution gain is limited to a factor of two beyond the diffraction limit.

TIRF-SIM: Total Internal Reflection Fluorescence SIM, which is a form of SIM that combines the low background and phototoxicitiy of TIRF with the two-fold resolution gain of SIM.

NL-SIM: Non-Linear SIM. A form of SIM in which spatially patterned light is used to create a nonlinear relationship between the intensity of the light and the intensity of the fluorescence emission. This nonlinearity introduces finer spatial structure (i.e., higher spatial frequencies) in the fluorescence emission distribution that can be used to extend the resolution beyond the two-fold limit of L-SIM.

SD NL-SIM: Saturated Depletion NL-SIM. A form of NL-SIM where spatially patterned light is used to return previously activated fluorphores back to their deactivated state, except for narrow sub-populations of activated fluorphores that remain at the nodes of the applied pattern. These narrow sub-populations contain the high spatial frequencies needed to extend SIM beyond its traditional two-fold resolution limit.

ISM: Image Scanning Microscopy. A super-resolution method conceptually similar to L-SIM, except that focused light, rather than broadly distributed, spatially structured excitation light is used in conjunction with widefield detection to extend resolution theoretically up to twice beyond the diffraction limit.

STED microscopy: Stimulated Emission Depletion microscopy. A super-resolution method in which focused light at a first wavelength is used to bring fluorescent molecules in a diffraction-limited focus to an excited state, and light in an annular intensity pattern is used to return all molecules except at those at the central node of the annulus back to the ground state by the process of stimulated emission. The remaining excited molecules at the node then emit photons by spontaneous emission and produce the detected signal. These are confined to a sub-diffractive volume, so a super-resolution image is generated if this process is repeated as the excitation focus and stimulation annulus are scanned together point-by-point across the speciemen.

RESOLFT microscopy: REversible Saturable Optical Fluorescence Transitions microscopy. A super-resolution method conceptually similar to STED, except that the excitation and partial stimulated deexcitation of conventional fluorophores is replaced by photoactivation and partial deactivation of reversibly photoswitchably fluorophores as the means to higher resolution. Deactivation in RESOLFT requires orders of magnitude less intense light than does deexcitation via stimulated emission in STED.

PS-RESOLFT: Point Scanning RESOLFT. The original form of RESOLFT, that uses a focused excitation spot and a focused deexcitation annulus with point detection and serial scanning in direct analogy to STED.

WF-RESOLFT: Wide Field RESOLFT. A form of RESOLFT wherein the point activation/deactivation with focused light is replaced with uniform, widefield activation followed by parallel deactivation of the photoswitchable fluorophore across an array of spatially structured intensity minima, with subsequent parallel, widefield readout of the remain activated fluorephores at these mimina. In this case, the pattern need be scanned over only the dimensions of the unit cell of the array to record a complete image, rather than the much larger size of the full field of view.

AOTF: acousto-optic tunable filter.

FOV: field of view

HWP: half wave plate

MTF: modulation transfer function

NA: numerical aperture

OTF: optical transfer function

QWP: quarter wave plate

SF: saturation factor

SLM: spatial light modulator

SNR: signal to noise ratio

SR: super-resolution

CCPs: clathrin coated pits

CLTA: clathrin light chain a

CLTB: clathrin light chain b

EEs: early endosomes

Fluorescence microscopy continues to play a key role in elucidating structure and function of living systems, thanks to its ability to image specific proteins with single molecule sensitivity, as well as its capacity to study in vivo dynamics in a minimally invasive manner. Its power has grown with the introduction of super-resolution (SR) techniques that extend its diffraction-limited spatial resolution (~200 nm for fluorescence light from green fluorescent protein (GFP)) by as much as an order of magnitude. However, while the SR imaging of fixed specimens, the most common modality, offers the highest resolution, it does so at the considerable risk of altering the very ultrastructure it hopes to reveal, due to both the fixation process itself and the extremely high density of fluorescent markers required to achieve such resolution. Furthermore, with the advent of genetically encoded markers for electron microscopy (EM), the continued preeminence of SR microscopy for protein-specific structural imaging at the nanoscale is no longer assured.

A different situation emerges for in vivo imaging, where electron microscopy (EM) is too destructive, and fixation is not involved. However, while this would appear to be the ideal niche of SR microscopy, SR techniques such as localization microscopy, stimulated emission depletion (STED) microscopy, and reversible saturable optical fluorescence transitions (RESOLFT) microscopy place extraordinary demands on the photon budget, represented by the product of the number of fluorescent molecules in the specimen and the number of photons each can emit before bleaching irreversibly. They also require specialized photoswitchable labels and excitation intensities (e.g., $10^3$ to $10^8$ W/cm$^2$), which are orders of magnitude greater than the 0.1 W/cm$^2$ intensity under which life evolved. As a result, time lapse measurements by these techniques rarely consist of more than a few frames, and phototoxic changes to cellular physiology can set in quickly, even at the lower end of this range. In addition, typical SR acquisition speeds of ~1 sec to several minutes per frame are too slow to follow processes that move faster than ~1 to 50 nm/sec without introducing motion induced artifacts, while common resolution metrics such as the Nyquist criterion for labeling density or the width of an isolated feature tend to overestimate the true spatial resolution substantially.

A notable exception is structured illumination microscopy (SIM) which, in vivo, can image in multiple colors using conventional fluorescent labels at rapid rates, e.g., 11 frames/sec at relatively low intensities, e.g., 1-100 W/cm². In the past, its resolution has been limited to only twice beyond the diffraction limit. This has provided the motivation for the development of other in vivo compatible SR methods, but to date, all suffer from substantial limitations as noted above.

The goal of fluorescence microscopy is to determine the spatial distribution S(x) of fluorophores in the specimen, on the assumption that these are bound to only the features of interest. If these fluorophores are standard fluorescent probes, spatially patterned excitation light of intensity $I_{exc}(x)$ produces a fluorescence emission distribution F(x) given by:

$$F(x)=S(x) \cdot E[I_{exc}(x)] \qquad (4)$$

where $E[I_{exc}(x)]$ gives the relative probability that a fluorophore at any position x will emit a photon under the influence of the excitation $I_{exc}(x)$. In the most common case where $I_{exc}(x)$ is far lower than the intensity required to drive the fluorophores to their lifetime-limited saturation of emission, $E[I_{exc}(x)] \propto I_{exc}(x)$, and the emission distribution F(x) just reflects the product of the fluorophore distribution S(x) with the excitation distribution $I_{exc}(x)$.

If, on the other hand, the fluorophores are phototransformable probes that can be switched from a non-fluorescent state to a fluorescent state under the influence of spatially patterned activation light of intensity $I_{act}(x)$, then the emission distribution also depends on which fluorophores have been activated. In this case, Eq (4) becomes:

$$F(x)=S(x) \cdot A[I_{act}(x)] \cdot E[I_{exc}(x)] \qquad (5)$$

where $A[I_{act}(x)]$ gives the relative probability that a fluorophore at any position x has been turned on by the activation light $I_{act}(x)$. Eq (5) also encompasses the case of standard fluorophores, in which case $A[I_{act}(x)]=1$.

Finally, if the fluorophores are photodepletable probes that can be switched from an active fluorescent state to an inactive fluorescent state under the influence of spatially patterned deactivation light of intensity $I_{dep}(x)$, then the emission distribution also depends on which fluorophores have been deactivated. In this case, Eq (5) becomes:

$$F(x)=S(x) \cdot A[I_{act}(x)] \cdot B[I_{dep}(x)] \cdot E[I_{exc}(x)] \qquad (6)$$

where $B[I_{dep}(x)]$ gives the relative probability that a fluorophore at any position x remains active after application of the deactivation light $I_{dep}(x)$. Eq (6) also encompasses the case of standard fluorophores, in which case $B[I_{dep}(x)]=1$.

For a microscope with a diffraction-limited detection PSF $H_{det}(x)$, the emission distribution F(x) produces an image D(x) given by their mutual convolution:

$$D(x)=F \otimes H_{det}(x)=\{S(x) \cdot A[I_{act}(x)] \cdot B[I_{dep}(x)] \cdot E[I_{exc}(x)]\} \otimes H_{det}(x) \qquad (7)$$

or, in Fourier space, $$\tilde{D}(k)=\tilde{F}(k) \cdot O_{det}(k)=FT\{S(x) \cdot A[I_{act}(x)] \cdot B[I_{dep}(x)] \cdot E[I_{exc}(x)]\} \cdot O_{det}(k) \qquad (8)$$

where FT is the Fourier transform operator. In every SR method, the final SR image $D_{SR}(x)$ is a method-specific function SR(ξ) of multiple such images $D_n(x)$, n=1 ... N:

$$D_{SR}(x)=SR[D_1(x),D_2(x), \ldots D_N(x)] \qquad (9)$$

For each such method, this can be case in the form:

$$D_{SR}(x)=S \otimes H_{SR}^{eff}(x) \qquad (10)$$

or, in Fourier space:

$$\tilde{D}_{SR}(k)=\tilde{S}(k) \cdot O_{SR}^{eff}(k) \qquad (11)$$

where $H_{SR}^{eff}(x)$ and $O_{SR}^{eff}(k)$ are the effective PSF and OTF of the method, respectively.

A. Live Cell Nonlinear SIM Via Patterned Activation of Photoswitchable Fluorophores An issue present in any form of live cell SR imaging is that higher resolution of an image must be accompanied by proportionally faster acquisition times to follow dynamic events of a given velocity. However, higher resolution also requires a quadratically-increasing number of raw measurements for each 2D image frame.

To achieve even higher resolution than high NA TIRF-SIM, we turned to nonlinear SIM (NL-SIM). The nonlinearity present in either the patterned saturation of fluorescence excitation at high intensity or the patterned depletion of photoswitchable fluorophores introduces additional harmonics H which permit resolution extension at wavelength λ via SIM to ≈λ/(2NA(H+1) with H≥2, compared to H=1 for the traditional linear form of SIM and H=0 for diffraction-limited widefield imaging with uniform illumination. An image resolution of ~50 nm has been demonstrated with both approaches, although not on living cells: saturated excitation was used to image densely labeled fluorescent beads at the likely-phototoxic peak intensity of 8 MW/cm², while saturated depletion (SD) imaged single fixed cells at 945 sec/frame, which is far too slow to follow most cellular processes.

SD provides the basis of resolution enhancement in STED and RESOLFT as well as SD NL-SIM. The degree of enhancement depends on the degree of saturation, where the degree of saturation can be defined in multiples of the saturation factor (SF) for which 1/e of the irradiated molecules remain in the original activated or excited state. When SF>1, then the intensity of the light that causes this condition can be said to be above the saturation limit. However, high SFs are very photon inefficient: only a fraction of the photobleaching-dictated number of switching cycles for any given molecule then contributes useful signal. Furthermore, high SFs require high intensities and/or long exposures, neither of which is compatible with fast, noninvasive live cell imaging.

To address these issues, patterned activation (PA) of optical labels, followed by patterned excitation and readout of the optical labels (e.g., green photoswitchable FP Skylan-NS) can be used to generate at least H=2 harmonics. Using this approach, a specimen labeled with photoswitchable optical emitters (e.g., green FP Skylan-NS) can be imaged with resolution of sub-100 nm resolution and with sub-second acquisition times in TIRF for live cell. This approach, termed PA NL-SIM, allowed us to achieve large amplitudes in both the first and second harmonics of the emission pattern, leading to SR images of high signal to noise ratio (SNR), even at low activation and excitation saturation factors ($SF_{act}$ and $SF_{exc}$) obtained with low intensities and short exposures for both activation and excitation).

Figure 37:
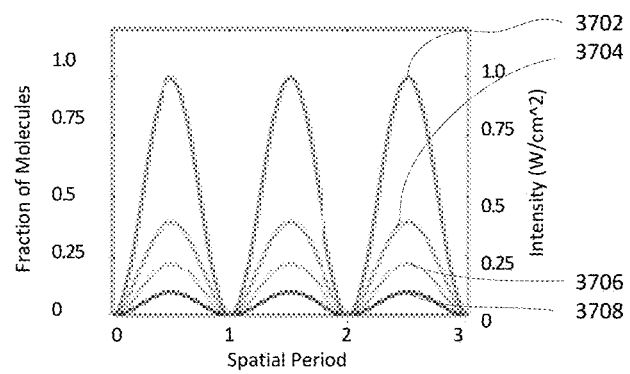
FIGS. 37, 38, 39, and 40 illustrate a process of PA NL-SIM, in accordance with the techniques describe herein.

FIGS. 37, 38, 39, and 40 illustrate a process of PA NL-SIM, in accordance with the techniques describe herein. As shown in FIG. 37, patterned activation radiation (e.g., with a peak intensity of 1.0 W/cm$^2$) can be applied to a sample containing phototransformable labels. The intensity of the patterned activation radiation over three spatial periods is shown by curve 3702, and the fraction of activated labels at different point in the spatial period is shown in curve 3704, when the activation radiation is applied for 0.2 ms, in curve 3706, when the activation radiation is applied for 0.5 ms, and in curve 3708, when the activation radiation is applied for 1.0 ms.

Figure 38:
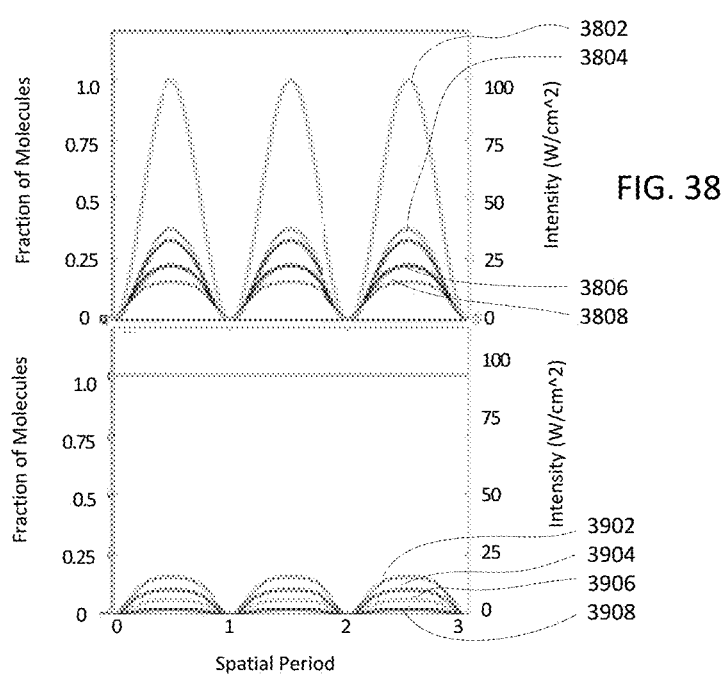

As shown in FIG. 38, positions of the activated labels can be read out by applying patterned excitation radiation with the same period and phase as the patterned activation radiation and (e.g., with a peak intensity of 100 W/cm$^2$) to the sample containing the activated labels. The intensity of the patterned excitation radiation over three spatial periods is shown by curve 3802, and the fraction of activated labels at that remain excited and able to provide fluorescence radiation at different points in the spatial period is shown in curve 3804, when the excitation radiation is applied for 0.3 ms, in curve 3806, when the excitation radiation is applied for 2 ms, in curve 3808, when the excitation radiation is applied for 5 ms, and in curve 3810, when the excitation radiation is applied for 10 ms.

Figure 39:
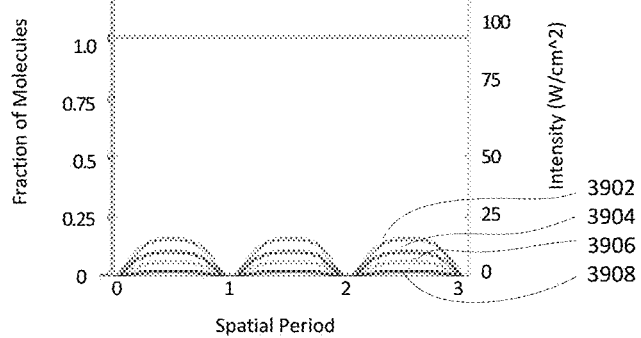

As shown in FIG. 39, the activated labels can be deactivated (e.g., bleached) by deactivation patterned radiation (e.g., additional patterned excitation radiation) with the same period and phase as the patterned activation radiation and with a peak intensity of 100 W/cm$^2$ to the sample containing the activated labels. The intensity of the patterned excitation radiation over three spatial periods is shown by curve 3802 (in FIG. 38), and the fraction of activated labels at that remain excited and able to provide fluorescence radiation at different points in the spatial period is shown in curve 3904, when the deactivation radiation is applied for 10 ms, in curve 3906, when the deactivation radiation is applied for 15 ms, in curve 3908, when the deactivation radiation is applied for 20 ms, and in curve 3910, when the deactivation radiation is applied for 40 ms.

Figure 40:
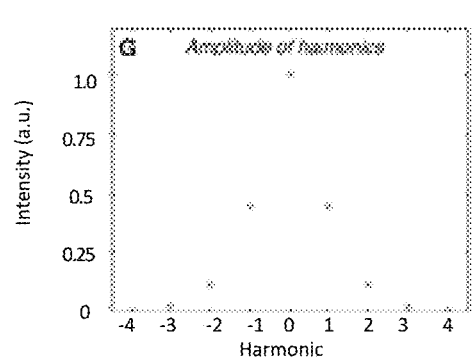

FIG. 40 shows the relative strengths of the resulting harmonics when the patterned radiation applied in PA NL-SIM process illustrated in FIGS. 37, 38, and 39, using a saturation factor for the activation radiation, $SF_{act}$, of 0.4.

FIGS. 41, 42, 43, and 44 illustrate a process of Saturated PA NL-SIM, in accordance with the techniques describe herein. As shown in FIG. 41, patterned activation radiation with a peak intensity of 4.0 W/cm$^2$ is applied to a sample containing phototransformable labels. The intensity of the patterned activation radiation over three spatial periods is shown by curve 4102, and the fraction of activated labels at different point in the spatial period is shown in curve 4104, when the activation radiation is applied for 0.05 ms, in curve 4106, when the activation radiation is applied for 0.25 ms, in curve 4108, when the activation radiation is applied for 0.5 ms, and in curve 4110, when the activation radiation is applied for 1.0 ms.

As shown in FIG. 42, positions of the activated labels can be read out by applying patterned excitation radiation with the same period and phase as the patterned activation radiation and with a peak intensity of 100 W/cm$^2$ to the sample containing the activated labels. The intensity of the patterned excitation radiation over three spatial periods is shown by curve 4202, and the fraction of activated labels at that remain excited and able to provide fluorescence radiation at different points in the spatial period is shown in curve 4204, when the excitation radiation is applied for 0.3 ms, in curve 4206, when the excitation radiation is applied for 2 ms, in curve 4208, when the excitation radiation is applied for 5 ms, and in curve 4210, when the excitation radiation is applied for 10 ms.

As shown in FIG. 43, the activated labels can be deactivated (e.g., bleached) by deactivation patterned radiation (e.g., additional patterned excitation radiation) with the same period and phase as the patterned activation radiation and with a peak intensity of 100 W/cm$^2$ to the sample containing the activated labels. The intensity of the patterned excitation radiation over three spatial periods is shown by curve 4202 (in FIG. 42), and the fraction of activated labels at that remain excited and able to provide fluorescence radiation at different points in the spatial period is shown in curve 4304, when the deactivation radiation is applied for 10 ms, in curve 4306, when the deactivation radiation is applied for 15 ms, in curve 4308, when the deactivation radiation is applied for 20 ms, and in curve 4310, when the deactivation radiation is applied for 40 ms.

The FIG. 44 shows the relative strengths of the resulting harmonics when the patterned radiation applied in PA NL-SIM process illustrated in FIGS. 41, 42, and 43, using a saturation factor for the activation radiation, $SF_{act}$, of 2.0.

As can be seen by a comparison of FIGS. 37-44, when the fraction of activated molecules is relatively small and the saturation factor is low, the activation is dominated by a single harmonic. However, when the activation of molecules saturates near unity (See e.g., curve 4110), then higher harmonics are introduced.

Thus, by keeping $SF_{act}$ low, only a small fraction of the total molecular population needed to be activated for every raw image and, with H=2, just N=(2H+1)$^2$=25 such raw images could be acquired to reconstruct each SIM image frame. Consequently, we could acquire substantially more frames at substantially higher SNR in far less time) by PA NL-SIM than by SD NL-SIM.

Figure 45:
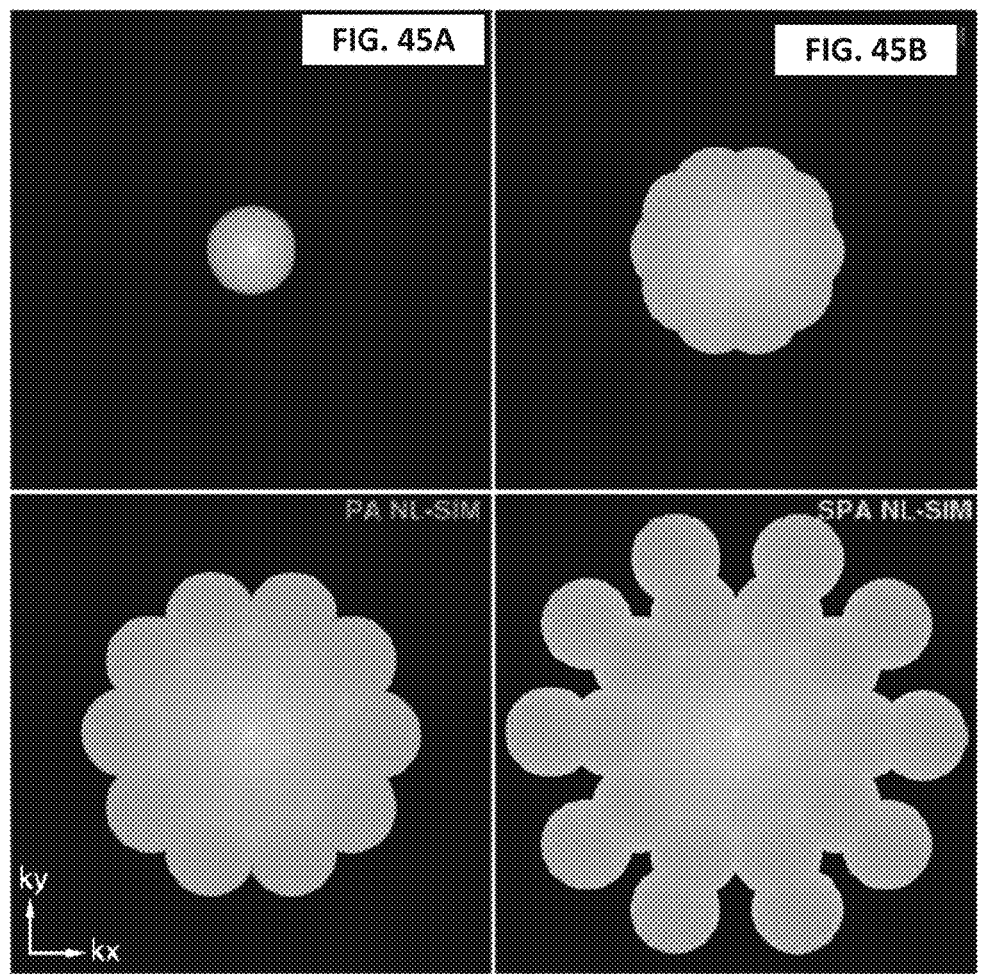
FIGS. 45A, 45B, 45C, and 45D show observable regions of reciprocal space representations of specimen structure shifted from the reciprocal space origin, where the different representations correspond to different orientations and/or phases of a structured pattern overlayed with the specimen structure.

FIGS. 45A, 45B, 45C, and 45D, which are analogous to FIG. 17E, show observable regions of reciprocal space representations of specimen structure shifted from the reciprocal space origin. FIGS. 45A, 45B, 45C, and 45D show the OTFs after compensation for spatial frequency rolloff for diffraction-limited TIRF (FIG. 45A), linear TIRF-SJM with three phases and three orientations (FIG. 45B), PA NL-SIM with five phases and five orientations (FIG. 45C), and saturated PA NL-SIM with seven phases, but only five orientations (FIG. 45D). By using seven phases, but only five orientations for saturated NL-SIM, so that only 35 raw images are required to reconstruct each SIM frame (rather than, N=(2H+1)$^2$=49, for the H=3 harmonics available in saturated PA NL-SIM), the imaging speed is faster, but results in anisotropic resolution extension, as shown in FIG. 48. A comparison of FIGS. 45A, 45B, 45C, and 45D illustrates the Fourier representation of resolution improvement in linear TIRF-SIM and nonlinear SIM compared to TIRF microscopy.

FIGS. 46A, 46B, 46C, and 46D, show linecuts through the OTFs of the corresponding figures of FIGS. 45A, 45B, 45C, and 45D, with a Gamma value of 0.2, and illustrate how PA NL-SIM can lead to a greater than 3× resolution improvement over TIRF, and how saturated PA NL-SIM can lead to a greater than 4× resolution improvement over TIRF.

We also used PA NL-SIM to image keratin and caveolin in living COS-7 cells, each labelled with with Skylan-NS, at a resolution of 59 nm. In the latter case, this was sufficient to resolve numerous caveolae moving by less than their radii during the acquisition time as rings, consistent with their invaginated appearance by EM. Rings of Skylan-NS-caveolin were somewhat more abundant than CCPs and, while most were below 100 nm in size, their distribution was broader than the 60-80 nm range observed in EM. However, some of the larger rings may represent multiple caveolae clustered around surface-docked vesicles. Caveolae also tended to loosely cluster in long narrow ribbons, although we saw tighter aggregations of rings as well, similar to those we saw in clathrin plaques.

Our time lapse imaging showed that most caveolae moved only a fraction of their size during the acquisition time, although more met this condition when slowed by operating at 23° C. than when imaged at 37° C. The smaller, laterally mobile fraction in each case appeared as distorted, discontinuous rings or quasi-periodic patches. These morphologies are indicative of motion-induced artifacts, and they underscore the difficulty of live cell SR imaging, by any method: higher resolution must be accompanied by proportionally faster acquisition times to follow dynamic events of a given velocity, yet higher resolution also requires a quadratically-increasing number of raw measurements for each 2D image frame. Even the comparatively brief 0.35 sec we needed here to acquire N=25 raw images for each PA NL-SIM image was insufficient to accurately depict caveolae moving by much more than our 59 nm resolution in this time.

Figure 46:
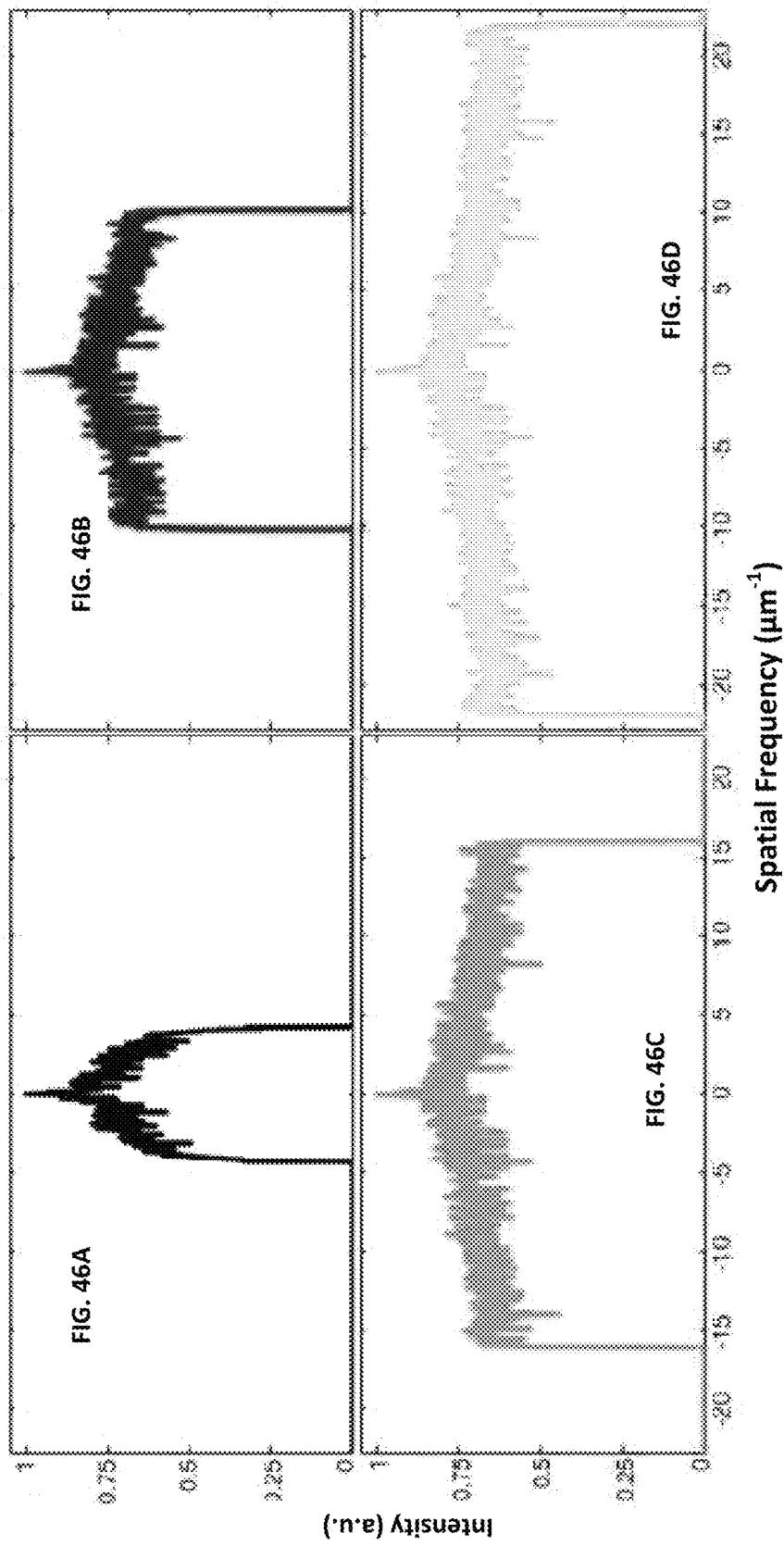
FIGS. 46A, 46B, 46C, and 46D, show linecuts through the OTFs of the corresponding figures of FIGS. 45A, 45B, 45C, and 45D, with a Gamma value of 0.2, and illustrate how PA NL-SIM can lead to a greater than 3× resolution improvement over TIRF, and how saturated PA NL-SIM can lead to a greater than 4× resolution improvement over TIRF.

Nevertheless, by further increasing $SF_{act}$, we were able to saturate the fraction of molecules in the activated state near the maxima of the patterned activation light. Saturated PA NL-SIM generates an additional harmonic (H=3) strong enough to further extend the resolution to 45 nm (as can be seen in FIGS. 44, 45D, and 46D) and allowed us to identify even smaller Skylan-NS-caveolin rings unresolvable without the extra harmonic. Using just N=35, rather than $(2H+1)^2=49$, raw images per frame, we balanced the resulting anisotropic resolution against the needs for rapid acquisition (0.49 sec/frame) and parsimonious use of the photon budget to image caveolin rings over 12 frames at 3 sec intervals.

B. Two-Color Live Imaging Via Combined TIRF-SIM and PA NL-SIM

By combining linear TIRF-SIM and PA NL-SIM, both in TIRF, we could study associations between fluorescent proteins, one conventional and one photoswitchable, in two colors at higher resolution than by linear TIRF-SIM alone. Images and movies of mCherry-Rab5a, a regulator of the formation, fusion, and transport of early endosomes (EEs), revealed irregularly shaped, dynamically remodeling patches of Rab5a consistent with the tubular/vesicular architecture of EEs seen in EM. Numerous patches also featured dark spots perhaps indicative of cargo or internal vacuoles depleted of Rab5a. Most patches moved randomly between successive 20 sec time intervals at velocities slow enough to avoid motion artifacts during each 0.34 sec acquisition. We also observed a sub-population of slowly growing Skylan-NS-Lifeact associated Rab5a patches that were constrained for minutes at a time. At the other extreme, we occasionally observed streaks of Rab5a moving parallel to nearby actin filaments at velocities of 3-5 μm/sec. These may represent EEs actively transported along microtubules (38) parallel to the filaments.

We also used PA NL-SIM and TIRF-SIM, respectively, to study the association of Skylan-NS-Lifeact with mCherry-α-actinin. Consistent with its role as an actin bundling protein, in COS-7 cells we found α-actinin at the treadmilling edge of the lamellepodium and at the basal surface in both filopodia and the leading edges of growing membrane ruffles. We also observed concentrations of α-actinin along the sides and at the branching ends of stress fibers that likely attach to cell-substrate adhesions. Finally, α-actinin was present at dense junctions of Lifeact-decorated filaments and Skylan-NS-Lifeact rings as described above were co-localized in every instance with a mCherry-α-actinin ring of similar size.

C. 3D Live Cell Imaging with Combined PA NL-SIM and Lattice Light Sheet Microscopy Although the ~50-200 nm extent of the evanescent excitation field we used in the examples above eliminated out-of-focus background and confined potentially phototoxic exposure to a minute fraction of the cellular volume, it also limited our observations to this sub-volume and restricted the total photon budget available for those targets unable to be replenished from the cytosol during the imaging interval.

To extend our observations to the entire cell, live cell three-dimensional SIM can be used. Unfortunately, traditional 3D-SIM with linear, widefield excitation brings limitations of its own: it is slow (~20 sec acquisition for whole adherent HeLa cells), limited to thin specimens (due to out-of-focus background), and requires high SNR for accurate image reconstruction. It is also potentially phototoxic and bleaches specimens rapidly, due to continuous whole-cell illumination. These problems would all be greatly magnified in its direct extension to PA NL-SIM.

Figure 47:
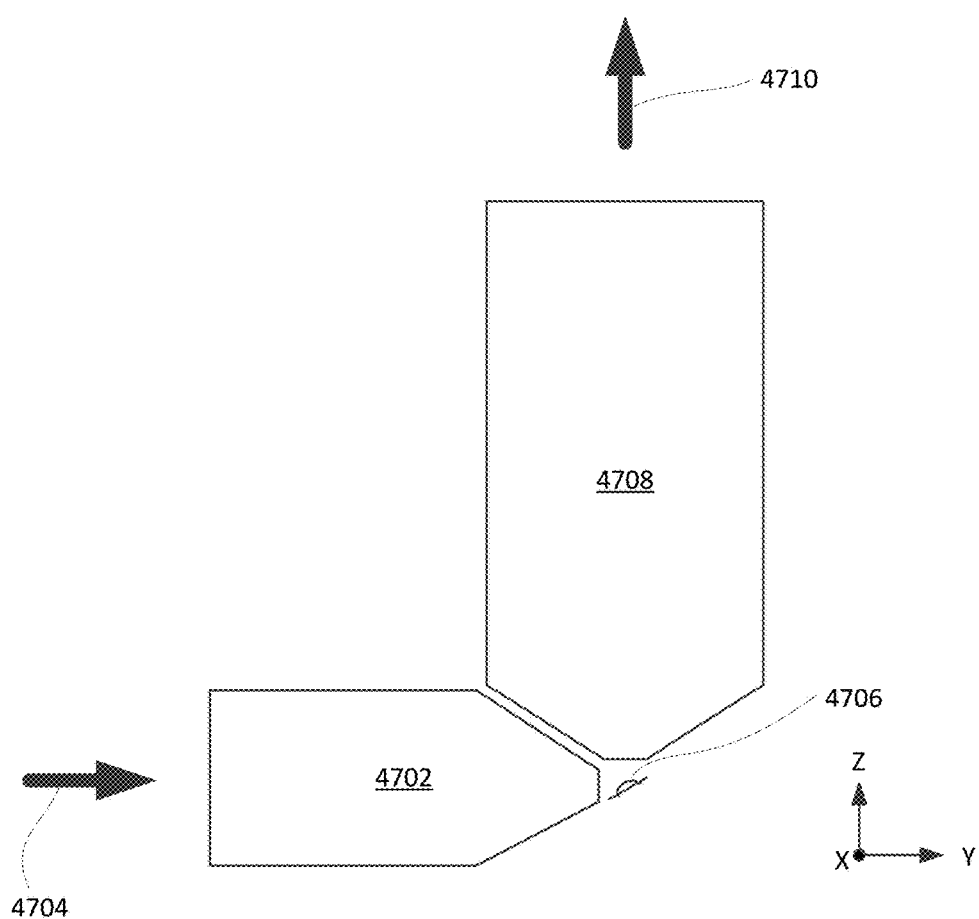
FIG. 47 is as schematic diagram of a system that can be used to apply PA NL-SIM to living cells in 3D.

Thus, to apply PA NL-SIM to living cells in 3D, we used lattice light sheet microscopy in which coherent, spatially-structured light sheets are used to create the optically emitting labels. FIG. 47 is as schematic diagram of a system that can be used to apply PA NL-SIM to living cells in 3D. In this technique, an excitation objective 4702 receives excitation light 4704 to projects a thin sheet of light through a specimen 4706, and the fluorescence generated in the illuminated plane is collected by a detection objective 4708 and then the collected fluorescence 4710 is imaged onto a detector (not shown). Thus, in contrast to the system shown in FIG. 36, in which activation and excitation light is provided to the sample via TIRF and the same objected is used to provide the activation and excitation light as is used to collect the fluorescence light, in the system shown in FIG. 47, the axis of the objective though with the activation and excitation light is provides is substantially perpendicular to the axis of the objective through which the fluorescence light is collected. Repeating this activation and excitation process plane-by-plane through the specimen and collecting the fluorescence light at each plane provides the information to produce a 3D image. Restriction of the light to the detection focal plane reduces or eliminates out-of-focus background, increases the z-axis resolution, and greatly reduces photo-bleaching and phototoxicity.

Figure 48A:
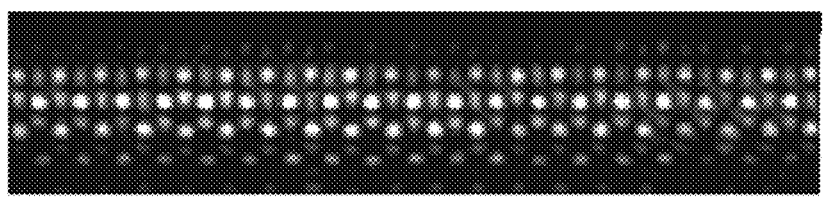
FIGS. 48A and 48B, show example spatial cross-sections of light sheets in the x-z plane that can have the 2D periodic structure of an optical lattice, with FIG. 48A being for the activation light and FIG. 48B being for the excitation light.
Figure 48B:
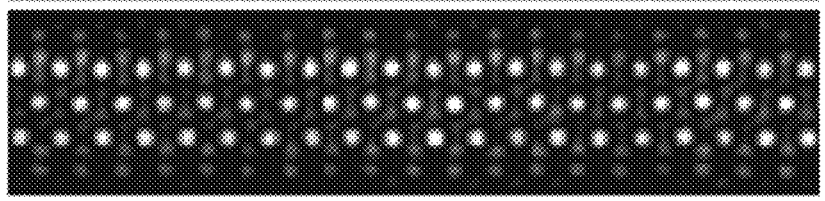

In some implementations, the activation and excitation radiation can be provided in the form of spatially-structured light sheets. FIGS. 48A and 48B, show example spatial cross-sections of light sheets in the x-z plane that can have the 2D periodic structure of an optical lattice, with FIG. 48A being for the activation light and FIG. 48B being for the excitation light.

Sweeping a light sheet back and forth along the x-axis can produce time-averaged uniform illumination, offering high speed and diffraction-limited xyz resolution (e.g., of 230×230×370 nm, as seen in a volume-rendered image of the actin. Stepping the sheet in x in five equal fractions of the lattice period and applying the algorithms of 3D-SIM to the resulting five raw images per plane extends the xyz resolution to 150×230×280 nm, but at the cost of at least five-fold slower imaging speed.

To further extend the 3D resolution via PA NL-SIM, phototransformable optical labels (PTOLSs) (e.g., Skylan-NS) in the sample could be activated with a sheet of activation light. The photoactivating light can be applied in the form of an optical lattice (e.g., a hexagonal lattice light sheet of $\lambda=405$ nm wavelength having H=2 harmonics. After photoactivating the target molecules, a sheet of excitation radiation can be applied, and the resulting fluorescence from the excited labels in the activated region can be imaged. The fluorescence can be excited with a lattice light sheet (e.g., a lattice light sheet created with light of $\lambda=488$ nm wavelength having the same hexagonal symmetry and period as the activation lattice. For activation well below saturation, the combination of the spatially-structured activation and excitation patterns can create a fluorescence emission pattern within the specimen having H=4 harmonics. Thus, to recover the information available from the presence of the higher harmonics, the activation and excitation sheets can be stepped in the x direction in 2H+1=9 equal fractions of the lattice period, while recording nine images. After repeating this process for multiple planes within the specimen, a 3D PA NL-SIM volume-rendered image could be reconstructed with resolution extended to 118×230×170 nm. The volumetric resolution of 3D lattice light sheet PA NL-SIM at the 0.6 NA excitation objective and 1.1 NA detection objective can be comparable to the 105×105×369 nm xyz resolution of widefield 3D-SIM at 1.2 NA. However, the lattice approach has two-fold higher axial resolution, and is four-fold better than traditional diffraction-limited microscopy.

Figure 36:
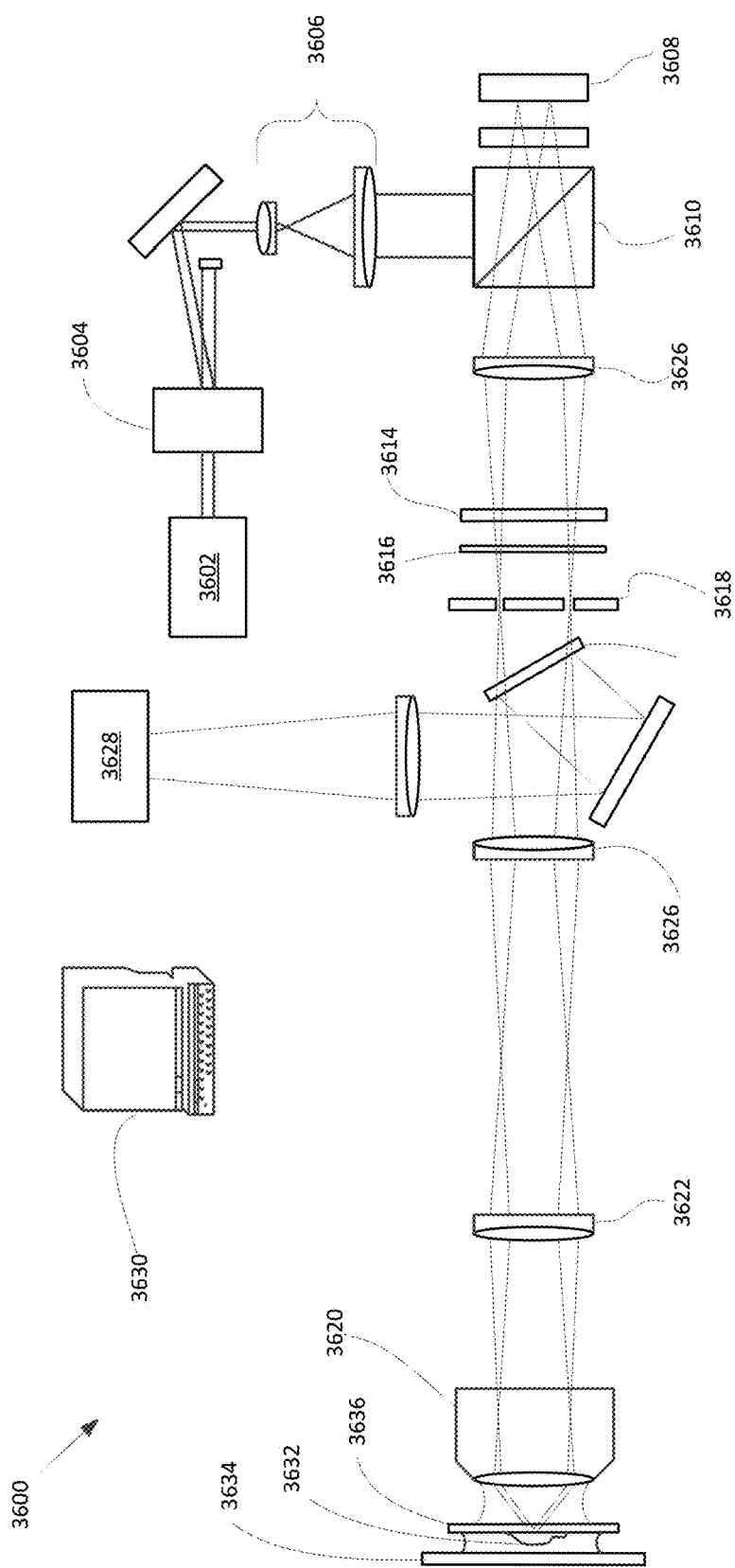
FIG. 36 is a schematic view of another system that can be used to implement the techniques described herein.

FIG. 36 is a schematic view of another system 3600 that can be used to implement the techniques described herein. One or more light sources 3602 (e.g., one or more lasers) can provide one or more radiation beams (e.g., beams of 405 nm activation light and 488 nm excitation and deactivation light) that can be combined and/or that can share an optical pathway. The beams can pass through an acousto-optic tunable filter 3604 that can be used to temporarily divert the beams from the sample and then expanded in a beam expander 3606 (e.g., to a 1/e² diameter of 12 mm), and sent to a wavefront modulating element (e.g., phase-only modulator). The wavefront modification element can include a polarizing beam splitter 3610, an achromatic half-wave plate 3612, and a ferroelectric spatial light modulator (SLM) 3608. In some implementations, a digital micromirror can be used in the wavefront modulating element. Light diffracted by the grating pattern displayed on SLM can pass through a polarization rotator that includes a liquid crystal cell 3614 and an achromatic quarter-wave plate 3616, which rotates the linear polarization of the diffracted light to maintain the s-polarization used to maximize the pattern contrast for all pattern orientations. A mask 3618 that includes a hollow barrel with slots for different pattern orientations can be driven by a galvanometric scanner to filter out diffraction orders created by the binary and pixelated nature of the SLM except for the desired diffraction orders (e.g., the ±1 diffraction orders). The desired diffraction orders are then imaged at the back focal plane of the objective 3620 as two spots at opposite sides of the pupil. After passage through the objective 3620, the two beams can intersect at the interface between the coverslip 3636 and the sample 3632 at an angle exceeding the critical angle for total internal reflection. An evanescent standing wave penetrating ~100 nm into the sample 3632 can be generated thereby, where the evanescent standing wave can include a spatially-structured pattern of activation radiation and/or excitation radiation that is a low-pass filtered image of the SLM pattern. The period, orientation, and relative phase of this pattern can be finely tuned by altering the corresponding pattern displayed on the SLM 3608. For each orientation and phase of the applied excitation pattern, the resulting fluorescence can be collected by the objective 3620, focused by a tube lens 3622 at an intermediate image plane, separated from excitation light by a dichroic mirror 3624 placed between two relay lenses 3626, and reimaged onto a detector 3628, where the structured fluorescence emission pattern is recorded. The specimen can be supported on a movable stage 3634.

The system 3600 can include one or more computing devices 3630 that can serve to control various components of the system 3600. For example, one or more computing devices 3630 can receive signals form the detector 3628 that represent detected fluorescence radiation. The one or more computing devices 3630 can include memory for storing detected radiation data for generating an image of the sample based on the detected radiation. The one or more computing devices 3630 can include one or more processors configured for generating a sub-diffraction-limited final image of the sample based on the stored data for the N positions of the non-linear fluorescence emission pattern within the sample. In addition, the one or more computing devices 3630 can control, for example, the motion of the stage 3634, the patterns applied to the SLM 3608, the AOTF 3604, the galvanometric scanner that drives the mask, etc.

To maximize the amplitudes of the nonlinear harmonics for PA NL-SIM, the spatially-structured (e.g., sinusoidal) patterns of activation light (e.g., 405 nm) and excitation and deactivation light (e.g., 488 nm) can be aligned to precisely overlap one another. As noted above, these patterns at the sample plane are created by displaying corresponding binary grating patterns on an SLM at a corresponding optically conjugate plane. In this case, the period $p_s$ at the specimen is related to the period $p_{SLM}$ at the SLM by:

$$p_s = M_\lambda \cdot p_{SLM} \qquad (1)$$

where M is the de-magnification factor between the two conjugate planes, and is dictated be the focal lengths of the relay lenses between the two planes. Unfortunately, chromatic aberration leads to slightly different focal lengths for even achromatic relay lenses for different wavelengths of light. For example, $M_{405}$ and $M_{488}$ can vary by ~2%. Considering that the sinusoidal interference pattern is composed of hundreds of periods across a typical field-of-view (FOV) of the specimen (e.g., a 45×45 µm² FOV), even a 2% difference can result in significant drift in the relative phases of the 405 and 488 nm excitation patterns across the FOV, leading to spatially variable amplitudes for the nonlinear harmonics and corresponding spatially variable errors in the resulting SIM reconstructions.

A straightforward way to compensate for chromatic aberration and achieve identical periods $p_{s,405}=p_{s,488}$ at the sample is to introduce a period difference $\Delta p_{SLM}$ between the two corresponding patterns at the SLM. In fact, in order to compensate completely and achieve well overlapped 405 and 488 nm excitation patterns over the whole FOV, two parameters can be measured: the initial period difference at the sample, $\Delta p_s^i = p_{s,488}^i - p_{s,405}^i$, when $p_{SLM}$ is the same for both wavelengths; and the phase difference, $\Delta \varphi_s = \varphi_{s,488} - \varphi_{s,405}$, when $p_s$ is the same. To to so, we can use a sample consisting of a dense but sub-monolayer spread of green fluorescent beads excitable at both 405 and 488 nm, and proceed as follows:

Step 1: Keeping $p_{SLM}$ constant, a number N of images of the of the sample sample can be acquired under both 405 and 488 nm sinusoidal excitation, with the phase shifted by $p_{SLM}/N$ for each image at a given wavelength. Then, the structured illumination (SI) reconstruction algorithm can be applied to each set of five images, from which $p_{s,405}^i$ and $p_{s,488}^i$ emerge as measured outputs. For a given period $p_{SLM,488}$ used at the SLM for 488 nm excitation, the corresponding period $p_{SLM,405}$ needed at the SLM for 405 nm excitation to produce the same period $p_s$ at the sample for both wavelengths is then given by:

$$p_{SLM,405} = \left(\frac{p_{s,488}^i}{p_{s,405}^i}\right) p_{SLM,488} \quad (2)$$

Step 2: After adjusting $p_{SLM,405}$ and $p_{SLM,488}$ to obtain the same period $p_s$ at the sample for both wavelengths, a constant phase offset can still exist between the two sinusoidal illumination patterns across the FOV. The phase φ for each wavelength can be measured by applying the sinusoidal illumination for that wavelength, and then recording the position $x_n$ along the modulation direction and intensity $I_n$ for each of N beads scattered across the field of view. Then, this data can be fitted with the function $I(x)=I_{max}[1+\sin(2\pi x/p_s+\varphi)]/2$ to find φ. A phase shift $\Delta\varphi=\varphi_{488}-\varphi_{405}$ is then applied to the SLM pattern for the 405 nm illumination to bring it into phase with the 488 nm illumination at the specimen.

Step 3: Lastly, we can confirm that both the period and phase of the sinusoidal illumination patterns at the two wavelengths match across the entire FOV by re-measuring the periods $p_{s,488}$, $p_{s,405}$ and the phases $\varphi_{488}$, $\varphi_{488}$ as described above and confirming that they are identical.

The spatially-structured illumination patterns can be generated using the wavefront modulating element (e.g., a binary ferroelectric SLM) 3608. The SLM can have sub-millisecond switching times so that the 9 (TIRF-SIM), 25 (PA NL-SIM), or more (saturated PA NL-SIM) raw images of different phase and orientation required to reconstruct a single SIM image can be obtain quickly (e.g., as fast as 100-400 ms). However, care must be taken to account for the finite pixel size of the SLM, especially considering that sub-pixel adjustment accuracy can be necessary to achieve precise pattern overlap at 405 and 488 nm, as described in the previous section. To do this, an algorithm that matches the two pattern periods to 0.02% precision, leading to a phase error no greater than 1.8° over the 45 µm field of view can be used.

Figure 49:
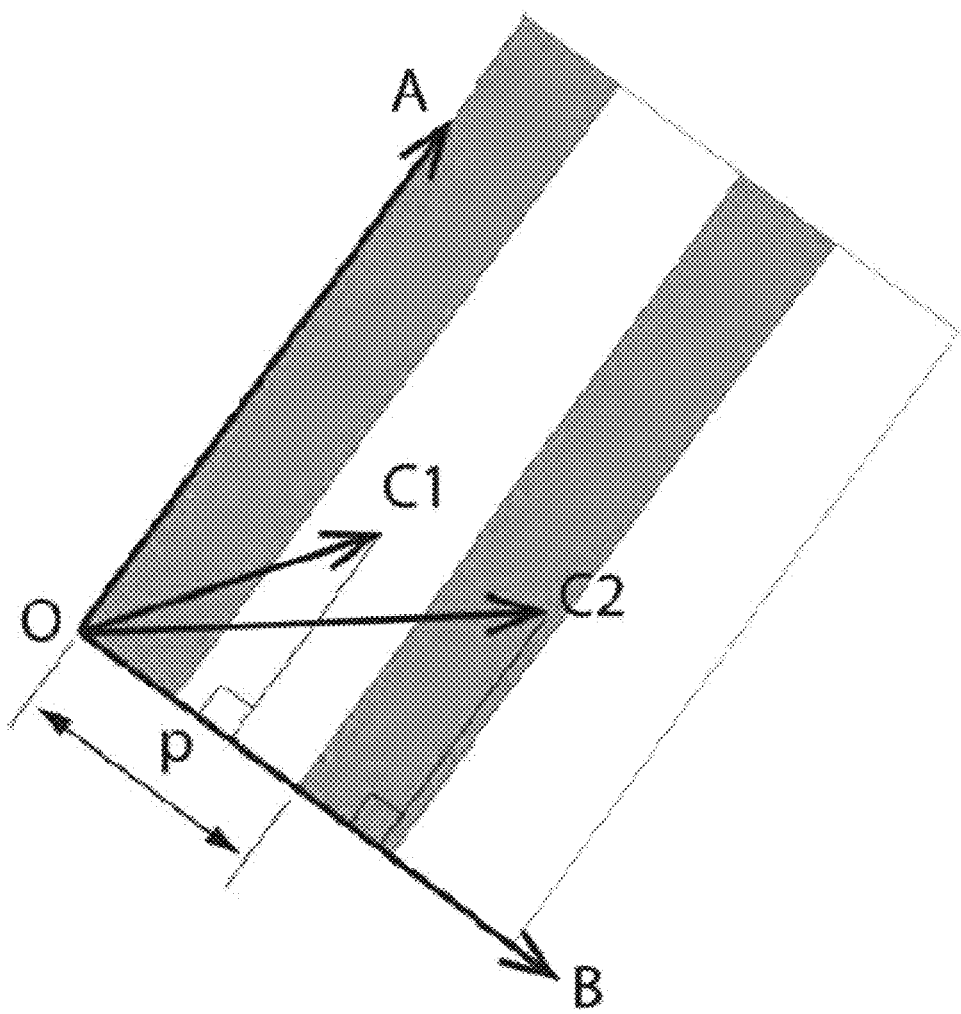
FIG. 49 is a schematic diagram illustrating a pattern generation algorithm.

FIG. 49 is a schematic diagram illustrating a pattern generation algorithm. In detail, a set of radial vectors $\{A_n\}$ can define the desired orientations of the grating pattern at the SLM. The angular orientation of this set of radial vectors relative to the x and y axes can be defined by pixel rows and columns of the SLM can be chosen such that each vector is at least 4° away from either axis. For each orientation represented by $A_n$, a vector $B_n$ that is orthogonal to $A_n$ can be defined. Likewise, for every pixel of the SLM, define a pixel vector can be defined (e.g., C1 or C2 in FIG. 49) from the point O at the intersection of $A_n$ and $B_n$ to the pixel. We can then calculate $F=[(C\cdot B) \bmod p]/p$, the fraction of the period p by which the pixel extends beyond an integral number of periods on the SLM. For a pattern with a desired off fraction D per period (D=0.5 in 2D SIM), the pixel is set to 0 if F<D and set to 1 otherwise. Finally, to define the pixel patterns required for the other N−1 phases of the illumination for a given orientation, the point O can be translated along $B_n$ in steps of p/N, and this process can be repeated with the new vector C for each pixel. This approach does not rely on unit-cell repetition, and therefore does not succumb to error accumulation over the entire span of the SLM.

When extending PA NL-SIM to 3D, it is useful to minimize out-of-focus fluorescence emission that can cause the shot noise in the DC harmonic to overwhelm the weak signals in the nonlinear harmonics. To accomplish this, as described above, we turned to the SIM mode of lattice light sheet microscopy. We introduced the nonlinear harmonics through patterned activation of Skylan-NS labels in the specimen. The excitation objective can be placed perpendicular to the detection objective (i.e., the excitation path from the excitation objective to the specimen can be perpendicular to the detection path from the specimen to the detection objective) to confine the illumination to the proximity of the latter's focal plane, as shown in FIG. 47. The lattice pattern projected on the SLM can be imaged onto the focal plane of the excitation objective 4702, after the excitation is first spatially filtered by an annular mask and relayed by a pair of galvanometers that phase step the pattern in the x direction and scan the light sheet in the z direction. Also, as in 2D PA NL-SIM, the periods and phases of the activation light (e.g., 405 nm) and the excitation and deactivation light (e.g., 488 nm) lattices can be matched by measuring their excitation profiles across the field of view using fluorescent beads and adjusting accordingly. The fluorescence emission can be collected by the detection objective 4708, and imaged by a tube lens onto a detector. A 3D image can be formed by repeating this process as the sample is translated through the light sheet with a piezoelectric stage along an axis s in the plane of the cover slip or by repeating the process as the light sheets are translated through sample, and a 3D super-resolution NL-SIM image is reconstructed as described below.

For NL-SIM, including PA NL-SIM and Saturated PA NL-SIM, we used a 1.49 NA TIRF objective, and with this objective, we were able to achieve high modulation contrast, while stably and precisely overlapping the 405 and 488 nm standing waves over the whole field-of-view. An excitation NA of 1.44 was used for both 488 and 560 nm light in this case, leading to 62 nm resolution for PA NL-SIM when using green emitting FPs. In addition, we used 1.57 NA objective in combination with a high refractive index immersion oil that did not absorb 405 nm light strongly, and therefore could be used to maintain precisely overlapped 405 and 488 nm standing waves with high modulation contrast at 37° C. and 5% $CO_2$. The excitation NA in this case was 1.52 for 488 nm light, leading to 59 nm resolution for PA NL-SIM when using green emitting FPs.

The exposure procedure for a single phase step in NL-SIM can include: (1) illumination of the sample with spatially-patterned activation radiation (e.g., 405 nm radiation) for a time period (e.g., 1 ms) to activate the fluorescent molecules; (2) illumination of the sample with spatially-patterned excitation radiation (e.g., 488 nm patterned illumination) for a time period (e.g., 5~30 ms) to read-out the activated molecules. In some implementations, (3) uniform (e.g., widefield) illumination with de-activating radiation (e.g., 488 nm radiation) can be applied for a time period (e.g., 2~10 ms) to read-out the remaining activated molecules and return the emitting labels in the sample back to the original unactivated state. The fluorescence from both steps (2) and (3) can be collected to reconstruct the SR image. Depending on the number of modulation harmonics H of significant amplitude in the image (e.g., H=2 for PA-NL-SIM and H=3 or possibly more for saturated PA NL-SIM), this sequence can be repeated for 2H+1 raw images at each of 2H+1 angular orientations equally spaced around 360° for a total of $(2H+1)^2$ raw images at each NL-SIM time point. In some implementations (e.g., with saturated PA-NL-SIM), to reduce the acquisition time, fewer than the full 2H+1 angular orientations could be used (e.g., only five orientations rather than seven for H=3).

Figure 51A:
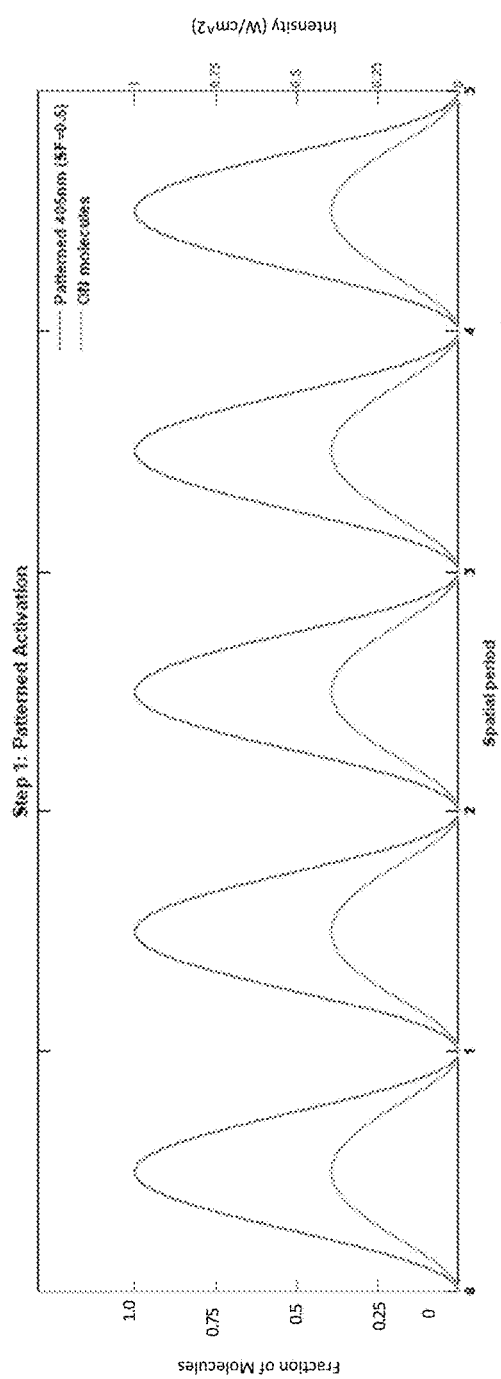
FIG. 51A and FIG. 51B are schematic diagrams, showing an example of spatially-structured excitation pattern being provided in-phase with a spatially-structured activation pattern, and the resulting fraction of molecules in the activated state.
Figure 51B:
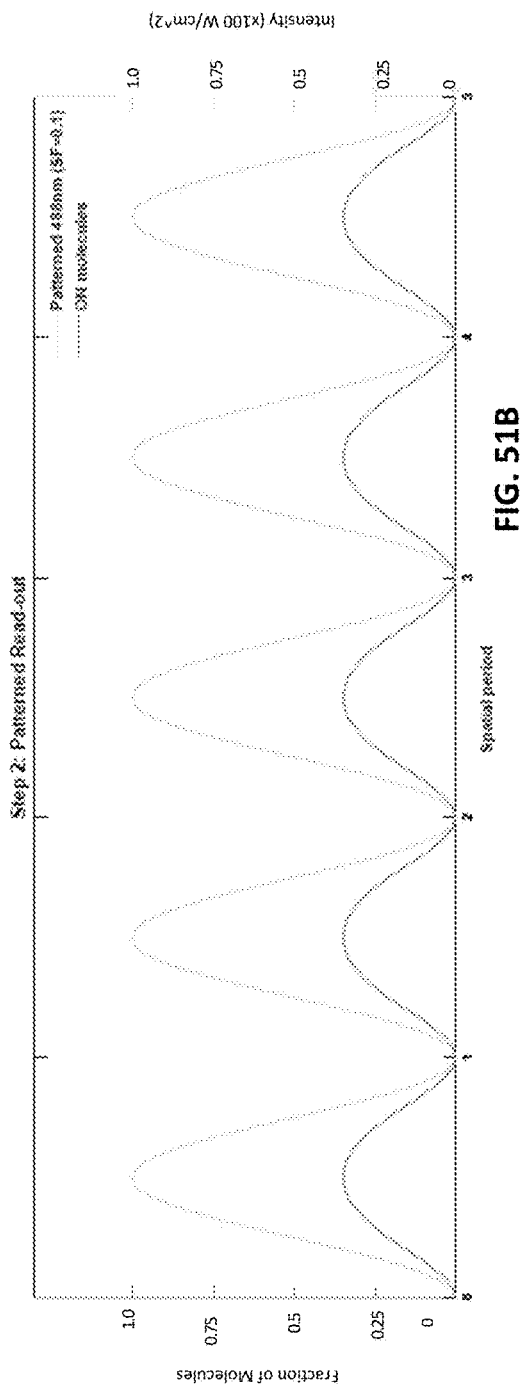

Control of the phase between the spatially-structured activation pattern and the spatially-structured excitation pattern can result in a non-linear fluorescence pattern that has harmonics of different strengths. For example, in some implementations, the spatially-structured excitation pattern can be in-phase with the spatially-structured activation pattern. FIG. 51A and FIG. 51B are schematic diagrams, showing an example of the spatially-structured excitation pattern being provided in-phase with the spatially-structured activation pattern, and the resulting fraction of molecules in the activated state. FIG. 51A shows spatially-structured activation pattern with a saturation factor of 0.5 applied to a hypothetical sample having a uniform distribution of photoswitchable optical labels and the resulting pattern of the fraction of activated labels. FIG. 51B shows spatially-structured excitation pattern with a saturation factor of 0.1 applied to the hypothetical sample, where the spatially-structured excitation pattern is in-phase with the spatially-structured activation pattern, and the resulting pattern of the fraction of activated labels.

Figure 52C:
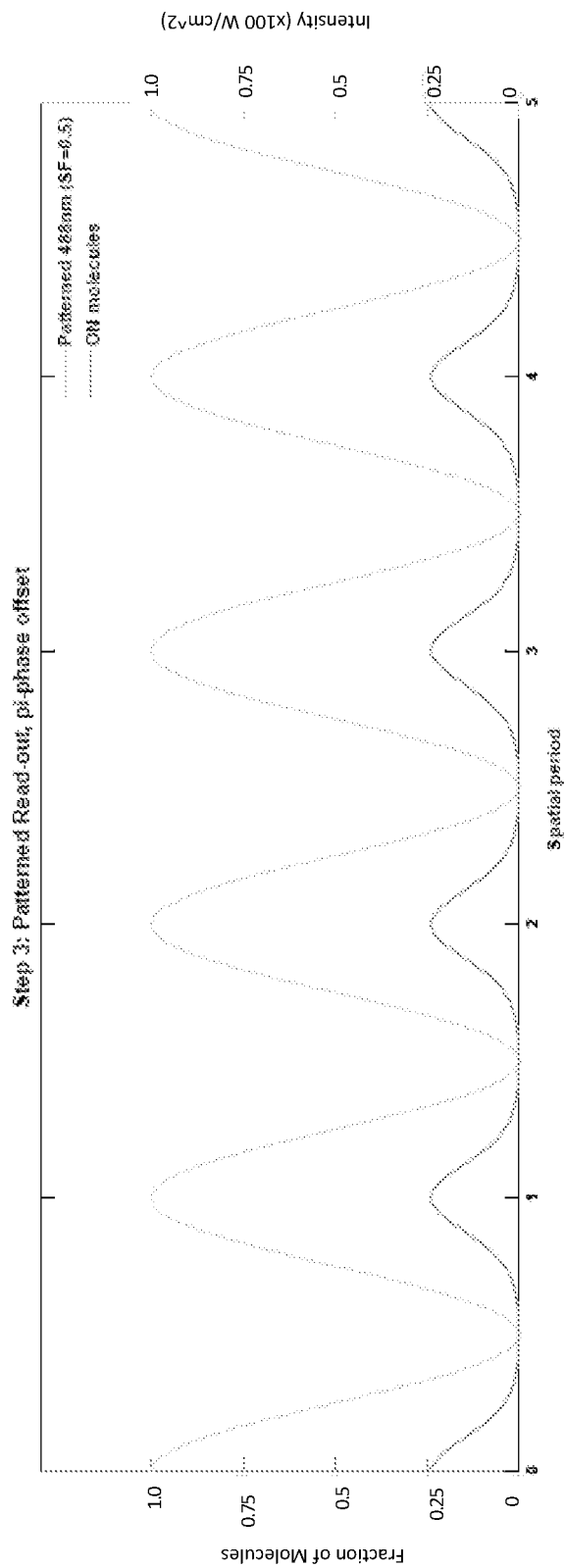

FIG. 52A, FIGS. 52B, and 52C are schematic diagrams, showing an example of spatially-structured excitation patterns being provided out-of-phase with the spatially-structured activation pattern, and the resulting fraction of molecules in the activated state. FIG. 52A shows spatially-structured activation pattern with a saturation factor of 0.5 applied to a hypothetical sample having a uniform distribution of photoswitchable optical labels and the resulting pattern of the fraction of activated labels. FIGS. 52B and 52C shows spatially-structured excitation patterns with a saturation factors of 3.0 and 0.5, respectively, that can be applied to the hypothetical sample in two successive readout steps, where the spatially-structured excitation pattern of FIG. 52B is out-of-phase by $\pi$ with the spatially-structured activation pattern and where the spatially-structured excitation pattern of FIG. 52C is out-of-phase by $\pi$ with the spatially-structured excitation pattern of FIG. 52B. The resulting fraction of molecules in the activated state shown in FIGS. 52B and 52C indicates that these patterns contain more information in higher harmonics than shown in FIG. 51B, when the spatially-structured excitation pattern being provided in-phase with the spatially-structured activation pattern. The fluoresence light gathered in different readout step can be processed separately to extract the information in the higher order harmonics available in the fluoresence light gathered in each readout step and then used to construct a sub-diffraction limited image of the sample. Other phase differences between the spatially-structured excitation pattern(s) used to excite fluoresence and the spatially-structured activation pattern can be used, and different numbers of readout steps can be used.

In two-color imaging combining linear TIRF-SIM and PA NL-SIM, at each time point, we acquired the PA NL-SIM image as discussed above. However, we could acquire the TIRF-SIM image with five instead of three orientations (i.e., 15 raw images for the TIRF-SIM channel at every time point), in order to match the orientations of the five-slot, galvanometer-driven barrel mask used to pick out the desired diffraction orders for the PA NL-SIM acquisition.

For 3D PA NL-SIM with lattice light sheet microscopy, various lattice patterns can be used (e.g., a hexagonal lattice) having a period large enough to contain two harmonics for each of the spatially-structured activation and excitation patterns—one harmonic just beyond the Abbe limit of the excitation objective, and the other at twice this period. The product of these patterns can create a fluorescence emission pattern containing H=4 harmonics. However, with a single excitation objective, we were limited to producing this pattern at only one orientation. Therefore, at a plane of the 3D stack, 2H+1=9 images could be acquired, resulting in improved resolution in both the lateral and axial directions of the pattern.

The raw image frames generated with patterned excitation can be processed and reconstructed into the super-resolved images by, for each pattern orientation with H modulation harmonics, collecting 2H+1 raw images and Fourier transforming each image into 2H+1 information components. These components can be assembled by initially translating each in Fourier space by a distance equal to the amplitude of the illumination pattern vector $nk_0$, where $k_0$ is the spatial frequency of the illumination pattern and n=−H to H. The pattern vector of each information component can be fine-tuned by finding the vector that maximizes the complex cross-correlation in the overlap region between successive components. The modulation amplitude of the harmonic and its starting phase can be found through complex linear regression. If the modulation amplitudes for the highest harmonics are too low for this empirical approach to work well, the theoretical values of their complex amplitudes can be used. After fine tuning the positions and complex amplitudes of the information components in the overlap regions, a generalized Wiener filter can be applied to this expanded transfer function to balance the amplitudes of the various spatial frequencies against the underlying noise. Next, an apodization function can be applied to minimize ringing artifacts when the result is Fourier transformed back to real space. In some implementations, a triangle apodization $A(k)=1-k/k_{max}$ can be used. In some implementations, we apply a gamma apodization $A(k)=1-(k/k_{max})^\gamma$, (e.g., using $\gamma=0.4$), so that the higher spatial frequencies are not suppressed more than necessary. Furthermore, we can strictly follow the azimuthally dependent support $k_{max}(\theta)$ of the expanded OTF to define the endpoint of the apodization function, which provides additional suppression of ringing artifacts. For the time series data, we independently implement this reconstruction process for each time point.

Samples can be prepared with optical labels in a variety of ways. A few examples are described here. For example, BSC-1, COS-7, U2OS and MEF cells (American Type Culture Collection) were grown to ~60-80% confluency in Dulbecco's modified eagle medium (DMEM) with high glucose and no phenol red supplemented with 15% fetal bovine serum (Life Technologies). BSC-1 cells stably expressed EGFP-clathrin-LCA. Other cells were transiently transfected with an Amaxa Nucleofector 96-well shuttle system (Lonza) with 1 ug DNA per 400,000 cells with nucleofection solution and a program optimized for each cell line per the manufactures instructions. Before imaging, 25 mm or 5 mm coverslips were coated with 10 ug/ml fibronectin (Millipore, FC010) for 24 hours prior to plating transfected cells. Imaging was performed in DMEM with HEPES containing no phenol red at temperatures specifically stated in each case.

In two-color imaging of clathrin coated pits and transferrin receptors (TfR) by high NA TIRF-SIM, MEF cells expressing clathrin light chain B fused to the C terminal of mEmerald were incubated with DMEM medium containing 250 μg/mL TfR bound to human transferrin conjugated with Alexa 568 (T23365, Life Technologies) for 15 min.

Fixed cells were treated for 15 min with fixation buffer containing 4% paraformaldehyde, 0.1% Gluteraldehyde in PHEM buffer (25 mM HEPES, 10 mM EGTA, 2 mM MgCl$_2$, and 120 mM PIPES in pH 7.3).

For each image frame, the clathrin coated pits (CCPs) were segmented using a watershed algorithm written in Matlab (MathWorks, 2014a), and their centroids measured individually. Subsequently, the centroid position was linked between time points using u-track 2.1. This linking operation collected successive position information for each pit over the entire endocytic process from initiation to final internalization. It was then straightforward to determine the lifetime for each endocytic event.

In order to precisely measure the pit diameter, we first measured the system magnification to the camera by imaging a standard fine counting grid (2280-32, Ted Pella, Inc.). The SIM image of each CCP was then deconvolved with the equivalent PSF of the SIM system to compensate for the broadening due to the finite resolution of the instrument. Finally, the diameter of each deconvolved pit was measured using an intensity-weighted average radius relative to the centroid of the pit. In certain cases, pits were color coded at each time point based on the time since their initiation to the current time point.

One challenge in this analysis was how to identify isolated pits rather than aggregates, and how to be sure that these represented true pits rather noise or disorganized patches of non-assembled clathrin. To accomplish this, we set some conditions during the analysis, such as that a pit must start as a spot and then evolve into a ring at at least one time point. When analyzing the correlation between pit lifetime and maximum diameter, we added the further constraint of including only those pits formed after the first frame, to insure that we could accurately measure the entire lifetime.

When measuring the associations of actin with clathrin, we first implemented the tracking algorithm above to obtain time-lapse CCP images for each endocytic event. We then created a mask for each CCP identified in each frame, equal to the CCP size plus an additional boundary of one pixel. We then applied these masks to each frame of lifeact data, and integrated the actin fluorescence within each CCP-derived mask. If the actin signal integrated over the area of a given mask increased during the final five frames of the life of the associated CCP, it was decided that actin was recruited to the CCP during the final stage of endocytosis.

Figure 50:
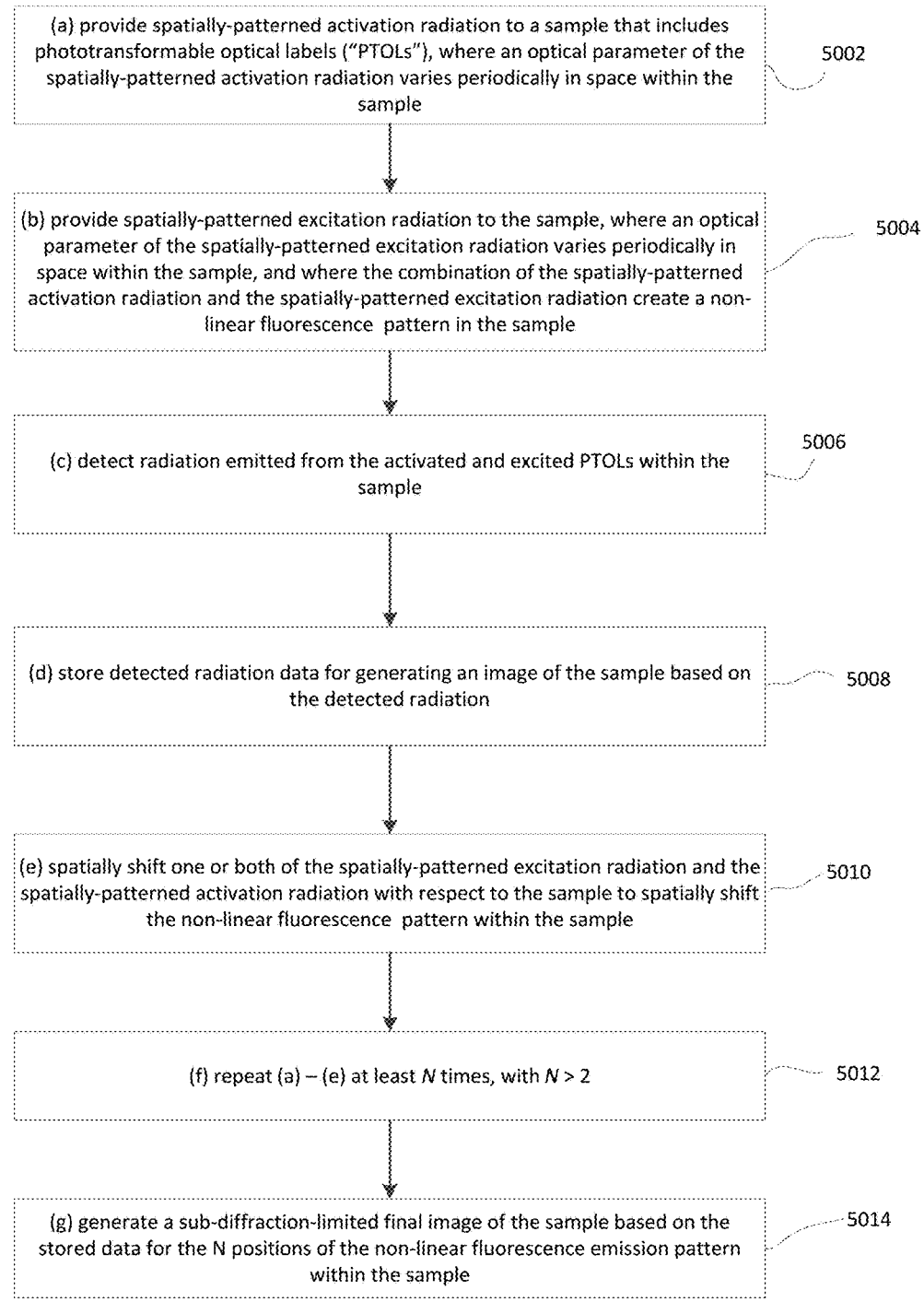
FIG. 50 is an example flowchart of a method for imaging a sample.

FIG. 50 is an example flowchart of a method 50 for imaging a sample. In the method 50, spatially-patterned activation radiation is provided to the sample, where the sample includes phototransformable optical labels ("PTOLs"), and where an optical parameter of the spatially-patterned activation radiation varies periodically in space within the sample (5002). A subset of the PTOLs having a density of activated PTOL that varies according to the periodicity of the optical parameter of the spatially-patterned activation radiation can activated by the activation radiation. Spatially-patterned excitation radiation is provided to the sample, where an optical parameter of the spatially-patterned excitation radiation varies periodically in space within the sample (5004). The combination of the spatially-patterned activation radiation and the spatially-patterned excitation radiation creates a non-linear fluorescence emission pattern within the sample, the pattern including H modulation harmonics, with H>1. Radiation emitted from the activated and excited PTOLs within the sample is detected (5006). Detected radiation data for generating an image of the sample based on the detected radiation is stored (5008). One or both of the spatially-patterned excitation radiation and the spatially-patterned activation radiation is spatially shifted with respect to the sample to spatially shift the non-linear fluorescence emission pattern within the sample (5010). Steps 5002 through 5010 are repeated at least N times, with N>2 (5012). In some implementations, N≥5 and in some implementations, N≥7. Then, a sub-diffraction-limited final image of the sample is generated based on the stored data for the N positions of the non-linear fluorescence emission pattern within the sample (5014).

In some implementations, a spatial period, Λ, of the periodic variation of the optical parameters of the activation and excitation radiation can be the same, and in some implementations, the periodic variation of both the activation radiation and the excitation radiation is a sinusoidal variation.

In some implementations, H≥2, and the detected signal includes spatial frequency components at −2Λ, −Λ, 0, Λ, and 2Λ. In some implementations, H≥3, and the detected signal includes spatial frequency components at −3Λ, −2Λ, −Λ, 0, Λ, 2Λ, and 3Λ.

In some implementations, the periodically varied optical parameter of the excitation and activation radiation is the intensity of the radiations and the intensities of both the activated and excited radiation is below the saturation limit, and in some implementations, the intensity of the activated radiation is above the saturation limit. In some implementations, the excitation radiation can have a wavelength, λ, and the detected radiation can have a wavelength λ/2, and in some implementations, the activation radiation can have a wavelength, λ', and the PTOLs can be activated through a two-photon activation process.

In some implementations, the patterns of the activation and excitation radiation are in-phase, and in some implementations, the patterns of the activation and excitation radiation are out of phase. When the patterns are out of phase, providing the spatially-patterned excitation radiation to the sample can includes providing first spatially-patterned excitation radiation to the sample, where the first spatially-patterned excitation radiation has a first phase, $\varphi_1$, relative to the pattern of the activation radiation, and providing second spatially-patterned excitation radiation to the sample, where the second spatially-patterned excitation radiation has a second phase, $\varphi_2$, relative to the pattern of the activation radiation, where in $\varphi_1 \neq \varphi_2$. For example, in some implementations, $\varphi_1 - \varphi_2 = 180$ degrees, and in some implementations, $\varphi_1 = 180$ degrees and $\varphi_2 = 0$ degrees.

In some implementations, providing the spatially-patterned activation radiation can include modulating a beam of activation radiation with a wavefront modulating element (WME) to provide a desired pattern of activation radiation in the sample. In some implementations, providing the spatially-patterned excitation radiation can include modulating a beam of excitation radiation with a WME to provide a desired pattern of excitation radiation in the sample. The WME can include a spatial light modulator (SLM) and/or a digitial micromirror (DMD), and in some implementations, the beams of activating and excitation radiation are modulated by the same WME. In some implementations, providing the the activating and excitation radiation have different wavelengths, and a pattern on the WME used to modulate the excitation radiation can have a different period than a pattern on the WME used to modulate the activation radiation. The different patterns for the different wavelengths on the WME can be chosen to provide patterns of excitation and activation radiation at the sample that have the same period.

In some implementations, providing the spatially-patterned activation radiation includes providing the activation radiation via TIRF illumination of the sample, and in some implementations, providing the spatially-patterned excitation radiation can include providing the excitation radiation via TIRF illumination of the sample.

In some implementations, providing the spatially-patterned activation/excitation radiation can include: providing a beam of activation/excitation radiation and sweeping the beam in the direction parallel to the plane of a first sheet, and varying the optical parameter of the radiation while sweeping the beam. In some implementations, the beam of excitation radiation can be a Bessel-like beam. For example, the Bessel-like beam can include a beam that has a ratio of a Rayleigh length, $z_R$ to a minimum beam waist, $w_o$, of more than $2\pi w_o/\lambda$ and less than $100\pi w_o/\lambda$, where $\lambda$ represents the wavelength of the excitation radiation or a beam that has a non-zero ratio of a minimum numerical aperture to a maximum numerical aperture of less than 0.95, or less than 0.90, or a beam that has a minimum numerical aperture greater than zero and a ratio of energy in a first side lobe of the beam to energy in the central lobe of the beam of less than 0.5.

In some implementations, providing the spatially-patterned excitation radiation in which an optical parameter of the second sheet varies periodically can include providing the beam of excitation radiation in the form of a light sheet, for example, a lattice light sheet.

In some implementations, steps 5002 through 5012 can be repeated a plurality of sequential times and generating a plurality of sub-diffraction-limited final images of the sample for each of the sequential times based on the stored data for each of the sequential times and for the N positions of the non-linear pattern of activated and excited PTOLs within the sample. In some implementations, the activation and excitation radiation can be provided to substantially the same plane in the sample at each of the sequential times. Then, a sequence of images in time of the sample can be generated, and the sequence of images can be used, for example, to generate a movie of events in the sample. In some implementations, the activation and excitation radiation can be provided to different planes in the sample at each of the sequential times, where the activation and excitation radiation are provided to the same plane in the sample at each of the sequential times, each of the different planes being substantially parallel to each other. Then, a sequence of images of the sample in space can be generated, and the sequence of images can be used, for example, to generate a 3D image of the sample.

In some implementations, an intensity of the excitation radiation can be less than about 125 W/cm$^2$ or less than about 500 W/cm$^2$, and in some implementations, repeating steps 5002 through 5010 can be performed in less than 0.5 seconds.

In some implementations, deactivating radiation can be provided each time that steps 5002 through 5010 are repeated. For example, deactivating radiation can be provided to the activated PTOLs to deactivate a portion of the activated PTOLs, such that the non-linear pattern within the sample includes H>2 modulation harmonics. For example, in some implementations, the deactivating radiation can be applied before to stimulate the emission of activated labels, to deplete some activated labels located near high-intensity regions of the deactivating radiation from contributing to the detected fluorescence radiation. In some implementations, the deactivating radiation has a wavelength that is different from the activating wavelength, and in some implementations, the deactivation radiation includes the spatially-patterned excitation radiation that is provided to the sample.

In some implementations, spatially shifting one or both of the spatially-patterned excitation radiation and the spatially-patterned activation radiation can include spatially shifting one or both of the spatially-patterned excitation radiation and the spatially-patterned activation in a linear direction with respect to the sample to spatially shift the non-linear pattern of activated and excited PTOLs within the sample in the linear direction. The method can further include shifting rotational orientation of the non-linear pattern of activated and excited PTOLs within the sample a number, M (e.g., M≥2H+1), of times and then repeating steps 5002 through 5010 at least N times, with N>2, for each rotational orientation of the pattern.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the implementations.

What is claimed is:

1. A method comprising:
(a) providing spatially-patterned activation radiation to a sample that includes phototransformable optical labels ("PTOLs"), wherein an optical parameter of the spatially-patterned activation radiation varies periodically in space within the sample;
(b) providing spatially-patterned excitation radiation to the sample, wherein an optical parameter of the spatially-patterned excitation radiation varies periodically in space within the sample,
wherein (a) and (b) create a non-linear fluorescence emission pattern within the sample, the pattern including H modulation harmonics, with H>1;
(c) detecting radiation emitted from the activated and excited PTOLs within the sample;
(d) storing detected radiation data for generating an image of the sample based on the detected radiation;
(e) spatially shifting one or both of the spatially-patterned excitation radiation and the spatially-patterned activation radiation with respect to the sample to spatially shift the non-linear fluorescence emission pattern within the sample;
(f) repeating (a)-(e) at least N times, with N>2; and
(g) generating a sub-diffraction-limited final image of the sample based on the stored data for the N positions of the non-linear fluorescence emission pattern within the sample.

2. The method of claim 1, wherein a spatial period, $\Lambda$, of the periodic variation of the optical parameters of the activation and excitation radiation is the same.

3. The method of claim 1, wherein the periodic variation of both the activation radiation and the excitation radiation is a sinusoidal variation.

4. The method of claim 2, wherein the patterns of the activation and excitation radiation are in-phase.

5. The method of claim 2, wherein the patterns of the activation and excitation radiation are out of phase.

6. The method of claim 5, wherein providing the spatially-patterned excitation radiation to the sample, includes:
providing first spatially-patterned excitation radiation to the sample, wherein the first spatially-patterned excitation radiation has a first phase, $\varphi_1$, relative to the pattern of the activation radiation; and
providing second spatially-patterned excitation radiation to the sample, wherein the second spatially-patterned excitation radiation has a second phase, $\varphi_2$, relative to the pattern of the activation radiation, wherein $\varphi_1 \neq \varphi_2$.

7. The method of claim 6, wherein $\varphi_1-\varphi_2=180$ degrees.

8. The method of claim 2, wherein providing the spatially-patterned excitation radiation to the sample, includes:
providing first spatially-patterned excitation radiation to the sample, wherein the first spatially-patterned excitation radiation has a phase of 180 degrees relative to the pattern of the activation radiation; and
providing second spatially-patterned excitation radiation to the sample, wherein the second spatially-patterned excitation radiation is in phase with the pattern of the activation radiation.

9. The method of claim 2, wherein the patterns of the activation and excitation radiation are 180 degrees out of phase.

10. The method of claim 2, wherein H≥2, and the detected signal includes spatial frequency components at $-2\Lambda$, $-\Lambda$, 0, $\Lambda$, and $2\Lambda$.

11. The method of claim 2, wherein H≥3, and the detected signal includes spatial frequency components at $-3\Lambda$, $-2\Lambda$, $-\Lambda$, 0, $\Lambda$, $2\Lambda$, and $3\Lambda$.

12. The method of claim 1, wherein the periodically varied optical parameter of the excitation and activation radiation is the intensity of the radiations and wherein the intensities of both the activated and excited radiation is below the saturation limit.

13. The method of claim 1, wherein the periodically varied optical parameter of the excitation and activation radiation is the intensity of the radiations and wherein the intensity of the activated radiation is above the saturation limit.

14. The method claim 1, wherein the periodically varied optical parameter of the excitation and activation radiation is the intensity of the radiations and wherein the intensity of the excitation radiation is above the saturation limit.

15. The method of claim 1, wherein the excitation radiation has a wavelength, $\lambda$, and the detected radiation has a wavelength $\lambda/2$.

16. The method of claim 1, wherein the activation radiation has a wavelength, $\lambda'$, and the PTOLs are activated through a two-photon activation process.

17. The method of claim 1, wherein N≥7.

18. The method of claim 1, wherein providing the spatially-patterned activation radiation includes modulating a beam of activation radiation with a wavefront modulating element (WME) to provide a desired pattern of activation radiation in the sample.

19. The method of claim 1, wherein providing the spatially-patterned excitation radiation includes modulating a beam of excitation radiation with a WME to provide a desired pattern of excitation radiation in the sample.

20. The method of claim 18, wherein the WME includes a spatial light modulator (SLM).

21. The method of claim 18, wherein the WME includes an digitial micromirror (DMD).

22. The method of claim 18, wherein the beams of activating and excitation radiation are modulated by the same WME.

23. The method of claim 22, wherein activating and excitation radiation have different wavelengths, and wherein a pattern on the WME used to modulate the excitation radiation has a different period than a pattern on the WME used to modulate the activation radiation.

24. The method of claim 23, wherein the different patterns for the different wavelengths on the WME are chosen to provide patterns of excitation and activation radiation at the sample that have the same period.

25. The method of claim 1, wherein providing the spatially-patterned activation radiation includes providing the activation radiation via TIRF illumination of the sample.

26. The method of claim 1, wherein providing the spatially-patterned excitation radiation includes providing the excitation radiation via TIRF illumination of the sample.

27. The method of claim 1, wherein providing the spatially-patterned activation radiation includes:
providing a beam of activation radiation; and
sweeping the beam of activation radiation in the direction parallel to the plane of a first sheet; and
varying the optical parameter of the activation radiation while sweeping the beam.

28. The method of claim 1, wherein providing the spatially-patterned excitation radiation in which an optical parameter of a second sheet varies periodically includes:
providing a beam of excitation radiation; and
sweeping the beam of excitation radiation in the direction parallel to the plane of the first sheet; and
varying the optical parameter of the excitation radiation while sweeping the beam of excitation radiation.

29. The method of claim 28, wherein the beam of excitation radiation includes a Bessel-like beam.

30. The method of claim 29, wherein the Bessel-like beam has a ratio of a Rayleigh length, $z_R$ to a minimum beam waist, $w_o$, of more than $2\pi w_o/\lambda$ and less than $100\pi w_o/\lambda$, wherein $\lambda$ represents the wavelength of the excitation radiation.

31. The method of claim 28, wherein the Bessel-like beam has a non-zero ratio of a minimum numerical aperture to a maximum numerical aperture of less than 0.95.

32. The method of claim 29, wherein the Bessel-like beam has a non-zero ratio of a minimum numerical aperture to a maximum numerical aperture of less than 0.90.

33. The method of claim 29, wherein the Bessel-like beam has a minimum numerical aperture greater than zero and a ratio of energy in a first side lobe of the beam to energy in the central lobe of the beam of less than 0.5.

34. The method of claim 1, wherein providing the spatially-patterned excitation radiation in which an optical parameter of the second sheet varies periodically includes:
providing the beam of excitation radiation in the form of a light sheet.

35. The method of claim 34, wherein the light sheet includes a lattice light sheet.

36. The method of claim 1, further comprising:
repeating (a)-(f) at a plurality of sequential times; and
generating a plurality of sub-diffraction-limited final images of the sample for each of the sequential times based on the stored data for each of the sequential times and for the N positions of the non-linear fluorescence emission pattern within the sample.

37. The method of claim 36, further comprising providing the activation and excitation radiation to substantially the same plane in the sample at each of the sequential times.

38. The method of claim 36, further comprising providing the activation and excitation radiation to different planes in the sample at each of the sequential times, wherein the activation and excitation radiation are provided to the same plane in the sample at each of the sequential times, each of the different planes being substantially parallel to each other.

39. The method of claim 1, wherein an intensity of the excitation radiation is less than about 125 W/cm$^2$.

40. The method of claim 1, wherein an intensity of the excitation radiation is less than about 500 W/cm$^2$.

41. The method of claim 1, wherein (f) is performed in less than 0.5 seconds.

42. The method of claim 1, further comprising providing deactivating radiation each time that (a)-(e) are repeated.

43. The method of claim 42, wherein the deactivating radiation is provided to the activated PTOLs to deactivate a portion of the activated PTOLs, such that the non-linear fluorescence emission pattern within the sample includes H>2 modulation harmonics.

44. The method of claim 42, wherein the deactivating radiation has a wavelength that is different from the activating wavelength.

45. The method of claim 42, wherein the deactivation radiation includes the spatially-patterned excitation radiation that is provided to the sample.

46. The method of claim 1, wherein spatially shifting one or both of the spatially-patterned excitation radiation and the spatially-patterned activation radiation includes spatially shifting one or both of the spatially-patterned excitation radiation and the spatially-patterned activation in a linear direction with respect to the sample to spatially shift the non-linear fluorescence emission pattern within the sample in the linear direction and further comprising:
shifting the rotational orientation of the non-linear fluorescence emission pattern within the sample a number, M, of times; and
repeating (a)-(e) at least N times, with N>2 for each rotational orientation of the pattern.

47. The method of claim 46, wherein the M≥2H+1.

48. An apparatus comprising:
a stage configured for supporting a sample;
a first light source and beam-forming optics configured for providing spatially-patterned activation radiation to a sample that includes phototransformable optical labels ("PTOLs"), wherein an optical parameter of the spatially-patterned activation radiation varies periodically in space within the sample;
a second light source and beam-forming optics configured for providing spatially-patterned excitation radiation to the sample, wherein an optical parameter of the spatially-patterned excitation radiation varies periodically in space within the sample, wherein the first and second light sources and beam-forming optics are configured for providing the spatially-patterned activation and excitation radiation to create a non-linear fluorescence emission pattern within the sample, the pattern including H modulation harmonics, with H>1;
wherein the stage and/or the first and second beam forming optics are configured for spatially shifting one or both of the spatially-patterned excitation radiation and the spatially-patterned activation radiation with respect to the sample to spatially shift the non-linear fluorescence emission pattern within the sample to at least N different positions, with N>2;
a detector configured for detecting radiation emitted from the non-linear fluorescence emission;
memory for storing detected radiation data for generating an image of the sample based on the detected radiation; and
one or more processors configured for generating a sub-diffraction-limited final image of the sample based on the stored data for the N positions of the non-linear fluorescence emission pattern within the sample.

49. The apparatus of claim 48, wherein a spatial period, Λ, of the periodic variation of the optical parameters of the activation and excitation radiation is the same.

50. The apparatus of claim 48, wherein the periodic variation of both the activation radiation and the excitation radiation is a sinusoidal variation.

51. The apparatus of claim 50, wherein the patterns of the activation and excitation radiation are in-phase.

52. The apparatus of claim 50, wherein the patterns of the activation and excitation radiation are out of phase.

53. The apparatus of claim 52, wherein providing the spatially-patterned excitation radiation to the sample, includes:
providing first spatially-patterned excitation radiation to the sample, wherein the first spatially-patterned excitation radiation has a first phase, $\varphi_1$, relative to the pattern of the activation radiation; and
providing second spatially-patterned excitation radiation to the sample, wherein the second spatially-patterned excitation radiation has a second phase, $\varphi_2$, relative to the pattern of the activation radiation, wherein in $\varphi_1 \neq \varphi_2$.

54. The apparatus of claim 53, wherein $\varphi_1 - \varphi_2 = 180$ degrees.

55. The apparatus of claim 50, wherein providing the spatially-patterned excitation radiation to the sample, includes:
providing first spatially-patterned excitation radiation to the sample, wherein the first spatially-patterned excitation radiation has a phase of 180 degrees relative to the pattern of the activation radiation; and
providing second spatially-patterned excitation radiation to the sample, wherein the second spatially-patterned excitation radiation is in phase with the pattern of the activation radiation.

56. The apparatus of claim 50, wherein the patterns of the activation and excitation radiation are 180 degrees out of phase.

57. The apparatus of claim 49, wherein H≥2, and the detected signal includes spatial frequency components at $-2\Lambda$, $-\Lambda$, 0, $\Lambda$, and $2\Lambda$.

58. The apparatus of claim 49, wherein H≥3, and the detected signal includes spatial frequency components at $-3\Lambda$, $-2\Lambda$, $-\Lambda$, 0, $\Lambda$, $2\Lambda$, and $3\Lambda$.

59. The apparatus of claim 56, wherein the periodically varied optical parameter of the excitation and activation radiation is the intensity of the radiations and wherein the intensities of both the activated and excited radiation is below the saturation limit.

60. The apparatus of claim 56, wherein the periodically varied optical parameter of the excitation and activation radiation is the intensity of the radiations and wherein the intensity of the activated radiation is above the saturation limit.

61. The apparatus of claim 59, wherein the periodically varied optical parameter of the excitation and activation radiation is the intensity of the radiations and wherein the intensity of the excitation radiation is above the saturation limit.

62. The apparatus of claim 48, wherein the excitation radiation has a wavelength, $\lambda$, and the detected radiation has a wavelength $\lambda/2$.

63. The apparatus of claim 48, wherein the activation radiation has a wavelength, $\lambda'$, and the PTOLs are activated through a two-photon activation process.

64. The apparatus of claim 48, wherein N≥7.

65. The apparatus of claim 48, further comprising a wavefront modulating element (WME) configured for modulating a beam of activation radiation to provide a desired pattern of activation radiation in the sample.

66. The apparatus of claim 48, further comprising a wavefront modulating element (WME) configured for modulating a beam of excitation radiation to provide a desired pattern of excitation radiation in the sample.

67. The apparatus of claim 65, wherein the WME includes a spatial light modulator (SLM).

68. The apparatus of claim 65, wherein the WME includes an digital micromirror (DMD).

69. The apparatus of claim 65, wherein the beams of activating and excitation radiation are modulated by the same WME.

70. The apparatus of claim 69, wherein activating and excitation radiation have different wavelengths, and wherein a pattern on the WME used to modulate the excitation radiation has a different period than a pattern on the WME used to modulate the activation radiation.

71. The apparatus of claim 70, wherein the different patterns for the different wavelengths on the WME are chosen to provide patterns of excitation and activation radiation at the sample that have the same period.

72. The apparatus of claim 48, wherein providing the spatially-patterned activation radiation includes providing the activation radiation via TIRF illumination of the sample.

73. The apparatus of claim 48, wherein providing the spatially-patterned excitation radiation includes providing the excitation radiation via TIRF illumination of the sample.

74. The apparatus of claim 48, wherein providing the spatially-patterned activation radiation includes:
providing a beam of activation radiation; and
sweeping the beam of activation radiation in the direction parallel to the plane of a first sheet; and
varying the optical parameter of the activation radiation while sweeping the beam.

75. The apparatus of claim 48, wherein providing the spatially-patterned excitation radiation in which an optical parameter of a second sheet varies periodically includes:
providing a beam of excitation radiation; and
sweeping the beam of excitation radiation in the direction parallel to the plane of the first sheet; and
varying the optical parameter of the excitation radiation while sweeping the beam of excitation radiation.

76. The apparatus of claim 75, wherein the beam of excitation radiation includes a Bessel-like beam.

77. The apparatus of claim 76, wherein the Bessel-like beam has a ratio of a Rayleigh length, $z_R$ to a minimum beam waist, $w_o$, of more than $2\pi w_o/\lambda$ and less than $100\pi w_o/\lambda$, wherein $\lambda$ represents the wavelength of the excitation radiation.

78. The apparatus of claim 75, wherein the Bessel-like beam has a non-zero ratio of a minimum numerical aperture to a maximum numerical aperture of less than 0.95.

79. The apparatus of claim 76, wherein the Bessel-like beam has a non-zero ratio of a minimum numerical aperture to a maximum numerical aperture of less than 0.90.

80. The apparatus of claim 76, wherein the Bessel-like beam has a minimum numerical aperture greater than zero and a ratio of energy in a first side lobe of the beam to energy in the central lobe of the beam of less than 0.5.

81. The apparatus of claim 48, wherein providing the spatially-patterned excitation radiation in which an optical parameter of the second sheet varies periodically includes:
providing the beam of excitation radiation in the form of a light sheet.

82. The apparatus of claim 81, wherein the light sheet includes a lattice light sheet.

83. The apparatus of claim 48, wherein the processor is further configured to:
generate a plurality of sub-diffraction-limited final images of the sample for each of a plurality of sequential times based on the stored data for each of the sequential times and for the N positions of the non-linear fluorescence emission pattern within the sample.

84. The apparatus of claim 83, wherein the activation and excitation radiation are provided to substantially the same plane in the sample at each of the sequential times.

85. The apparatus of claim 83, wherein the activation and excitation radiation are provided to different planes in the sample at each of the sequential times, wherein the activation and excitation radiation are provided to the same plane in the sample at each of the sequential times, each of the different planes being substantially parallel to each other.

86. The apparatus of claim 48, wherein an intensity of the excitation radiation is less than about 125 W/cm$^2$.

87. The apparatus of claim 48, wherein an intensity of the excitation radiation is less than about 500 W/cm$^2$.

88. The apparatus of claim 48, a third light source for providing deactivating radiation.

89. The apparatus of claim 88, wherein the deactivating radiation is provided to the activated PTOLs to deactivate a portion of the activated PTOLs, such that the non-linear fluorescence emission pattern within the sample includes H>2 modulation harmonics.

90. The apparatus of claim 88, wherein the deactivating radiation has a wavelength that is different from the activating wavelength.

91. The apparatus of claim 48, wherein the second light source is further configured to provide deactivation radiation to the sample.

92. The apparatus of claim 91, wherein the deactivation radiation is provided in the form of the spatially-structured excitation pattern.

93. The apparatus of claim 91, wherein the deactivation radiation is provided in the form of substantially spatially uniform excitation radiation.

94. The apparatus of claim 48, wherein spatially shifting one or both of the spatially-patterned excitation radiation and the spatially-patterned activation radiation includes spatially shifting one or both of the spatially-patterned excitation radiation and the spatially-patterned activation in a linear direction with respect to the sample to spatially shift the non-linear fluorescence emission pattern within the sample in the linear direction and further comprising:
    shifting the rotational orientation of the non-linear fluorescence emission pattern within the sample a number, M, of times; and
    repeating (a)-(e) at least N times, with N>2 for each rotational orientation of the pattern.

95. The apparatus of claim 94, wherein the M≥2H+1.

* * * * *